(12) United States Patent
Kuroki et al.

(10) Patent No.: US 7,309,718 B2
(45) Date of Patent: Dec. 18, 2007

(54) DIBENZOCYCLOHEPTENE COMPOUND

(75) Inventors: Yoshiaki Kuroki, Ube (JP); Hitoshi Ueno, Ube (JP); Tetsushi Katsube, Ube (JP); Tetsuo Kawaguchi, Ube (JP); Eiji Okanari, Ube (JP); Ichiro Tanaka, Ube (JP); Masayuki Tanaka, Ube (JP); Masahiko Hagihara, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 585 days.

(21) Appl. No.: 10/481,752

(22) PCT Filed: Jun. 27, 2002

(86) PCT No.: PCT/JP02/06469

§ 371 (c)(1),
(2), (4) Date: Dec. 23, 2003

(87) PCT Pub. No.: WO03/002539

PCT Pub. Date: Jan. 9, 2003

(65) Prior Publication Data

US 2004/0180884 A1    Sep. 16, 2004

(30) Foreign Application Priority Data

Jun. 27, 2001  (JP) ............................. 2001-193859

(51) Int. Cl.
*A61K 31/19* (2006.01)
*C07C 61/00* (2006.01)
*C07C 63/00* (2006.01)

(52) U.S. Cl. ...................... 514/557; 562/400; 562/405

(58) Field of Classification Search ................ 514/557; 562/400, 405
See application file for complete search history.

(56) References Cited

U.S. PATENT DOCUMENTS 4,235,820 A * 11/1980 Evans .......................... 564/379
6,602,901 B2 * 8/2003 Jeppesen et al. ............ 514/443
6,723,731 B2 * 4/2004 Jeppesen et al. ............ 514/292

FOREIGN PATENT DOCUMENTS

| EP | 468785 A2 | 1/1992 |
|---|---|---|
| EP | 685478 A1 | 12/1995 |
| WO | WO 01/47889 A1 | 7/2001 |

* cited by examiner

*Primary Examiner*—Kamal A. Saeed
*Assistant Examiner*—Susannah Chung
(74) *Attorney, Agent, or Firm*—Birch, Stewart, Kolasch & Birch, LLP

(57) ABSTRACT

The present invention discloses a dibenzocycloheptene compound represented by the formula (I):

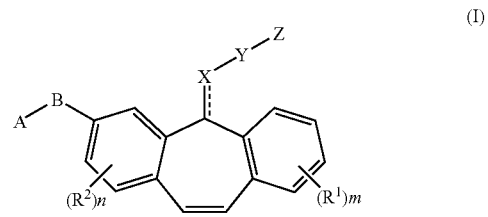

wherein $R^1$: hydrogen atom, halogen atom, etc., $R^2$: hydrogen atom, halogen atom, etc., A: 5-membered or 6-membered heteroaromatic ring group containing 1 to 3 hetero atom(s) selected from the group consisting of nitrogen atom, oxygen atom and sulfur atom, and the heteroaromatic ring group, etc. may have halogen atom, nitrogen atom, etc. as substituent(s), B: formula; —CH=CH—, formula; —CH$_2$O—, etc., Y: $C_1$-$C_{10}$ alkylene group which may have halogen atom, etc. as substituent(s), etc., Z: carboxyl group which may be protected, etc., m: an integer of 1 to 4, n: an integer of 1 to 3, ----- represents a single bond or a double bond, or a pharmaceutically acceptable salt thereof and a medical composition containing the same as an effective ingredient which has leukotriene $C_4$ antagonistic action and leukotriene $E_4$ antagonistic action in addition to potent leukotriene $D_4$ antagonistic action, and useful as antiasthmatic agent, antiallergic agent and anti-inflammatory agent.

20 Claims, No Drawings

DIBENZOCYCLOHEPTENE COMPOUND

TECHNICAL FIELD

The present invention relates to a dibenzocycloheptene compound which has, in addition to potent leukotriene $D_4$ antagonistic action, leukotriene $C_4$ antagonistic action and leukotriene $E_4$ antagonistic action, and useful as an antiazma agent, an antiallergic agent and anti-inflammatory agent, or a pharmaceutically acceptable salt thereof.

BACKGROUND ART

As a compound having leukotriene $D_4$ antagonistic action similarly in the present invention and having a structure similar to the compound of the present invention, there has been known, for example, a compound disclosed in WO94/19345, and as a compound having a structure partially similar to the same, there have been known 5-[3-[3-(2-quinolinylmethoxy)phenoxy]propyl]-1H-tetrazole (RG7152; J. Med. Chem., 33, 1186 (1990)), 5-[[2-[[4-(2-quinolinylmethoxy)phenoxy]methyl]phenyl]methyl]-1H-tetrazole (RG12525; J. Med. Chem., 33, 1194 (1990)), and a compound disclosed in WO95/18107.

In the present invention, as a result of research for long years about syntheses of compounds having potent leukotriene $D_4$ antagonistic action, as well as having antagonistic actions to leukotriene $C_4$ and leukotriene $E_4$ and their pharmaceutical effects, the inventors have found that novel dibenzocycloheptene compounds have excellent leukotriene $D_4$ antagonistic action, as well as having leukotriene $C_4$ and leukotriene $E_4$ antagonistic action with good balance, and have high safety, excellent oral absorbability and durability of the action to accomplish the present invention.

SUMMARY OF THE INVENTION

The present invention relates to a dibenzocycloheptene compound represented by the formula (I):

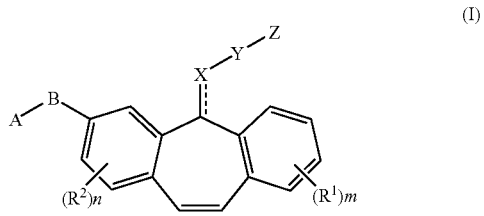

wherein $R^1$ represents a hydrogen atom, a halogen atom, a hydroxy group, a nitro group, a cyano group, a carbamoyl group, a formyl group, a carboxyl group, a 1H-tetrazol-5-yl group, a $C_1$-$C_4$ alkyl group, a fluoro $C_1$-$C_4$ alkyl group, a hydroxy $C_1$-$C_4$ alkyl group, a $C_2$-$C_4$ alkenyl group, a $C_2$-$C_4$ alkynyl group, a $C_1$-$C_4$ alkoxy group, a fluoro $C_1$-$C_4$ alkoxy group, a $C_1$-$C_4$ alkylthio group, a $C_1$-$C_4$ alkylsulfinyl group or a $C_1$-$C_4$ alkylsulfonyl group, $R^2$ represents a hydrogen atom, a halogen atom, a nitro group, a cyano group, a $C_1$-$C_4$ alkyl group or a $C_1$-$C_4$ alkoxy group, A represents a 5-membered or 6-membered heteroaromatic ring group containing 1 to 3 hetero atoms selected from the group consisting of a nitrogen atom, an oxygen atom and a sulfur atom or a fused heteroaromatic ring group in which the heteroaromatic ring group and a benzene ring are fused, the heteroaromatic ring group or fused heteroaromatic ring group may have a substituent(s) selected from a halogen atom, a nitro group, a cyano group, a $C_1$-$C_4$ alkyl group, a fluoro $C_1$-$C_4$ alkyl group, a $C_1$-$C_4$ alkoxy group, a fluoro $C_1$-$C_4$ alkoxy group, a $C_1$-$C_4$ alkylthio group or a $C_3$-$C_4$ alkylene group, B represents a formula: —CH=CH—, —CH$_2$O—, —CH$_2$CH$_2$—, —CH$_2$S—, —OCH$_2$— or —SCH$_2$—, X represents an oxygen atom, a sulfur atom, methylene group or a formula: =CH—, Y represents a $C_1$-$C_{10}$ alkylene group which may have a substituent(s) selected from a halogen atom, $C_1$-$C_4$ alkyl group and $C_1$-$C_4$ alkoxy group, or a group represented by the formula (a):

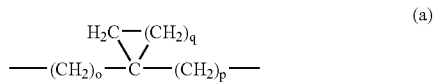

wherein o and p each represent an integer of 0 to 2, and q represents an integer of 1 to 4, Z represents a carboxyl group which may be protected; 1H-tetrazol-5-yl group; the formula —NH—SO$_2$—R$^3$; or the formula —CO—NH—SO$_2$—R$^3$
wherein R$^3$ represents a $C_1$-$C_4$ alkyl group, a fluoro $C_1$-$C_4$ alkyl group or a phenyl group which may have a halogen atom, a $C_1$-$C_4$ alkyl group, a fluoro $C_1$-$C_4$ alkyl group, a $C_1$-$C_4$ alkoxy group, a fluoro $C_1$-$C_4$ alkoxy group, a nitro group or a cyano group as a substituent(s), m is an integer of 1 to 4, when m is 2 or more, a plural number of R$^1$ may be different from each other, n is an integer of 1 to 3, and when n is 2 or more, a plural number of R$^2$ may be different from each other, ⁓⁓⁓ represents a single bond or a double bond, or a pharmaceutically acceptable salt thereof.

BEST MODE FOR CARRYING OUT THE INVENTION

In the compound represented by the above-mentioned formula (I), as the halogen atom of R$^1$, there may be mentioned, for example, a fluorine atom, a chlorine atom, bromine atom or iodine atom, preferably a fluorine atom, a chlorine atom or bromine atom, more preferably a fluorine atom or a chlorine atom.

As the $C_1$-$C_4$ alkyl group of R$^1$, there may be mentioned, for example, a straight or branched $C_1$-$C_4$ alkyl group such as methyl, ethyl, propyl, isopropyl, butyl, isobutyl, sec-butyl or t-butyl group, preferably methyl, ethyl, propyl or isopropyl group, more preferably methyl or ethyl group, particularly preferably methyl group.

As the fluoro $C_1$-$C_4$ alkyl group of R$^1$, there may be mentioned, for example, a straight or branched $C_1$-$C_4$ alkyl group substituted by 1 to 3 fluorine atoms such as fluoromethyl, difluoromethyl, trifluoromethyl, 2-fluoroethyl, 2,2,2-trifluoroethyl, 2-fluoropropyl, 3-fluoropropyl or 4-fluorobutyl group, preferably fluoromethyl, difluoromethyl, trifluoromethyl or 2-fluoroethyl group, more preferably fluoromethyl, difluoromethyl or trifluoromethyl group, particularly preferably difluoromethyl or trifluoromethyl group.

As the hydroxy $C_1$-$C_4$ alkyl group of R$^1$, there may be mentioned, for example, a straight or branched $C_1$-$C_4$ alkyl group substituted by hydroxy group such as a hydroxymethyl, 1-hydroxyethyl, 2-hydroxyethyl, 1-hydroxy-1-methylethyl, 1-hydroxypropyl, 2-hydroxypropyl, 3-hydroxypropyl, 1-hydroxybutyl or 4-hydroxybutyl group, preferably hydroxymethyl, 1-hydroxyethyl, 2-hydroxyethyl, 1-hydroxy-1-methylethyl, 1-hydroxypropyl or 2-hydroxypropyl group, more preferably hydroxymethyl, 1-hydroxyethyl, 1-hydroxy-1-methylethyl or 1-hydroxypropyl group, particularly preferably hydroxymethyl or 1-hydroxy-1-methylethyl group.

As the $C_2$-$C_4$ alkenyl group of $R^1$, there may be mentioned, for example, a straight or branched $C_2$-$C_4$ alkenyl group such as vinyl, 1-propenyl, allyl, isopropenyl, 1-butenyl, 2-butenyl, 3-butenyl, 1-methyl-1-propenyl, 2-methyl-1-propenyl or 2-methyl-2-propenyl group, preferably vinyl, 1-propenyl, allyl, 1-butenyl, 2-butenyl or 2-methyl-1-propenyl group, more preferably vinyl, 1-propenyl or allyl group, particularly preferably vinyl group.

As the $C_2$-$C_4$ alkynyl group of $R^1$, there may be mentioned, for example, a straight $C_2$-$C_4$ alkynyl group such as ethynyl, 1-propynyl, propargyl, 1-butynyl, 2-butynyl or 3-butynyl group, preferably ethynyl, 1-propynyl or 1-butynyl group, more preferably ethynyl or 1-propynyl group, particularly preferably ethynyl group.

As the $C_1$-$C_4$ alkoxy group of $R^1$, there may be mentioned, for example, a straight or branched $C_1$-$C_4$ alkoxy group such as methoxy, ethoxy, propoxy, isopropoxy, butoxy, isobutoxy, sec-butoxy or t-butoxy group, preferably methoxy, ethoxy, propoxy or isopropoxy group, more preferably methoxy or ethoxy group, particularly preferably methoxy group.

As the fluoro $C_1$-$C_4$ alkoxy group of $R^1$, there may be mentioned, for example, a straight or branched $C_1$-$C_4$ alkoxy group substituted by 1 to 3 fluorine atoms such as fluoromethoxy, difluoromethoxy, trifluoromethoxy, 2-fluoroethoxy, 2,2,2-trifluoroethoxy, 2-fluoropropoxy, 3-fluoropropoxy or 4-fluorobutoxy group, preferably fluoromethoxy, difluoromethoxy, trifluoromethoxy or 2-fluoroethoxy group, more preferably fluoromethoxy, difluoromethoxy or trifluoromethoxy group, particularly preferably difluoromethoxy or trifluoromethoxy group.

As the $C_1$-$C_4$ alkylthio group of $R^1$, there may be mentioned, for example, a straight or branched $C_1$-$C_4$ alkylthio group such as methylthio, ethylthio, propylthio, isopropylthio, butylthio, isobutylthio, sec-butylthio or t-butylthio group, preferably methylthio, ethylthio, propylthio or isopropylthio group, more preferably methylthio or ethylthio group, particularly preferably methylthio group.

As the $C_1$-$C_4$ alkylsulfinyl group of $R^1$, there may be mentioned, for example, a straight or branched $C_1$-$C_4$ alkylsulfinyl group such as methylsulfinyl, ethylsulfinyl, propylsulfinyl, isopropylsulfinyl, butylsulfinyl, isobutylsulfinyl, sec-butylsulfinyl or t-butylsulfinyl group, preferably methylsulfinyl, ethylsulfinyl, propylsulfinyl or isopropylsulfinyl group, more preferably methylsulfinyl or ethylsulfinyl group, particularly preferably methylsulfinyl group.

As the $C_1$-$C_4$ alkylsulfonyl group of $R^1$, there may be mentioned, for example, a straight or branched $C_1$-$C_4$ alkylsulfonyl group such as methylsulfonyl, ethylsulfonyl, propylsulfonyl, isopropylsulfonyl, butylsulfonyl, isobutylsulfonyl, sec-butylsulfonyl or t-butylsulfonyl group, preferably methylsulfonyl, ethylsulfonyl, propylsulfonyl or isopropylsulfonyl group, more preferably methylsulfonyl or ethylsulfonyl group, particularly preferably methylsulfonyl group.

In particular, as $R^1$ in the formula (I), there may be preferably mentioned a hydrogen atom, a fluorine atom, a chlorine atom, bromine atom, a hydroxy group, a nitro group, a cyano group, a carbamoyl group, a formyl group, a carboxyl group, 1H-tetrazol-5-yl group, methyl group, ethyl group, propyl group, isopropyl group, fluoromethyl group, difluoromethyl group, trifluoromethyl group, 2-fluoroethyl group, hydroxymethyl group, 1-hydroxyethyl group, 2-hydroxyethyl group, 1-hydroxy-1-methylethyl group, 1-hydroxypropyl group, 2-hydroxypropyl group, vinyl group, 1-propenyl group, allyl group, 1-butenyl group, 2-butenyl group, 2-methyl-1-propenyl group, ethynyl group, 1-propynyl group, 1-butynyl group, methoxy group, ethoxy group, propoxy group, isopropoxy group, fluoromethoxy group, difluoromethoxy group, trifluoromethoxy group, 2-fluoroethoxy group, methylthio group, ethylthio group, propylthio group, isopropylthio group, methylsulfinyl group, ethylsulfinyl group, propylsulfinyl group, isopropylsulfinyl group, methylsulfonyl group, ethylsulfonyl group, propylsulfonyl group or isopropylsulfonyl group, more preferably a hydrogen atom, a fluorine atom, a chlorine atom, a hydroxy group, a nitro group, a cyano group, a carbamoyl group, a formyl group, 1H-tetrazol-5-yl group, methyl group, ethyl group, fluoromethyl group, difluoromethyl group, trifluoromethyl group, hydroxymethyl group, 1-hydroxyethyl group, 1-hydroxy-1-methylethyl group, 1-hydroxypropyl group, vinyl group, 1-propenyl group, allyl group, ethynyl group, 1-propynyl group, 1-butynyl group, methoxy group, ethoxy group, fluoromethoxy group, difluoromethoxy group, trifluoromethoxy group, methylthio group, ethylthio group, methylsulfinyl group, ethylsulfinyl group, methylsulfonyl group or ethylsulfonyl group, further more preferably hydrogen atom, fluorine atom, chlorine atom, nitro group, cyano group, formyl group, 1H-tetrazol-5-yl group, methyl group, difluoromethyl group, trifluoromethyl group, hydroxymethyl group, 1-hydroxy-1-methylethyl group, vinyl group, ethynyl group, methoxy group, difluoromethoxy group, trifluoromethoxy group, methylthio group, methylsulfinyl group or methylsulfonyl group, particularly preferably hydrogen atom, fluorine atom, chlorine atom, cyano group, trifluoromethyl group, hydroxymethyl group, 1-hydroxy-1-methylethyl group, ethynyl group, methoxy group, difluoromethoxy group, trifluoromethoxy group, methylsulfinyl group or methylsulfonyl group.

In the formula (I), a halogen atom, $C_1$-$C_4$ alkyl group and $C_1$-$C_4$ alkoxy group of $R^2$ have the same meanings as those of the above-mentioned $R^1$, and as $R^2$, there may be preferably mentioned hydrogen atom, fluorine atom, chlorine atom, bromine atom, nitro group, cyano group, methyl group, ethyl group, propyl group, isopropyl group, methoxy group, ethoxy group, propoxy group or isopropoxy group, more preferably hydrogen atom, fluorine atom, chlorine atom, nitro group, cyano group, methyl group, ethyl group, methoxy group or ethoxy group, further more preferably hydrogen atom, fluorine atom, chlorine atom, methyl group or methoxy group, particularly preferably hydrogen atom.

In the formula (I), "a 5-membered or 6-membered heteroaromatic ring group containing 1 to 3 hetero atom(s) selected from the group consisting of a nitrogen atom, an oxygen atom and a sulfur atom or a fused heteroaromatic ring group in which the heteroaromatic ring group and a benzene are fused" of A, there may be mentioned, for example, a 5-membered heteroaromatic ring group such as furan, thiophen, oxazol, thiazol, imidazol, pyrazol or thiadiazol group; a 6-membered heteroaromatic ring group such as pyridin, pyrimidin, pyridazin or pyrazin group; or a fused heteroaromatic ring group such as benzofuran, benzothiophen, benzoxazol, benzothiazol, benzimidazol, quinolin, quinazolin or quinoxalin group, preferably oxazol, thiazol, imidazol, pyrazol, thiadiazol, pyridine, pyrimidin, pyridazin, pyrazin, benzoxazol, benzothiazol, benzimidazol, quinolin, quinazolin or quinoxalin group, more preferably thiazol, thiadiazol, pyridine, pyrimidin, benzoxazol, benzothiazol, quinolin or quinazolin group, particularly preferably pyridine, benzothiazol or quinolin group.

The above-mentioned heteroaromatic ring group or fused heteroaromatic ring group may have a substituent(s), and as the substituent(s), there may be mentioned, for example, a halogen atom with the same meaning as $R^1$; a $C_1$-$C_4$ alkyl group with the same meaning as $R^1$; a fluoro $C_1$-$C_4$ alkyl group with the same meaning as $R^1$; a $C_1$-$C_4$ alkoxy group with the same meaning as $R^1$; a fluoro $C_1$-$C_4$ alkoxy group with the same meaning as $R^1$; a $C_1$-$C_4$ alkylthio group with the same meaning as $R^1$; nitro group; cyano group; or a $C_3$-$C_4$ alkylene group such as trimethylene, tetramethylene group (said alkylene group bonds to an adjacent carbon atom on the heteroaromatic ring to form a 5-membered ring or 6-membered ring), preferably fluorine atom, chlorine atom, bromine atom, nitro, cyano, methyl, ethyl, propyl, isopropyl, butyl, isobutyl, t-butyl, fluoromethyl, difluoromethyl, trifluoromethyl, 2-fluoroethyl, methoxy, ethoxy, propoxy, isopropoxy, fluoromethoxy, difluoromethoxy, trifluoromethoxy, 2-fluoroethoxy, methylthio, ethylthio, propylthio, isopropylthio, trimethylene or tetramethylene group, more preferably a fluorine atom, a chlorine atom, nitro, cyano, methyl, ethyl, isopropyl, t-butyl, fluoromethyl, difluoromethyl, trifluoromethyl, methoxy, ethoxy, fluoromethoxy, difluoromethoxy, trifluoromethoxy, methylthio, ethylthio, trimethylene or tetramethylene group, further more preferably fluorine atom, chlorine atom, nitro, cyano, methyl, isopropyl, t-butyl, difluoromethyl, trifluoromethyl, methoxy, difluoromethoxy, trifluoromethoxy, methylthio or tetramethylene group, particularly preferably fluorine atom, chlorine atom, trifluoromethyl or tetramethylene group.

A number of the substituent(s) on the heteroaromatic ring group or fused heteroaromatic ring group is 1 to 4, preferably 1 to 2.

As A in the formula (I), it is specifically mentioned, preferably 2-oxazolyl, 2-thiazolyl, 2- or 4-imidazolyl, 3-pyrazolyl, 1,3,4-thiadiazol-2-yl, 2-pyridyl, 2- or 4-pyrimidinyl, 3-pyridazinyl, 2-pyrazinyl, 2-benzoxazolyl, 2-benzothiazolyl, 2-benzoimidazolyl, quinolin-2-yl, quinazolin-2-yl, quinoxalin-2-yl, 4-methyl-2-thiazolyl, 4-ethyl-2-thiazolyl, 4-isopropyl-2-thiazolyl, 4-t-butyl-2-thiazolyl, 4-trifluoromethyl-2-thiazolyl, 5-methyl-1,3,4-thiadiazol-2-yl, 5-ethyl-1,3,4-thiadiazol-2-yl, 5-isopropyl-1,3,4-thiadiazol-2-yl, 5-t-butyl-1,3,4-thiadiazol-2-yl, 5-trifluoromethyl-1,3,4-thiadiazol-2-yl, 5,6-difluoro-2-pyridyl, 5,6-dichloro-2-pyridyl, 5,6-dimethyl-2-pyridyl, 5,6-diethyl-2-pyridyl, 6-trifluoromethyl-2-pyridyl, 6-methylthio-2-pyridyl, 5H-6,7-dihydrocyclopenta[b]pyridin-2-yl, 5,6,7,8-tetrahydroquinolin-2-yl, 5,6-difluoro-2-pyrimidinyl, 5,6-dichloro-2-pyrimidinyl, 5,6-dimethyl-2-pyrimidinyl, 6-trifluoromethyl-2-pyrimidinyl, 5H-6,7-dihydrocyclopenta[d]pyrimidin-2-yl, 5,6,7,8-tetrahydroquinazolin-2-yl, 6-fluoro-2-benzoxazolyl, 5-fluoro-2-benzoxazolyl, 5,6-difluoro-2-benzoxazolyl, 6-chloro-2-benzoxazolyl, 5-chloro-2-benzoxazolyl, 5,6-dichloro-2-benzoxazolyl, 5-chloro-6-fluoro-2-benzoxazolyl, 5-methyl-2-benzoxazolyl, 5-cyano-2-benzoxazolyl, 5-trifluoromethyl-2-benzoxazolyl, 5-methylthio-2-benzoxazolyl, 6-fluoro-2-benzothiazolyl, 5-fluoro-2-benzothiazolyl, 5,6-difluoro-2-benzothiazolyl, 6-chloro-2-benzothiazolyl, 5-chloro-2-benzothiazolyl, 5,6-dichloro-2-benzothiazolyl, 5-chloro-6-fluoro-2-benzothiazolyl, 5-methyl-2-benzothiazolyl, 5-cyano-2-benzothiazolyl, 5-trifluoromethyl-2-benzothiazolyl, 5-methylthio-2-benzothiazolyl, 5-fluoroquinolin-2-yl, 6-fluoroquinolin-2-yl, 7-fluoroquinolin-2-yl, 5-chloroquinolin-2-yl, 6-chloroquinolin-2-yl, 7-chloroquinolin-2-yl, 7-methylquinolin-2-yl, 7-trifluoromethylquinolin-2-yl, 7-methoxyquinolin-2-yl, 7-difluoromethoxyquinolin-2-yl, 7-trifluoromethoxyquinolin-2-yl, 5,7-difluoroquinolin-2-yl, 6,7-difluoroquinolin-2-yl, 5,7-dichloroquinolin-2-yl, 6,7-dichloroquinolin-2-yl, 5-chloro-7-fluoroquinolin-2-yl, 6-chloro-7-fluoroquinolin-2-yl, 7-chloro-5-fluoroquinolin-2-yl, 7-chloro-6-fluoroquinolin-2-yl, 7-chloro-6-cyanoquinolin-2-yl, 7-cyano-6-fluoroquinolin-2-yl, 6-fluoro-7-trifluoromethylquinolin-2-yl, 5,6,7-trifluoroquinolin-2-yl, 5-fluoroquinazolin-2-yl, 6-fluoroquinazolin-2-yl, 7-fluoroquinazolin-2-yl, 5-chloroquinazolin-2-yl, 6-chloroquinazolin-2-yl, 7-chloroquinazolin-2-yl, 7-methylquinazolin-2-yl, 7-trifluoromethylquinazolin-2-yl, 7-methoxyquinazolin-2-yl, 7-difluoromethoxyquinazolin-2-yl, 7-trifluoromethoxyquinazolin-2-yl, 5,7-difluoroquinazolin-2-yl, 6,7-difluoroquinazolin-2-yl, 5,7-dichloroquinazolin-2-yl, 6,7-dichloroquinazolin-2-yl, 5-chloro-7-fluoroquinazolin-2-yl, 6-chloro-7-fluoroquinazolin-2-yl, 7-chloro-5-fluoroquinazolin-2-yl, 7-chloro-6-fluoroquinazolin-2-yl, 7-chloro-6-cyanoquinazolin-2-yl, 7-cyano-6-fluoroquinazolin-2-yl, 6-fluoro-7-trifluoromethylquinazolin-2-yl or 5,6,7-trifluoroquinazolin-2-yl group, more preferably 2-thiazolyl, 1,3,4-thiadiazol-2-yl, 2-pyridyl, 2-pyrimidinyl, 2-benzoxazolyl, 2-benzothiazolyl, quinolin-2-yl, quinazolin-2-yl, 4-methyl-2-thiazolyl, 4-isopropyl-2-thiazolyl, 4-t-butyl-2-thiazolyl, 4-trifluoromethyl-2-thiazolyl, 5-methyl-1,3,4-thiadiazol-2-yl, 5-isopropyl-1,3,4-thiadiazol-2-yl, 5-t-butyl-1,3,4-thiadiazol-2-yl, 5-trifluoromethyl-1,3,4-thiadiazol-2-yl, 5,6-difluoro-2-pyridyl, 5,6-dichloro-2-pyridyl, 5,6-dimethyl-2-pyridyl, 5H-6,7-dihydrocyclopenta[b]pyridin-2-yl, 5,6,7,8-tetrahydroquinolin-2-yl, 5,6-difluoro-2-pyrimidinyl, 5,6-dichloro-2-pyrimidinyl, 5,6-dimethyl-2-pyrimidinyl, 6-trifluoromethyl-2-pyrimidinyl, 5H-6,7-dihydrocyclopenta[d]pyrimidin-2-yl, 5,6,7,8-tetrahydroquinazolin-2-yl, 6-fluoro-2-benzoxazolyl, 5-fluoro-2-benzoxazolyl, 5,6-difluoro-2-benzoxazolyl, 6-chloro-2-benzoxazolyl, 5-chloro-2-benzoxazolyl, 5,6-dichloro-2-benzoxazolyl, 5-chloro-6-fluoro-2-benzoxazolyl, 5-methyl-2-benzoxazolyl, 5-cyano-2-benzoxazolyl, 5-trifluoromethyl-2-benzoxazolyl, 5-methylthio-2-benzoxazolyl, 6-fluoro-2-benzothiazolyl, 5-fluoro-2-benzothiazolyl, 5,6-difluoro-2-benzothiazolyl, 6-chloro-2-benzothiazolyl, 5-chloro-2-benzothiazolyl, 5,6-dichloro-2-benzothiazolyl, 5-chloro-6-fluoro-2-benzothiazolyl, 5-methyl-2-benzothiazolyl, 5-cyano-2-benzothiazolyl, 5-trifluoromethyl-2-benzothiazolyl, 5-methylthio-2-benzothiazolyl, 5-fluoroquinolin-2-yl, 6-fluoroquinolin-2-yl, 7-fluoroquinolin-2-yl, 5-chloroquinolin-2-yl, 6-chloroquinolin-2-yl, 7-chloroquinolin-2-yl, 7-methylquinolin-2-yl, 7-trifluoromethylquinolin-2-yl, 7-methoxyquinolin-2-yl, 7-difluoromethoxyquinolin-2-yl, 7-trifluoromethoxyquinolin-2-yl, 5,7-difluoroquinolin-2-yl, 6,7-difluoroquinolin-2-yl, 5,7-dichloroquinolin-2-yl, 6,7-dichloroquinolin-2-yl, 5-chloro-7-fluoroquinolin-2-yl, 6-chloro-7-fluoroquinolin-2-yl, 7-chloro-5-fluoroquinolin-2-yl, 7-chloro-6-fluoroquinolin-2-yl, 7-chloro-6-cyanoquinolin-2-yl, 7-cyano-6-fluoroquinolin-2-yl, 6-fluoro-7-trifluoromethylquinolin-2-yl, 5,6,7-trifluoroquinolin-2-yl, 5-fluoroquinazolin-2-yl, 6-fluoroquinazolin-2-yl, 7-fluoroquinazolin-2-yl, 5-chloroquinazolin-2-yl, 6-chloroquinazolin-2-yl, 7-chloroquinazolin-2-yl, 7-methylquinazolin-2-yl, 7-trifluoromethylquinazolin-2-yl, 7-methoxyquinazolin-2-yl, 7-difluoromethoxyquinazolin-2-yl, 7-trifluoromethoxyquinazolin-2-yl, 5,7-difluoroquinazolin-2-yl, 6,7-difluoroquinazolin-2-yl, 5,7-dichloroquinazolin-2-yl, 6,7-dichloroquinazolin-2-yl, 5-chloro-7-fluoroquinazolin-2-yl, 6-chloro-7-fluoroquinazolin-2-yl, 7-chloro-5-fluoroquinazolin-2-yl, 7-chloro-6-fluoroquinazolin-2-yl, 7-chloro-6-cyanoquinazolin-2-yl, 7-cyano-6-fluoroquinazolin-2-yl, 6-fluoro-7-trifluoromethylquinazolin-2-yl or 5,6,7-trifluoroquinazolin-2-yl group, further more preferably 2-pyridyl, 2-benzothiazolyl, quinolin-2-yl, 5,6-difluoro-2-pyridyl, 5,6-dichloro-2-pyridyl, 5,6-dimethyl-2-pyridyl, 5,6,7,8-tetrahydroquinolin-2-yl, 6-fluoro-2-benzothiazolyl, 5-fluoro-2-benzothiazolyl, 5,6-difluoro-2-benzothiazolyl, 6-chloro-2-benzothiazolyl, 5-chloro-2-benzothiazolyl, 5,6-dichloro-2-benzothiazolyl, 5-chloro-6-fluoro-2-benzothiazolyl, 5-methyl-2-benzothiazolyl, 5-cyano-2-benzothiazolyl, 5-trifluoromethyl-2-benzothiazolyl, 5-methylthio-2-benzothiazolyl, 5-fluoroquinolin-2-yl, 6-fluoroquinolin-2-yl, 7-fluoroquinolin-2-yl, 5-chloroquinolin-2-yl, 6-chloroquinolin-2-yl, 7-chloroquinolin-2-yl, 7-methylquinolin-2-yl, 7-trifluoromethylquinolin-2-yl, 7-methoxyquinolin-2-yl, 7-difluoromethoxyquinolin-2-yl, 7-trifluoromethoxyquinolin-2-yl, 5,7-difluoroquinolin-2-yl, 6,7-difluoroquinolin-2-yl, 5,7-dichloroquinolin-2-yl, 6,7-dichloroquinolin-2-yl, 5-chloro-7-fluoroquinolin-2-yl, 6-chloro-7-fluoroquinolin-2-yl, 7-chloro-5-fluoroquinolin-2-yl, 7-chloro-6-fluoroquinolin-2-yl, 7-chloro-6-cyanoquinolin-2-yl, 7-cyano-6-fluoroquinolin-2-yl, 6-fluoro-7-trifluoromethylquinolin-2-yl or 5,6,7-trifluoroquinolin-2-yl group, particularly preferably 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl or 7-chloro-6-fluoroquinolin-2-yl.

In the above-mentioned formula (I), B is, for example, a formula: —CH=CH—, a formula: —CH$_2$O—, a formula: —CH$_2$CH$_2$—, a formula: —CH$_2$S—, a formula: —OCH$_2$— or a formula: —SCH$_2$—, preferably a formula: —CH=CH—, a formula: —OCH$_2$— or a formula: —CH$_2$O—.

In the above-mentioned formula (I), X is an oxygen atom, a sulfur atom, a methylene group or a formula: =CH—, preferably an oxygen atom or a sulfur atom.

As the $C_1$-$C_{10}$ alkylene group of Y in the above-mentioned formula (I), there may be mentioned, for example, a straight $C_1$-$C_{10}$ alkylene group such as methylene, ethylene, trimethylene, tetramethylene, pentamethylene, hexamethylene, heptamethylene, octamethylene, nonamethylene or decamethylene group, preferably a $C_1$-$C_6$ alkylene group, more preferably a $C_1$-$C_4$ alkylene group, particularly preferably methylene, ethylene or trimethylene group.

Said alkylene group may have a substituent(s), and a halogen atom, a $C_1$-$C_4$ alkyl group and a $C_1$-$C_4$ alkoxy group as said substituent(s) thereof have the same meanings as those mentioned in the above-mentioned $R^1$, respectively.

As the substituent(s) for the alkylene group of Y, there may be preferably mentioned fluorine atom, chlorine atom, methyl, ethyl, propyl, methoxy, ethoxy or propoxy group, more preferably fluorine atom, methyl, ethyl or methoxy group, particularly preferably fluorine atom or methyl group.

As the group represented by the formula (a) of Y, there may be preferably mentioned a group wherein o=0, p=0 and q=1 (hereinafter referred to as (a-1) group), a group wherein o=0, p=1 and q=1 (hereinafter referred to as (a-2) group), a group wherein o=0, p=1 and q=2 (hereinafter referred to as (a-3) group), a group wherein o=1, p=0 and q=1 (hereinafter referred to as (a-4) group), a group wherein o=1, p=1 and q=1 (hereinafter referred to as (a-5) group), a group wherein o=1, p=1 and q=2 (hereinafter referred to as (a-6) group) or a group wherein o=1, p=1 and q=3 (hereinafter referred to as (a-7) group), more preferably a (a-4) group, a (a-5) group or a (a-6) group, particularly more preferably (a-5) group.

As the preferred group of Y in the formula (I), there may be specifically mentioned methylene, ethylene, trimethylene, tetramethylene, pentamethylene, fluoromethylene, difluoromethylene, 1-fluoroethylene, 2-fluoroethylene, 1,1-difluoroethylene, 2,2-difluoroethylene, ethylidene, 1-methylethylene, 2-methylethylene, 1,1-dimethylethylene, 2,2-dimethylethylene, 1-ethylethylene, 2-ethylethylene, 1-methoxyethylene, 2-methoxyethylene, 1-fluorotrimethylene, 2-fluorotrimethylene, 3-fluorotrimethylene, 1,1-difluorotrimethylene, 2,2-difluorotrimethylene, 3,3-difluorotrimethylene, 1-methyltrimethylene, 2-methyltrimethylene, 1,1-dimethyltrimethylene, 2,2-dimethyltrimethylene, 3,3-dimethyltrimethylene, 2,2-diethyltrimethylene, 2-methoxytrimethylene, 3-methoxytrimethylene, 2,2-dimethoxytrimethylene, 3,3-dimethoxytrimethylene, (a-1) group, (a-2) group, (a-3) group, (a-4) group, (a-5) group or (a-6) group, more preferably methylene, ethylene, trimethylene, fluoromethylene, difluoromethylene, 1-fluoroethylene, 2-fluoroethylene, 1,1-difluoroethylene, 2,2-difluoroethylene, ethylidene, 1-methylethylene, 2-methylethylene, 1-fluorotrimethylene, 2-fluorotrimethylene, 3-fluorotrimethylene, 1,1-difluorotrimethylene, 2,2-difluorotrimethylene, 3,3-difluorotrimethylene, 1-methyltrimethylene, 2-methyltrimethylene, 1,1-dimethyltrimethylene, 2,2-dimethyltrimethylene, 3,3-dimethyltrimethylene, (a-4) group, (a-5) group or (a-6) group, further more preferably methylene, ethylene, trimethylene, difluoromethylene, 1-fluoroethylene, 2-fluoroethylene, 1,1-difluoroethylene, 2,2-difluoroethylene, ethylidene, 1-methylethylene, 2-methylethylene, 2,2-difluorotrimethylene, 1-methyltrimethylene, 2-methyltrimethylene, 1,1-dimethyltrimethylene, 2,2-dimethyltrimethylene, 3,3-dimethyltrimethylene or (a-5) group, particularly preferably methylene, ethylene, trimethylene, ethylidene, 1-methylethylene, 2-methylethylene or (a-5) group.

In a group of the formula: —NH—SO$_2$—$R^3$ or the formula: —CO—NH—SO$_2$—$R^3$ group shown by Z, $C_1$-$C_4$ alkyl group of $R^3$; a fluoro $C_1$-$C_4$ alkyl group of $R^3$; or a halogen atom, $C_1$-$C_4$ alkyl group, fluoro $C_1$-$C_4$ alkyl group, $C_1$-$C_4$ alkoxy group or fluoro $C_1$-$C_4$ alkoxy group which is a substituent(s) on a phenyl group of $R^3$ have the same meanings as those mentioned in the above-mentioned $R^1$, respectively.

As $R^3$, there may be preferably mentioned methyl, ethyl, propyl, fluoromethyl, difluoromethyl, trifluoromethyl, 2-fluoroethyl, 2,2,2-trifluoroethyl, phenyl, (o-, m- or p-)fluorophenyl, (o-, m- or p-)chlorophenyl, (o-, m- or p-)methylphenyl, (o-, m- or p-)ethylphenyl, (o-, m- or p-)(trifluoromethyl)phenyl, (o-, m- or p-)methoxyphenyl, (o-, m- or p-)ethoxyphenyl, (o-, m- or p-)(difluoromethoxy)phenyl, (o-, m- or p-)(trifluoromethoxy)phenyl, (o-, m- or p-)nitrophenyl or (o-, m- or p-)cyanophenyl group, more preferably methyl, ethyl, trifluoromethyl, 2-fluoroethyl, 2,2,2-trifluoroethyl, phenyl, (o- or p-)fluorophenyl, (o- or p-)chlorophenyl, (o- or p-)methylphenyl, (o- or p-)(trifluoromethyl)phenyl, (o- or p-)methoxyphenyl, (o- or p-)(difluoromethoxy)phenyl, (o- or p-)(trifluoromethoxy)phenyl, (o- or p-)nitrophenyl or (o- or p-)cyanophenyl group, further more preferably methyl, ethyl, trifluoromethyl, phenyl, p-fluorophenyl, p-chlorophenyl, (o- or p-)methylphenyl, p-(trifluoromethyl)phenyl, (o- or p-)methoxyphenyl, p-(difluoromethoxy)phenyl, p-(trifluoromethoxy)phenyl, p-nitrophenyl or p-cyanophenyl group, particularly preferably methyl, trifluoromethyl, phenyl, o-methylphenyl or p-methylphenyl group.

As a preferred group of Z in the formula (I), there may be specifically mentioned carboxy, 1H-tetrazol-5-yl, methanesulfonylamino, ethanesulfonylamino, trifluoromethanesulfonylamino, phenylsulfonylamino, p-fluorophenylsulfonylamino, p-chlorophenylsulfonylamino, o-methylphenylsulfonylamino, p-methylphenylsulfonylamino, p-trifluoromethylphenylsulfonylamino, o-methoxyphenylsulfonylamino, p-methoxyphenylsulfonylamino, p-difluoromethoxyphenylsulfonylamino, p-trifluoromethoxyphenylsulfonylamino, p-nitrophenylsulfonylamino, p-cyanophenylsulfonylamino, methanesulfonylaminocarbonyl, ethanesulfonylaminocarbonyl, trifluoromethanesulfonylaminocarbonyl, phenylsulfonylaminocarbonyl, p-fluorophenylsulfonylaminocarbonyl, p-chlorophenylsulfonylaminocarbonyl, o-methylphenylsulfonylaminocarbonyl, p-methylphenylsulfonylaminocarbonyl, p-trifluoromethylphenylsulfonylaminocarbonyl, o-methoxyphenylsulfonylaminocarbonyl, p-methoxyphenylsulfonylaminocarbonyl, p-difluoromethoxyphenylsulfonylaminocarbonyl, p-trifluoromethoxyphenylsulfonylaminocarbonyl, p-nitrophenylsulfonylaminocarbonyl or p-cyanophenylsulfonylaminocarbonyl group, more preferably carboxy, 1H-tetrazol-5-yl, methanesulfonylamino, trifluoromethanesulfonylamino, phenylsulfonylamino, o-methylphenylsulfonylamino, p-methylphenylsulfonylamino, methanesulfonylaminocarbonyl, trifluoromethanesulfonylaminocarbonyl, phenylsulfonylaminocarbonyl, o-methylphenylsulfonylaminocarbonyl or p-methylphenylsulfonylaminocarbonyl group, further more preferably carboxy, methanesulfonylamino, trifluoromethanesulfonylamino, methanesulfonylaminocarbonyl or trifluoromethanesulfonylaminocarbonyl group, particularly preferably carboxyl group.

Incidentally, when Z is a carboxyl group, the carboxyl group may be protected by a protective group. As the protective group, it is not specifically limited so long as it can be easily deprotected in a living body to be changed to a carboxyl group, and there may be mentioned, for example, a $C_1$-$C_4$ alkyl group having the same meanings as those defined in $R^1$; a $C_7$-$C_{10}$ aralkyl group such as benzyl, phenylethyl or phenylpropyl group; a $C_1$-$C_4$ alkyl group substituted by a $C_2$-$C_5$ alkanoyloxy group, such as acetoxymethyl, 1-acetoxyethyl, 1-acetoxypropyl, 1-acetoxybutyl, propanoyloxymethyl, 1-propanoyloxyethyl, butanoyloxymethyl, 1-butanoyloxymethyl, pivaloyloxymethyl, 1-pivaloyloxyethyl, 1-pivaloyloxypropyl or 1-pivaloyloxybutyl group; a $C_1$-$C_4$ alkyl group substituted by a ($C_1$-$C_4$ alkoxy)carbonyloxy group, such as methoxycarbonyloxymethyl, 1-(methoxycarbonyloxy)ethyl, ethoxycarbonyloxymethyl, 1-(ethoxycarbonyloxy)ethyl, propoxycarbonyloxymethyl, oxymethylcarbonyloxymethyl, 1-(isopropoxycarbonyloxy)ethyl, butoxycarbonyloxymethyl, 1-(butoxycarbonyloxy)ethyl, t-butoxycarbonyloxymethyl or 1-(t-butoxycarbonyloxy)ethyl group; a $C_1$-$C_4$ alkyl group substituted by a N,N-di($C_1$-$C_4$ alkyl)aminocarbonyl group such as N,N-dimethylaminocarbonylmethyl, 2-(N,N-dimethylaminocarbonyl)ethyl or N,N-diethylaminocarbonylmethyl group; a $C_1$-$C_4$ alkyl group substituted by a N,N-di($C_1$-$C_4$ alkyl)amino group or a 5- to 6-membered cyclic amino group which may contain an oxygen atom such as 2-(N,N-dimethylamino)ethyl, 2-(N,N-diethylamino)ethyl, 3-(N,N-dimethylamino)propyl, 2-piperidinoethyl, 2-(4-methyl)piperidinoethyl, 3-piperidinopropyl or 2-morpholinoethyl group; or (5-methyl-2-oxo-1,3-dioxolen-4-yl)methyl group, and the like.

As a protective group for the carboxyl group, it is preferably a $C_1$-$C_4$ alkyl group; benzyl group; a $C_1$-$C_2$ alkyl group substituted by a $C_2$-$C_5$ alkanoyloxy group; a $C_1$-$C_2$ alkyl group substituted by a ($C_1$-$C_4$ alkoxy)carbonyloxy group; or (5-methyl-2-oxo-1,3-dioxolen-4-yl)methyl group, more preferably methyl, ethyl, propyl, isopropyl, butyl, isobutyl, acetoxymethyl, 1-acetoxyethyl, pivaloyloxymethyl or 1-pivaloyloxyethyl group.

In the above-mentioned formula (I), m is an integer of 1 to 4, m is preferably 1, 2 or 3, and particularly preferably 1 or 2. When m is 2 or more, $R^1$s may be different from each other.

In the above-mentioned formula (I), n is an integer of 1 to 3, preferably n is 1 or 2, particularly preferably 1. When n is 2 or more, $R^2$s may be different from each other.

In the Compound (I) of the present invention, there exist an optical isomer(s) (including diastereomer) due to an asymmetric carbon atom(s) in the molecule, or there exist a case in which a geometric isomer due to a double bond exists, and these respective isomers are also included in the present invention.

Also, the Compound (I) of the present invention can be converted into a pharmaceutically acceptable salt, if necessary. Such a pharmaceutically acceptable salt may be mentioned an acid addition salt of a mineral acid such as hydrochloride, hydrobromide, hydroiodide, sulfate or phosphate; an acid addition salt of an organic acid such as trifluoroacetate, methanesulfonate, ethanesulfonate, benzenesulfonate, p-toluenesulfonate, oxalate, maleate, fumarate, tartarate or citrate; a metal salt of a carboxylic acid such as a sodium salt, a potassium salt, a calcium salt, a magnesium salt, a manganese salt, an iron salt or an aluminum salt; or a salt with an organic base such as an ammonium salt, a triethylamine salt, a guanidine salt, a hydrazine salt, a quinine salt or a cinchonine salt, and the like.

Incidentally, the Compound (I) of the present invention can also exist as a hydrate.

In the dibenzocycloheptene compound having the above-mentioned formula (I) of the present invention, it is preferably (1). a dibenzocycloheptene compound wherein $R^1$ of the compound represented by the formula (I) is selected from the group consisting of hydrogen atom, fluorine atom, chlorine atom, bromine atom, hydroxy group, nitro group, a cyano group, carbamoyl group, formyl group, carboxyl group, 1H-tetrazol-5-yl group, methyl group, ethyl group, propyl group, isopropyl group, fluoromethyl group, difluoromethyl group, triflubromethyl group, 2-fluoroethyl group, hydroxymethyl group, 1-hydroxyethyl group, 2-hydroxyethyl group, 1-hydroxy-1-methylethyl group, 1-hydroxypropyl group, 2-hydroxypropyl group, vinyl group, 1-propenyl group, allyl group, 1-butenyl group, 2-butenyl group, 2-methyl-1-propenyl group, ethynyl group, 1-propynyl group, 1-butynyl group, methoxy group, ethoxy group, propoxy group, isopropoxy group, fluoromethoxy group, difluoromethoxy group, trifluoromethoxy group, 2-fluoroethoxy group, methylthio group, ethylthio group, propylthio group, isopropylthio group, methylsulfinyl group, ethylsulfinyl group, propylsulfinyl group, isopropylsulfinyl group, methylsulfonyl group, ethylsulfonyl group, propylsulfonyl group and isopropylsulfonyl group, (2). a dibenzocycloheptene compound wherein $R^1$ of the compound represented by the formula (I) is selected from the group consisting of hydrogen atom, fluorine atom, chlorine atom, hydroxy group, nitro group, cyano group, carbamoyl group, formyl group, 1H-tetrazol-5-yl group, methyl group, ethyl group, fluoromethyl group, difluoromethyl group, trifluoromethyl group, hydroxymethyl group, 1-hydroxyethyl group, 1-hydroxy-1-methylethyl group, 1-hydroxypropyl group, vinyl group, 1-propenyl group, allyl group, ethynyl group, 1-propynyl group, 1-butynyl group, methoxy group, ethoxy group, fluoromethoxy group, difluoromethoxy group, trifluoromethoxy group, methylthio group, ethylthio group, methylsulfinyl group, ethylsulfinyl group, methylsulfonyl group and ethylsulfonyl group, (3). a dibenzocycloheptene compound wherein $R^1$ of the compound represented by the formula (I) is selected from the group consisting of a hydrogen atom, a fluorine atom, a chlorine atom, a nitro group, a cyano group, a formyl group, 1H-tetrazol-5-yl group, methyl group, difluoromethyl group, trifluoromethyl group, hydroxymethyl group, 1-hydroxy-1-methylethyl group, vinyl group, ethynyl group, methoxy group, difluoromethoxy group, trifluoromethoxy group, methylthio group, methylsulfinyl group and methylsulfonyl group, (4). a dibenzocycloheptene compound wherein $R^1$ of the compound represented by the formula (I) is selected from the group consisting of a hydrogen atom, a fluorine atom, a chlorine atom, a cyano group, trifluoromethyl group, hydroxymethyl group, 1-hydroxy-1-methylethyl group, ethynyl group, methoxy group, difluoromethoxy group, trifluoromethoxy group, methylsulfinyl group and methylsulfonyl group, (5). a dibenzocycloheptene compound wherein $R^2$ of the compound represented by the formula (I) is selected from the group consisting of a hydrogen atom, a fluorine atom, a chlorine atom, bromine atom, a nitro group, a cyano group, methyl group, ethyl group, propyl group, isopropyl group, methoxy group, ethoxy group, propoxy group and isopropoxy group, (6). a dibenzocycloheptene compound wherein $R^2$ of the compound represented by the formula (I) is selected from the group consisting of a hydrogen atom, a fluorine atom, a chlorine atom, a nitro group, a cyano group, methyl group, ethyl group, methoxy group and ethoxy group, (7). a dibenzocycloheptene compound wherein $R^2$ of the compound represented by the formula (I) is selected from the group consisting of a hydrogen atom, a fluorine atom, a chlorine atom, methyl group and methoxy group, (8). a dibenzocycloheptene compound wherein $R^2$ of the compound represented by the formula (I) is a hydrogen atom, (9). a dibenzocycloheptene compound wherein A of the compound represented by the formula (I) is selected from the group consisting of 2-thiazolyl, 1,3,4-thiadiazol-2-yl, 2-pyridyl, 2-pyrimidinyl, 2-benzoxazolyl, 2-benzothiazolyl, quinolin-2-yl, quinazolin-2-yl, 4-methyl-2-thiazolyl, 4-isopropyl-2-thiazolyl, 4-t-butyl-2-thiazolyl, 4-trifluoromethyl-2-thiazolyl, 5-methyl-1,3,4-thiadiazol-2-yl, 5-isopropyl-1,3,4-thiadiazol-2-yl, 5-t-butyl-1,3,4-thiadiazol-2-yl, 5-trifluoromethyl-1,3,4-thiadiazol-2-yl, 5,6-difluoro-2-pyridyl, 5,6-dichloro-2-pyridyl, 5,6-dimethyl-2-pyridyl, 5H-6,7-dihydrocyclopenta[b]pyridin-2-yl, 5,6,7,8-tetrahydroquinolin-2-yl, 5,6-difluoro-2-pyrimidinyl, 5,6-dichloro-2-pyrimidinyl, 5,6-dimethyl-2-pyrimidinyl, 6-trifluoromethyl-2-pyrimidinyl, 5H-6,7-dihydrocyclopenta[d]pyrimidin-2-yl, 5,6,7,8-tetrahydroquinazolin-2-yl, 6-fluoro-2-benzoxazolyl, 5-fluoro-2-benzoxazolyl, 5,6-difluoro-2-benzoxazolyl, 6-chloro-2-benzoxazolyl, 5-chloro-2-benzoxazolyl, 5,6-dichloro-2-benzoxazolyl, 5-chloro-6-fluoro-2-benzoxazolyl, 5-methyl-2-benzoxazolyl, 5-cyano-2-benzoxazolyl, 5-trifluoromethyl-2-benzoxazolyl, 5-methylthio-2-benzoxazolyl, 6-fluoro-2-benzothiazolyl, 5-fluoro-2-benzothiazolyl, 5,6-difluoro-2-benzothiazolyl, 6-chloro-2-benzothiazolyl, 5-chloro-2-benzothiazolyl, 5,6-dichloro-2-benzothiazolyl, 5-chloro-6-fluoro-2-benzothiazolyl, 5-methyl-2-benzothiazolyl, 5-cyano-2-benzothiazolyl, 5-trifluoromethyl-2-benzothiazolyl, 5-methylthio-2-benzothiazolyl, 5-fluoroquinolin-2-yl, 6-fluoroquinolin-2-yl, 7-fluoroquinolin-2-yl, 5-chloroquinolin-2-yl, 6-chloroquinolin-2-yl, 7-chloroquinolin-2-yl, 7-methylquinolin-2-yl, 7-trifluoromethylquinolin-2-yl, 7-methoxyquinolin-2-yl, 7-difluoromethoxyquinolin-2-yl, 7-trifluoromethoxyquinolin-2-yl, 5,7-difluoroquinolin-2-yl, 6,7-difluoroquinolin-2-yl, 5,7-dichloroquinolin-2-yl, 6,7-dichloroquinolin-2-yl, 5-chloro-7-fluoroquinolin-2-yl, 6-chloro-7-fluoroquinolin-2-yl, 7-chloro-5-fluoroquinolin-2-yl, 7-chloro-6-fluoroquinolin-2-yl, 7-chloro-6-cyanoquinolin-2-yl, 7-cyano-6-fluoroquinolin-2-yl, 6-fluoro-7-trifluoromethylquinolin-2-yl, 5,6,7-trifluoroquinolin-2-yl, 5-fluoroquinazolin-2-yl, 6-fluoroquinazolin-2-yl, 7-fluoroquinazolin-2-yl, 5-chloroquinazolin-2-yl, 6-chloroquinazolin-2-yl, 7-chloroquinazolin-2-yl, 7-methylquinazolin-2-yl, 7-trifluoromethylquinazolin-2-yl, 7-methoxyquinazolin-2-yl, 7-difluoromethoxyquinazolin-2-yl, 7-trifluoromethoxyquinazolin-2-yl, 5,7-difluoroquinazolin-2-yl, 6,7-difluoroquinazolin-2-yl, 5,7-dichloroquinazolin-2-yl, 6,7-dichloroquinazolin-2-yl, 5-chloro-7-fluoroquinazolin-2-yl, 6-chloro-7-fluoroquinazolin-2-yl, 7-chloro-5-fluoroquinazolin-2-yl, 7-chloro-6-fluoroquinazolin-2-yl, 7-chloro-6-cyanoquinazolin-2-yl, 7-cyano-6-fluoroquinazolin-2-yl, 6-fluoro-7-trifluoromethylquinazolin-2-yl and 5,6,7-trifluoroquinazolin-2-yl group, (10). a dibenzocycloheptene compound wherein A of the compound represented by the formula (I) is selected from the group consisting of 2-pyridyl, 2-benzothiazolyl, quinolin-2-yl, 5,6-difluoro-2-pyridyl, 5,6-dichloro-2-pyridyl, 5,6-dimethyl-2-pyridyl, 5,6,7,8-tetrahydroquinolin-2-yl, 6-fluoro-2-benzothiazolyl, 5-fluoro-2-benzothiazolyl, 5,6-difluoro-2-benzothiazolyl, 6-chloro-2-benzothiazolyl, 5-chloro-2-benzothiazolyl, 5,6-dichloro-2-benzothiazolyl, 5-chloro-6-fluoro-2-benzothiazolyl, 5-methyl-2-benzothiazolyl, 5-cyano-2-benzothiazolyl, 5-trifluoromethyl-2-benzothiazolyl, 5-methylthio-2-benzothiazolyl, 5-fluoroquinolin-2-yl, 6-fluoroquinolin-2-yl, 7-fluoroquinolin-2-yl, 5-chloroquinolin-2-yl, 6-chloroquinolin-2-yl, 7-chloroquinolin-2-yl, 7-methylquinolin-2-yl, 7-trifluoromethylquinolin-2-yl, 7-methoxyquinolin-2-yl, 7-difluoromethoxyquinolin-2-yl, 7-trifluoromethoxyquinolin-2-yl, 5,7-difluoroquinolin-2-yl, 6,7-difluoroquinolin-2-yl, 5,7-dichloroquinolin-2-yl, 6,7-dichloroquinolin-2-yl, 5-chloro-7-fluoroquinolin-2-yl, 6-chloro-7-fluoroquinolin-2-yl, 7-chloro-5-fluoroquinolin-2-yl, 7-chloro-6-fluoroquinolin-2-yl, 7-chloro-6-cyanoquinolin-2-yl, 7-cyano-6-fluoroquinolin-2-yl, 6-fluoro-7-trifluoromethylquinolin-2-yl and 5,6,7-trifluoroquinolin-2-yl group, (11). a dibenzocycloheptene compound wherein A of the compound represented by the formula (I) is selected from the group consisting of 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl and 7-chloro-6-fluoroquinolin-2-yl group, (12). a dibenzocycloheptene compound wherein B of the compound represented by the formula (I) is a formula: —CH═CH—, a formula: —OCH$_2$— or a formula: —CH$_2$O—, (13). a dibenzocycloheptene compound wherein X of the compound represented by the formula (I) is an oxygen atom or a sulfur atom, (14). a dibenzocycloheptene compound wherein Y of the compound represented by the formula (I) is selected from the group consisting of methylene, ethylene, trimethylene, tetramethylene, pentamethylene, fluoromethylene, difluoromethylene, 1-fluoroethylene, 2-fluoroethylene, 1,1-difluoroethylene, 2,2-difluoroethylene, ethylidene, 1-methylethylene, 2-methylethylene, 1,1-dimethylethylene, 2,2-dimethylethylene, 1-ethylethylene, 2-ethylethylene, 1-methoxyethylene, 2-methoxyethylene, 1-fluorotrimethylene, 2-fluorotrimethylene, 3-fluorotrimethylene, 1,1-difluorotrimethylene, 2,2-difluorotrimethylene, 3,3-difluorotrimethylene, 1-methyltrimethylene, 2-methyltrimethylene, 1,1-dimethyltrimethylene, 2,2-dimethyltrimethylene, 3,3-dimethyltrimethylene, 2,2-diethyltrimethylene, 2-methoxytrimethylene, 3-methoxytrimethylene, 2,2-dimethoxytrimethylene, 3,3-dimethoxytrimethylene, (a-1) group, (a-2) group, (a-3) group, (a-4) group, (a-5) group and (a-6) group, (15). a dibenzocycloheptene compound wherein Y of the compound represented by the formula (I) is selected from the group consisting of methylene, ethylene, trimethylene, fluoromethylene, difluoromethylene, 1-fluoroethylene, 2-fluoroethylene, 1,1-difluoroethylene, 2,2-difluoroethylene, ethylidene, 1-methylethylene, 2-methylethylene, 1-fluorotrimethylene, 2-fluorotrimethylene, 3-fluorotrimethylene, 1,1-difluorotrimethylene, 2,2-difluorotrimethylene, 3,3-difluorotrimethylene, 1-methyltrimethylene, 2-methyltrimethylene, 1,1-dimethyltrimethylene, 2,2-dimethyltrimethylene, 3,3-dimethyltrimethylene, (a-4) group, (a-5) group and (a-6) group, (16). a dibenzocycloheptene compound wherein Y of the compound represented by the formula (I) is selected from the group consisting of methylene, ethylene, trimethylene, difluoromethylene, 1-fluoroethylene, 2-fluoroethylene, 1,1-difluoroethylene, 2,2-difluoroethylene, ethylidene, 1-methylethylene, 2-methylethylene, 2,2-difluorotrimethylene, 1-methyltrimethylene, 2-methyltrimethylene, 1,1-dimethyltrimethylene, 2,2-dimethyltrimethylene, 3,3-dimethyltrimethylene and (a-5) group, (17). a dibenzocycloheptene compound wherein Y of the compound represented by the formula (I) is selected from the group consisting of methylene, ethylene, trimethylene, ethylidene, 1-methylethylene, 2-methylethylene and (a-5) group, (18). a dibenzocycloheptene compound wherein Z of the compound represented by the formula (I) is selected from the group consisting of carboxy, 1H-tetrazol-5-yl, methanesulfonylamino, ethanesulfonylamino, trifluoromethanesulfonylamino, phenylsulfonylamino, p-fluorophenylsulfonylamino, p-chlorophenylsulfonylamino, o-methylphenylsulfonylamino, p-methylphenylsulfonylamino, p-trifluoromethylphenylsulfonylamino, o-methoxyphenylsulfonylamino, p-methoxyphenylsulfonylamino, p-difluoromethoxyphenylsulfonylamino, p-trifluoromethoxyphenylsulfonylamino, p-nitrophenylsulfonylamino, p-cyanophenylsulfonylamino, methanesulfonylaminocarbonyl, ethanesulfonylaminocarbonyl, trifluoromethanesulfonylaminocarbonyl, phenylsulfonylaminocarbonyl, p-fluorophenylsulfonylaminocarbonyl, p-chlorophenylsulfonylaminocarbonyl, o-methylphenylsulfonylaminocarbonyl, p-methylphenylsulfonylaminocarbonyl, p-trifluoromethylphenylsulfonylaminocarbonyl, o-methoxyphenylsulfonylaminocarbonyl, p-methoxyphenylsulfonylaminocarbonyl, p-difluoromethoxyphenylsulfonylaminocarbonyl, p-trifluoromethoxyphenylsulfonylaminocarbonyl, p-nitrophenylsulfonylaminocarbonyl and p-cyanophenylsulfonylaminocarbonyl group, (19). a dibenzocycloheptene compound wherein Z of the compound represented by the formula (I) is selected from the group consisting of carboxy, 1H-tetrazol-5-yl, methanesulfonylamino, trifluoromethanesulfonylamino, phenylsulfonylamino, o-methylphenylsulfonylamino, p-methylphenylsulfonylamino, methanesulfonylaminocarbonyl, trifluoromethanesulfonylaminocarbonyl, phenylsulfonylaminocarbonyl, o-methylphenylsulfonylaminocarbonyl and p-methylphenylsulfonylaminocarbonyl group, (20). a dibenzocycloheptene compound wherein Z of the compound represented by the formula (I) is selected from the group consisting of carboxy, methanesulfonylamino, trifluoromethanesulfonylamino, methanesulfonylaminocarbonyl and trifluoromethanesulfonylaminocarbonyl group, (21). a dibenzocycloheptene compound wherein Z of the compound represented by the formula (I) is carboxyl group, (22). a dibenzocycloheptene compound wherein when Z of the compound represented by the formula (I) is carboxyl group, the protective group is selected from the group consisting of $C_1$-$C_4$ alkyl group; benzyl group; $C_1$-$C_2$ alkyl group substituted by $C_2$-$C_5$ alkanoyloxy group; $C_1$-$C_2$ alkyl group substituted by ($C_1$-$C_4$ alkoxy)carbonyloxy group; and (5-methyl-2-oxo-1,3-dioxolen-4-yl)methyl group, (23). a dibenzocycloheptene compound wherein when Z of the compound represented by the formula (I) is carboxyl group, the protective group is selected from the group consisting of methyl, ethyl, propyl, isopropyl, butyl, isobutyl, acetoxymethyl, 1-acetoxyethyl, pivaloyloxymethyl and 1-pivaloyloxyethyl group, (24). a dibenzocycloheptene compound wherein m of the compound represented by the formula (I) is 1, 2 or 3, (25). a dibenzocycloheptene compound wherein m of the compound represented by the formula (I) is 1 or 2, (26). a dibenzocycloheptene compound wherein n of the compound represented by the formula (I) is 1 or 2, (27). a dibenzocycloheptene compound wherein n of the compound represented by the formula (I) is 1, and with respect to $R^1$, the preferable order is increased in the order of (1) to (4), with respect to $R^2$, the preferable order is increased in the order of (5) to (8), with respect to A, the preferable order is increased in the order of (9) to (11), with respect to Y, the preferable order is increased in the order of (14) to (17), with respect to Z, the preferable order is increased in the order of (18) to (21), with respect to the protective group when Z is a carboxyl group, the preferable order is increased in the order of (22) to (23), with respect to m, the preferable order is increased in the order of (24) to (25), and with respect to n, the preferable order is increased in the order of (26) to (27).

Also, as the dibenzocycloheptene compound having the above-mentioned formula (I), a dibenzocycloheptene compound comprising a combination of two or more of the abovementioned (1) to (27) is preferred.

For example, the following may be mentioned, (28). a compound wherein $R^1$ of the compound represented by the formula (I) is selected from the group consisting of hydrogen atom, fluorine atom, chlorine atom, nitro group, cyano group, formyl group, 1H-tetrazol-5-yl group, methyl group, difluoromethyl group, trifluoromethyl group, hydroxymethyl group, 1-hydroxy-1-methylethyl group, vinyl group, ethynyl group, methoxy group, difluoromethoxy group, trifluoromethoxy group, methylthio group, methylsulfinyl group and methylsulfonyl group, $R^2$ is selected from the group consisting of hydrogen atom, fluorine atom, chlorine atom, methyl group and methoxy group, A is selected from the group consisting of 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl and 7-chloro-6-fluoroquinolin-2-yl group, B is a formula: —CH═CH—, a formula: —OCH$_2$— or a formula: —CH$_2$O—, X is selected from the group consisting of an oxygen atom or a sulfur atom, Y is selected from the group consisting of methylene, ethylene, trimethylene, difluoromethylene, 1-fluoroethylene, 2-fluoroethylene, 1,1-difluoroethylene, 2,2-difluoroethylene, ethylidene, 1-methylethylene, 2-methylethylene, 2,2-difluorotrimethylene, 1-methyltrimethylene, 2-methyltrimethylene, 1,1-dimethyltrimethylene, 2,2-dimethyltrimethylene, 3,3-dimethyltrimethylene and (a-5) group, Z is selected from the group consisting of carboxy, methanesulfonylamino, trifluoromethanesulfonylamino, methanesulfonylaminocarbonyl and trifluoromethanesulfonylaminocarbonyl group, m is 1 or 2, and n is 1.

(29). a compound wherein $R^1$ of the compound represented by the formula (I) is selected from the group consisting of hydrogen atom, fluorine atom, chlorine atom, cyano group, trifluoromethyl group, hydroxymethyl group, 1-hydroxy-1-methylethyl group, ethynyl group, methoxy group, difluoromethoxy group, trifluoromethoxy group, methylsulfinyl group and methylsulfonyl group, $R^2$ is a hydrogen atom, A is selected from the group consisting of 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl and 7-chloro-6-fluoroquinolin-2-yl group, B is a formula: —CH═CH—, a formula: —OCH$_2$— or a formula: —CH$_2$O—, X is an oxygen atom or a sulfur atom, Y is selected from the group consisting of methylene, ethylene, trimethylene, ethylidene, 1-methylethylene, 2-methylethylene and (a-5) group, Z is carboxy group, m is 1 or 2, and n is 1.

As preferred compounds in the compound (I), compounds in the following Table 1 can be specifically exemplified.

TABLE 1

(I)

| No. | A | B | $(R^2)n$ | $(R^1)m$ | X—Y—Z |
|---|---|---|---|---|---|
| 1 | 6,7-diF-Q | —CH═CH— | H | H | —OCH$_2$COOH |
| 2 | 6,7-diF-Q | —CH═CH— | H | H | —OCH(CH$_3$)COOH |
| 3 | 6,7-diF-Q | —CH═CH— | H | H | —OCH$_2$CH$_2$COOH |
| 4 | 6,7-diF-Q | —CH═CH— | H | H | —OCH$_2$CH(CH$_3$)COOH |
| 5 | 6,7-diF-Q | —CH═CH— | H | H | —OCH$_2$C(CH$_2$CH$_2$)CH$_2$COOH |
| 6 | 6,7-diF-Q | —CH═CH— | H | H | —SCH$_2$COOH |
| 7 | 6,7-diF-Q | —CH═CH— | H | H | —SCH(CH$_3$)COOH |
| 8 | 6,7-diF-Q | —CH═CH— | H | H | —SCH$_2$CH$_2$COOH |
| 9 | 6,7-diF-Q | —CH═CH— | H | H | —SCH$_2$CH(CH$_3$)COOH |
| 10 | 6,7-diF-Q | —CH═CH— | H | H | —SCH$_2$C(CH$_3$)$_2$COOH |
| 11 | 6,7-diF-Q | —CH═CH— | H | H | —SCH$_2$CH(CH$_2$CH$_3$)COOH |
| 12 | 6,7-diF-Q | —CH═CH— | H | H | —SCH(CH$_3$)CH$_2$COOH |
| 13 | 6,7-diF-Q | —CH═CH— | H | H | —SC(CH$_3$)$_2$CH$_2$COOH |
| 14 | 6,7-diF-Q | —CH═CH— | H | H | —SCH$_2$CH$_2$CH$_2$COOH |
| 15 | 6,7-diF-Q | —CH═CH— | H | H | —SCH$_2$CH(CH$_3$)CH$_2$COOH |
| 16 | 6,7-diF-Q | —CH═CH— | H | H | —SCH$_2$C(CH$_3$)$_2$CH$_2$COOH |
| 17 | 6,7-diF-Q | —CH═CH— | H | H | —SCH$_2$C(CH$_2$CH$_2$)CH$_2$COOH |
| 18 | 6,7-diF-Q | —CH═CH— | H | H | —SCH$_2$CF$_2$COOH |
| 19 | 6,7-diF-Q | —CH═CH— | H | H | —SCH$_2$CF$_2$CH$_2$COOH |
| 20 | 6,7-diF-Q | —CH═CH— | H | H | —SCH$_2$-Tet |
| 21 | 6,7-diF-Q | —CH═CH— | H | H | —SCH$_2$CH$_2$-Tet |
| 22 | 6,7-diF-Q | —CH═CH— | H | H | —SCH$_2$NHSO$_2$CF$_3$ |
| 23 | 6,7-diF-Q | —CH═CH— | H | H | —SCH$_2$CONHSO$_2$CH$_3$ |
| 24 | 6,7-diF-Q | —CH═CH— | H | H | —SCH$_2$CONHSO$_2$CF$_3$ |
| 25 | 6,7-diF-Q | —CH═CH— | H | H | —SCH$_2$CONHSO$_2$Ph |
| 26 | 6,7-diF-Q | —CH═CH— | H | H | —SCH$_2$CONHSO$_2$(2-CH$_3$—Ph) |
| 27 | 6,7-diF-Q | —CH═CH— | H | H | —SCH$_2$CH$_2$NHSO$_2$CF$_3$ |
| 28 | 6,7-diF-Q | —CH═CH— | H | H | —SCH$_2$CH$_2$CONHSO$_2$CH$_3$ |
| 29 | 6,7-diF-Q | —CH═CH— | H | H | —SCH$_2$CH$_2$CONHSO$_2$CF$_3$ |
| 30 | 6,7-diF-Q | —CH═CH— | H | H | —SCH$_2$CH$_2$CONHSO$_2$Ph |
| 31 | 6,7-diF-Q | —CH═CH— | H | H | —SCH$_2$CH$_2$CONHSO$_2$(2-CH$_3$—Ph) |
| 32 | 6,7-diF-Q | —CH═CH— | H | H | —CH$_2$COOH |
| 33 | 6,7-diF-Q | —CH═CH— | H | H | —CH$_2$CH$_2$COOH |
| 34 | 6,7-diF-Q | —CH═CH— | H | H | —CH$_2$CH$_2$CH$_2$COOH |
| 35 | 6,7-diF-Q | —CH═CH— | H | 9-F | —OCH$_2$COOH |
| 36 | 6,7-diF-Q | —CH═CH— | H | 9-F | —OCH(CH$_3$)COOH |
| 37 | 6,7-diF-Q | —CH═CH— | H | 9-F | —OCH$_2$CH$_2$COOH |

TABLE 1-continued (I)

| No. | A | B | (R²)n | (R¹)m | X—Y—Z |
|---|---|---|---|---|---|
| 38 | 6,7-diF-Q | —CH=CH— | H | 9-F | —SCH₂COOH |
| 39 | 6,7-diF-Q | —CH=CH— | H | 9-F | —SCH(CH₃)COOH |
| 40 | 6,7-diF-Q | —CH=CH— | H | 9-F | —SCH₂CH₂COOH |
| 41 | 6,7-diF-Q | —CH=CH— | H | 9-F | —SCH₂CH(CH₃)COOH |
| 42 | 6,7-diF-Q | —CH=CH— | H | 9-F | —SCH₂CH(CH₂CH₃)COOH |
| 43 | 6,7-diF-Q | —CH=CH— | H | 9-F | —SCH₂C(CH₂CH₂)CH₂COOH |
| 44 | 6,7-diF-Q | —CH=CH— | H | 8-F | —OCH₂COOH |
| 45 | 6,7-diF-Q | —CH=CH— | H | 8-F | —OCH₂CH₂COOH |
| 46 | 6,7-diF-Q | —CH=CH— | H | 8-F | —SCH₂COOH |
| 47 | 6,7-diF-Q | —CH=CH— | H | 8-F | —SCH₂CH₂COOH |
| 48 | 6,7-diF-Q | —CH=CH— | H | 8-F | —SCH₂CH(CH₃)COOH |
| 49 | 6,7-diF-Q | —CH=CH— | H | 8-F | —SCH₂C(CH₂CH₂)CH₂COOH |
| 50 | 6,7-diF-Q | —CH=CH— | H | 7-F | —OCH₂COOH |
| 51 | 6,7-diF-Q | —CH=CH— | H | 7-F | —OCH₂CH₂COOH |
| 52 | 6,7-diF-Q | —CH=CH— | H | 7-F | —SCH₂COOH |
| 53 | 6,7-diF-Q | —CH=CH— | H | 7-F | —SCH₂CH₂COOH |
| 54 | 6,7-diF-Q | —CH=CH— | H | 7-F | —SCH₂CH(CH₃)COOH |
| 55 | 6,7-diF-Q | —CH=CH— | H | 6-F | —OCH₂COOH |
| 56 | 6,7-diF-Q | —CH=CH— | H | 6-F | —OCH(CH₃)COOH |
| 57 | 6,7-diF-Q | —CH=CH— | H | 6-F | —OCH₂CH₂COOH |
| 58 | 6,7-diF-Q | —CH=CH— | H | 6-F | —OCH₂CH(CH3)COOH |
| 59 | 6,7-diF-Q | —CH=CH— | H | 6-F | —OCH₂C(CH₂CH₂)CH₂COOH |
| 60 | 6,7-diF-Q | —CH=CH— | H | 6-F | —SCH₂COOH |
| 61 | 6,7-diF-Q | —CH=CH— | H | 6-F | —SCH(CH₃)COOH |
| 62 | 6,7-diF-Q | —CH=CH— | H | 6-F | —SCH₂CH₂COOH |
| 63 | 6,7-diF-Q | —CH=CH— | H | 6-F | —SCH₂CH(CH₃)COOH |
| 64 | 6,7-diF-Q | —CH=CH— | H | 6-F | —SCH₂C(CH₂CH₂)CH₂COOH |
| 65 | 6,7-diF-Q | —CH=CH— | H | 9-Cl | —OCH₂COOH |
| 66 | 6,7-diF-Q | —CH=CH— | H | 9-Cl | —OCH(CH₃)COOH |
| 67 | 6,7-diF-Q | —CH=CH— | H | 9-Cl | —OCH₂CH₂COOH |
| 68 | 6,7-diF-Q | —CH=CH— | H | 9-Cl | —OCH₂CH(CH3)COOH |
| 69 | 6,7-diF-Q | —CH=CH— | H | 9-Cl | —OCH₂C(CH₂CH₂)CH₂COOH |
| 70 | 6,7-diF-Q | —CH=CH— | H | 9-Cl | —SCH₂COOH |
| 71 | 6,7-diF-Q | —CH=CH— | H | 9-Cl | —SCH(CH₃)COOH |
| 72 | 6,7-diF-Q | —CH=CH— | H | 9-Cl | —SCH₂CH₂COOH |
| 73 | 6,7-diF-Q | —CH=CH— | H | 9-Cl | —SCH₂CH(CH₃)COOH |
| 74 | 6,7-diF-Q | —CH=CH— | H | 9-Cl | —SCH₂C(CH₂CH₂)CH₂COOH |
| 75 | 6,7-diF-Q | —CH=CH— | H | 8-Cl | —SCH₂C(CH₂CH₂)CH₂COOH |
| 76 | 6,7-diF-Q | —CH=CH— | H | 8-Cl | —OCH₂COOH |
| 77 | 6,7-diF-Q | —CH=CH— | H | 8-Cl | —OCH₂CH₂COOH |
| 78 | 6,7-diF-Q | —CH=CH— | H | 8-Cl | —SCH₂COOH |
| 79 | 6,7-diF-Q | —CH=CH— | H | 8-Cl | —SCH₂CH₂COOH |
| 80 | 6,7-diF-Q | —CH=CH— | H | 8-Cl | —SCH₂CH(CH₃)COOH |
| 81 | 6,7-diF-Q | —CH=CH— | H | 7-Cl | —SCH₂C(CH₂CH₂)CH₂COOH |
| 82 | 6,7-diF-Q | —CH=CH— | H | 7-Cl | —OCH₂COOH |
| 83 | 6,7-diF-Q | —CH=CH— | H | 7-Cl | —OCH₂CH₂COOH |
| 84 | 6,7-diF-Q | —CH=CH— | H | 7-Cl | —SCH₂COOH |
| 85 | 6,7-diF-Q | —CH=CH— | H | 7-Cl | —SCH₂CH₂COOH |
| 86 | 6,7-diF-Q | —CH=CH— | H | 7-Cl | —SCH₂CH(CH₃)COOH |
| 87 | 6,7-diF-Q | —CH=CH— | H | 6-Cl | —OCH₂COOH |
| 88 | 6,7-diF-Q | —CH=CH— | H | 6-Cl | —OCH(CH₃)COOH |
| 89 | 6,7-diF-Q | —CH=CH— | H | 6-Cl | —OCH₂CH₂COOH |
| 90 | 6,7-diF-Q | —CH=CH— | H | 6-Cl | —OCH₂CH(CH3)COOH |
| 91 | 6,7-diF-Q | —CH=CH— | H | 6-Cl | —OCH₂C(CH₂CH₂)CH₂COOH |
| 92 | 6,7-diF-Q | —CH=CH— | H | 6-Cl | —SCH₂COOH |
| 93 | 6,7-diF-Q | —CH=CH— | H | 6-Cl | —SCH(CH₃)COOH |
| 94 | 6,7-diF-Q | —CH=CH— | H | 6-Cl | —SCH₂CH₂COOH |
| 95 | 6,7-diF-Q | —CH=CH— | H | 6-Cl | —SCH₂CH(CH₃)COOH |
| 96 | 6,7-diF-Q | —CH=CH— | H | 6-Cl | —SCH₂C(CH₂CH₂)CH₂COOH |
| 97 | 6,7-diF-Q | —CH=CH— | H | 9-CN | —OCH₂COOH |
| 98 | 6,7-diF-Q | —CH=CH— | H | 9-CN | —OCH(CH₃)COOH |
| 99 | 6,7-diF-Q | —CH=CH— | H | 9-CN | —OCH₂CH₂COOH |
| 100 | 6,7-diF-Q | —CH=CH— | H | 9-CN | —OCH₂CH(CH₃)COOH |
| 101 | 6,7-diF-Q | —CH=CH— | H | 9-CN | —OCH₂C(CH₂CH₂)CH₂COOH |
| 102 | 6,7-diF-Q | —CH=CH— | H | 9-CN | —SCH₂COOH |

TABLE 1-continued (I)

| No. | A | B | (R²)n | (R¹)m | X—Y—Z |
|---|---|---|---|---|---|
| 103 | 6,7-diF-Q | —CH=CH— | H | 9-CN | —SCH(CH₃)COOH |
| 104 | 6,7-diF-Q | —CH=CH— | H | 9-CN | —SCH₂CH₂COOH |
| 105 | 6,7-diF-Q | —CH=CH— | H | 9-CN | —SCH₂CH(CH₃)COOH |
| 106 | 6,7-diF-Q | —CH=CH— | H | 9-CN | —SCH₂C(CH₂CH₂)CH₂COOH |
| 107 | 6,7-diF-Q | —CH=CH— | H | 8-CN | —OCH₂COOH |
| 108 | 6,7-diF-Q | —CH=CH— | H | 8-CN | —OCH₂CH₂COOH |
| 109 | 6,7-diF-Q | —CH=CH— | H | 8-CN | —SCH₂COOH |
| 110 | 6,7-diF-Q | —CH=CH— | H | 8-CN | —SCH₂CH₂COOH |
| 111 | 6,7-diF-Q | —CH=CH— | H | 8-CN | —SCH₂CH(CH₃)COOH |
| 112 | 6,7-diF-Q | —CH=CH— | H | 8-CN | —SCH₂C(CH₂CH₂)CH₂COOH |
| 113 | 6,7-diF-Q | —CH=CH— | H | 7-CN | —OCH₂COOH |
| 114 | 6,7-diF-Q | —CH=CH— | H | 7-CN | —OCH₂CH₂COOH |
| 115 | 6,7-diF-Q | —CH=CH— | H | 7-CN | —SCH₂COOH |
| 116 | 6,7-diF-Q | —CH=CH— | H | 7-CN | —SCH₂CH₂COOH |
| 117 | 6,7-diF-Q | —CH=CH— | H | 7-CN | —SCH₂CH(CH₃)COOH |
| 118 | 6,7-diF-Q | —CH=CH— | H | 9-CH₃ | —OCH₂COOH |
| 119 | 6,7-diF-Q | —CH=CH— | H | 9-CH₃ | —OCH₂CH₂COOH |
| 120 | 6,7-diF-Q | —CH=CH— | H | 9-CH₃ | —SCH₂COOH |
| 121 | 6,7-diF-Q | —CH=CH— | H | 9-CH₃ | —SCH₂CH₂COOH |
| 122 | 6,7-diF-Q | —CH=CH— | H | 9-CH₃ | —SCH₂CH(CH₃)COOH |
| 123 | 6,7-diF-Q | —CH=CH— | H | 9-CH₃ | —SCH₂CH(CH₂CH₃)COOH |
| 124 | 6,7-diF-Q | —CH=CH— | H | 9-CH₃ | —SCH₂C(CH₂CH₂)CH₂COOH |
| 125 | 6,7-diF-Q | —CH=CH— | H | 8-CH₃ | —OCH₂COOH |
| 126 | 6,7-diF-Q | —CH=CH— | H | 8-CH₃ | —OCH₂CH₂COOH |
| 127 | 6,7-diF-Q | —CH=CH— | H | 8-CH₃ | —SCH₂COOH |
| 128 | 6,7-diF-Q | —CH=CH— | H | 8-CH₃ | —SCH₂CH₂COOH |
| 129 | 6,7-diF-Q | —CH=CH— | H | 8-CH₃ | —SCH₂CH(CH₃)COOH |
| 130 | 6,7-diF-Q | —CH=CH— | H | 8-CH₃ | —SCH₂C(CH₂CH₂)CH₂COOH |
| 131 | 6,7-diF-Q | —CH=CH— | H | 7-CH₃ | —OCH₂COOH |
| 132 | 6,7-diF-Q | —CH=CH— | H | 7-CH₃ | —OCH₂CH₂COOH |
| 133 | 6,7-diF-Q | —CH=CH— | H | 7-CH₃ | —SCH₂COOH |
| 134 | 6,7-diF-Q | —CH=CH— | H | 7-CH₃ | —SCH₂CH₂COOH |
| 135 | 6,7-diF-Q | —CH=CH— | H | 7-CH₃ | —SCH₂CH(CH₃)COOH |
| 136 | 6,7-diF-Q | —CH=CH— | H | 9-CF₃ | —OCH₂COOH |
| 137 | 6,7-diF-Q | —CH=CH— | H | 9-CF₃ | —OCH(CH₃)COOH |
| 138 | 6,7-diF-Q | —CH=CH— | H | 9-CF₃ | —OCH₂CH₂COOH |
| 139 | 6,7-diF-Q | —CH=CH— | H | 9-CF₃ | —OCH₂CH(CH3)COOH |
| 140 | 6,7-diF-Q | —CH=CH— | H | 9-CF₃ | —OCH₂C(CH₂CH₂)CH₂COOH |
| 141 | 6,7-diF-Q | —CH=CH— | H | 9-CF₃ | —SCH₂COOH |
| 142 | 6,7-diF-Q | —CH=CH— | H | 9-CF₃ | —SCH(CH₃)COOH |
| 143 | 6,7-diF-Q | —CH=CH— | H | 9-CF₃ | —SCH₂CH₂COOH |
| 144 | 6,7-diF-Q | —CH=CH— | H | 9-CF₃ | —SCH₂CH(CH₃)COOH |
| 145 | 6,7-diF-Q | —CH=CH— | H | 9-CF₃ | —SCH₂C(CH₂CH₂)CH₂COOH |
| 146 | 6,7-diF-Q | —CH=CH— | H | 8-CF₃ | —OCH₂COOH |
| 147 | 6,7-diF-Q | —CH=CH— | H | 8-CF₃ | —OCH₂CH₂COOH |
| 148 | 6,7-diF-Q | —CH=CH— | H | 8-CF₃ | —SCH₂COOH |
| 149 | 6,7-diF-Q | —CH=CH— | H | 8-CF₃ | —SCH₂CH₂COOH |
| 150 | 6,7-diF-Q | —CH=CH— | H | 8-CF₃ | —SCH₂CH(CH₃)COOH |
| 151 | 6,7-diF-Q | —CH=CH— | H | 8-CF₃ | —SCH₂C(CH₂CH₂)CH₂COOH |
| 152 | 6,7-diF-Q | —CH=CH— | H | 7-CF₃ | —OCH₂COOH |
| 153 | 6,7-diF-Q | —CH=CH— | H | 7-CF₃ | —OCH₂CH₂COOH |
| 154 | 6,7-diF-Q | —CH=CH— | H | 7-CF₃ | —SCH₂COOH |
| 155 | 6,7-diF-Q | —CH=CH— | H | 7-CF₃ | —SCH₂CH₂COOH |
| 156 | 6,7-diF-Q | —CH=CH— | H | 7-CF₃ | —SCH₂CH(CH₃)COOH |
| 157 | 6,7-diF-Q | —CH=CH— | H | 9-C≡CH | —OCH₂COOH |
| 158 | 6,7-diF-Q | —CH=CH— | H | 9-C≡CH | —OCH(CH₃)COOH |
| 159 | 6,7-diF-Q | —CH=CH— | H | 9-C≡CH | —OCH₂CH₂COOH |
| 160 | 6,7-diF-Q | —CH=CH— | H | 9-C≡CH | —OCH₂CH(CH3)COOH |
| 161 | 6,7-diF-Q | —CH=CH— | H | 9-C≡CH | —OCH₂C(CH₂CH₂)CH₂COOH |
| 162 | 6,7-diF-Q | —CH=CH— | H | 9-C≡CH | —SCH₂COOH |
| 163 | 6,7-diF-Q | —CH=CH— | H | 9-C≡CH | —SCH(CH₃)COOH |
| 164 | 6,7-diF-Q | —CH=CH— | H | 9-C≡CH | —SCH₂CH₂COOH |
| 165 | 6,7-diF-Q | —CH=CH— | H | 9-C≡CH | —SCH₂CH(CH₃)COOH |
| 166 | 6,7-diF-Q | —CH=CH— | H | 9-C≡CH | —SCH₂C(CH₂CH₂)CH₂COOH |
| 167 | 6,7-diF-Q | —CH=CH— | H | 8-C≡CH | —OCH₂COOH |

TABLE 1-continued (I)

| No. | A | B | (R²)n | (R¹)m | X—Y—Z |
|---|---|---|---|---|---|
| 168 | 6,7-diF-Q | —CH=CH— | H | 8-C≡CH | —OCH$_2$CH$_2$COOH |
| 169 | 6,7-diF-Q | —CH=CH— | H | 8-C≡CH | —SCH$_2$COOH |
| 170 | 6,7-diF-Q | —CH=CH— | H | 8-C≡CH | —SCH$_2$CH$_2$COOH |
| 171 | 6,7-diF-Q | —CH=CH— | H | 8-C≡CH | —SCH$_2$CH(CH$_3$)COOH |
| 172 | 6,7-diF-Q | —CH=CH— | H | 8-C≡CH | —SCH$_2$C(CH$_2$CH$_2$)CH$_2$COOH |
| 173 | 6,7-diF-Q | —CH=CH— | H | 7-C≡CH | —OCH$_2$COOH |
| 174 | 6,7-diF-Q | —CH=CH— | H | 7-C≡CH | —OCH$_2$CH$_2$COOH |
| 175 | 6,7-diF-Q | —CH=CH— | H | 7-C≡CH | —SCH$_2$COOH |
| 176 | 6,7-diF-Q | —CH=CH— | H | 7-C≡CH | —SCH$_2$CH$_2$COOH |
| 177 | 6,7-diF-Q | —CH=CH— | H | 7-C≡CH | —SCH$_2$CH(CH$_3$)COOH |
| 178 | 6,7-diF-Q | —CH=CH— | H | 9-CH$_2$OH | —OCH$_2$COOH |
| 179 | 6,7-diF-Q | —CH=CH— | H | 9-CH$_2$OH | —SCH$_2$CH$_2$COOH |
| 180 | 6,7-diF-Q | —CH=CH— | H | 8-CH$_2$OH | —OCH$_2$COOH |
| 181 | 6,7-diF-Q | —CH=CH— | H | 8-CH$_2$OH | —SCH$_2$CH$_2$COOH |
| 182 | 6,7-diF-Q | —CH=CH— | H | 7-CH$_2$OH | —OCH$_2$COOH |
| 183 | 6,7-diF-Q | —CH=CH— | H | 7-CH$_2$OH | —SCH$_2$CH$_2$COOH |
| 184 | 6,7-diF-Q | —CH=CH— | H | 9-C(CH$_3$)$_2$OH | —OCH$_2$COOH |
| 185 | 6,7-diF-Q | —CH=CH— | H | 9-C(CH$_3$)$_2$OH | —SCH$_2$CH$_2$COOH |
| 186 | 6,7-diF-Q | —CH=CH— | H | 8-C(CH$_3$)$_2$OH | —OCH$_2$COOH |
| 187 | 6,7-diF-Q | —CH=CH— | H | 8-C(CH$_3$)$_2$OH | —SCH$_2$CH$_2$COOH |
| 188 | 6,7-diF-Q | —CH=CH— | H | 7-C(CH$_3$)$_2$OH | —OCH$_2$COOH |
| 189 | 6,7-diF-Q | —CH=CH— | H | 7-C(CH$_3$)$_2$OH | —SCH$_2$CH$_2$COOH |
| 190 | 6,7-diF-Q | —CH=CH— | H | 9-OCH$_3$ | —OCH$_2$COOH |
| 191 | 6,7-diF-Q | —CH=CH— | H | 9-OCH$_3$ | —SCH$_2$CH$_2$COOH |
| 192 | 6,7-diF-Q | —CH=CH— | H | 8-OCH$_3$ | —OCH$_2$COOH |
| 193 | 6,7-diF-Q | —CH=CH— | H | 8-OCH$_3$ | —SCH$_2$CH$_2$COOH |
| 194 | 6,7-diF-Q | —CH=CH— | H | 7-OCH$_3$ | —OCH$_2$COOH |
| 195 | 6,7-diF-Q | —CH=CH— | H | 7-OCH$_3$ | —SCH$_2$CH$_2$COOH |
| 196 | 6,7-diF-Q | —CH=CH— | H | 9-OCHF$_2$ | —OCH$_2$COOH |
| 197 | 6,7-diF-Q | —CH=CH— | H | 9-OCHF$_2$ | —SCH$_2$CH$_2$COOH |
| 198 | 6,7-diF-Q | —CH=CH— | H | 8-OCHF$_2$ | —OCH$_2$COOH |
| 199 | 6,7-diF-Q | —CH=CH— | H | 8-OCHF$_2$ | —SCH$_2$CH$_2$COOH |
| 200 | 6,7-diF-Q | —CH=CH— | H | 7-OCHF$_2$ | —OCH$_2$COOH |
| 201 | 6,7-diF-Q | —CH=CH— | H | 7-OCHF$_2$ | —SCH$_2$CH$_2$COOH |
| 202 | 6,7-diF-Q | —CH=CH— | H | 9-OCF$_3$ | —OCH$_2$COOH |
| 203 | 6,7-diF-Q | —CH=CH— | H | 9-OCF$_3$ | —SCH$_2$CH$_2$COOH |
| 204 | 6,7-diF-Q | —CH=CH— | H | 8-OCF$_3$ | —OCH$_2$COOH |
| 205 | 6,7-diF-Q | —CH=CH— | H | 8-OCF$_3$ | —SCH$_2$CH$_2$COOH |
| 206 | 6,7-diF-Q | —CH=CH— | H | 7-OCF$_3$ | —OCH$_2$COOH |
| 207 | 6,7-diF-Q | —CH=CH— | H | 7-OCF$_3$ | —SCH$_2$CH$_2$COOH |
| 208 | 6,7-diF-Q | —CH=CH— | H | 9-SOCH$_3$ | —OCH$_2$COOH |
| 209 | 6,7-diF-Q | —CH=CH— | H | 9-SOCH$_3$ | —SCH$_2$CH$_2$COOH |
| 210 | 6,7-diF-Q | —CH=CH— | H | 8-SOCH$_3$ | —OCH$_2$COOH |
| 211 | 6,7-diF-Q | —CH=CH— | H | 8-SOCH$_3$ | —SCH$_2$CH$_2$COOH |
| 212 | 6,7-diF-Q | —CH=CH— | H | 7-SOCH$_3$ | —OCH$_2$COOH |
| 213 | 6,7-diF-Q | —CH=CH— | H | 7-SOCH$_3$ | —SCH$_2$CH$_2$COOH |
| 214 | 6,7-diF-Q | —CH=CH— | H | 9-SO$_2$CH$_3$ | —OCH$_2$COOH |
| 215 | 6,7-diF-Q | —CH=CH— | H | 9-SO$_2$CH$_3$ | —SCH$_2$CH$_2$COOH |
| 216 | 6,7-diF-Q | —CH=CH— | H | 8-SO$_2$CH$_3$ | —OCH$_2$COOH |
| 217 | 6,7-diF-Q | —CH=CH— | H | 8-SO$_2$CH$_3$ | —SCH$_2$CH$_2$COOH |
| 218 | 6,7-diF-Q | —CH=CH— | H | 7-SO$_2$CH$_3$ | —OCH$_2$COOH |
| 219 | 6,7-diF-Q | —CH=CH— | H | 7-SO$_2$CH$_3$ | —SCH$_2$CH$_2$COOH |
| 220 | 6,7-diF-Q | —CH=CH— | H | 9-CH=CH$_2$ | —SCH$_2$CH$_2$COOH |
| 221 | 6,7-diF-Q | —CH=CH— | H | 8-CH=CH$_2$ | —SCH$_2$CH$_2$COOH |
| 222 | 6,7-diF-Q | —CH=CH— | H | 7-CH=CH$_2$ | —SCH$_2$CH$_2$COOH |
| 223 | 6,7-diF-Q | —CH=CH— | H | 9-NO$_2$ | —OCH$_2$COOH |
| 224 | 6,7-diF-Q | —CH=CH— | H | 9-NO$_2$ | —SCH$_2$CH$_2$COOH |
| 225 | 6,7-diF-Q | —CH=CH— | H | 8-NO$_2$ | —OCH$_2$COOH |
| 226 | 6,7-diF-Q | —CH=CH— | H | 8-NO$_2$ | —SCH$_2$CH$_2$COOH |

TABLE 1-continued (I)

| No. | A | B | (R²)n | (R¹)m | X—Y—Z |
|---|---|---|---|---|---|
| 227 | 6,7-diF-Q | —CH=CH— | H | 7-NO₂ | —OCH₂COOH |
| 228 | 6,7-diF-Q | —CH=CH— | H | 7-NO₂ | —SCH₂CH₂COOH |
| 229 | 6,7-diF-Q | —CH=CH— | 1-F | H | —SCH₂CH₂COOH |
| 230 | 6,7-diF-Q | —CH=CH— | 2-F | H | —SCH₂CH₂COOH |
| 231 | 6,7-diF-Q | —CH=CH— | 1-Cl | H | —SCH₂CH₂COOH |
| 232 | 6,7-diF-Q | —CH=CH— | 2-Cl | H | —SCH₂CH₂COOH |
| 233 | 6,7-diF-Q | —CH=CH— | 1-CH₃ | H | —SCH₂CH₂COOH |
| 234 | 6,7-diF-Q | —CH=CH— | 2-CH₃ | H | —SCH₂CH₂COOH |
| 235 | 6,7-diF-Q | —CH=CH— | 1-OCH₃ | H | —SCH₂CH₂COOH |
| 236 | 6,7-diF-Q | —CH=CH— | 2-OCH₃ | H | —SCH₂CH₂COOH |
| 237 | 6,7-diF-Q | —CH=CH— | 1-NO₂ | H | —SCH₂CH₂COOH |
| 238 | 6,7-diF-Q | —CH=CH— | 2-NO₂ | H | —SCH₂CH₂COOH |
| 239 | 6,7-diF-Q | —CH=CH— | 1-CN | H | —SCH₂CH₂COOH |
| 240 | 6,7-diF-Q | —CH=CH— | 2-CN | H | —SCH₂CH₂COOH |
| 241 | 6,7-diF-Q | —CH₂O— | H | H | —OCH₂COOH |
| 242 | 6,7-diF-Q | —CH₂O— | H | H | —OCH(CH3)COOH |
| 243 | 6,7-diF-Q | —CH₂O— | H | H | —OCH₂CH₂COOH |
| 244 | 6,7-diF-Q | —CH₂O— | H | H | —OCH₂CH(CH₃)COOH |
| 245 | 6,7-diF-Q | —CH₂O— | H | H | —OCH₂C(CH₂CH₂)CH₂COOH |
| 246 | 6,7-diF-Q | —CH₂O— | H | H | —SCH₂COOH |
| 247 | 6,7-diF-Q | —CH₂O— | H | H | —SCH(CH3)COOH |
| 248 | 6,7-diF-Q | —CH₂O— | H | H | —SCH₂CH₂COOH |
| 249 | 6,7-diF-Q | —CH₂O— | H | H | —SCH₂CH(CH₃)COOH |
| 250 | 6,7-diF-Q | —CH₂O— | H | H | —SCH₂C(CH₃)₂COOH |
| 251 | 6,7-diF-Q | —CH₂O— | H | H | —SCH₂CH(CH₂CH₃)COOH |
| 252 | 6,7-diF-Q | —CH₂O— | H | H | —SCH(CH₃)CH₂COOH |
| 253 | 6,7-diF-Q | —CH₂O— | H | H | —SC(CH₃)₂CH₂COOH |
| 254 | 6,7-diF-Q | —CH₂O— | H | H | —SCH₂CH₂CH₂COOH |
| 255 | 6,7-diF-Q | —CH₂O— | H | H | —SCH₂CH(CH₃)CH₂COOH |
| 256 | 6,7-diF-Q | —CH₂O— | H | H | —SCH₂C(CH₃)₂CH₂COOH |
| 257 | 6,7-diF-Q | —CH₂O— | H | H | —SCH₂C(CH₂CH₂)CH₂COOH |
| 258 | 6,7-diF-Q | —CH₂O— | H | H | —SCH₂CF₂COOH |
| 259 | 6,7-diF-Q | —CH₂O— | H | H | —SCH₂CF₂CH₂COOH |
| 260 | 6,7-diF-Q | —CH₂C— | H | H | —SCH₂-Tet |
| 261 | 6,7-diF-Q | —CH₂O— | H | H | —SCH₂CH₂-Tet |
| 262 | 6,7-diF-Q | —CH₂O— | H | H | —SCH₂NHSO₂CF₃ |
| 263 | 6,7-diF-Q | —CH₂O— | H | H | —SCH₂CONHSO₂CH₃ |
| 264 | 6,7-diF-Q | —CH₂O— | H | H | —SCH₂CONHSO₂CF₃ |
| 265 | 6,7-diF-Q | —CH₂O— | H | H | —SCH₂CONHSO₂Ph |
| 266 | 6,7-diF-Q | —CH₂O— | H | H | —SCH₂CONHSO₂(2-CH₃—Ph) |
| 267 | 6,7-diF-Q | —CH₂O— | H | H | —SCH₂CH₂NHSO₂CF₃ |
| 268 | 6,7-diF-Q | —CH₂O— | H | H | —SCH₂CH₂CONHSO₂CH₃ |
| 269 | 6,7-diF-Q | —CH₂O— | H | H | —SCH₂CH₂CONHSO₂CF₃ |
| 270 | 6,7-diF-Q | —CH₂O— | H | H | —SCH₂CH₂CONHSO₂Ph |
| 271 | 6,7-diF-Q | —CH₂O— | H | H | —SCH₂CH₂CONHSO₂(2-CH₃—Ph) |
| 272 | 6,7-diF-Q | —CH₂O— | H | H | —CH₂COOH |
| 273 | 6,7-diF-Q | —CH₂O— | H | H | —CH₂CH₂COOH |
| 274 | 6,7-diF-Q | —CH₂O— | H | H | —CH₂CH₂CH₂COOH |
| 275 | 6,7-diF-Q | —CH₂O— | H | 9-F | —OCH₂COOH |
| 276 | 6,7-diF-Q | —CH₂O— | H | 9-F | —OCH(CH₃)COOH |
| 277 | 6,7-diF-Q | —CH₂O— | H | 9-F | —OCH₂CH₂COOH |
| 278 | 6,7-diF-Q | —CH₂O— | H | 9-F | —OCH₂CH(CH3)COOH |
| 279 | 6,7-diF-Q | —CH₂O— | H | 9-F | —OCH₂C(CH₂CH₂)CH₂COOH |
| 280 | 6,7-diF-Q | —CH₂O— | H | 9-F | —SCH₂COOH |
| 281 | 6,7-diF-Q | —CH₂O— | H | 9-F | —SCH(CH₃)COOH |
| 282 | 6,7-diF-Q | —CH₂O— | H | 9-F | —SCH₂CH₂COOH |
| 283 | 6,7-diF-Q | —CH₂O— | H | 9-F | —SCH₂CH(CH₃)COOH |
| 284 | 6,7-diF-Q | —CH₂O— | H | 9-F | —SCH₂C(CH₂CH₂)CH₂COOH |
| 285 | 6,7-diF-Q | —CH₂O— | H | 8-F | —OCH₂COOH |
| 286 | 6,7-diF-Q | —CH₂O— | H | 8-F | —OCH₂CH₂COOH |
| 287 | 6,7-diF-Q | —CH₂O— | H | 8-F | —SCH₂COOH |
| 288 | 6,7-diF-Q | —CH₂O— | H | 8-F | —SCH₂CH₂COOH |
| 289 | 6,7-diF-Q | —CH₂O— | H | 8-F | —SCH₂CH(CH₃)COOH |
| 290 | 6,7-diF-Q | —CH₂O— | H | 8-F | —SCH₂C(CH₂CH₂)CH₂COOH |
| 291 | 6,7-diF-Q | —CH₂O— | H | 7-F | —OCH₂COOH |

TABLE 1-continued

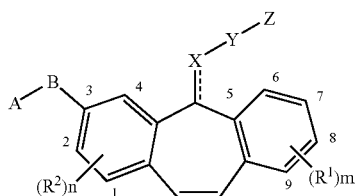
(I)

| No. | A | B | (R²)n | (R¹)m | X—Y—Z |
|---|---|---|---|---|---|
| 292 | 6,7-diF-Q | —CH$_2$O— | H | 7-F | —OCH$_2$CH$_2$COOH |
| 293 | 6,7-diF-Q | —CH$_2$O— | H | 7-F | —SCH$_2$COOH |
| 294 | 6,7-diF-Q | —CH$_2$O— | H | 7-F | —SCH$_2$CH$_2$COOH |
| 295 | 6,7-diF-Q | —CH$_2$O— | H | 7-F | —SCH$_2$CH(CH$_3$)COOH |
| 296 | 6,7-diF-Q | —CH$_2$O— | H | 6-F | —OCH$_2$COOH |
| 297 | 6,7-diF-Q | —CH$_2$O— | H | 6-F | —OCH(CH$_3$)COOH |
| 298 | 6,7-diF-Q | —CH$_2$O— | H | 6-F | —OCH$_2$CH$_2$COOH |
| 299 | 6,7-diF-Q | —CH$_2$O— | H | 6-F | —OCH$_2$CH(CH3)COOH |
| 300 | 6,7-diF-Q | —CH$_2$O— | H | 6-F | —OCH$_2$C(CH$_2$CH$_2$)CH$_2$COOH |
| 301 | 6,7-diF-Q | —CH$_2$O— | H | 6-F | —SCH$_2$COOH |
| 302 | 6,7-diF-Q | —CH$_2$O— | H | 6-F | —SCH(CH$_3$)COOH |
| 303 | 6,7-diF-Q | —CH$_2$O— | H | 6-F | —SCH$_2$CH$_2$COOH |
| 304 | 6,7-diF-Q | —CH$_2$O— | H | 6-F | —SCH$_2$CH(CH$_3$)COOH |
| 305 | 6,7-diF-Q | —CH$_2$O— | H | 6-F | —SCH$_2$C(CH$_2$CH$_2$)CH$_2$COOH |
| 306 | 6,7-diF-Q | —CH$_2$O— | H | 9-Cl | —OCH$_2$COOH |
| 307 | 6,7-diF-Q | —CH$_2$O— | H | 9-Cl | —OCH(CH$_3$)COOH |
| 308 | 6,7-diF-Q | —CH$_2$O— | H | 9-Cl | —OCH$_2$COOH |
| 309 | 6,7-diF-Q | —CH$_2$O— | H | 9-Cl | —OCH$_2$CH(CH3)COOH |
| 310 | 6,7-diF-Q | —CH$_2$O— | H | 9-Cl | —OCH$_2$C(CH$_2$CH$_2$)CH$_2$COOH |
| 311 | 6,7-diF-Q | —CH$_2$O— | H | 9-Cl | —SCH$_2$COOH |
| 312 | 6,7-diF-Q | —CH$_2$O— | H | 9-Cl | —SCH(CH$_3$)COOH |
| 313 | 6,7-diF-Q | —CH$_2$O— | H | 9-Cl | —SCH$_2$CH$_2$COOH |
| 314 | 6,7-diF-Q | —CH$_2$O— | H | 9-Cl | —SCH$_2$CH(CH$_3$)COOH |
| 315 | 6,7-diF-Q | —CH$_2$O— | H | 9-Cl | —SCH$_2$C(CH$_2$CH$_2$)CH$_2$COOH |
| 316 | 6,7-diF-Q | —CH$_2$O— | H | 8-Cl | —SCH$_2$C(CH$_2$CH$_2$)CH$_2$COOH |
| 317 | 6,7-diF-Q | —CH$_2$O— | H | 8-Cl | —OCH$_2$COOH |
| 318 | 6,7-diF-Q | —CH$_2$O— | H | 8-Cl | —OCH$_2$CH$_2$COOH |
| 319 | 6,7-diF-Q | —CH$_2$O— | H | 8-Cl | —SCH$_2$COOH |
| 320 | 6,7-diF-Q | —CH$_2$O— | H | 8-Cl | —SCH$_2$CH$_2$COOH |
| 321 | 6,7-diF-Q | —CH$_2$O— | H | 8-Cl | —SCH$_2$CH(CH$_3$)COOH |
| 322 | 6,7-diF-Q | —CH$_2$O— | H | 7-Cl | —OCH$_2$COOH |
| 323 | 6,7-diF-Q | —CH$_2$O— | H | 7-Cl | —OCH$_2$CH$_2$COOH |
| 324 | 6,7-diF-Q | —CH$_2$O— | H | 7-Cl | —SCH$_2$COOH |
| 325 | 6,7-diF-Q | —CH$_2$O— | H | 7-Cl | —SCH$_2$CH$_2$COOH |
| 326 | 6,7-diF-Q | —CH$_2$O— | H | 7-Cl | —SCH$_2$CH(CH$_3$)COOH |
| 327 | 6,7-diF-Q | —CH$_2$O— | H | 9-CN | —OCH$_2$COOH |
| 328 | 6,7-diF-Q | —CH$_2$O— | H | 9-CN | —OCH(CH$_3$)COOH |
| 329 | 6,7-diF-Q | —CH$_2$O— | H | 9-CN | —OCH$_2$CH$_2$COOH |
| 330 | 6,7-diF-Q | —CH$_2$O— | H | 9-CN | —OCH$_2$CH(CH$_3$)COOH |
| 331 | 6,7-diF-Q | —CH$_2$O— | H | 9-CN | —OCH$_2$C(CH$_2$CH$_2$)CH$_2$COOH |
| 332 | 6,7-diF-Q | —CH$_2$O— | H | 9-CN | —SCH$_2$COOH |
| 333 | 6,7-diF-Q | —CH$_2$O— | H | 9-CN | —SCH(CH$_3$)COOH |
| 334 | 6,7-diF-Q | —CH$_2$O— | H | 9-CN | —SCH$_2$CH$_2$COOH |
| 335 | 6,7-diF-Q | —CH$_2$O— | H | 9-CN | —SCH$_2$CH(CH$_3$)COOH |
| 336 | 6,7-diF-Q | —CH$_2$O— | H | 9-CN | —SCH$_2$C(CH$_2$CH$_2$)CH$_2$COOH |
| 337 | 6,7-diF-Q | —CH$_2$O— | H | 8-CN | —OCH$_2$COOH |
| 338 | 6,7-diF-Q | —CH$_2$O— | H | 8-CN | —OCH$_2$CH$_2$COOH |
| 339 | 6,7-diF-Q | —CH$_2$O— | H | 8-CN | —SCH$_2$COOH |
| 340 | 6,7-diF-Q | —CH$_2$O— | H | 8-CN | —SCH$_2$CH$_2$COOH |
| 341 | 6,7-diF-Q | —CH$_2$O— | H | 8-CN | —SCH$_2$CH(CH$_3$)COOH |
| 342 | 6,7-diF-Q | —CH$_2$O— | H | 8-CN | —SCH$_2$C(CH$_2$CH$_2$)CH$_2$COOH |
| 343 | 6,7-diF-Q | —CH$_2$O— | H | 7-CN | —OCH$_2$COOH |
| 344 | 6,7-diF-Q | —CH$_2$O— | H | 7-CN | —OCH$_2$CH$_2$COOH |
| 345 | 6,7-diF-Q | —CH$_2$O— | H | 7-CN | —SCH$_2$COOH |
| 346 | 6,7-diF-Q | —CH$_2$O— | H | 7-CN | —SCH$_2$CH$_2$COOH |
| 347 | 6,7-diF-Q | —CH$_2$O— | H | 7-CN | —SCH$_2$CH(CH$_3$)COOH |
| 348 | 6,7-diF-Q | —CH$_2$O— | H | 9-CH$_3$ | —OCH$_2$COOH |
| 349 | 6,7-diF-Q | —CH$_2$O— | H | 9-CH$_3$ | —OCH$_2$CH$_2$COOH |
| 350 | 6,7-diF-Q | —CH$_2$O— | H | 9-CH$_3$ | —SCH$_2$COOH |
| 351 | 6,7-diF-Q | —CH$_2$O— | H | 9-CH$_3$ | —SCH$_2$CH$_2$COOH |
| 352 | 6,7-diF-Q | —CH$_2$O— | H | 9-CH$_3$ | —SCH$_2$CH(CH$_3$)COOH |
| 353 | 6,7-diF-Q | —CH$_2$O— | H | 9-CH$_3$ | —SCH$_2$CH(CH$_2$CH$_3$)COOH |
| 354 | 6,7-diF-Q | —CH$_2$O— | H | 9-CH$_3$ | —SCH$_2$C(CH$_2$CH$_2$)CH$_2$COOH |
| 355 | 6,7-diF-Q | —CH$_2$O— | H | 8-CH$_3$ | —OCH$_2$COOH |
| 356 | 6,7-diF-Q | —CH$_2$O— | H | 8-CH$_3$ | —OCH$_2$CH$_2$COOH |

TABLE 1-continued

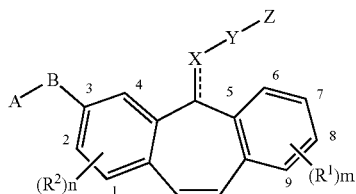

(I)

| No. | A | B | (R²)n | (R¹)m | X—Y—Z |
|---|---|---|---|---|---|
| 357 | 6,7-diF-Q | —CH₂O— | H | 8-CH₃ | —SCH₂COOH |
| 358 | 6,7-diF-Q | —CH₂O— | H | 8-CH₃ | —SCH₂CH₂COOH |
| 359 | 6,7-diF-Q | —CH₂O— | H | 8-CH₃ | —SCH₂CH(CH₃)COOH |
| 360 | 6,7-diF-Q | —CH₂O— | H | 8-CH₃ | —SCH₂C(CH₂CH₂)CH₂COOH |
| 361 | 6,7-diF-Q | —CH₂O— | H | 7-CH₃ | —OCH₂COOH |
| 362 | 6,7-diF-Q | —CH₂O— | H | 7-CH₃ | —OCH₂CH₂COOH |
| 363 | 6,7-diF-Q | —CH₂O— | H | 7-CH₃ | —SCH₂COOH |
| 364 | 6,7-diF-Q | —CH₂O— | H | 7-CH₃ | —SCH₂CH₂COOH |
| 365 | 6,7-diF-Q | —CH₂O— | H | 7-CH₃ | —SCH₂CH(CH₃)COOH |
| 366 | 6,7-diF-Q | —CH₂O— | H | 9-CF₃ | —OCH₂COOH |
| 367 | 6,7-diF-Q | —CH₂O— | H | 9-CF₃ | —OCH(CH₃)COOH |
| 368 | 6,7-diF-Q | —CH₂O— | H | 9-CF₃ | —OCH₂CH₂COOH |
| 369 | 6,7-diF-Q | —CH₂O— | H | 9-CF₃ | —OCH₂CH(CH3)COOH |
| 370 | 6,7-diF-Q | —CH₂O— | H | 9-CF₃ | —OCH₂C(CH₂CH₂)CH₂COOH |
| 371 | 6,7-diF-Q | —CH₂O— | H | 9-CF₃ | —SCH₂COOH |
| 372 | 6,7-diF-Q | —CH₂O— | H | 9-CF₃ | —SCH(CH₃)COOH |
| 373 | 6,7-diF-Q | —CH₂O— | H | 9-CF₃ | —SCH₂CH₂COOH |
| 374 | 6,7-diF-Q | —CH₂O— | H | 9-CF₃ | —SCH₂CH(CH₃)COOH |
| 375 | 6,7-diF-Q | —CH₂O— | H | 9-CF₃ | —SCH₂C(CH₂CH₂)CH₂COOH |
| 376 | 6,7-diF-Q | —CH₂O— | H | 8-CF₃ | —OCH₂COOH |
| 377 | 6,7-diF-Q | —CH₂O— | H | 8-CF₃ | —OCH₂CH₂COOH |
| 378 | 6,7-diF-Q | —CH₂O— | H | 8-CF₃ | —SCH₂COOH |
| 379 | 6,7-diF-Q | —CH₂O— | H | 8-CF₃ | —SCH₂CH₂COOH |
| 380 | 6,7-diF-Q | —CH₂O— | H | 8-CF₃ | —SCH₂CH(CH₃)COOH |
| 381 | 6,7-diF-Q | —CH₂O— | H | 8-CF₃ | —SCH₂C(CH₂CH₂)CH₂COOH |
| 382 | 6,7-diF-Q | —CH₂O— | H | 7-CF₃ | —OCH₂COOH |
| 383 | 6,7-diF-Q | —CH₂O— | H | 7-CF₃ | —OCH₂CH₂COOH |
| 384 | 6,7-diF-Q | —CH₂O— | H | 7-CF₃ | —SCH₂COOH |
| 385 | 6,7-diF-Q | —CH₂O— | H | 7-CF₃ | —SCH₂CH₂COOH |
| 386 | 6,7-diF-Q | —CH₂O— | H | 7-CF₃ | —SCH₂CH(CH₃)COOH |
| 387 | 6,7-diF-Q | —CH₂O— | H | 9-C≡CH | —OCH₂COOH |
| 388 | 6,7-diF-Q | —CH₂O— | H | 9-C≡CH | —OCH(CH₃)COOH |
| 389 | 6,7-diF-Q | —CH₂O— | H | 9-C≡CH | —OCH₂CH₂COOH |
| 390 | 6,7-diF-Q | —CH₂O— | H | 9-C≡CH | —OCH₂CH(CH₃)COOH |
| 391 | 6,7-diF-Q | —CH₂O— | H | 9-C≡CH | —OCH₂C(CH₂CH₂)CH₂COOH |
| 392 | 6,7-diF-Q | —CH₂O— | H | 9-C≡CH | —SCH₂COOH |
| 393 | 6,7-diF-Q | —CH₂O— | H | 9-C≡CH | —SCH(CH₃)COOH |
| 394 | 6,7-diF-Q | —CH₂O— | H | 9-C≡CH | —SCH₂CH₂COOH |
| 395 | 6,7-diF-Q | —CH₂O— | H | 9-C≡CH | —SCH₂CH(CH₃)COOH |
| 396 | 6,7-diF-Q | —CH₂O— | H | 9-C≡CH | —SCH₂C(CH₂CH₂)CH₂COOH |
| 397 | 6,7-diF-Q | —CH₂O— | H | 8-C≡CH | —OCH₂COOH |
| 398 | 6,7-diF-Q | —CH₂O— | H | 8-C≡CH | —OCH₂CH₂COOH |
| 399 | 6,7-diF-Q | —CH₂O— | H | 8-C≡CH | —SCH₂COOH |
| 400 | 6,7-diF-Q | —CH₂O— | H | 8-C≡CH | —SCH₂CH₂COOH |
| 401 | 6,7-diF-Q | —CH₂O— | H | 8-C≡CH | —SCH₂CH(CH₃)COOH |
| 402 | 6,7-diF-Q | —CH₂O— | H | 8-C≡CH | —SCH₂C(CH₂CH₂)CH₂COOH |
| 403 | 6,7-diF-Q | —CH₂O— | H | 7-C≡CH | —OCH₂COOH |
| 404 | 6,7-diF-Q | —CH₂O— | H | 7-C≡CH | —OCH₂CH₂COOH |
| 405 | 6,7-diF-Q | —CH₂O— | H | 7-C≡CH | —SCH₂COOH |
| 406 | 6,7-diF-Q | —CH₂O— | H | 7-C≡CH | —SCH₂CH₂COOH |
| 407 | 6,7-diF-Q | —CH₂O— | H | 7-C≡CH | —SCH₂CH(CH₃)COOH |
| 408 | 6,7-diF-Q | —CH₂O— | H | 9-CH₂OH | —OCH₂COOH |
| 409 | 6,7-diF-Q | —CH₂O— | H | 9-CH₂OH | —SCH₂CH₂COOH |
| 410 | 6,7-diF-Q | —CH₂O— | H | 8-CH₂OH | —OCH₂COOH |
| 411 | 6,7-diF-Q | —CH₂O— | H | 8-CH₂OH | —SCH₂CH₂COOH |
| 412 | 6,7-diF-Q | —CH₂O— | H | 7-CH₂OH | —OCH₂COOH |
| 413 | 6,7-diF-Q | —CH₂O— | H | 7-CH₂OH | —SCH₂CH₂COOH |
| 414 | 6,7-diF-Q | —CH₂O— | H | 9-C(CH₃)₂OH | —OCH₂COOH |
| 415 | 6,7-diF-Q | —CH₂O— | H | 9-C(CH₃)₂OH | —SCH₂CH₂COOH |
| 416 | 6,7-diF-Q | —CH₂O— | H | 8-C(CH₃)₂OH | —OCH₂COOH |
| 417 | 6,7-diF-Q | —CH₂O— | H | 8-C(CH₃)₂OH | —SCH₂CH₂COOH |

TABLE 1-continued (I)

| No. | A | B | (R²)n | (R¹)m | X—Y—Z |
|---|---|---|---|---|---|
| 418 | 6,7-diF-Q | —CH₂O— | H | 7-C(CH₃)₂OH | —OCH₂COOH |
| 419 | 6,7-diF-Q | —CH₂O— | H | 7-C(CH₃)₂OH | —SCH₂CH₂COOH |
| 420 | 6,7-diF-Q | —CH₂O— | H | 9-OCH₃ | —OCH₂COOH |
| 421 | 6,7-diF-Q | —CH₂O— | H | 9-OCH₃ | —SCH₂CH₂COOH |
| 422 | 6,7-diF-Q | —CH₂O— | H | 8-OCH₃ | —OCH₂COOH |
| 423 | 6,7-diF-Q | —CH₂O— | H | 8-OCH₃ | —SCH₂CH₂COOH |
| 424 | 6,7-diF-Q | —CH₂O— | H | 7-OCH₃ | —OCH₂COOH |
| 425 | 6,7-diF-Q | —CH₂O— | H | 7-OCH₃ | —SCH₂CH₂COOH |
| 426 | 6,7-diF-Q | —CH₂O— | H | 9-OCHF₂ | —OCH₂COOH |
| 427 | 6,7-diF-Q | —CH₂O— | H | 9-OCHF₂ | —SCH₂CH₂COOH |
| 428 | 6,7-diF-Q | —CH₂O— | H | 8-OCHF₂ | —OCH₂COOH |
| 429 | 6,7-diF-Q | —CH₂O— | H | 8-OCHF₂ | —SCH₂CH₂COOH |
| 430 | 6,7-diF-Q | —CH₂O— | H | 7-OCHF₂ | —OCH₂COOH |
| 431 | 6,7-diF-Q | —CH₂O— | H | 7-OCHF₂ | —SCH₂CH₂COOH |
| 432 | 6,7-diF-Q | —CH₂O— | H | 9-OCF₃ | —OCH₂COOH |
| 433 | 6,7-diF-Q | —CH₂O— | H | 9-OCF₃ | —SCH₂CH₂COOH |
| 434 | 6,7-diF-Q | —CH₂O— | H | 8-OCF₃ | —OCH₂COOH |
| 435 | 6,7-diF-Q | —CH₂O— | H | 8-OCF₃ | —SCH₂CH₂COOH |
| 436 | 6,7-diF-Q | —CH₂O— | H | 7-OCF₃ | —OCH₂COOH |
| 437 | 6,7-diF-Q | —CH₂O— | H | 7-OCF₃ | —SCH₂CH₂COOH |
| 438 | 6,7-diF-Q | —CH₂O— | H | 9-SOCH₃ | —OCH₂COOH |
| 439 | 6,7-diF-Q | —CH₂O— | H | 9-SOCH₃ | —SCH₂CH₂COOH |
| 440 | 6,7-diF-Q | —CH₂O— | H | 8-SOCH₃ | —OCH₂COOH |
| 441 | 6,7-diF-Q | —CH₂O— | H | 8-SOCH₃ | —SCH₂CH₂COOH |
| 442 | 6,7-diF-Q | —CH₂O— | H | 7-SOCH₃ | —OCH₂COOH |
| 443 | 6,7-diF-Q | —CH₂O— | H | 7-SOCH₃ | —SCH₂CH₂COOH |
| 444 | 6,7-diF-Q | —CH₂O— | H | 9-SO₂CH₃ | —OCH₂COOH |
| 445 | 6,7-diF-Q | —CH₂O— | H | 9-SO₂CH₃ | —SCH₂CH₂COOH |
| 446 | 6,7-diF-Q | —CH₂O— | H | 8-SO₂CH₃ | —OCH₂COOH |
| 447 | 6,7-diF-Q | —CH₂O— | H | 8-SO₂CH₃ | —SCH₂CH₂COOH |
| 448 | 6,7-diF-Q | —CH₂O— | H | 7-SO₂CH₃ | —OCH₂COOH |
| 449 | 6,7-diF-Q | —CH₂O— | H | 7-SO₂CH₃ | —SCH₂CH₂COOH |
| 450 | 6,7-diF-Q | —CH₂O— | H | 9-CH=CH₂ | —SCH₂CH₂COOH |
| 451 | 6,7-diF-Q | —CH₂O— | H | 8-CH=CH₂ | —SCH₂CH₂COOH |
| 452 | 6,7-diF-Q | —CH₂O— | H | 7-CH=CH₂ | —SCH₂CH₂COOH |
| 453 | 6,7-diF-Q | —CH₂O— | H | 9-NO₂ | —OCH₂COOH |
| 454 | 6,7-diF-Q | —CH₂O— | H | 9-NO₂ | —SCH₂CH₂COOH |
| 455 | 6,7-diF-Q | —CH₂O— | H | 8-NO₂ | —OCH₂COOH |
| 456 | 6,7-diF-Q | —CH₂O— | H | 8-NO₂ | —SCH₂CH₂COOH |
| 457 | 6,7-diF-Q | —CH₂O— | H | 7-NO₂ | —OCH₂COOH |
| 458 | 6,7-diF-Q | —CH₂O— | H | 7-NO₂ | —SCH₂CH₂COOH |
| 459 | 6,7-diF-Q | —CH₂O— | 1-F | H | —SCH₂CH₂COOH |
| 460 | 6,7-diF-Q | —CH₂O— | 2-F | H | —SCH₂CH₂COOH |
| 461 | 6,7-diF-Q | —CH₂O— | 1-Cl | H | —SCH₂CH₂COOH |
| 462 | 6,7-diF-Q | —CH₂O— | 2-Cl | H | —SCH₂CH₂COOH |
| 463 | 6,7-diF-Q | —CH₂O— | 1-CH₃ | H | —SCH₂CH₂COOH |
| 464 | 6,7-diF-Q | —CH₂O— | 2-CH₃ | H | —SCH₂CH₂COOH |
| 465 | 6,7-diF-Q | —CH₂O— | 1-OCH₃ | H | —SCH₂CH₂COOH |
| 466 | 6,7-diF-Q | —CH₂O— | 2-OCH₃ | H | —SCH₂CH₂COOH |
| 467 | 6,7-diF-Q | —CH₂O— | 1-NO₂ | H | —SCH₂CH₂COOH |
| 468 | 6,7-diF-Q | —CH₂O— | 2-NO₂ | H | —SCH₂CH₂COOH |
| 469 | 6,7-diF-Q | —CH₂O— | 1-CN | H | —SCH₂CH₂COOH |
| 470 | 6,7-diF-Q | —CH₂O— | 2-CN | H | —SCH₂CH₂COOH |
| 471 | 7-Cl,6-F-Q | —CH=CH— | H | H | —OCH₂COOH |
| 472 | 7-Cl,6-F-Q | —CH=CH— | H | H | —OCH(CH₃)COOH |
| 473 | 7-Cl,6-F-Q | —CH=CH— | H | H | —OCH₂CH₂COOH |
| 474 | 7-Cl,6-F-Q | —CH=CH— | H | H | —OCH₂CH(CH₃)COOH |
| 475 | 7-Cl,6-F-Q | —CH=CH— | H | H | —OCH₂C(CH₂CH₂)CH₂COOH |
| 476 | 7-Cl,6-F-Q | —CH=CH— | H | H | —SCH₂COOH |
| 477 | 7-Cl,6-F-Q | —CH=CH— | H | H | —SCH(CH₃)COOH |
| 478 | 7-Cl,6-F-Q | —CH=CH— | H | H | —SCH₂CH₂COOH |
| 479 | 7-Cl,6-F-Q | —CH=CH— | H | H | —SCH₂CH(CH₃)COOH |
| 480 | 7-Cl,6-F-Q | —CH=CH— | H | H | —SCH₂C(CH₃)₂COOH |

TABLE 1-continued (I)

$$\text{structure with A-B at position 3, (R}^2\text{)n at positions 1,2, X=Y-Z at position 5, (R}^1\text{)m at positions 6-9}$$

| No. | A | B | (R²)n | (R¹)m | X—Y—Z |
|---|---|---|---|---|---|
| 481 | 7-Cl,6-F-Q | —CH=CH— | H | H | —SCH₂CH(CH₂CH₃)COOH |
| 482 | 7-Cl,6-F-Q | —CH=CH— | H | H | —SCH(CH₃)CH₂COOH |
| 483 | 7-Cl,6-F-Q | —CH=CH— | H | H | —SO(CH₃)₂CH₂COOH |
| 484 | 7-Cl,6-F-Q | —CH=CH— | H | H | —SCH₂CH₂COOH |
| 485 | 7-Cl,6-F-Q | —CH=CH— | H | H | —SCH₂CH(CH₃)CH₂COOH |
| 486 | 7-Cl,6-F-Q | —CH=CH— | H | H | —SCH₂C(CH₃)₂CH₂COOH |
| 487 | 7-Cl,6-F-Q | —CH=CH— | H | H | —SCH₂C(CH₂CH₂)CH₂COOH |
| 488 | 7-Cl,6-F-Q | —CH=CH— | H | H | —SCH₂CF₂COOH |
| 489 | 7-Cl,6-F-Q | —CH=CH— | H | H | —SCH₂CF₂CH₂COOH |
| 490 | 7-Cl,6-F-Q | —CH=CH— | H | H | —SCH₂-Tet |
| 491 | 7-Cl,6-F-Q | —CH=CH— | H | H | —SCH₂CH₂-Tet |
| 492 | 7-Cl,6-F-Q | —CH=CH— | H | H | —SCH₂NHSO₂CF₃ |
| 493 | 7-Cl,6-F-Q | —CH=CH— | H | H | —SCH₂CONHSO₂CH₃ |
| 494 | 7-Cl,6-F-Q | —CH=CH— | H | H | —SCH₂CONHSO₂CF₃ |
| 495 | 7-Cl,6-F-Q | —CH=CH— | H | H | —SCH₂CONHSO₂Ph |
| 496 | 7-Cl,6-F-Q | —CH=CH— | H | H | —SCH₂CONHSO₂(2-CH₃—Ph) |
| 497 | 7-Cl,6-F-Q | —CH=CH— | H | H | —SCH₂CH₂NHSO₂CF₃ |
| 498 | 7-Cl,6-F-Q | —CH=CH— | H | H | —SCH₂CH₂CONHSO₂CH₃ |
| 499 | 7-Cl,6-F-Q | —CH=CH— | H | H | —SCH₂CH₂CONHSO₂CF₃ |
| 500 | 7-Cl,6-F-Q | —CH=CH— | H | H | —SCH₂CH₂CONHSO₂Ph |
| 501 | 7-Cl,6-F-Q | —CH=CH— | H | H | —SCH₂CH₂CONHSO₂(2-CH₃—Ph) |
| 502 | 7-Cl,6-F-Q | —CH=CH— | H | H | —CH₂COOH |
| 503 | 7-Cl,6-F-Q | —CH=CH— | H | H | —CH₂CH₂COOH |
| 504 | 7-Cl,6-F-Q | —CH=CH— | H | H | —CH₂CH₂CH₂COOH |
| 505 | 7-Cl,6-F-Q | —CH=CH— | H | 9-F | —OCH₂COOH |
| 506 | 7-Cl,6-F-Q | —CH=CH— | H | 9-F | —OCH(CH₃)COOH |
| 507 | 7-Cl,6-F-Q | —CH=CH— | H | 9-F | —OCH₂CH₂COOH |
| 508 | 7-Cl,6-F-Q | —CH=CH— | H | 9-F | —SCH₂COOH |
| 509 | 7-Cl,6-F-Q | —CH=CH— | H | 9-F | —SCH(CH₃)COOH |
| 510 | 7-Cl,6-F-Q | —CH=CH— | H | 9-F | —SCH₂CH₂COOH |
| 511 | 7-Cl,6-F-Q | —CH=CH— | H | 9-F | —SCH₂CH(CH₃)COOH |
| 512 | 7-Cl,6-F-Q | —CH=CH— | H | 9-F | —SCH₂CH(CH₂CH₃)COOH |
| 513 | 7-Cl,6-F-Q | —CH=CH— | H | 9-F | —SCH₂C(CH₂CH₂)CH₂COOH |
| 514 | 7-Cl,6-F-Q | —CH=CH— | H | 8-F | —OCH₂COOH |
| 515 | 7-Cl,6-F-Q | —CH=CH— | H | 8-F | —OCH₂CH₂COOH |
| 516 | 7-Cl,6-F-Q | —CH=CH— | H | 8-F | —SCH₂COOH |
| 517 | 7-Cl,6-F-Q | —CH=CH— | H | 8-F | —SCH₂CH₂COOH |
| 518 | 7-Cl,6-F-Q | —CH=CH— | H | 8-F | —SCH₂CH(CH₃)COOH |
| 519 | 7-Cl,6-F-Q | —CH=CH— | H | 8-F | —SCH₂C(CH₂CH₂)CH₂COOH |
| 520 | 7-Cl,6-F-Q | —CH=CH— | H | 7-F | —OCH₂COOH |
| 521 | 7-Cl,6-F-Q | —CH=CH— | H | 7-F | —OCH₂CH₂COOH |
| 522 | 7-Cl,6-F-Q | —CH=CH— | H | 7-F | —SCH₂COOH |
| 523 | 7-Cl,6-F-Q | —CH=CH— | H | 7-F | —SCH₂CH₂COOH |
| 524 | 7-Cl,6-F-Q | —CH=CH— | H | 7-F | —SCH₂CH(CH₃)COOH |
| 525 | 7-Cl,6-F-Q | —CH=CH— | H | 6-F | —OCH₂COOH |
| 526 | 7-Cl,6-F-Q | —CH=CH— | H | 6-F | —OCH(CH₃)COOH |
| 527 | 7-Cl,6-F-Q | —CH=CH— | H | 6-F | —OCH₂CH₂COOH |
| 528 | 7-Cl,6-F-Q | —CH=CH— | H | 6-F | —OCH₂CH(CH3)COOH |
| 529 | 7-Cl,6-F-Q | —CH=CH— | H | 6-F | —OCH₂C(CH₂CH₂)CH₂COOH |
| 530 | 7-Cl,6-F-Q | —CH=CH— | H | 6-F | —SCH₂COOH |
| 531 | 7-Cl,6-F-Q | —CH=CH— | H | 6-F | —SCH(CH₃)COOH |
| 532 | 7-Cl,6-F-Q | —CH=CH— | H | 6-F | —SCH₂CH₂COOH |
| 533 | 7-Cl,6-F-Q | —CH=CH— | H | 6-F | —SCH₂CH(CH₃)COOH |
| 534 | 7-Cl,6-F-Q | —CH=CH— | H | 6-F | —SCH₂C(CH₂CH₂)CH₂COOH |
| 535 | 7-Cl,6-F-Q | —CH=CH— | H | 9-Cl | —OCH₂COOH |
| 536 | 7-Cl,6-F-Q | —CH=CH— | H | 9-Cl | —OCH(CH₃)COOH |
| 537 | 7-Cl,6-F-Q | —CH=CH— | H | 9-Cl | —OCH₂CH₂COOH |
| 538 | 7-Cl,6-F-Q | —CH=CH— | H | 9-Cl | —OCH₂CH(CH₃)COOH |
| 539 | 7-Cl,6-F-Q | —CH=CH— | H | 9-Cl | —OCH₂C(CH₂CH₂)CH₂COOH |
| 540 | 7-Cl,6-F-Q | —CH=CH— | H | 9-Cl | —SCH₂COOH |
| 541 | 7-Cl,6-F-Q | —CH=CH— | H | 9-Cl | —SCH(CH₃)COOH |
| 542 | 7-Cl,6-F-Q | —CH=CH— | H | 9-Cl | —SCH₂CH₂COOH |
| 543 | 7-Cl,6-F-Q | —CH=CH— | H | 9-Cl | —SCH₂CH(CH₃)COOH |
| 544 | 7-Cl,6-F-Q | —CH=CH— | H | 9-Cl | —SCH₂C(CH₂CH₂)CH₂COOH |
| 545 | 7-Cl,6-F-Q | —CH=CH— | H | 8-Cl | —SCH₂C(CH₂CH₂)CH₂COOH |

TABLE 1-continued (I)

| No. | A | B | (R²)n | (R¹)m | X—Y—Z |
|---|---|---|---|---|---|
| 546 | 7-Cl,6-F-Q | —CH=CH— | H | 8-Cl | —OCH₂COOH |
| 547 | 7-Cl,6-F-Q | —CH=CH— | H | 8-Cl | —OCH₂CH₂COOH |
| 548 | 7-Cl,6-F-Q | —CH=CH— | H | 8-Cl | —SCH₂COOH |
| 549 | 7-Cl,6-F-Q | —CH=CH— | H | 8-Cl | —SCH₂CH₂COOH |
| 550 | 7-Cl,6-F-Q | —CH=CH— | H | 8-Cl | —SCH₂CH(CH₃)COOH |
| 551 | 7-Cl,6-F-Q | —CH=CH— | H | 7-Cl | —SCH₂C(CH₂CH₂)CH₂COOH |
| 552 | 7-Cl,6-F-Q | —CH=CH— | H | 7-Cl | —OCH₂COOH |
| 553 | 7-Cl,6-F-Q | —CH=CH— | H | 7-Cl | —OCH₂CH₂COOH |
| 554 | 7-Cl,6-F-Q | —CH=CH— | H | 7-Cl | —SCH₂COOH |
| 555 | 7-Cl,6-F-Q | —CH=CH— | H | 7-Cl | —SCH₂CH₂COOH |
| 556 | 7-Cl,6-F-Q | —CH=CH— | H | 7-Cl | —SCH₂CH(CH₃)COOH |
| 557 | 7-Cl,6-F-Q | —CH=CH— | H | 6-Cl | —OCH₂COOH |
| 558 | 7-Cl,6-F-Q | —CH=CH— | H | 6-Cl | —OCH(CH₃)COOH |
| 559 | 7-Cl,6-F-Q | —CH=CH— | H | 6-Cl | —OCH₂CH₂COOH |
| 560 | 7-Cl,6-F-Q | —CH=CH— | H | 6-Cl | —OCH₂CH(CH3)COOH |
| 561 | 7-Cl,6-F-Q | —CH=CH— | H | 6-Cl | —OCH₂C(CH₂CH₂)CH₂COOH |
| 562 | 7-Cl,6-F-Q | —CH=CH— | H | 6-Cl | —SCH₂COOH |
| 563 | 7-Cl,6-F-Q | —CH=CH— | H | 6-Cl | —SCH(CH₃)COOH |
| 564 | 7-Cl,6-F-Q | —CH=CH— | H | 6-Cl | —SCH₂CH₂COOH |
| 565 | 7-Cl,6-F-Q | —CH=CH— | H | 6-Cl | —SCH₂CH(CH₃)COOH |
| 566 | 7-Cl,6-F-Q | —CH=CH— | H | 6-Cl | —SCH₂C(CH₂CH₂)CH₂COOH |
| 567 | 7-Cl,6-F-Q | —CH=CH— | H | 9-CN | —OCH₂COOH |
| 568 | 7-Cl,6-F-Q | —CH=CH— | H | 9-CN | —OCH(CH₃)COOH |
| 569 | 7-Cl,6-F-Q | —CH=CH— | H | 9-CN | —OCH₂CH₂COOH |
| 570 | 7-Cl,6-F-Q | —CH=CH— | H | 9-CN | —OCH₂CH(CH3)COOH |
| 571 | 7-Cl,6-F-Q | —CH=CH— | H | 9-CN | —OCH₂C(CH₂CH₂)CH₂COOH |
| 572 | 7-Cl,6-F-Q | —CH=CH— | H | 9-CN | —SCH₂COOH |
| 573 | 7-Cl,6-F-Q | —CH=CH— | H | 9-CN | —SCH(CH₃)COOH |
| 574 | 7-Cl,6-F-Q | —CH=CH— | H | 9-CN | —SCH₂CH₂COOH |
| 575 | 7-Cl,6-F-Q | —CH=CH— | H | 9-CN | —SCH₂CH(CH₃)COOH |
| 576 | 7-Cl,6-F-Q | —CH=CH— | H | 9-CN | —SCH₂C(CH₂CH₂)CH₂COOH |
| 577 | 7-Cl,6-F-Q | —CH=CH— | H | 8-CN | —OCH₂COOH |
| 578 | 7-Cl,6-F-Q | —CH=CH— | H | 8-CN | —OCH₂CH₂COOH |
| 579 | 7-Cl,6-F-Q | —CH=CH— | H | 8-CN | —SCH₂COOH |
| 580 | 7-Cl,6-F-Q | —CH=CH— | H | 8-CN | —SCH₂CH₂COOH |
| 581 | 7-Cl,6-F-Q | —CH=CH— | H | 8-CN | —SCH₂CH(CH₃)COOH |
| 582 | 7-Cl,6-F-Q | —CH=CH— | H | 8-CN | —SCH₂C(CH₂CH₂)CH₂COOH |
| 583 | 7-Cl,6-F-Q | —CH=CH— | H | 7-CN | —OCH₂COOH |
| 584 | 7-Cl,6-F-Q | —CH=CH— | H | 7-CN | —OCH₂CH₂COOH |
| 585 | 7-Cl,6-F-Q | —CH=CH— | H | 7-CN | —SCH₂COOH |
| 586 | 7-Cl,6-F-Q | —CH=CH— | H | 7-CN | —SCH₂CH₂COOH |
| 587 | 7-Cl,6-F-Q | —CH=CH— | H | 7-CN | —SCH₂CH(CH₃)COOH |
| 588 | 7-Cl,6-F-Q | —CH=CH— | H | 9-CH₃ | —OCH₂COOH |
| 589 | 7-Cl,6-F-Q | —CH=CH— | H | 9-CH₃ | —OCH₂CH₂COOH |
| 590 | 7-Cl,6-F-Q | —CH=CH— | H | 9-CH₃ | —SCH₂COOH |
| 591 | 7-Cl,6-F-Q | —CH=CH— | H | 9-CH₃ | —SCH₂CH₂COOH |
| 592 | 7-Cl,6-F-Q | —CH=CH— | H | 9-CH₃ | —SCH₂CH(CH₃)COOH |
| 593 | 7-Cl,6-F-Q | —CH=CH— | H | 9-CH₃ | —SCH₂CH(CH₂CH₃)COOH |
| 594 | 7-Cl,6-F-Q | —CH=CH— | H | 9-CH₃ | —SCH₂C(CH₂CH₂)CH₂COOH |
| 595 | 7-Cl,6-F-Q | —CH=CH— | H | 8-CH₃ | —OCH₂COOH |
| 596 | 7-Cl,6-F-Q | —CH=CH— | H | 8-CH₃ | —OCH₂CH₂COOH |
| 597 | 7-Cl,6-F-Q | —CH=CH— | H | 8-CH₃ | —SCH₂COOH |
| 598 | 7-Cl,6-F-Q | —CH=CH— | H | 8-CH₃ | —SCH₂CH₂COOH |
| 599 | 7-Cl,6-F-Q | —CH=CH— | H | 8-CH₃ | —SCH₂CH(CH₃)COOH |
| 600 | 7-Cl,6-F-Q | —CH=CH— | H | 8-CH₃ | —SCH₂C(CH₂CH₂)CH₂COOH |
| 601 | 7-Cl,6-F-Q | —CH=CH— | H | 7-CH₃ | —OCH₂COOH |
| 602 | 7-Cl,6-F-Q | —CH=CH— | H | 7-CH₃ | —OCH₂CH₂COOH |
| 603 | 7-Cl,6-F-Q | —CH=CH— | H | 7-CH₃ | —SCH₂COOH |
| 604 | 7-Cl,6-F-Q | —CH=CH— | H | 7-CH₃ | —SCH₂CH₂COOH |
| 605 | 7-Cl,6-F-Q | —CH=CH— | H | 7-CH₃ | —SCH₂CH(CH₃)COOH |
| 606 | 7-Cl,6-F-Q | —CH=CH— | H | 9-CF₃ | —OCH₂COOH |
| 607 | 7-Cl,6-F-Q | —CH=CH— | H | 9-CF₃ | —OCH(CH₃)COOH |
| 608 | 7-Cl,6-F-Q | —CH=CH— | H | 9-CF₃ | —OCH₂CH₂COOH |
| 609 | 7-Cl,6-F-Q | —CH=CH— | H | 9-CF₃ | —OCH₂CH(CH3)COOH |
| 610 | 7-Cl,6-F-Q | —CH=CH— | H | 9-CF₃ | —OCH₂C(CH₂CH₂)CH₂COOH |

TABLE 1-continued

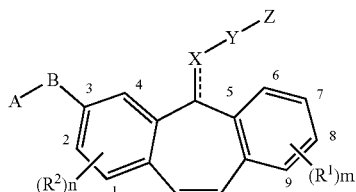

(I)

| No. | A | B | (R²)n | (R¹)m | X—Y—Z |
|---|---|---|---|---|---|
| 611 | 7-Cl,6-F-Q | —CH=CH— | H | 9-CF₃ | —SCH₂COOH |
| 612 | 7-Cl,6-F-Q | —CH=CH— | H | 9-CF₃ | —SCH(CH₃)COOH |
| 613 | 7-Cl,6-F-Q | —CH=CH— | H | 9-CF₃ | —SCH₂CH₂COOH |
| 614 | 7-Cl,6-F-Q | —CH=CH— | H | 9-CF₃ | —SCH₂CH(CH₃)COOH |
| 615 | 7-Cl,6-F-Q | —CH=CH— | H | 9-CF₃ | —SCH₂C(CH₂CH₂)CH₂COOH |
| 616 | 7-Cl,6-F-Q | —CH=CH— | H | 8-CF₃ | —OCH₂COOH |
| 617 | 7-Cl,6-F-Q | —CH=CH— | H | 8-CF₃ | —OCH₂CH₂COOH |
| 618 | 7-Cl,6-F-Q | —CH=CH— | H | 8-CF₃ | —SCH₂COOH |
| 619 | 7-Cl,6-F-Q | —CH=CH— | H | 8-CF₃ | —SCH₂CH₂COOH |
| 620 | 7-Cl,6-F-Q | —CH=CH— | H | 8-CF₃ | —SCH₂CH(CH₃)COOH |
| 621 | 7-Cl,6-F-Q | —CH=CH— | H | 8-CF₃ | —SCH₂C(CH₂CH₂)CH₂COOH |
| 622 | 7-Cl,6-F-Q | —CH=CH— | H | 7-CF₃ | —OCH₂COOH |
| 623 | 7-Cl,6-F-Q | —CH=CH— | H | 7-CF₃ | —OCH₂CH₂COOH |
| 624 | 7-Cl,6-F-Q | —CH=CH— | H | 7-CF₃ | —SCH₂COOH |
| 625 | 7-Cl,6-F-Q | —CH=CH— | H | 7-CF₃ | —SCH₂CH₂COOH |
| 626 | 7-Cl,6-F-Q | —CH=CH— | H | 7-CF₃ | —SCH₂CH(CH₃)COOH |
| 627 | 7-Cl,6-F-Q | —CH=CH— | H | 9-C≡CH | —OCH₂COOH |
| 628 | 7-Cl,6-F-Q | —CH=CH— | H | 9-C≡CH | —OCH(CH₃)COOH |
| 629 | 7-Cl,6-F-Q | —CH=CH— | H | 9-C≡CH | —OCH₂CH₂COOH |
| 630 | 7-Cl,6-F-Q | —CH=CH— | H | 9-C≡CH | —OCH₂CH(CH3)COOH |
| 631 | 7-Cl,6-F-Q | —CH=CH— | H | 9-C≡CH | —OCH₂C(CH₂CH₂)CH₂COOH |
| 632 | 7-Cl,6-F-Q | —CH=CH— | H | 9-C≡CH | —SCH₂COOH |
| 633 | 7-Cl,6-F-Q | —CH=CH— | H | 9-C≡CH | —SCH(CH₃)COOH |
| 634 | 7-Cl,6-F-Q | —CH=CH— | H | 9-C≡CH | —SCH₂CH₂COOH |
| 635 | 7-Cl,6-F-Q | —CH=CH— | H | 9-C≡CH | —SCH₂CH(CH₃)COOH |
| 636 | 7-Cl,6-F-Q | —CH=CH— | H | 9-C≡CH | —SCH₂C(CH₂CH₂)CH₂COOH |
| 637 | 7-Cl,6-F-Q | —CH=CH— | H | 8-C≡CH | —OCH₂COOH |
| 638 | 7-Cl,6-F-Q | —CH=CH— | H | 8-C≡CH | —OCH₂CH₂COOH |
| 639 | 7-Cl,6-F-Q | —CH=CH— | H | 8-C≡CH | —SCH₂COOH |
| 640 | 7-Cl,6-F-Q | —CH=CH— | H | 8-C≡CH | —SCH₂CH₂COOH |
| 641 | 7-Cl,6-F-Q | —CH=CH— | H | 8-C≡CH | —SCH₂CH(CH₃)COOH |
| 642 | 7-Cl,6-F-Q | —CH=CH— | H | 8-C≡CH | —SCH₂C(CH₂CH₂)CH₂COOH |
| 643 | 7-Cl,6-F-Q | —CH=CH— | H | 7-C≡CH | —OCH₂COOH |
| 644 | 7-Cl,6-F-Q | —CH=CH— | H | 7-C≡CH | —OCH₂CH₂COOH |
| 645 | 7-Cl,6-F-Q | —CH=CH— | H | 7-C≡CH | —SCH₂COOH |
| 646 | 7-Cl,6-F-Q | —CH=CH— | H | 7-C≡CH | —SCH₂CH₂COOH |
| 647 | 7-Cl,6-F-Q | —CH=CH— | H | 7-C≡CH | —SCH₂CH(CH₃)COOH |
| 648 | 7-Cl,6-F-Q | —CH=CH— | H | 9-CH₂OH | —OCH₂COOH |
| 649 | 7-Cl,6-F-Q | —CH=CH— | H | 9-CH₂OH | —SCH₂CH₂COOH |
| 650 | 7-Cl,6-F-Q | —CH=CH— | H | 8-CH₂OH | —OCH₂COOH |
| 651 | 7-Cl,6-F-Q | —CH=CH— | H | 8-CH₂OH | —SCH₂CH₂COOH |
| 652 | 7-Cl,6-F-Q | —CH=CH— | H | 7-CH₂OH | —OCH₂COOH |
| 653 | 7-Cl,6-F-Q | —CH=CH— | H | 7-CH₂OH | —SCH₂CH₂COOH |
| 654 | 7-Cl,6-F-Q | —CH=CH— | H | 9-C(CH₃)₂OH | —OCH₂COOH |
| 655 | 7-Cl,6-F-Q | —CH=CH— | H | 9-C(CH₃)₂OH | —SCH₂CH₂COOH |
| 656 | 7-Cl,6-F-Q | —CH=CH— | H | 8-C(CH₃)₂OH | —OCH₂COOH |
| 657 | 7-Cl,6-F-Q | —CH=CH— | H | 8-C(CH₃)₂OH | —SCH₂CH₂COOH |
| 658 | 7-Cl,6-F-Q | —CH=CH— | H | 7-C(CH₃)₂OH | —OCH₂COOH |
| 659 | 7-Cl,6-F-Q | —CH=CH— | H | 7-C(CH₃)₂OH | —SCH₂CH₂COOH |
| 660 | 7-Cl,6-F-Q | —CH=CH— | H | 9-OCH₃ | —OCH₂COOH |
| 661 | 7-Cl,6-F-Q | —CH=CH— | H | 9-OCH₃ | —SCH₂CH₂COOH |
| 662 | 7-Cl,6-F-Q | —CH=CH— | H | 8-OCH₃ | —OCH₂COOH |
| 663 | 7-Cl,6-F-Q | —CH=CH— | H | 8-OCH₃ | —SCH₂CH₂COOH |
| 664 | 7-Cl,6-F-Q | —CH=CH— | H | 7-OCH₃ | —OCH₂COOH |
| 665 | 7-Cl,6-F-Q | —CH=CH— | H | 7-OCH₃ | —SCH₂CH₂COOH |
| 666 | 7-Cl,6-F-Q | —CH=CH— | H | 9-OCHF₂ | —OCH₂COOH |
| 667 | 7-Cl,6-F-Q | —CH=CH— | H | 9-OCHF₂ | —SCH₂CH₂COOH |
| 668 | 7-Cl,6-F-Q | —CH=CH— | H | 8-OCHF₂ | —OCH₂COOH |
| 669 | 7-Cl,6-F-Q | —CH=CH— | H | 8-OCHF₂ | —SCH₂CH₂COOH |

TABLE 1-continued

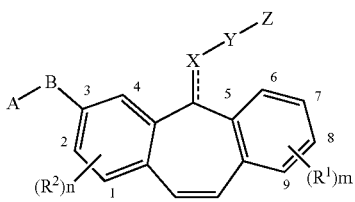

(I)

| No. | A | B | (R²)n | (R¹)m | X—Y—Z |
|---|---|---|---|---|---|
| 670 | 7-Cl,6-F-Q | —CH=CH— | H | 7-OCHF₂ | —OCH₂COOH |
| 671 | 7-Cl,6-F-Q | —CH=CH— | H | 7-OCHF₂ | —SCH₂CH₂COOH |
| 672 | 7-Cl,6-F-Q | —CH=CH— | H | 9-OCF₃ | —OCH₂COOH |
| 673 | 7-Cl,6-F-Q | —CH=CH— | H | 9-OCF₃ | —SCH₂CH₂COOH |
| 674 | 7-Cl,6-F-Q | —CH=CH— | H | 8-OCF₃ | —OCH₂COOH |
| 675 | 7-Cl,6-F-Q | —CH=CH— | H | 8-OCF₃ | —SCH₂CH₂COOH |
| 676 | 7-Cl,6-F-Q | —CH=CH— | H | 7-OCF₃ | —OCH₂COOH |
| 677 | 7-Cl,6-F-Q | —CH=CH— | H | 7-OCF₃ | —SCH₂CH₂COOH |
| 678 | 7-Cl,6-F-Q | —CH=CH— | H | 9-SOCH₃ | —OCH₂COOH |
| 679 | 7-Cl,6-F-Q | —CH=CH— | H | 9-SOCH₃ | —SCH₂CH₂COOH |
| 680 | 7-Cl,6-F-Q | —CH=CH— | H | 8-SOCH₃ | —OCH₂COOH |
| 681 | 7-Cl,6-F-Q | —CH=CH— | H | 8-SOCH₃ | —SCH₂CH₂COOH |
| 682 | 7-Cl,6-F-Q | —CH=CH— | H | 7-SOCH₃ | —OCH₂COOH |
| 683 | 7-Cl,6-F-Q | —CH=CH— | H | 7-SOCH₃ | —SCH₂CH₂COOH |
| 684 | 7-Cl,6-F-Q | —CH=CH— | H | 9-SO₂CH₃ | —OCH₂COOH |
| 685 | 7-Cl,6-F-Q | —CH=CH— | H | 9-SO₂CH₃ | —SCH₂CH₂COOH |
| 686 | 7-Cl,6-F-Q | —CH=CH— | H | 8-SO₂CH₃ | —OCH₂COOH |
| 687 | 7-Cl,6-F-Q | —CH=CH— | H | 8-SO₂CH₃ | —SCH₂CH₂COOH |
| 688 | 7-Cl,6-F-Q | —CH=CH— | H | 7-SO₂CH₃ | —OCH₂COOH |
| 689 | 7-Cl,6-F-Q | —CH=CH— | H | 7-SO₂CH₃ | —SCH₂CH₂COOH |
| 690 | 7-Cl,6-F-Q | —CH=CH— | H | 9-CH=CH₂ | —SCH₂CH₂COOH |
| 691 | 7-Cl,6-F-Q | —CH=CH— | H | 8-CH=CH₂ | —SCH₂CH₂COOH |
| 692 | 7-Cl,6-F-Q | —CH=CH— | H | 7-CH=CH₂ | —SCH₂CH₂COOH |
| 693 | 7-Cl,6-F-Q | —CH=CH— | H | 9-NO₂ | —OCH₂COOH |
| 694 | 7-Cl,6-F-Q | —CH=CH— | H | 9-NO₂ | —SCH₂CH₂COOH |
| 695 | 7-Cl,6-F-Q | —CH=CH— | H | 8-NO₂ | —OCH₂COOH |
| 696 | 7-Cl,6-F-Q | —CH=CH— | H | 8-NO₂ | —SCH₂CH₂COOH |
| 697 | 7-Cl,6-F-Q | —CH=CH— | H | 7-NO₂ | —OCH₂COOH |
| 698 | 7-Cl,6-F-Q | —CH=CH— | H | 7-NO₂ | —SCH₂CH₂COOH |
| 699 | 7-Cl,6-F-Q | —CH=CH— | 1-F | H | —SCH₂CH₂COOH |
| 700 | 7-Cl,6-F-Q | —CH=CH— | 2-F | H | —SCH₂CH₂COOH |
| 701 | 7-Cl,6-F-Q | —CH=CH— | 1-Cl | H | —SCH₂CH₂COOH |
| 702 | 7-Cl,6-F-Q | —CH=CH— | 2-Cl | H | —SCH₂CH₂COOH |
| 703 | 7-Cl,6-F-Q | —CH=CH— | 1-CH₃ | H | —SCH₂CH₂COOH |
| 704 | 7-Cl,6-F-Q | —CH=CH— | 2-CH₃ | H | —SCH₂CH₂COOH |
| 705 | 7-Cl,6-F-Q | —CH=CH— | 1-OCH₃ | H | —SCH₂CH₂COOH |
| 706 | 7-Cl,6-F-Q | —CH=CH— | 2-OCH₃ | H | —SCH₂CH₂COOH |
| 707 | 7-Cl,6-F-Q | —CH=CH— | 1-NO₂ | H | —SCH₂CH₂COOH |
| 708 | 7-Cl,6-F-Q | —CH=CH— | 2-NO₂ | H | —SCH₂CH₂COOH |
| 709 | 7-Cl,6-F-Q | —CH=CH— | 1-CN | H | —SCH₂CH₂COOH |
| 710 | 7-Cl,6-F-Q | —CH=CH— | 2-CN | H | —SCH₂CH₂COOH |
| 711 | 7-Cl,6-F-Q | —CH₂O— | H | H | —OCH₂COOH |
| 712 | 7-Cl,6-F-Q | —CH₂O— | H | H | —OCH(CH3)COOH |
| 713 | 7-Cl,6-F-Q | —CH₂O— | H | H | —OCH₂CH₂COOH |
| 714 | 7-Cl,6-F-Q | —CH₂O— | H | H | —OCH₂CH(CH₃)COOH |
| 715 | 7-Cl,6-F-Q | —CH₂O— | H | H | —OCH₂C(CH₂CH₂)CH₂COOH |
| 716 | 7-Cl,6-F-Q | —CH₂O— | H | H | —SCH₂COOH |
| 717 | 7-Cl,6-F-Q | —CH₂O— | H | H | —SCH(CH3)COOH |
| 718 | 7-Cl,6-F-Q | —CH₂O— | H | H | —SCH₂CH₂COOH |
| 719 | 7-Cl,6-F-Q | —CH₂O— | H | H | —SCH₂CH(CH₃)COOH |
| 720 | 7-Cl,6-F-Q | —CH₂O— | H | H | —SCH₂C(CH₃)₂COOH |
| 721 | 7-Cl,6-F-Q | —CH₂O— | H | H | —SCH₂CH(CH₂CH₃)COOH |
| 722 | 7-Cl,6-F-Q | —CH₂O— | H | H | —SCH(CH₃)CH₂COOH |
| 723 | 7-Cl,6-F-Q | —CH₂O— | H | H | —SC(CH₃)₂CH₂COOH |
| 724 | 7-Cl,6-F-Q | —CH₂O— | H | H | —SCH₂CH₂CH₂COOH |
| 725 | 7-Cl,6-F-Q | —CH₂O— | H | H | —SCH₂CH(CH₃)CH₂COOH |
| 726 | 7-Cl,6-F-Q | —CH₂O— | H | H | —SCH₂C(CH₃)₂CH₂COOH |
| 727 | 7-Cl,6-F-Q | —CH₂O— | H | H | —SCH₂C(CH₂CH₂)CH₂COOH |
| 728 | 7-Cl,6-F-Q | —CH₂O— | H | H | —SCH₂CF₂COOH |
| 729 | 7-Cl,6-F-Q | —CH₂O— | H | H | —SCH₂CF₂CH₂COOH |
| 730 | 7-Cl,6-F-Q | —CH₂O— | H | H | —SCH₂-Tet |
| 731 | 7-Cl,6-F-Q | —CH₂O— | H | H | —SCH₂CH₂-Tet |
| 732 | 7-Cl,6-F-Q | —CH₂O— | H | H | —SCH₂NHSO₂CF₃ |
| 733 | 7-Cl,6-F-Q | —CH₂O— | H | H | —SCH₂CONHSO₂CH₃ |
| 734 | 7-Cl,6-F-Q | —CH₂O— | H | H | —SCH₂CONHSO₂CF₃ |

TABLE 1-continued

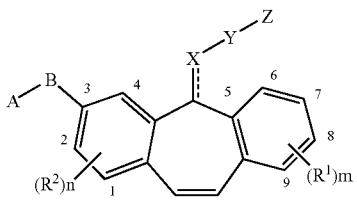
(I)

| No. | A | B | (R²)n | (R¹)m | X—Y—Z |
|---|---|---|---|---|---|
| 735 | 7-Cl,6-F-Q | —CH₂O— | H | H | —SCH₂CONHSO₂Ph |
| 736 | 7-Cl,6-F-Q | —CH₂O— | H | H | —SCH₂CONHSO₂(2-CH₃—Ph) |
| 737 | 7-Cl,6-F-Q | —CH₂O— | H | H | —SCH₂CH₂NHSO₂CF₃ |
| 738 | 7-Cl,6-F-Q | —CH₂O— | H | H | —SCH₂CH₂CONHSO₂CH₃ |
| 739 | 7-Cl,6-F-Q | —CH₂O— | H | H | —SCH₂CH₂CONHSO₂CF₃ |
| 740 | 7-Cl,6-F-Q | —CH₂O— | H | H | —SCH₂CH₂CONHSO₂Ph |
| 741 | 7-Cl,6-F-Q | —CH₂O— | H | H | —SCH₂CH₂CONHSO₂(2-CH₃—Ph) |
| 742 | 7-Cl,6-F-Q | —CH₂O— | H | H | —CH₂COOH |
| 743 | 7-Cl,6-F-Q | —CH₂O— | H | H | —CH₂CH₂COOH |
| 744 | 7-Cl,6-F-Q | —CH₂O— | H | H | —CH₂CH₂CH₂COOH |
| 745 | 7-Cl,6-F-Q | —CH₂O— | H | 9-F | —OCH₂COOH |
| 746 | 7-Cl,6-F-Q | —CH₂O— | H | 9-F | —OCH(CH₃)COOH |
| 747 | 7-Cl,6-F-Q | —CH₂O— | H | 9-F | —OCH₂CH₂COOH |
| 748 | 7-Cl,6-F-Q | —CH₂O— | H | 9-F | —OCH₂CH(CH3)COOH |
| 749 | 7-Cl,6-F-Q | —CH₂O— | H | 9-F | —OCH₂C(CH₂CH₂)CH₂COOH |
| 750 | 7-Cl,6-F-Q | —CH₂O— | H | 9-F | —SCH₂COOH |
| 751 | 7-Cl,6-F-Q | —CH₂O— | H | 9-F | —SCH(CH₃)COOH |
| 752 | 7-Cl,6-F-Q | —CH₂O— | H | 9-F | —SCH₂CH₂COOH |
| 753 | 7-Cl,6-F-Q | —CH₂O— | H | 9-F | —SCH₂CH(CH₃)COOH |
| 754 | 7-Cl,6-F-Q | —CH₂O— | H | 9-F | —SCH₂C(CH₂CH₂)CH₂COOH |
| 755 | 7-Cl,6-F-Q | —CH₂O— | H | 8-F | —OCH₂COOH |
| 756 | 7-Cl,6-F-Q | —CH₂O— | H | 8-F | —OCH₂CH₂COOH |
| 757 | 7-Cl,6-F-Q | —CH₂O— | H | 8-F | —SCH₂COOH |
| 758 | 7-Cl,6-F-Q | —CH₂O— | H | 8-F | —SCH₂CH₂COOH |
| 759 | 7-Cl,6-F-Q | —CH₂O— | H | 8-F | —SCH₂CH(CH₃)COOH |
| 760 | 7-Cl,6-F-Q | —CH₂O— | H | 8-F | —SCH₂C(CH₂CH₂)CH₂COOH |
| 761 | 7-Cl,6-F-Q | —CH₂O— | H | 7-F | —OCH₂COOH |
| 762 | 7-Cl,6-F-Q | —CH₂O— | H | 7-F | —OCH₂CH₂COOH |
| 763 | 7-Cl,6-F-Q | —CH₂O— | H | 7-F | —SCH₂COOH |
| 764 | 7-Cl,6-F-Q | —CH₂O— | H | 7-F | —SCH₂CH₂COOH |
| 765 | 7-Cl,6-F-Q | —CH₂O— | H | 7-F | —SCH₂CH(CH₃)COOH |
| 766 | 7-Cl,6-F-Q | —CH₂O— | H | 6-F | —OCH₂COOH |
| 767 | 7-Cl,6-F-Q | —CH₂O— | H | 6-F | —OCH(CH₃)COOH |
| 768 | 7-Cl,6-F-Q | —CH₂O— | H | 6-F | —OCH₂CH₂COOH |
| 769 | 7-Cl,6-F-Q | —CH₂O— | H | 6-F | —OCH₂CH(CH3)COOH |
| 770 | 7-Cl,6-F-Q | —CH₂O— | H | 6-F | —OCH₂C(CH₂CH₂)CH₂COOH |
| 771 | 7-Cl,6-F-Q | —CH₂O— | H | 6-F | —SCH₂COOH |
| 772 | 7-Cl,6-F-Q | —CH₂O— | H | 6-F | —SCH(CH₃)COOH |
| 773 | 7-Cl,6-F-Q | —CH₂O— | H | 6-F | —SCH₂CH₂COOH |
| 774 | 7-Cl,6-F-Q | —CH₂O— | H | 6-F | —SCH₂CH(CH₃)COOH |
| 775 | 7-Cl,6-F-Q | —CH₂O— | H | 6-F | —SCH₂C(CH₂CH₂)CH₂COOH |
| 776 | 7-Cl,6-F-Q | —CH₂O— | H | 9-Cl | —OCH₂COOH |
| 777 | 7-Cl,6-F-Q | —CH₂O— | H | 9-Cl | —OCH(CH₃)COOH |
| 778 | 7-Cl,6-F-Q | —CH₂O— | H | 9-Cl | —OCH₂CH₂COOH |
| 779 | 7-Cl,6-F-Q | —CH₂O— | H | 9-Cl | —OCH₂CH(CH3)COOH |
| 780 | 7-Cl,6-F-Q | —CH₂O— | H | 9-Cl | —OCH₂C(CH₂CH₂)CH₂COOH |
| 781 | 7-Cl,6-F-Q | —CH₂O— | H | 9-Cl | —SCH₂COOH |
| 782 | 7-Cl,6-F-Q | —CH₂O— | H | 9-Cl | —SCH(CH₃)COOH |
| 783 | 7-Cl,6-F-Q | —CH₂O— | H | 9-Cl | —SCH₂CH₂COOH |
| 784 | 7-Cl,6-F-Q | —CH₂O— | H | 9-Cl | —SCH₂CH(CH₃)COOH |
| 785 | 7-Cl,6-F-Q | —CH₂O— | H | 9-Cl | —SCH₂C(CH₂CH₂)CH₂COOH |
| 786 | 7-Cl,6-F-Q | —CH₂O— | H | 8-Cl | —SCH₂C(CH₂CH₂)CH₂COOH |
| 787 | 7-Cl,6-F-Q | —CH₂O— | H | 8-Cl | —OCH₂COOH |
| 788 | 7-Cl,6-F-Q | —CH₂O— | H | 8-Cl | —OCH₂CH₂COOH |
| 789 | 7-Cl,6-F-Q | —CH₂O— | H | 8-Cl | —SCH₂COOH |
| 790 | 7-Cl,6-F-Q | —CH₂O— | H | 8-Cl | —SCH₂CH₂COOH |
| 791 | 7-Cl,6-F-Q | —CH₂O— | H | 8-Cl | —SCH₂CH(CH₃)COOH |
| 792 | 7-Cl,6-F-Q | —CH₂O— | H | 7-Cl | —OCH₂COOH |
| 793 | 7-Cl,6-F-Q | —CH₂O— | H | 7-Cl | —OCH₂CH₂COOH |
| 794 | 7-Cl,6-F-Q | —CH₂O— | H | 7-Cl | —SCH₂COOH |
| 795 | 7-Cl,6-F-Q | —CH₂O— | H | 7-Cl | —SCH₂CH₂COOH |
| 796 | 7-Cl,6-F-Q | —CH₂O— | H | 7-Cl | —SCH₂CH(CH₃)COOH |
| 797 | 7-Cl,6-F-Q | —CH₂O— | H | 9-CN | —OCH₂COOH |
| 798 | 7-Cl,6-F-Q | —CH₂O— | H | 9-CN | —OCH(CH₃)COOH |
| 799 | 7-Cl,6-F-Q | —CH₂O— | H | 9-CN | —OCH₂CH₂COOH |

TABLE 1-continued (I)

| No. | A | B | (R²)n | (R¹)m | X—Y—Z |
|-----|---|---|-------|-------|-------|
| 800 | 7-Cl,6-F-Q | —CH₂O— | H | 9-CN | —OCH₂CH(CH3)COOH |
| 801 | 7-Cl,6-F-Q | —CH₂O— | H | 9-CN | —OCH₂C(CH₂CH₂)CH₂COOH |
| 802 | 7-Cl,6-F-Q | —CH₂O— | H | 9-CN | —SCH₂COOH |
| 803 | 7-Cl,6-F-Q | —CH₂O— | H | 9-CN | —SCH(CH₃)COOH |
| 804 | 7-Cl,6-F-Q | —CH₂O— | H | 9-CN | —SCH₂CH₂COOH |
| 805 | 7-Cl,6-F-Q | —CH₂O— | H | 9-CN | —SCH₂CH(CH₃)COOH |
| 806 | 7-Cl,6-F-Q | —CH₂O— | H | 9-CN | —SCH₂C(CH₂CH₂)CH₂COOH |
| 807 | 7-Cl,6-F-Q | —CH₂O— | H | 8-CN | —OCH₂COOH |
| 808 | 7-Cl,6-F-Q | —CH₂O— | H | 8-CN | —OCH₂CH₂COOH |
| 809 | 7-Cl,6-F-Q | —CH₂O— | H | 8-CN | —SCH₂COOH |
| 810 | 7-Cl,6-F-Q | —CH₂O— | H | 8-CN | —SCH₂CH₂COOH |
| 811 | 7-Cl,6-F-Q | —CH₂O— | H | 8-CN | —SCH₂CH(CH₃)COOH |
| 812 | 7-Cl,6-F-Q | —CH₂O— | H | 8-CN | —SCH₂C(CH₂CH₂)CH₂COOH |
| 813 | 7-Cl,6-F-Q | —CH₂O— | H | 7-CN | —OCH₂COOH |
| 814 | 7-Cl,6-F-Q | —CH₂O— | H | 7-CN | —OCH₂CH₂COOH |
| 815 | 7-Cl,6-F-Q | —CH₂O— | H | 7-CN | —SCH₂COOH |
| 816 | 7-Cl,6-F-Q | —CH₂O— | H | 7-CN | —SCH₂CH₂COOH |
| 817 | 7-Cl,6-F-Q | —CH₂O— | H | 7-CN | —SCH₂CH(CH₃)COOH |
| 818 | 7-Cl,6-F-Q | —CH₂O— | H | 9-CH₃ | —OCH₂COOH |
| 819 | 7-Cl,6-F-Q | —CH₂O— | H | 9-CH₃ | —OCH₂CH₂COOH |
| 820 | 7-Cl,6-F-Q | —CH₂O— | H | 9-CH₃ | —SCH₂COOH |
| 821 | 7-Cl,6-F-Q | —CH₂O— | H | 9-CH₃ | —SCH₂CH₂COOH |
| 822 | 7-Cl,6-F-Q | —CH₂O— | H | 9-CH₃ | —SCH₂CH(CH₃)COOH |
| 823 | 7-Cl,6-F-Q | —CH₂O— | H | 9-CH₃ | —SCH₂CH(CH₂CH₃)COOH |
| 824 | 7-Cl,6-F-Q | —CH₂O— | H | 9-CH₃ | —SCH₂C(CH₂CH₂)CH₂COOH |
| 825 | 7-Cl,6-F-Q | —CH₂O— | H | 8-CH₃ | —OCH₂COOH |
| 826 | 7-Cl,6-F-Q | —CH₂O— | H | 8-CH₃ | —OCH₂CH₂COOH |
| 827 | 7-Cl,6-F-Q | —CH₂O— | H | 8-CH₃ | —SCH₂COOH |
| 828 | 7-Cl,6-F-Q | —CH₂O— | H | 8-CH₃ | —SCH₂CH₂COOH |
| 829 | 7-Cl,6-F-Q | —CH₂O— | H | 8-CH₃ | —SCH₂CH(CH₃)COOH |
| 830 | 7-Cl,6-F-Q | —CH₂O— | H | 8-CH₃ | —SCH₂C(CH₂CH₂)CH₂COOH |
| 831 | 7-Cl,6-F-Q | —CH₂O— | H | 7-CH₃ | —OCH₂COOH |
| 832 | 7-Cl,6-F-Q | —CH₂O— | H | 7-CH₃ | —OCH₂CH₂COOH |
| 833 | 7-Cl,6-F-Q | —CH₂O— | H | 7-CH₃ | —SCH₂COOH |
| 834 | 7-Cl,6-F-Q | —CH₂O— | H | 7-CH₃ | —SCH₂CH₂COOH |
| 835 | 7-Cl,6-F-Q | —CH₂O— | H | 7-CH₃ | —SCH₂CH(CH₃)COOH |
| 836 | 7-Cl,6-F-Q | —CH₂O— | H | 9-CF₃ | —OCH₂COOH |
| 837 | 7-Cl,6-F-Q | —CH₂O— | H | 9-CF₃ | —OCH(CH₃)COOH |
| 838 | 7-Cl,6-F-Q | —CH₂O— | H | 9-CF₃ | —OCH₂CH₂COOH |
| 839 | 7-Cl,6-F-Q | —CH₂O— | H | 9-CF₃ | —OCH₂CH(CH3)COOH |
| 840 | 7-Cl,6-F-Q | —CH₂O— | H | 9-CF₃ | —OCH₂C(CH₂CH₂)CH₂COOH |
| 841 | 7-Cl,6-F-Q | —CH₂O— | H | 9-CF₃ | —SCH₂COOH |
| 842 | 7-Cl,6-F-Q | —CH₂O— | H | 9-CF₃ | —SCH(CH₃)COOH |
| 843 | 7-Cl,6-F-Q | —CH₂O— | H | 9-CF₃ | —SCH₂CH₂COOH |
| 844 | 7-Cl,6-F-Q | —CH₂O— | H | 9-CF₃ | —SCH₂CH(CH₃)COOH |
| 845 | 7-Cl,6-F-Q | —CH₂O— | H | 9-CF₃ | —SCH₂C(CH₂CH₂)CH₂COOH |
| 846 | 7-Cl,6-F-Q | —CH₂O— | H | 8-CF₃ | —OCH₂COOH |
| 847 | 7-Cl,6-F-Q | —CH₂O— | H | 8-CF₃ | —OCH₂CH₂COOH |
| 848 | 7-Cl,6-F-Q | —CH₂O— | H | 8-CF₃ | —SCH₂COOH |
| 849 | 7-Cl,6-F-Q | —CH₂O— | H | 8-CF₃ | —SCH₂CH₂COOH |
| 850 | 7-Cl,6-F-Q | —CH₂O— | H | 8-CF₃ | —SCH₂CH(CH₃)COOH |
| 851 | 7-Cl,6-F-Q | —CH₂O— | H | 8-CF₃ | —SCH₂C(CH₂CH₂)CH₂COOH |
| 852 | 7-Cl,6-F-Q | —CH₂O— | H | 7-CF₃ | —OCH₂COOH |
| 853 | 7-Cl,6-F-Q | —CH₂O— | H | 7-CF₃ | —OCH₂CH₂COOH |
| 854 | 7-Cl,6-F-Q | —CH₂O— | H | 7-CF₃ | —SCH₂COOH |
| 855 | 7-Cl,6-F-Q | —CH₂O— | H | 7-CF₃ | —SCH₂CH₂COOH |
| 856 | 7-Cl,6-F-Q | —CH₂O— | H | 7-CF₃ | —SCH₂CH(CH₃)COOH |
| 857 | 7-Cl,6-F-Q | —CH₂O— | H | 9-C≡CH | —OCH₂COOH |
| 858 | 7-Cl,6-F-Q | —CH₂O— | H | 9-C≡CH | —OCH(CH₃)COOH |
| 859 | 7-Cl,6-F-Q | —CH₂O— | H | 9-C≡CH | —OCH₂CH₂COOH |
| 860 | 7-Cl,6-F-Q | —CH₂O— | H | 9-C≡CH | —OCH₂CH(CH3)COOH |
| 861 | 7-Cl,6-F-Q | —CH₂O— | H | 9-C≡CH | —OCH₂C(CH₂CH₂)CH₂COOH |
| 862 | 7-Cl,6-F-Q | —CH₂O— | H | 9-C≡CH | —SCH₂COOH |
| 863 | 7-Cl,6-F-Q | —CH₂O— | H | 9-C≡CH | —SCH(CH₃)COOH |
| 864 | 7-Cl,6-F-Q | —CH₂O— | H | 9-C≡CH | —SCH₂CH₂COOH |

TABLE 1-continued

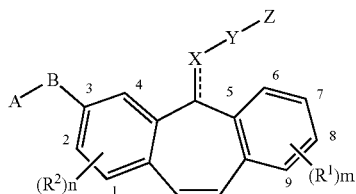

(I)

| No. | A | B | (R²)n | (R¹)m | X—Y—Z |
|---|---|---|---|---|---|
| 865 | 7-Cl,6-F-Q | —CH₂O— | H | 9-C≡CH | —SCH₂CH(CH₃)COOH |
| 866 | 7-Cl,6-F-Q | —CH₂O— | H | 9-C≡CH | —SCH₂C(CH₂CH₂)CH₂COOH |
| 867 | 7-Cl,6-F-Q | —CH₂O— | H | 8-C≡CH | —OCH₂COOH |
| 868 | 7-Cl,6-F-Q | —CH₂O— | H | 8-C≡CH | —OCH₂CH₂COOH |
| 869 | 7-Cl,6-F-Q | —CH₂O— | H | 8-C≡CH | —SCH₂COOH |
| 870 | 7-Cl,6-F-Q | —CH₂O— | H | 8-C≡CH | —SCH₂CH₂COOH |
| 871 | 7-Cl,6-F-Q | —CH₂O— | H | 8-C≡CH | —SCH₂CH(CH₃)COOH |
| 872 | 7-Cl,6-F-Q | —CH₂O— | H | 8-C≡CH | —SCH₂C(CH₂CH₂)CH₂COOH |
| 873 | 7-Cl,6-F-Q | —CH₂O— | H | 7-C≡CH | —OCH₂COOH |
| 874 | 7-Cl,6-F-Q | —CH₂O— | H | 7-C≡CH | —OCH₂CH₂COOH |
| 875 | 7-Cl,6-F-Q | —CH₂O— | H | 7-C≡CH | —SCH₂COOH |
| 876 | 7-Cl,6-F-Q | —CH₂O— | H | 7-C≡CH | —SCH₂CH₂COOH |
| 877 | 7-Cl,6-F-Q | —CH₂O— | H | 7-C≡CH | —SCH₂CH(CH₃)COOH |
| 878 | 7-Cl,6-F-Q | —CH₂O— | H | 9-CH₂OH | —OCH₂COOH |
| 879 | 7-Cl,6-F-Q | —CH₂O— | H | 9-CH₂OH | —SCH₂CH₂COOH |
| 880 | 7-Cl,6-F-Q | —CH₂O— | H | 8-CH₂OH | —OCH₂COOH |
| 881 | 7-Cl,6-F-Q | —CH₂O— | H | 8-CH₂OH | —SCH₂CH₂COOH |
| 885 | 7-Cl,6-F-Q | —CH₂O— | H | 9-C(CH₃)₂OH | —SCH₂CH₂COOH |
| 886 | 7-Cl,6-F-Q | —CH₂O— | H | 8-C(CH₃)₂OH | —OCH₂COOH |
| 887 | 7-Cl,6-F-Q | —CH₂O— | H | 8-C(CH₃)₂OH | —SCH₂CH₂COOH |
| 888 | 7-Cl,6-F-Q | —CH₂O— | H | 7-C(CH₃)₂OH | —OCH₂COOH |
| 889 | 7-Cl,6-F-Q | —CH₂O— | H | 7-C(CH₃)₂OH | —SCH₂CH₂COOH |
| 890 | 7-Cl,6-F-Q | —CH₂O— | H | 9-OCH₃ | —OCH₂COOH |
| 891 | 7-Cl,6-F-Q | —CH₂O— | H | 9-OCH₃ | —SCH₂CH₂COOH |
| 892 | 7-Cl,6-F-Q | —CH₂O— | H | 8-OCH₃ | —OCH₂COOH |
| 893 | 7-Cl,6-F-Q | —CH₂O— | H | 8-OCH₃ | —SCH₂CH₂COOH |
| 894 | 7-Cl,6-F-Q | —CH₂O— | H | 7-OCH₃ | —OCH₂COOH |
| 895 | 7-Cl,6-F-Q | —CH₂O— | H | 7-OCH₃ | —SCH₂CH₂COOH |
| 896 | 7-Cl,6-F-Q | —CH₂O— | H | 9-OCHF₂ | —OCH₂COOH |
| 897 | 7-Cl,6-F-Q | —CH₂O— | H | 9-OCHF₂ | —SCH₂CH₂COOH |
| 898 | 7-Cl,6-F-Q | —CH₂O— | H | 8-OCHF₂ | —OCH₂COOH |
| 899 | 7-Cl,6-F-Q | —CH₂O— | H | 8-OCHF₂ | —SCH₂CH₂COOH |
| 900 | 7-Cl,6-F-Q | —CH₂O— | H | 7-OCHF₂ | —OCH₂COOH |
| 901 | 7-Cl,6-F-Q | —CH₂O— | H | 7-OCHF₂ | —SCH₂CH₂COOH |
| 902 | 7-Cl,6-F-Q | —CH₂O— | H | 9-OCF₃ | —OCH₂COOH |
| 903 | 7-Cl,6-F-Q | —CH₂O— | H | 9-OCF₃ | —SCH₂CH₂COOH |
| 904 | 7-Cl,6-F-Q | —CH₂O— | H | 8-OCF₃ | —OCH₂COOH |
| 905 | 7-Cl,6-F-Q | —CH₂O— | H | 8-OCF₃ | —SCH₂CH₂COOH |
| 906 | 7-Cl,6-F-Q | —CH₂O— | H | 7-OCF₃ | —OCH₂COOH |
| 907 | 7-Cl,6-F-Q | —CH₂O— | H | 7-OCF₃ | —SCH₂CH₂COOH |
| 908 | 7-Cl,6-F-Q | —CH₂O— | H | 9-SOCH₃ | —OCH₂COOH |
| 909 | 7-Cl,6-F-Q | —CH₂O— | H | 9-SOCH₃ | —SCH₂CH₂COOH |
| 910 | 7-Cl,6-F-Q | —CH₂O— | H | 8-SOCH₃ | —OCH₂COOH |
| 911 | 7-Cl,6-F-Q | —CH₂O— | H | 8-SOCH₃ | —SCH₂CH₂COOH |
| 912 | 7-Cl,6-F-Q | —CH₂O— | H | 7-SOCH₃ | —OCH₂COOH |
| 913 | 7-Cl,6-F-Q | —CH₂O— | H | 7-SOCH₃ | —SCH₂CH₂COOH |
| 914 | 7-Cl,6-F-Q | —CH₂O— | H | 9-SO₂CH₃ | —OCH₂COOH |
| 915 | 7-Cl,6-F-Q | —CH₂O— | H | 9-SO₂CH₃ | —SCH₂CH₂COOH |
| 916 | 7-Cl,6-F-Q | —CH₂O— | H | 8-SO₂CH₃ | —OCH₂COOH |
| 917 | 7-Cl,6-F-Q | —CH₂O— | H | 8-SO₂CH₃ | —SCH₂CH₂COOH |
| 918 | 7-Cl,6-F-Q | —CH₂O— | H | 7-SO₂CH₃ | —OCH₂COOH |
| 919 | 7-Cl,6-F-Q | —CH₂O— | H | 7-SO₂CH₃ | —SCH₂CH₂COOH |
| 920 | 7-Cl,6-F-Q | —CH₂O— | H | 9-CH=CH₂ | —SCH₂CH₂COOH |
| 921 | 7-Cl,6-F-Q | —CH₂O— | H | 8-CH=CH₂ | —SCH₂CH₂COOH |
| 922 | 7-Cl,6-F-Q | —CH₂O— | H | 7-CH=CH₂ | —SCH₂CH₂COOH |
| 923 | 7-Cl,6-F-Q | —CH₂O— | H | 9-NO₂ | —OCH₂COOH |
| 924 | 7-Cl,6-F-Q | —CH₂O— | H | 9-NO₂ | —SCH₂CH₂COOH |
| 925 | 7-Cl,6-F-Q | —CH₂O— | H | 8-NO₂ | —OCH₂COOH |
| 926 | 7-Cl,6-F-Q | —CH₂O— | H | 8-NO₂ | —SCH₂CH₂COOH |
| 927 | 7-Cl,6-F-Q | —CH₂O— | H | 7-NO₂ | —OCH₂COOH |

TABLE 1-continued (I)

| No. | A | B | (R²)n | (R¹)m | X—Y—Z |
|---|---|---|---|---|---|
| 928 | 7-Cl,6-F-Q | —CH₂O— | H | 7-NO₂ | —SCH₂CH₂COOH |
| 929 | 7-Cl,6-F-Q | —CH₂O— | 1-F | H | —SCH₂CH₂COOH |
| 930 | 7-Cl,6-F-Q | —CH₂O— | 2-F | H | —SCH₂CH₂COOH |
| 931 | 7-Cl,6-F-Q | —CH₂O— | 1-Cl | H | —SCH₂CH₂COOH |
| 932 | 7-Cl,6-F-Q | —CH₂O— | 2-Cl | H | —SCH₂CH₂COOH |
| 933 | 7-Cl,6-F-Q | —CH₂O— | 1-CH₃ | H | —SCH₂CH₂COOH |
| 934 | 7-Cl,6-F-Q | —CH₂O— | 2-CH₃ | H | —SCH₂CH₂COOH |
| 935 | 7-Cl,6-F-Q | —CH₂O— | 1-OCH₃ | H | —SCH₂CH₂COOH |
| 936 | 7-Cl,6-F-Q | —CH₂O— | 2-OCH₃ | H | —SCH₂CH₂COOH |
| 937 | 7-Cl,6-F-Q | —CH₂O— | 1-NO₂ | H | —SCH₂CH₂COOH |
| 938 | 7-Cl,6-F-Q | —CH₂O— | 2-NO₂ | H | —SCH₂CH₂COOH |
| 939 | 7-Cl,6-F-Q | —CH₂O— | 1-CN | H | —SCH₂CH₂COOH |
| 940 | 7-Cl,6-F-Q | —CH₂O— | 2-CN | H | —SCH₂CH₂COOH |
| 941 | 7-F-Q | —CH=CH— | H | H | —OCH₂COOH |
| 942 | 7-F-Q | —CH=CH— | H | H | —OCH(CH₃)COOH |
| 943 | 7-F-Q | —CH=CH— | H | H | —OCH₂CH₂COOH |
| 944 | 7-F-Q | —CH=CH— | H | H | —OCH₂CH(CH₃)COOH |
| 945 | 7-F-Q | —CH=CH— | H | H | —OCH₂C(CH₂CH₂)CH₂COOH |
| 946 | 7-F-Q | —CH=CH— | H | H | —SCH₂COOH |
| 947 | 7-F-Q | —CH=CH— | H | H | —SCH(CH₃)COOH |
| 948 | 7-F-Q | —CH=CH— | H | H | —SCH₂CH₂COOH |
| 949 | 7-F-Q | —CH=CH— | H | H | —SCH₂CH(CH₃)COOH |
| 950 | 7-F-Q | —CH=CH— | H | H | —SCH₂C(CH₃)₂COOH |
| 951 | 7-F-Q | —CH=CH— | H | H | —SCH₂CH(CH₂CH₃)COOH |
| 952 | 7-F-Q | —CH=CH— | H | H | —SCH(CH₃)CH₂COOH |
| 953 | 7-F-Q | —CH=CH— | H | H | —SC(CH₃)₂CH₂COOH |
| 954 | 7-F-Q | —CH=CH— | H | H | —SCH₂CH₂CH₂COOH |
| 955 | 7-F-Q | —CH=CH— | H | H | —SCH₂CH(CH₃)CH₂COOH |
| 956 | 7-F-Q | —CH=CH— | H | H | —SCH₂C(CH₃)₂CH₂COOH |
| 957 | 7-F-Q | —CH=CH— | H | H | —SCH₂C(CH₂CH₂)CH₂COOH |
| 958 | 7-F-Q | —CH=CH— | H | H | —SCH₂CF₂COOH |
| 959 | 7-F-Q | —CH=CH— | H | H | —SCH₂CF₂CH₂COOH |
| 960 | 7-F-Q | —CH=CH— | H | H | —SCH₂-Tet |
| 961 | 7-F-Q | —CH=CH— | H | H | —SCH₂CH₂-Tet |
| 962 | 7-F-Q | —CH=CH— | H | H | —SCH₂NHSO₂CF₃ |
| 963 | 7-F-Q | —CH=CH— | H | H | —SCH₂CONHSO₂CH₃ |
| 964 | 7-F-Q | —CH=CH— | H | H | —SCH₂CONHSO₂CF₃ |
| 965 | 7-F-Q | —CH=CH— | H | H | —SCH₂CONHSO₂Ph |
| 966 | 7-F-Q | —CH=CH— | H | H | —SCH₂CONHSO₂(2-CH₃—Ph) |
| 967 | 7-F-Q | —CH=CH— | H | H | —SCH₂CH₂NHSO₂CF₃ |
| 968 | 7-F-Q | —CH=CH— | H | H | —SCH₂CH₂CONHSO₂CH₃ |
| 969 | 7-F-Q | —CH=CH— | H | H | —SCH₂CH₂CONHSO₂CF₃ |
| 970 | 7-F-Q | —CH=CH— | H | H | —SCH₂CH₂CONHSO₂Ph |
| 971 | 7-F-Q | —CH=CH— | H | H | —SCH₂CH₂CONHSO₂(2-CH₃—Ph) |
| 972 | 7-F-Q | —CH=CH— | H | H | —CH₂COOH |
| 973 | 7-F-Q | —CH=CH— | H | H | —CH₂CH₂COOH |
| 974 | 7-F-Q | —CH=CH— | H | H | —CH₂CH₂CH₂COOH |
| 975 | 7-F-Q | —CH=CH— | H | 9-F | —OCH₂COOH |
| 976 | 7-F-Q | —CH=CH— | H | 9-F | —OCH(CH₃)COOH |
| 977 | 7-F-Q | —CH=CH— | H | 9-F | —OCH₂CH₂COOH |
| 978 | 7-F-Q | —CH=CH— | H | 9-F | —SCH₂COOH |
| 979 | 7-F-Q | —CH=CH— | H | 9-F | —SCH(CH₃)COOH |
| 980 | 7-F-Q | —CH=CH— | H | 9-F | —SCH₂CH₂COOH |
| 981 | 7-F-Q | —CH=CH— | H | 9-F | —SCH₂CH(CH₃)COOH |
| 982 | 7-F-Q | —CH=CH— | H | 9-F | —SCH₂CH(CH₂CH₃)COOH |
| 983 | 7-F-Q | —CH=CH— | H | 9-F | —SCH₂C(CH₂CH₂)CH₂COOH |
| 984 | 7-F-Q | —CH=CH— | H | 8-F | —OCH₂COOH |
| 985 | 7-F-Q | —CH=CH— | H | 8-F | —OCH₂CH₂COOH |
| 986 | 7-F-Q | —CH=CH— | H | 8-F | —SCH₂COOH |
| 987 | 7-F-Q | —CH=CH— | H | 8-F | —SCH₂CH₂COOH |
| 988 | 7-F-Q | —CH=CH— | H | 8-F | —SCH₂CH(CH₃)COOH |
| 989 | 7-F-Q | —CH=CH— | H | 8-F | —SCH₂C(CH₂CH₂)CH₂COOH |
| 990 | 7-F-Q | —CH=CH— | H | 7-F | —OCH₂COOH |
| 991 | 7-F-Q | —CH=CH— | H | 7-F | —OCH₂CH₂COOH |
| 992 | 7-F-Q | —CH=CH— | H | 7-F | —SCH₂COOH |

TABLE 1-continued (I)

| No. | A | B | (R²)n | (R¹)m | X—Y—Z |
|---|---|---|---|---|---|
| 993 | 7-F-Q | —CH=CH— | H | 7-F | —SCH$_2$CH$_2$COOH |
| 994 | 7-F-Q | —CH=CH— | H | 7-F | —SCH$_2$CH(CH$_3$)COOH |
| 995 | 7-F-Q | —CH=CH— | H | 6-F | —OCH$_2$COOH |
| 996 | 7-F-Q | —CH=CH— | H | 6-F | —OCH(CH$_3$)COOH |
| 997 | 7-F-Q | —CH=CH— | H | 6-F | —OCH$_2$CH$_2$COOH |
| 998 | 7-F-Q | —CH=CH— | H | 6-F | —OCH$_2$CH(CH3)COOH |
| 999 | 7-F-Q | —CH=CH— | H | 6-F | —OCH$_2$C(CH$_2$CH$_2$)CH$_2$COOH |
| 1000 | 7-F-Q | —CH=CH— | H | 6-F | —SCH$_2$COOH |
| 1001 | 7-F-Q | —CH=CH— | H | 6-F | —SCH(CH$_3$)COOH |
| 1002 | 7-F-Q | —CH=CH— | H | 6-F | —SCH$_2$CH$_2$COOH |
| 1003 | 7-F-Q | —CH=CH— | H | 6-F | —SCH$_2$CH(CH$_3$)COOH |
| 1004 | 7-F-Q | —CH=CH— | H | 6-F | —SCH$_2$C(CH$_2$CH$_2$)CH$_2$COOH |
| 1005 | 7-F-Q | —CH=CH— | H | 9-Cl | —OCH$_2$COOH |
| 1006 | 7-F-Q | —CH=CH— | H | 9-Cl | —OCH(CH$_3$)COOH |
| 1007 | 7-F-Q | —CH=CH— | H | 9-Cl | —OCH$_2$CH$_2$COOH |
| 1008 | 7-F-Q | —CH=CH— | H | 9-Cl | —OCH$_2$CH(CH$_3$)COOH |
| 1009 | 7-F-Q | —CH=CH— | H | 9-Cl | —OCH$_2$C(CH$_2$CH$_2$)CH$_2$COOH |
| 1010 | 7-F-Q | —CH=CH— | H | 9-Cl | —SCH$_2$COOH |
| 1011 | 7-F-Q | —CH=CH— | H | 9-Cl | —SCH(CH$_3$)COOH |
| 1012 | 7-F-Q | —CH=CH— | H | 9-Cl | —SCH$_2$CH$_2$COOH |
| 1013 | 7-F-Q | —CH=CH— | H | 9-Cl | —SCH$_2$CH(CH$_3$)COOH |
| 1014 | 7-F-Q | —CH=CH— | H | 9-Cl | —SCH$_2$C(CH$_2$CH$_2$)CH$_2$COOH |
| 1015 | 7-F-Q | —CH=CH— | H | 8-Cl | —SCH$_2$C(CH$_2$CH$_2$)CH$_2$COOH |
| 1016 | 7-F-Q | —CH=CH— | H | 8-Cl | —OCH$_2$COOH |
| 1017 | 7-F-Q | —CH=CH— | H | 8-Cl | —OCH$_2$CH$_2$COOH |
| 1018 | 7-F-Q | —CH=CH— | H | 8-Cl | —SCH$_2$COOH |
| 1019 | 7-F-Q | —CH=CH— | H | 8-Cl | —SCH$_2$CH$_2$COOH |
| 1020 | 7-F-Q | —CH=CH— | H | 8-Cl | —SCH$_2$CH(CH$_3$)COOH |
| 1021 | 7-F-Q | —CH=CH— | H | 8-Cl | —SCH$_2$C(CH$_2$CH$_2$)CH$_2$COOH |
| 1022 | 7-F-Q | —CH=CH— | H | 7-Cl | —OCH$_2$COOH |
| 1023 | 7-F-Q | —CH=CH— | H | 7-Cl | —OCH$_2$CH$_2$COOH |
| 1024 | 7-F-Q | —CH=CH— | H | 7-Cl | —SCH$_2$COOH |
| 1025 | 7-F-Q | —CH=CH— | H | 7-Cl | —SCH$_2$CH$_2$COOH |
| 1026 | 7-F-Q | —CH=CH— | H | 7-Cl | —SCH$_2$CH(CH$_3$)COOH |
| 1027 | 7-F-Q | —CH=CH— | H | 6-Cl | —OCH$_2$COOH |
| 1028 | 7-F-Q | —CH=CH— | H | 6-Cl | —OCH(CH$_3$)COOH |
| 1029 | 7-F-Q | —CH=CH— | H | 6-Cl | —OCH$_2$CH$_2$COOH |
| 1030 | 7-F-Q | —CH=CH— | H | 6-Cl | —OCH$_2$CH(CH3)COOH |
| 1031 | 7-F-Q | —CH=CH— | H | 6-Cl | —OCH$_2$C(CH$_2$CH$_2$)CH$_2$COOH |
| 1032 | 7-F-Q | —CH=CH— | H | 6-Cl | —SCH$_2$COOH |
| 1033 | 7-F-Q | —CH=CH— | H | 6-Cl | —SCH(CH$_3$)COOH |
| 1034 | 7-F-Q | —CH=CH— | H | 6-Cl | —SCH$_2$CH$_2$COOH |
| 1035 | 7-F-Q | —CH=CH— | H | 6-Cl | —SCH$_2$CH(CH$_3$)COOH |
| 1036 | 7-F-Q | —CH=CH— | H | 6-Cl | —SCH$_2$C(CH$_2$CH$_2$)CH$_2$COOH |
| 1037 | 7-F-Q | —CH=CH— | H | 9-CN | —OCH$_2$COOH |
| 1038 | 7-F-Q | —CH=CH— | H | 9-CN | —OCH(CH$_3$)COOH |
| 1039 | 7-F-Q | —CH=CH— | H | 9-CN | —OCH$_2$CH$_2$COOH |
| 1040 | 7-F-Q | —CH=CH— | H | 9-CN | —OCH$_2$CH(CH3)COOH |
| 1041 | 7-F-Q | —CH=CH— | H | 9-CN | —OCH$_2$C(CH$_2$CH$_2$)CH$_2$COOH |
| 1042 | 7-F-Q | —CH=CH— | H | 9-CN | —SCH$_2$COOH |
| 1043 | 7-F-Q | —CH=CH— | H | 9-CN | —SCH(CH$_3$)COOH |
| 1044 | 7-F-Q | —CH=CH— | H | 9-CN | —SCH$_2$CH$_2$COOH |
| 1045 | 7-F-Q | —CH=CH— | H | 9-CN | —SCH$_2$CH(CH$_3$)COOH |
| 1046 | 7-F-Q | —CH=CH— | H | 9-CN | —SCH$_2$C(CH$_2$CH$_2$)CH$_2$COOH |
| 1047 | 7-F-Q | —CH=CH— | H | 8-CN | —OCH$_2$COOH |
| 1048 | 7-F-Q | —CH=CH— | H | 8-CN | —OCH$_2$CH$_2$COOH |
| 1049 | 7-F-Q | —CH=CH— | H | 8-CN | —SCH$_2$COOH |
| 1050 | 7-F-Q | —CH=CH— | H | 8-CN | —SCH$_2$CH$_2$COOH |
| 1051 | 7-F-Q | —CH=CH— | H | 8-CN | —SCH$_2$CH(CH$_3$)COOH |
| 1052 | 7-F-Q | —CH=CH— | H | 8-CN | —SCH$_2$C(CH$_2$CH$_2$)CH$_2$COOH |
| 1053 | 7-F-Q | —CH=CH— | H | 7-CN | —OCH$_2$COOH |
| 1054 | 7-F-Q | —CH=CH— | H | 7-CN | —OCH$_2$CH$_2$COOH |
| 1055 | 7-F-Q | —CH=CH— | H | 7-CN | —SCH$_2$COOH |
| 1056 | 7-F-Q | —CH=CH— | H | 7-CN | —SCH$_2$CH$_2$COOH |
| 1057 | 7-F-Q | —CH=CH— | H | 7-CN | —SCH$_2$CH(CH$_3$)COOH |

TABLE 1-continued (I)

| No. | A | B | (R²)n | (R¹)m | X—Y—Z |
|---|---|---|---|---|---|
| 1058 | 7-F-Q | —CH=CH— | H | 9-CH₃ | —OCH₂COOH |
| 1059 | 7-F-Q | —CH=CH— | H | 9-CH₃ | —OCH₂CH₂COOH |
| 1060 | 7-F-Q | —CH=CH— | H | 9-CH₃ | —SCH₂COOH |
| 1061 | 7-F-Q | —CH=CH— | H | 9-CH₃ | —SCH₂CH₂COOH |
| 1062 | 7-F-Q | —CH=CH— | H | 9-CH₃ | —SCH₂CH(CH₃)COOH |
| 1063 | 7-F-Q | —CH=CH— | H | 9-CH₃ | —SCH₂CH(CH₂CH₃)COOH |
| 1064 | 7-F-Q | —CH=CH— | H | 9-CH₃ | —SCH₂C(CH₂CH₂)CH₂COOH |
| 1065 | 7-F-Q | —CH=CH— | H | 8-CH₃ | —OCH₂COOH |
| 1066 | 7-F-Q | —CH=CH— | H | 8-CH₃ | —OCH₂CH₂COOH |
| 1067 | 7-F-Q | —CH=CH— | H | 8-CH₃ | —SCH₂COOH |
| 1068 | 7-F-Q | —CH=CH— | H | 8-CH₃ | —SCH₂CH₂COOH |
| 1069 | 7-F-Q | —CH=CH— | H | 8-CH₃ | —SCH₂CH(CH₃)COOH |
| 1070 | 7-F-Q | —CH=CH— | H | 8-CH₃ | —SCH₂C(CH₂CH₂)CH₂COOH |
| 1071 | 7-F-Q | —CH=CH— | H | 7-CH₃ | —OCH₂COOH |
| 1072 | 7-F-Q | —CH=CH— | H | 7-CH₃ | —OCH₂CH₂COOH |
| 1073 | 7-F-Q | —CH=CH— | H | 7-CH₃ | —SCH₂COOH |
| 1074 | 7-F-Q | —CH=CH— | H | 7-CH₃ | —SCH₂CH₂COOH |
| 1075 | 7-F-Q | —CH=CH— | H | 7-CH₃ | —SCH₂CH(CH₃)COOH |
| 1076 | 7-F-Q | —CH=CH— | H | 9-CF₃ | —OCH₂COOH |
| 1077 | 7-F-Q | —CH=CH— | H | 9-CF₃ | —OCH(CH₃)COOH |
| 1078 | 7-F-Q | —CH=CH— | H | 9-CF₃ | —OCH₂CH₂COOH |
| 1079 | 7-F-Q | —CH=CH— | H | 9-CF₃ | —OCH₂CH(CH3)COOH |
| 1080 | 7-F-Q | —CH=CH— | H | 9-CF₃ | —OCH₂C(CH₂CH₂)CH₂COOH |
| 1081 | 7-F-Q | —CH=CH— | H | 9-CF₃ | —SCH₂COOH |
| 1082 | 7-F-Q | —CH=CH— | H | 9-CF₃ | —SCH(CH₃)COOH |
| 1083 | 7-F-Q | —CH=CH— | H | 9-CF₃ | —SCH₂CH₂COOH |
| 1084 | 7-F-Q | —CH=CH— | H | 9-CF₃ | —SCH₂CH(CH₃)COOH |
| 1085 | 7-F-Q | —CH=CH— | H | 9-CF₃ | —SCH₂C(CH₂CH₂)CH₂COOH |
| 1086 | 7-F-Q | —CH=CH— | H | 8-CF₃ | —OCH₂COOH |
| 1087 | 7-F-Q | —CH=CH— | H | 8-CF₃ | —OCH₂CH₂COOH |
| 1088 | 7-F-Q | —CH=CH— | H | 8-CF₃ | —SCH₂COOH |
| 1089 | 7-F-Q | —CH=CH— | H | 8-CF₃ | —SCH₂CH₂COOH |
| 1090 | 7-F-Q | —CH=CH— | H | 8-CF₃ | —SCH₂CH(CH₃)COOH |
| 1091 | 7-F-Q | —CH=CH— | H | 8-CF₃ | —SCH₂C(CH₂CH₂)CH₂COOH |
| 1092 | 7-F-Q | —CH=CH— | H | 7-CF₃ | —OCH₂COOH |
| 1093 | 7-F-Q | —CH=CH— | H | 7-CF₃ | —OCH₂CH₂COOH |
| 1094 | 7-F-Q | —CH=CH— | H | 7-CF₃ | —SCH₂COOH |
| 1095 | 7-F-Q | —CH=CH— | H | 7-CF₃ | —SCH₂CH₂COOH |
| 1096 | 7-F-Q | —CH=CH— | H | 7-CF₃ | —SCH₂CH(CH₃)COOH |
| 1097 | 7-F-Q | —CH=CH— | H | 9-C≡CH | —OCH₂COOH |
| 1098 | 7-F-Q | —CH=CH— | H | 9-C≡CH | —OCH(CH₃)COOH |
| 1099 | 7-F-Q | —CH=CH— | H | 9-C≡CH | —OCH₂CH₂COOH |
| 1100 | 7-F-Q | —CH=CH— | H | 9-C≡CH | —OCH₂CH(CH3)COOH |
| 1101 | 7-F-Q | —CH=CH— | H | 9-C≡CH | —OCH₂C(CH₂CH₂)CH₂COOH |
| 1102 | 7-F-Q | —CH=CH— | H | 9-C≡CH | —SCH₂COOH |
| 1103 | 7-F-Q | —CH=CH— | H | 9-C≡CH | —SCH(CH₃)COOH |
| 1104 | 7-F-Q | —CH=CH— | H | 9-C≡CH | —SCH₂CH₂COOH |
| 1105 | 7-F-Q | —CH=CH— | H | 9-C≡CH | —SCH₂CH(CH₃)COOH |
| 1106 | 7-F-Q | —CH=CH— | H | 9-C≡CH | —SCH₂C(CH₂CH₂)CH₂COOH |
| 1107 | 7-F-Q | —CH=CH— | H | 8-C≡CH | —OCH₂COOH |
| 1108 | 7-F-Q | —CH=CH— | H | 8-C≡CH | —OCH₂CH₂COOH |
| 1109 | 7-F-Q | —CH=CH— | H | 8-C≡CH | —SCH₂COOH |
| 1110 | 7-F-Q | —CH=CH— | H | 8-C≡CH | —SCH₂CH₂COOH |
| 1111 | 7-F-Q | —CH=CH— | H | 8-C≡CH | —SCH₂CH(CH₃)COOH |
| 1112 | 7-F-Q | —CH=CH— | H | 8-C≡CH | —SCH₂C(CH₂CH₂)CH₂COOH |
| 1113 | 7-F-Q | —CH=CH— | H | 7-C≡CH | —OCH₂COOH |
| 1114 | 7-F-Q | —CH=CH— | H | 7-C≡CH | —OCH₂CH₂COOH |
| 1115 | 7-F-Q | —CH=CH— | H | 7-C≡CH | —SCH₂COOH |
| 1116 | 7-F-Q | —CH=CH— | H | 7-C≡CH | —SCH₂CH₂COOH |
| 1117 | 7-F-Q | —CH=CH— | H | 7-C≡CH | —SCH₂CH(CH₃)COOH |
| 1118 | 7-F-Q | —CH=CH— | H | 9-CH₂OH | —OCH₂COOH |
| 1119 | 7-F-Q | —CH=CH— | H | 9-CH₂OH | —SCH₂CH₂COOH |
| 1120 | 7-F-Q | —CH=CH— | H | 8-CH₂OH | —OCH₂COOH |
| 1121 | 7-F-Q | —CH=CH— | H | 8-CH₂OH | —SCH₂CH₂COOH |
| 1122 | 7-F-Q | —CH=CH— | H | 7-CH₂OH | —OCH₂COOH |

TABLE 1-continued

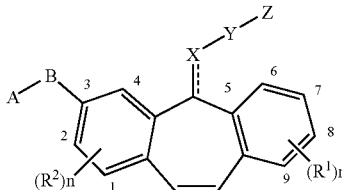

| No. | A | B | (R²)n | (R¹)m | X—Y—Z |
|---|---|---|---|---|---|
| 1123 | 7-F-Q | —CH=CH— | H | 7-CH₂OH | —SCH₂CH₂COOH |
| 1124 | 7-F-Q | —CH=CH— | H | 9-C(CH₃)₂OH | —OCH₂COOH |
| 1125 | 7-F-Q | —CH=CH— | H | 9-C(CH₃)₂OH | —SCH₂CH₂COOH |
| 1126 | 7-F-Q | —CH=CH— | H | 8-C(CH₃)₂OH | —OCH₂COOH |
| 1127 | 7-F-Q | —CH=CH— | H | 8-C(CH₃)₂OH | —SCH₂CH₂COOH |
| 1128 | 7-F-Q | —CH=CH— | H | 7-C(CH₃)₂OH | —OCH₂COOH |
| 1129 | 7-F-Q | —CH=CH— | H | 7-C(CH₃)₂OH | —SCH₂CH₂COOH |
| 1130 | 7-F-Q | —CH=CH— | H | 9-OCH₃ | —OCH₂COOH |
| 1131 | 7-F-Q | —CH=CH— | H | 9-OCH₃ | —SCH₂CH₂COOH |
| 1132 | 7-F-Q | —CH=CH— | H | 8-OCH₃ | —OCH₂COOH |
| 1133 | 7-F-Q | —CH=CH— | H | 8-OCH₃ | —SCH₂CH₂COOH |
| 1134 | 7-F-Q | —CH=CH— | H | 7-OCH₃ | —OCH₂COOH |
| 1135 | 7-F-Q | —CH=CH— | H | 7-OCH₃ | —SCH₂CH₂COOH |
| 1136 | 7-F-Q | —CH=CH— | H | 9-OCHF₂ | —OCH₂COOH |
| 1137 | 7-F-Q | —CH=CH— | H | 9-OCHF₂ | —SCH₂CH₂COOH |
| 1138 | 7-F-Q | —CH=CH— | H | 8-OCHF₂ | —OCH₂COOH |
| 1139 | 7-F-Q | —CH=CH— | H | 8-OCHF₂ | —SCH₂CH₂COOH |
| 1140 | 7-F-Q | —CH=CH— | H | 7-OCHF₂ | —OCH₂COOH |
| 1141 | 7-F-Q | —CH=CH— | H | 7-OCHF₂ | —SCH₂CH₂COOH |
| 1142 | 7-F-Q | —CH=CH— | H | 9-OCF₃ | —OCH₂COOH |
| 1143 | 7-F-Q | —CH=CH— | H | 9-OCF₃ | —SCH₂CH₂COOH |
| 1144 | 7-F-Q | —CH=CH— | H | 8-OCF₃ | —OCH₂COOH |
| 1145 | 7-F-Q | —CH=CH— | H | 8-OCF₃ | —SCH₂CH₂COOH |
| 1146 | 7-F-Q | —CH=CH— | H | 7-OCF₃ | —OCH₂COOH |
| 1147 | 7-F-Q | —CH=CH— | H | 7-OCF₃ | —SCH₂CH₂COOH |
| 1148 | 7-F-Q | —CH=CH— | H | 9-SOCH₃ | —OCH₂COOH |
| 1149 | 7-F-Q | —CH=CH— | H | 9-SOCH₃ | —SCH₂CH₂COOH |
| 1150 | 7-F-Q | —CH=CH— | H | 8-SOCH₃ | —OCH₂COOH |
| 1151 | 7-F-Q | —CH=CH— | H | 8-SOCH₃ | —SCH₂CH₂COOH |
| 1152 | 7-F-Q | —CH=CH— | H | 7-SOCH₃ | —OCH₂COOH |
| 1153 | 7-F-Q | —CH=CH— | H | 7-SOCH₃ | —SCH₂CH₂COOH |
| 1154 | 7-F-Q | —CH=CH— | H | 9-SO₂CH₃ | —OCH₂COOH |
| 1155 | 7-F-Q | —CH=CH— | H | 9-SO₂CH₃ | —SCH₂CH₂COOH |
| 1156 | 7-F-Q | —CH=CH— | H | 8-SO₂CH₃ | —OCH₂COOH |
| 1157 | 7-F-Q | —CH=CH— | H | 8-SO₂CH₃ | —SCH₂CH₂COOH |
| 1158 | 7-F-Q | —CH=CH— | H | 7-SO₂CH₃ | —OCH₂COOH |
| 1159 | 7-F-Q | —CH=CH— | H | 7-SO₂CH₃ | —SCH₂CH₂COOH |
| 1160 | 7-F-Q | —CH=CH— | H | 9-CH=CH₂ | —SCH₂CH₂COOH |
| 1161 | 7-F-Q | —CH=CH— | H | 8-CH=CH₂ | —SCH₂CH₂COOH |
| 1162 | 7-F-Q | —CH=CH— | H | 7-CH=CH₂ | —SCH₂CH₂COOH |
| 1163 | 7-F-Q | —CH=CH— | H | 9-NO₂ | —OCH₂COOH |
| 1164 | 7-F-Q | —CH=CH— | H | 9-NO₂ | —SCH₂OH₂COOH |
| 1165 | 7-F-Q | —CH=CH— | H | 8-NO₂ | —OCH₂COOH |
| 1166 | 7-F-Q | —CH=CH— | H | 8-NO₂ | —SCH₂CH₂COOH |
| 1167 | 7-F-Q | —CH=CH— | H | 7-NO₂ | —OCH₂COOH |
| 1168 | 7-F-Q | —CH=CH— | H | 7-NO₂ | —SCH₂CH₂COOH |
| 1169 | 7-F-Q | —CH=CH— | 1-F | H | —SCH₂CH₂COOH |
| 1170 | 7-F-Q | —CH=CH— | 2-F | H | —SCH₂CH₂COOH |
| 1171 | 7-F-Q | —CH=CH— | 1-Cl | H | —SCH₂CH₂COOH |
| 1172 | 7-F-Q | —CH=CH— | 2-Cl | H | —SCH₂CH₂COOH |
| 1173 | 7-F-Q | —CH=CH— | 1-CH₃ | H | —SCH₂CH₂COOH |
| 1174 | 7-F-Q | —CH=CH— | 2-CH₃ | H | —SCH₂CH₂COOH |
| 1175 | 7-F-Q | —CH=CH— | 1-OCH₃ | H | —SCH₂CH₂COOH |
| 1176 | 7-F-Q | —CH=CH— | 2-OCH₃ | H | —SCH₂CH₂COOH |
| 1177 | 7-F-Q | —CH=CH— | 1-NO₂ | H | —SCH₂CH₂COOH |
| 1178 | 7-F-Q | —CH=CH— | 2-NO₂ | H | —SCH₂CH₂COOH |
| 1179 | 7-F-Q | —CH=CH— | 1-CN | H | —SCH₂CH₂COOH |
| 1180 | 7-F-Q | —CH=CH— | 2-CN | H | —SCH₂CH₂COOH |
| 1181 | 7-F-Q | —CH₂O— | H | H | —OCH₂COOH |

TABLE 1-continued (I)

| No. | A | B | (R²)n | (R¹)m | X—Y—Z |
|---|---|---|---|---|---|
| 1182 | 7-F-Q | —CH₂O— | H | H | —OCH(CH3)COOH |
| 1183 | 7-F-Q | —CH₂O— | H | H | —OCH₂CH₂COOH |
| 1184 | 7-F-Q | —CH₂O— | H | H | —OCH₂CH(CH₃)COOH |
| 1185 | 7-F-Q | —CH₂O— | H | H | —OCH₂C(CH₂CH₂)CH₂COOH |
| 1186 | 7-F-Q | —CH₂O— | H | H | —SCH₂COOH |
| 1187 | 7-F-Q | —CH₂O— | H | H | —SCH(CH3)COOH |
| 1188 | 7-F-Q | —CH₂O— | H | H | —SCH₂CH₂COOH |
| 1189 | 7-F-Q | —CH₂O— | H | H | —SCH₂CH(CH₃)COOH |
| 1190 | 7-F-Q | —CH₂O— | H | H | —SCH₂C(CH₃)₂COOH |
| 1191 | 7-F-Q | —CH₂O— | H | H | —SCH₂CH(CH₂CH₃)COOH |
| 1192 | 7-F-Q | —CH₂O— | H | H | —SCH(CH₃)CH₂COOH |
| 1193 | 7-F-Q | —CH₂O— | H | H | —SO(CH₃)₂CH₂COOH |
| 1194 | 7-F-Q | —CH₂O— | H | H | —SCH₂CH₂CH₂COOH |
| 1195 | 7-F-Q | —CH₂O— | H | H | —SCH₂CH(CH₃)CH₂COOH |
| 1196 | 7-F-Q | —CH₂O— | H | H | —SCH₂C(CH₃)₂CH₂COOH |
| 1197 | 7-F-Q | —CH₂O— | H | H | —SCH₂C(CH₂CH₂)CH₂COOH |
| 1198 | 7-F-Q | —CH₂O— | H | H | —SCH₂CF₂COOH |
| 1199 | 7-F-Q | —CH₂O— | H | H | —SCH₂CF₂CH₂COOH |
| 1200 | 7-F-Q | —CH₂O— | H | H | —SCH₂-Tet |
| 1201 | 7-F-Q | —CH₂O— | H | H | —SCH₂CH₂-Tet |
| 1202 | 7-F-Q | —CH₂O— | H | H | —SCH₂NHSO₂CF₃ |
| 1203 | 7-F-Q | —CH₂O— | H | H | —SCH₂CONHSO₂CH₃ |
| 1204 | 7-F-Q | —CH₂O— | H | H | —SCH₂CONHSO₂CF₃ |
| 1205 | 7-F-Q | —CH₂O— | H | H | —SCH₂CONHSO₂Ph |
| 1206 | 7-F-Q | —CH₂O— | H | H | —SCH₂CONHSO₂(2-CH₃—Ph) |
| 1207 | 7-F-Q | —CH₂O— | H | H | —SCH₂CH₂NHSO₂CF₃ |
| 1208 | 7-F-Q | —CH₂O— | H | H | —SCH₂CH₂CONHSO₂CH₃ |
| 1209 | 7-F-Q | —CH₂O— | H | H | —SCH₂CH₂CONHSO₂CF₃ |
| 1210 | 7-F-Q | —CH₂O— | H | H | —SCH₂CH₂CONHSO₂Ph |
| 1211 | 7-F-Q | —CH₂O— | H | H | —SCH₂CH₂CONHSO₂(2-CH₃—Ph) |
| 1212 | 7-F-Q | —CH₂O— | H | H | —CH₂COOH |
| 1213 | 7-F-Q | —CH₂O— | H | H | —CH₂CH₂COOH |
| 1214 | 7-F-Q | —CH₂O— | H | H | —CH₂CH₂CH₂COOH |
| 1215 | 7-F-Q | —CH₂O— | H | 9-F | —OCH₂COOH |
| 1216 | 7-F-Q | —CH₂O— | H | 9-F | —OCH(CH₃)COOH |
| 1217 | 7-F-Q | —CH₂O— | H | 9-F | —OCH₂CH₂COOH |
| 1218 | 7-F-Q | —CH₂O— | H | 9-F | —OCH₂CH(CH3)COOH |
| 1219 | 7-F-Q | —CH₂O— | H | 9-F | —OCH₂C(CH₂CH₂)CH₂COOH |
| 1220 | 7-F-Q | —CH₂O— | H | 9-F | —SCH₂COOH |
| 1221 | 7-F-Q | —CH₂O— | H | 9-F | —SCH(CH₃)COOH |
| 1222 | 7-F-Q | —CH₂O— | H | 9-F | —SCH₂CH₂COOH |
| 1223 | 7-F-Q | —CH₂O— | H | 9-F | —SCH₂CH(CH₃)COOH |
| 1224 | 7-F-Q | —CH₂O— | H | 9-F | —SCH₂C(CH₂CH₂)CH₂COOH |
| 1225 | 7-F-Q | —CH₂O— | H | 8-F | —OCH₂COOH |
| 1226 | 7-F-Q | —CH₂O— | H | 8-F | —OCH₂CH₂COOH |
| 1227 | 7-F-Q | —CH₂O— | H | 8-F | —SCH₂COOH |
| 1228 | 7-F-Q | —CH₂O— | H | 8-F | —SCH₂CH₂COOH |
| 1229 | 7-F-Q | —CH₂O— | H | 8-F | —SCH₂CH(CH₃)COOH |
| 1230 | 7-F-Q | —CH₂O— | H | 8-F | —SCH₂C(CH₂CH₂)CH₂COOH |
| 1231 | 7-F-Q | —CH₂O— | H | 7-F | —OCH₂COOH |
| 1232 | 7-F-Q | —CH₂O— | H | 7-F | —OCH₂CH₂COOH |
| 1233 | 7-F-Q | —CH₂O— | H | 7-F | —SCH₂COOH |
| 1234 | 7-F-Q | —CH₂O— | H | 7-F | —SCH₂CH₂COOH |
| 1235 | 7-F-Q | —CH₂O— | H | 7-F | —SCH₂CH(CH₃)COOH |
| 1236 | 7-F-Q | —CH₂O— | H | 6-F | —OCH₂COOH |
| 1237 | 7-F-Q | —CH₂O— | H | 6-F | —OCH(CH₃)COOH |
| 1238 | 7-F-Q | —CH₂O— | H | 6-F | —OCH₂CH₂COOH |
| 1239 | 7-F-Q | —CH₂O— | H | 8-F | —OCH₂CH(CH₃)COOH |
| 1240 | 7-F-Q | —CH₂O— | H | 6-F | —OCH₂C(CH₂CH₂)CH₂COOH |
| 1241 | 7-F-Q | —CH₂O— | H | 6-F | —SCH₂COOH |
| 1242 | 7-F-Q | —CH₂O— | H | 6-F | —SCH(CH₃)COOH |
| 1243 | 7-F-Q | —CH₂O— | H | 6-F | —SCH₂CH₂COOH |
| 1244 | 7-F-Q | —CH₂O— | H | 6-F | —SCH₂CH(CH₃)COOH |
| 1245 | 7-F-Q | —CH₂O— | H | 6-F | —SCH₂C(CH₂CH₂)CH₂COOH |
| 1246 | 7-F-Q | —CH₂O— | H | 9-Cl | —OCH₂COOH |

TABLE 1-continued (I)

$$\text{structure with A-B substituent on ring at positions 2,3,4; carbon 5 bearing X=Y-Z; positions 6,7,8,9 on other ring; (R}^2\text{)n at position 1; (R}^1\text{)m at position 9}$$

| No. | A | B | (R²)n | (R¹)m | X—Y—Z |
|---|---|---|---|---|---|
| 1247 | 7-F-Q | —CH₂O— | H | 9-Cl | —OCH(CH₃)COOH |
| 1248 | 7-F-Q | —CH₂O— | H | 9-Cl | —OCH₂CH₂COOH |
| 1249 | 7-F-Q | —CH₂O— | H | 9-Cl | —OCH₂CH(CH3)COOH |
| 1250 | 7-F-Q | —CH₂O— | H | 9-Cl | —OCH₂C(CH₂CH₂)CH₂COOH |
| 1251 | 7-F-Q | —CH₂O— | H | 9-Cl | —SCH₂COOH |
| 1252 | 7-F-Q | —CH₂O— | H | 9-Cl | —SCH(CH₃)COOH |
| 1253 | 7-F-Q | —CH₂O— | H | 9-Cl | —SCH₂CH₂COOH |
| 1254 | 7-F-Q | —CH₂O— | H | 9-Cl | —SCH₂CH(CH₃)COOH |
| 1255 | 7-F-Q | —CH₂O— | H | 9-Cl | —SCH₂C(CH₂CH₂)CH₂COOH |
| 1256 | 7-F-Q | —CH₂O— | H | 8-Cl | —SCH₂C(CH₂CH₂)CH₂COOH |
| 1257 | 7-F-Q | —CH₂O— | H | 8-Cl | —OCH₂COOH |
| 1258 | 7-F-Q | —CH₂O— | H | 8-Cl | —OCH₂CH₂COOH |
| 1259 | 7-F-Q | —CH₂O— | H | 8-Cl | —SCH₂COOH |
| 1260 | 7-F-Q | —CH₂O— | H | 8-Cl | —SCH₂CH₂COOH |
| 1261 | 7-F-Q | —CH₂O— | H | 8-Cl | —SCH₂CH(CH₃)COOH |
| 1295 | 7-F-Q | —CH₂O— | H | 8-CH₃ | —OCH₂COOH |
| 1296 | 7-F-Q | —CH₂O— | H | 8-CH₃ | —OCH₂CH₂COOH |
| 1297 | 7-F-Q | —CH₂O— | H | 8-CH₃ | —SCH₂COOH |
| 1298 | 7-F-Q | —CH₂O— | H | 8-CH₃ | —SCH₂CH₂COOH |
| 1299 | 7-F-Q | —CH₂O— | H | 8-CH₃ | —SCH₂CH(CH₃)COOH |
| 1300 | 7-F-Q | —CH₂O— | H | 8-CH₃ | —SCH₂C(CH₂CH₂)CH₂COOH |
| 1301 | 7-F-Q | —CH₂O— | H | 7-CH₃ | —OCH₂COOH |
| 1302 | 7-F-Q | —CH₂O— | H | 7-CH₃ | —OCH₂CH₂COOH |
| 1303 | 7-F-Q | —CH₂O— | H | 7-CH₃ | —SCH₂COOH |
| 1304 | 7-F-Q | —CH₂O— | H | 7-CH₃ | —SCH₂CH₂COOH |
| 1305 | 7-F-Q | —CH₂O— | H | 7-CH₃ | —SCH₂CH(CH₃)COOH |
| 1306 | 7-F-Q | —CH₂O— | H | 9-CF₃ | —OCH₂COOH |
| 1307 | 7-F-Q | —CH₂O— | H | 9-CF₃ | —OCH(CH₃)COOH |
| 1308 | 7-F-Q | —CH₂O— | H | 9-CF₃ | —OCH₂CH₂COOH |
| 1309 | 7-F-Q | —CH₂O— | H | 9-CF₃ | —OCH₂CH(CH3)COOH |
| 1310 | 7-F-Q | —CH₂O— | H | 9-CF₃ | —OCH₂C(CH₂CH₂)CH₂COOH |
| 1311 | 7-F-Q | —CH₂O— | H | 9-CF₃ | —SCH₂COOH |
| 1312 | 7-F-Q | —CH₂O— | H | 9-CF₃ | —SCH(CH₃)COOH |
| 1313 | 7-F-Q | —CH₂O— | H | 9-CF₃ | —SCH₂CH₂COOH |
| 1314 | 7-F-Q | —CH₂O— | H | 9-CF₃ | —SCH₂CH(CH₃)COOH |
| 1315 | 7-F-Q | —CH₂O— | H | 9-CF₃ | —SCH₂C(CH₂CH₂)CH₂COOH |
| 1316 | 7-F-Q | —CH₂O— | H | 8-CF₃ | —OCH₂COOH |
| 1317 | 7-F-Q | —CH₂O— | H | 8-CF₃ | —OCH₂CH₂COOH |
| 1318 | 7-F-Q | —CH₂O— | H | 8-CF₃ | —SCH₂COOH |
| 1319 | 7-F-Q | —CH₂O— | H | 8-CF₃ | —SCH₂CH₂COOH |
| 1320 | 7-F-Q | —CH₂O— | H | 8-CF₃ | —SCH₂CH(CH₃)COOH |
| 1321 | 7-F-Q | —CH₂O— | H | 8-CF₃ | —SCH₂C(CH₂CH₂)CH₂COOH |
| 1322 | 7-F-Q | —CH₂O— | H | 7-CF₃ | —OCH₂COOH |
| 1323 | 7-F-Q | —CH₂O— | H | 7-CF₃ | —OCH₂CH₂COOH |
| 1324 | 7-F-Q | —CH₂O— | H | 7-CF₃ | —SCH₂COOH |
| 1325 | 7-F-Q | —CH₂O— | H | 7-CF₃ | —SCH₂CH₂COOH |
| 1326 | 7-F-Q | —CH₂O— | H | 7-CF₃ | —SCH₂CH(CH₃)COOH |
| 1327 | 7-F-Q | —CH₂O— | H | 9-C≡CH | —OCH₂COOH |
| 1328 | 7-F-Q | —CH₂O— | H | 9-C≡CH | —OCH(CH₃)COOH |
| 1329 | 7-F-Q | —CH₂O— | H | 9-C≡CH | —OCH₂CH₂COOH |
| 1330 | 7-F-Q | —CH₂O— | H | 9-C≡CH | —OCH₂CH(CH3)COOH |
| 1331 | 7-F-Q | —CH₂O— | H | 9-C≡CH | —OCH₂C(CH₂CH₂)CH₂COOH |
| 1332 | 7-F-Q | —CH₂O— | H | 9-C≡CH | —SCH₂COOH |
| 1333 | 7-F-Q | —CH₂O— | H | 9-C≡CH | —SCH(CH₃)COOH |
| 1334 | 7-F-Q | —CH₂O— | H | 9-C≡CH | —SCH₂CH₂COOH |
| 1335 | 7-F-Q | —CH₂O— | H | 9-C≡CH | —SCH₂CH(CH₃)COOH |
| 1336 | 7-F-Q | —CH₂O— | H | 9-C≡CH | —SCH₂C(CH₂CH₂)CH₂COOH |
| 1337 | 7-F-Q | —CH₂O— | H | 8-C≡CH | —OCH₂COOH |
| 1338 | 7-F-Q | —CH₂O— | H | 8-C≡CH | —OCH₂CH₂COOH |
| 1339 | 7-F-Q | —CH₂O— | H | 8-C≡CH | —SCH₂COOH |
| 1340 | 7-F-Q | —CH₂O— | H | 8-C≡CH | —SCH₂CH₂COOH |
| 1341 | 7-F-Q | —CH₂O— | H | 8-C≡CH | —SCH₂CH(CH₃)COOH |
| 1342 | 7-F-Q | —CH₂O— | H | 8-C≡CH | —SCH₂C(CH₂CH₂)CH₂COOH |
| 1343 | 7-F-Q | —CH₂O— | H | 7-C≡CH | —OCH₂COOH |
| 1344 | 7-F-Q | —CH₂O— | H | 7-C≡CH | —OCH₂CH₂COOH |

TABLE 1-continued (I)

| No. | A | B | (R²)n | (R¹)m | X—Y—Z |
|---|---|---|---|---|---|
| 1345 | 7-F-Q | —CH₂O— | H | 7-C≡CH | —SCH₂COOH |
| 1346 | 7-F-Q | —CH₂O— | H | 7-C≡CH | —SCH₂CH₂COOH |
| 1347 | 7-F-Q | —CH₂O— | H | 7-C≡CH | —SCH₂CH(CH₃)COOH |
| 1348 | 7-F-Q | —CH₂O— | H | 9-CH₂OH | —OCH₂COOH |
| 1349 | 7-F-Q | —CH₂O— | H | 9-CH₂OH | —SCH₂CH₂COOH |
| 1350 | 7-F-Q | —CH₂O— | H | 8-CH₂OH | —OCH₂COOH |
| 1351 | 7-F-Q | —CH₂O— | H | 8-CH₂OH | —SCH₂CH₂COOH |
| 1352 | 7-F-Q | —CH₂O— | H | 7-CH₂OH | —OCH₂COOH |
| 1353 | 7-F-Q | —CH₂O— | H | 7-CH₂OH | —SCH₂CH₂COOH |
| 1354 | 7-F-Q | —CH₂O— | H | 9-C(CH₃)₂OH | —OCH₂COOH |
| 1355 | 7-F-Q | —CH₂O— | H | 9-C(CH₃)₂OH | —SCH₂CH₂COOH |
| 1356 | 7-F-Q | —CH₂O— | H | 8-C(CH₃)₂OH | —OCH₂COOH |
| 1357 | 7-F-Q | —CH₂O— | H | 8-C(CH₃)₂OH | —SCH₂CH₂COOH |
| 1358 | 7-F-Q | —CH₂O— | H | 7-C(CH₃)₂OH | —OCH₂COOH |
| 1359 | 7-F-Q | —CH₂O— | H | 7-C(CH₃)₂OH | —SCH₂CH₂COOH |
| 1360 | 7-F-Q | —CH₂O— | H | 9-OCH₃ | —OCH₂COOH |
| 1361 | 7-F-Q | —CH₂O— | H | 9-OCH₃ | —SCH₂CH₂COOH |
| 1362 | 7-F-Q | —CH₂O— | H | 8-OCH₃ | —OCH₂COOH |
| 1363 | 7-F-Q | —CH₂O— | H | 8-OCH₃ | —SCH₂CH₂COOH |
| 1364 | 7-F-Q | —CH₂O— | H | 7-OCH₃ | —OCH₂COOH |
| 1365 | 7-F-Q | —CH₂O— | H | 7-OCH₃ | —SCH₂CH₂COOH |
| 1366 | 7-F-Q | —CH₂O— | H | 9-OCHF₂ | —OCH₂COOH |
| 1367 | 7-F-Q | —CH₂O— | H | 9-OCHF₂ | —SCH₂CH₂COOH |
| 1368 | 7-F-Q | —CH₂O— | H | 8-OCHF₂ | —OCH₂COOH |
| 1369 | 7-F-Q | —CH₂O— | H | 8-COHF₂ | —SCH₂CH₂COOH |
| 1370 | 7-F-Q | —CH₂O— | H | 7-OCHF₂ | —OCH₂COOH |
| 1371 | 7-F-Q | —CH₂O— | H | 7-OCHF₂ | —SCH₂CH₂COOH |
| 1372 | 7-F-Q | —CH₂O— | H | 9-OCF₃ | —OCH₂COOH |
| 1373 | 7-F-Q | —CH₂O— | H | 9-OCF₃ | —SCH₂CH₂COOH |
| 1374 | 7-F-Q | —CH₂O— | H | 8-OCF₃ | —OCH₂COOH |
| 1375 | 7-F-Q | —CH₂O— | H | 8-OCF₃ | —SCH₂CH₂COOH |
| 1376 | 7-F-Q | —CH₂O— | H | 7-OCF₃ | —OCH₂COOH |
| 1377 | 7-F-Q | —CH₂O— | H | 7-OCF₃ | —SCH₂CH₂COOH |
| 1378 | 7-F-Q | —CH₂O— | H | 9-SOCH₃ | —OCH₂COOH |
| 1379 | 7-F-Q | —CH₂O— | H | 9-SOCH₃ | —SCH₂CH₂COOH |
| 1380 | 7-F-Q | —CH₂O— | H | 8-SOCH₃ | —OCH₂COOH |
| 1381 | 7-F-Q | —CH₂O— | H | 8-SOCH₃ | —SCH₂CH₂COOH |
| 1382 | 7-F-Q | —CH₂O— | H | 7-SOCH₃ | —OCH₂COOH |
| 1383 | 7-F-Q | —CH₂O— | H | 7-SOCH₃ | —SCH₂CH₂COOH |
| 1384 | 7-F-Q | —CH₂O— | H | 9-SO₂CH₃ | —OCH₂COOH |
| 1385 | 7-F-Q | —CH₂O— | H | 9-SO₂CH₃ | —SCH₂CH₂COOH |
| 1386 | 7-F-Q | —CH₂O— | H | 8-SO₂CH₃ | —OCH₂COOH |
| 1387 | 7-F-Q | —CH₂O— | H | 8-SO₂CH₃ | —SCH₂CH₂COOH |
| 1388 | 7-F-Q | —CH₂O— | H | 7-SO₂CH₃ | —OCH₂COOH |
| 1389 | 7-F-Q | —CH₂O— | H | 7-SO₂CH₃ | —SCH₂CH₂COOH |
| 1390 | 7-F-Q | —CH₂O— | H | 9-CH=CH₂ | —SCH₂CH₂COOH |
| 1391 | 7-F-Q | —CH₂O— | H | 8-CH=CH₂ | —SCH₂CH₂COOH |
| 1392 | 7-F-Q | —CH₂O— | H | 7-CH=CH₂ | —SCH₂CH₂COOH |
| 1393 | 7-F-Q | —CH₂O— | H | 9-NO₂ | —OCH₂COOH |
| 1394 | 7-F-Q | —CH₂O— | H | 9-NO₂ | —SCH₂CH₂COOH |
| 1395 | 7-F-Q | —CH₂O— | H | 8-NO₂ | —OCH₂COOH |
| 1396 | 7-F-Q | —CH₂O— | H | 8-NO₂ | —SCH₂CH₂COOH |
| 1397 | 7-F-Q | —CH₂O— | H | 7-NO₂ | —OCH₂COOH |
| 1398 | 7-F-Q | —CH₂O— | H | 7-NO₂ | —SCH₂CH₂COOH |
| 1399 | 7-F-Q | —CH₂O— | 1-F | H | —SCH₂CH₂COOH |
| 1400 | 7-F-Q | —CH₂O— | 2-F | H | —SCH₂CH₂COOH |
| 1401 | 7-F-Q | —CH₂O— | 1-Cl | H | —SCH₂CH₂COOH |
| 1402 | 7-F-Q | —CH₂O— | 2-Cl | H | —SCH₂CH₂COOH |
| 1403 | 7-F-Q | —CH₂O— | 1-CH₃ | H | —SCH₂CH₂COOH |

TABLE 1-continued (I)

| No. | A | B | (R²)n | (R¹)m | X—Y—Z |
|---|---|---|---|---|---|
| 1404 | 7-F-Q | —CH₂O— | 2-CH₃ | H | —SCH₂CH₂COOH |
| 1405 | 7-F-Q | —CH₂O— | 1-OCH₃ | H | —SCH₂CH₂COOH |
| 1406 | 7-F-Q | —CH₂O— | 2-OCH₃ | H | —SCH₂CH₂COOH |
| 1407 | 7-F-Q | —CH₂O— | 1-NO₂ | H | —SCH₂CH₂COOH |
| 1408 | 7-F-Q | —CH₂O— | 2-NO₂ | H | —SCH₂CH₂COOH |
| 1409 | 7-F-Q | —CH₂O— | 1-CN | H | —SCH₂CH₂COOH |
| 1410 | 7-F-Q | —CH₂O— | 2-CN | H | —SCH₂CH₂COOH |
| 1411 | 7-Cl-Q | —CH=CH— | H | H | —OCH₂COOH |
| 1412 | 7-Cl-Q | —CH=CH— | H | H | —OCH(CH₃)COOH |
| 1413 | 7-Cl-Q | —CH=CH— | H | H | —OCH₂CH₂COOH |
| 1414 | 7-Cl-Q | —CH=CH— | H | H | —OCH₂CH(CH₃)COOH |
| 1415 | 7-Cl-Q | —CH=CH— | H | H | —OCH₂C(CH₂CH₂)CH₂COOH |
| 1416 | 7-Cl-Q | —CH=CH— | H | H | —SCH₂COOH |
| 1417 | 7-Cl-Q | —CH=CH— | H | H | —SCH(CH₃)COOH |
| 1418 | 7-Cl-Q | —CH=CH— | H | H | —SCH₂CH₂COOH |
| 1419 | 7-Cl-Q | —CH=CH— | H | H | —SCH₂CH(CH₃)COOH |
| 1420 | 7-Cl-Q | —CH=CH— | H | H | —SCH₂C(CH₃)₂COOH |
| 1421 | 7-Cl-Q | —CH=CH— | H | H | —SCH(CH₂CH₃)COOH |
| 1422 | 7-Cl-Q | —CH=CH— | H | H | —SCH(CH₃)CH₂COOH |
| 1423 | 7-Cl-Q | —CH=CH— | H | H | —SC(CH₃)₂CH₂COOH |
| 1424 | 7-Cl-Q | —CH=CH— | H | H | —SCH₂CH₂CH₂COOH |
| 1425 | 7-Cl-Q | —CH=CH— | H | H | —SCH₂CH(CH₃)CH₂COOH |
| 1426 | 7-Cl-Q | —CH=CH— | H | H | —SCH₂C(CH₃)₂CH₂COOH |
| 1427 | 7-Cl-Q | —CH=CH— | H | H | —SCH₂C(CH₂CH₂)CH₂COOH |
| 1428 | 7-Cl-Q | —CH=CH— | H | H | —SCH₂CF₂COOH |
| 1429 | 7-Cl-Q | —CH=CH— | H | H | —SCH₂CF₂CH₂COOH |
| 1430 | 7-Cl-Q | —CH=CH— | H | H | —SCH₂-Tet |
| 1431 | 7-Cl-Q | —CH=CH— | H | H | —SCH₂CH₂-Tet |
| 1432 | 7-Cl-Q | —CH=CH— | H | H | —SCH₂NHSO₂CF₃ |
| 1433 | 7-Cl-Q | —CH=CH— | H | H | —SCH₂CONHSO₂CH₃ |
| 1434 | 7-Cl-Q | —CH=CH— | H | H | —SCH₂CONHSO₂CF₃ |
| 1435 | 7-Cl-Q | —CH=CH— | H | H | —SCH₂CONHSO₂Ph |
| 1436 | 7-Cl-Q | —CH=CH— | H | H | —SCH₂CONHSO₂(2-CH₃—Ph) |
| 1437 | 7-Cl-Q | —CH=CH— | H | H | —SCH₂CH₂NHSO₂CF₃ |
| 1438 | 7-Cl-Q | —CH=CH— | H | H | —SCH₂CH₂CONHSO₂CH₃ |
| 1439 | 7-Cl-Q | —CH=CH— | H | H | —SCH₂CH₂CONHSO₂CF₃ |
| 1440 | 7-Cl-Q | —CH=CH— | H | H | —SCH₂CH₂CONHSO₂Ph |
| 1441 | 7-Cl-Q | —CH=CH— | H | H | —SCH₂CH₂CONHSO₂(2-CH₃—Ph) |
| 1442 | 7-Cl-Q | —CH=CH— | H | H | —CH₂COOH |
| 1443 | 7-Cl-Q | —CH=CH— | H | H | —CH₂CH₂COOH |
| 1444 | 7-Cl-Q | —CH=CH— | H | H | —CH₂CH₂CH₂COOH |
| 1445 | 7-Cl-Q | —CH=CH— | H | 9-F | —OCH₂COOH |
| 1446 | 7-Cl-Q | —CH=CH— | H | 9-F | —OCH(CH₃)COOH |
| 1447 | 7-Cl-Q | —CH=CH— | H | 9-F | —OCH₂CH₂COOH |
| 1448 | 7-Cl-Q | —CH=CH— | H | 9-F | —SCH₂COOH |
| 1449 | 7-Cl-Q | —CH=CH— | H | 9-F | —SCH(CH₃)COOH |
| 1450 | 7-Cl-Q | —CH=CH— | H | 9-F | —SCH₂CH₂COOH |
| 1451 | 7-Cl-Q | —CH=CH— | H | 9-F | —SCH₂CH(CH₃)COOH |
| 1452 | 7-Cl-Q | —CH=CH— | H | 9-F | —SCH₂CH(CH₂CH₃)COOH |
| 1453 | 7-Cl-Q | —CH=CH— | H | 9-F | —SCH₂C(CH₂CH₂)CH₂COOH |
| 1454 | 7-Cl-Q | —CH=CH— | H | 8-F | —OCH₂COOH |
| 1455 | 7-Cl-Q | —CH=CH— | H | 8-F | —OCH₂CH₂COOH |
| 1456 | 7-Cl-Q | —CH=CH— | H | 8-F | —SCH₂COOH |
| 1457 | 7-Cl-Q | —CH=CH— | H | 8-F | —SCH₂CH₂COOH |
| 1458 | 7-Cl-Q | —CH=CH— | H | 8-F | —SCH₂CH(CH₃)COOH |
| 1459 | 7-Cl-Q | —CH=CH— | H | 8-F | —SCH₂C(CH₂CH₂)CH₂COOH |
| 1460 | 7-Cl-Q | —CH=CH— | H | 7-F | —OCH₂COOH |
| 1461 | 7-Cl-Q | —CH=CH— | H | 7-F | —OCH₂CH₂COOH |
| 1462 | 7-Cl-Q | —CH=CH— | H | 7-F | —SCH₂COOH |
| 1463 | 7-Cl-Q | —CH=CH— | H | 7-F | —SCH₂CH₂COOH |
| 1464 | 7-Cl-Q | —CH=CH— | H | 7-F | —SCH₂CH(CH₃)COOH |
| 1465 | 7-Cl-Q | —CH=CH— | H | 6-F | —OCH₂COOH |
| 1466 | 7-Cl-Q | —CH=CH— | H | 6-F | —OCH(CH₃)COOH |
| 1467 | 7-Cl-Q | —CH=CH— | H | 6-F | —OCH₂COOH |
| 1468 | 7-Cl-Q | —CH=CH— | H | 6-F | —OCH₂CH(CH3)COOH |

TABLE 1-continued

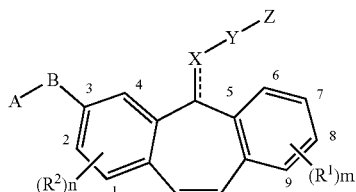

(I)

| No. | A | B | (R²)n | (R¹)m | X—Y—Z |
|---|---|---|---|---|---|
| 1469 | 7-Cl-Q | —CH=CH— | H | 6-F | —OCH₂C(CH₂CH₂)CH₂COOH |
| 1470 | 7-Cl-Q | —CH=CH— | H | 6-F | —SCH₂COOH |
| 1471 | 7-Cl-Q | —CH=CH— | H | 6-F | —SCH(CH₃)COOH |
| 1472 | 7-Cl-Q | —CH=CH— | H | 6-F | —SCH₂CH₂COOH |
| 1473 | 7-Cl-Q | —CH=CH— | H | 6-F | —SCH₂CH(CH₃)COOH |
| 1474 | 7-Cl-Q | —CH=CH— | H | 6-F | —SCH₂C(CH₂CH₂)CH₂COOH |
| 1475 | 7-Cl-Q | —CH=CH— | H | 9-Cl | —OCH₂COOH |
| 1476 | 7-Cl-Q | —CH=CH— | H | 9-Cl | —OCH(CH₃)COOH |
| 1477 | 7-Cl-Q | —CH=CH— | H | 9-Cl | —OCH₂CH₂COOH |
| 1478 | 7-Cl-Q | —CH=CH— | H | 9-Cl | —OCH₂CH(CH3)COOH |
| 1479 | 7-Cl-Q | —CH=CH— | H | 9-Cl | —OCH₂C(CH₂CH₂)CH₂COOH |
| 1480 | 7-Cl-Q | —CH=CH— | H | 9-Cl | —SCH₂COOH |
| 1481 | 7-Cl-Q | —CH=CH— | H | 9-Cl | —SCH(CH₃)COOH |
| 1482 | 7-Cl-Q | —CH=CH— | H | 9-Cl | —SCH₂CH₂COOH |
| 1483 | 7-Cl-Q | —CH=CH— | H | 9-Cl | —SCH₂CH(CH₃)COOH |
| 1484 | 7-Cl-Q | —CH=CH— | H | 9-Cl | —SCH₂C(CH₂CH₂)CH₂COOH |
| 1485 | 7-Cl-Q | —CH=CH— | H | 8-Cl | —SCH₂C(CH₂CH₂)CH₂COOH |
| 1486 | 7-Cl-Q | —CH=CH— | H | 8-Cl | —OCH₂COOH |
| 1487 | 7-Cl-Q | —CH=CH— | H | 8-Cl | —OCH₂CH₂COOH |
| 1488 | 7-Cl-Q | —CH=CH— | H | 8-Cl | —SCH₂COOH |
| 1489 | 7-Cl-Q | —CH=CH— | H | 8-Cl | —SCH₂CH₂COOH |
| 1490 | 7-Cl-Q | —CH=CH— | H | 8-Cl | —SCH₂CH(CH₃)COOH |
| 1491 | 7-Cl-Q | —CH=CH— | H | 8-Cl | —SCH₂C(CH₂CH₂)CH₂COOH |
| 1492 | 7-Cl-Q | —CH=CH— | H | 7-Cl | —OCH₂COOH |
| 1493 | 7-Cl-Q | —CH=CH— | H | 7-Cl | —OCH₂CH₂COOH |
| 1494 | 7-Cl-Q | —CH=CH— | H | 7-Cl | —SCH₂COOH |
| 1495 | 7-Cl-Q | —CH=CH— | H | 7-Cl | —SCH₂CH₂COOH |
| 1496 | 7-Cl-Q | —CH=CH— | H | 7-Cl | —SCH₂CH(CH₃)COOH |
| 1497 | 7-Cl-Q | —CH=CH— | H | 6-Cl | —OCH₂COOH |
| 1498 | 7-Cl-Q | —CH=CH— | H | 6-Cl | —OCH(CH₃)COOH |
| 1499 | 7-Cl-Q | —CH=CH— | H | 6-Cl | —OCH₂CH₂COOH |
| 1500 | 7-Cl-Q | —CH=CH— | H | 6-Cl | —OCH₂CH(CH3)COOH |
| 1501 | 7-Cl-Q | —CH=CH— | H | 6-Cl | —OCH₂C(CH₂CH₂)CH₂COOH |
| 1502 | 7-Cl-Q | —CH=CH— | H | 6-Cl | —SCH₂COOH |
| 1503 | 7-Cl-Q | —CH=CH— | H | 6-Cl | —SCH(CH₃)COOH |
| 1504 | 7-Cl-Q | —CH=CH— | H | 6-Cl | —SCH₂CH₂COOH |
| 1505 | 7-Cl-Q | —CH=CH— | H | 6-Cl | —SCH₂CH(CH₃)COOH |
| 1506 | 7-Cl-Q | —CH=CH— | H | 6-Cl | —SCH₂C(CH₂CH₂)CH₂COOH |
| 1507 | 7-Cl-Q | —CH=CH— | H | 9-CN | —OCH₂COOH |
| 1508 | 7-Cl-Q | —CH=CH— | H | 9-CN | —OCH(CH₃)COOH |
| 1509 | 7-Cl-Q | —CH=CH— | H | 9-CN | —OCH₂CH₂COOH |
| 1510 | 7-Cl-Q | —CH=CH— | H | 9-CN | —OCH₂CH(CH₃)COOH |
| 1511 | 7-Cl-Q | —CH=CH— | H | 9-CN | —OCH₂C(CH₂CH₂)CH₂COOH |
| 1512 | 7-Cl-Q | —CH=CH— | H | 9-CN | —SCH₂COOH |
| 1513 | 7-Cl-Q | —CH=CH— | H | 9-CN | —SCH(CH₃)COOH |
| 1514 | 7-Cl-Q | —CH=CH— | H | 9-CN | —SCH₂CH₂COOH |
| 1515 | 7-Cl-Q | —CH=CH— | H | 9-CN | —SCH₂CH(CH₃)COOH |
| 1516 | 7-Cl-Q | —CH=CH— | H | 9-CN | —SCH₂C(CH₂CH₂)CH₂COOH |
| 1517 | 7-Cl-Q | —CH=CH— | H | 8-CN | —OCH₂COOH |
| 1518 | 7-Cl-Q | —CH=CH— | H | 8-CN | —OCH₂CH₂COOH |
| 1519 | 7-Cl-Q | —CH=CH— | H | 8-CN | —SCH₂COOH |
| 1520 | 7-Cl-Q | —CH=CH— | H | 8-CN | —SCH₂CH₂COOH |
| 1521 | 7-Cl-Q | —CH=CH— | H | 8-CN | —SCH₂CH(CH₃)COOH |
| 1522 | 7-Cl-Q | —CH=CH— | H | 8-CN | —SCH₂C(CH₂CH₂)CH₂COOH |
| 1523 | 7-Cl-Q | —CH=CH— | H | 7-CN | —OCH₂COOH |
| 1524 | 7-Cl-Q | —CH=CH— | H | 7-CN | —OCH₂CH₂COOH |
| 1525 | 7-Cl-Q | —CH=CH— | H | 7-CN | —SCH₂COOH |
| 1526 | 7-Cl-Q | —CH=CH— | H | 7-CN | —SCH₂CH₂COOH |
| 1527 | 7-Cl-Q | —CH=CH— | H | 7-CN | —SCH₂CH(CH₃)COOH |
| 1528 | 7-Cl-Q | —CH=CH— | H | 9-CH₃ | —OCH₂COOH |
| 1529 | 7-Cl-Q | —CH=CH— | H | 9-CH₃ | —OCH₂CH₂COOH |
| 1530 | 7-Cl-Q | —CH=CH— | H | 9-CH₃ | —SCH₂COOH |
| 1531 | 7-Cl-Q | —CH=CH— | H | 9-CH₃ | —SCH₂CH₂COOH |
| 1532 | 7-Cl-Q | —CH=CH— | H | 9-CH₃ | —SCH₂CH(CH₃)COOH |
| 1533 | 7-Cl-Q | —CH=CH— | H | 9-CH₃ | —SCH₂CH(CH₂CH₃)COOH |

TABLE 1-continued

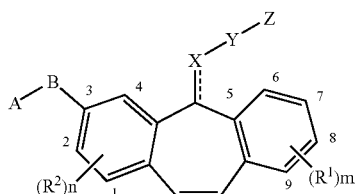

(I)

| No. | A | B | (R²)n | (R¹)m | X—Y—Z |
|---|---|---|---|---|---|
| 1534 | 7-Cl-Q | —CH=CH— | H | 9-CH₃ | —SCH₂C(CH₂CH₂)CH₂COOH |
| 1535 | 7-Cl-Q | —CH=CH— | H | 8-CH₃ | —OCH₂COOH |
| 1536 | 7-Cl-Q | —CH=CH— | H | 8-CH₃ | —OCH₂CH₂COOH |
| 1537 | 7-Cl-Q | —CH=CH— | H | 8-CH₃ | —SCH₂COOH |
| 1538 | 7-Cl-Q | —CH=CH— | H | 8-CH₃ | —SCH₂CH₂COOH |
| 1539 | 7-Cl-Q | —CH=CH— | H | 8-CH₃ | —SCH₂CH(CH₃)COOH |
| 1540 | 7-Cl-Q | —CH=CH— | H | 8-CH₃ | —SCH₂C(CH₂CH₂)CH₂COOH |
| 1541 | 7-Cl-Q | —CH=CH— | H | 7-CH₃ | —OCH₂COOH |
| 1542 | 7-Cl-Q | —CH=CH— | H | 7-CH₃ | —OCH₂CH₂COOH |
| 1543 | 7-Cl-Q | —CH=CH— | H | 7-CH₃ | —SCH₂COOH |
| 1544 | 7-Cl-Q | —CH=CH— | H | 7-CH₃ | —SCH₂CH₂COOH |
| 1545 | 7-Cl-Q | —CH=CH— | H | 7-CH₃ | —SCH₂CH(CH₃)COOH |
| 1546 | 7-Cl-Q | —CH=CH— | H | 9-CF₃ | —OCH₂COOH |
| 1547 | 7-Cl-Q | —CH=CH— | H | 9-CF₃ | —OCH(CH₃)COOH |
| 1548 | 7-Cl-Q | —CH=CH— | H | 9-CF₃ | —OCH₂CH₂COOH |
| 1549 | 7-Cl-Q | —CH=CH— | H | 9-CF₃ | —OCH₂CH(CH3)COOH |
| 1550 | 7-Cl-Q | —CH=CH— | H | 9-CF₃ | —OCH₂C(CH₂CH₂)CH₂COOH |
| 1551 | 7-Cl-Q | —CH=CH— | H | 9-CF₃ | —SCH₂COOH |
| 1552 | 7-Cl-Q | —CH=CH— | H | 9-CF₃ | —SCH(CH₃)COOH |
| 1553 | 7-Cl-Q | —CH=CH— | H | 9-CF₃ | —SCH₂CH₂COOH |
| 1554 | 7-Cl-Q | —CH=CH— | H | 9-CF₃ | —SCH₂CH(CH₃)COOH |
| 1555 | 7-Cl-Q | —CH=CH— | H | 9-CF₃ | —SCH₂C(CH₂CH₂)CH₂COOH |
| 1556 | 7-Cl-Q | —CH=CH— | H | 8-CF₂ | —OCH₂COOH |
| 1557 | 7-Cl-Q | —CH=CH— | H | 8-CF₃ | —OCH₂CH₂COOH |
| 1558 | 7-Cl-Q | —CH=CH— | H | 8-CF₃ | —SCH₂COOH |
| 1559 | 7-Cl-Q | —CH=CH— | H | 8-CF₃ | —SCH₂CH₂COOH |
| 1560 | 7-Cl-Q | —CH=CH— | H | 8-CF₃ | —SCH₂CH(CH₃)COOH |
| 1561 | 7-Cl-Q | —CH=CH— | H | 8-CF₃ | —SCH₂C(CH₂CH₂)CH₂COOH |
| 1562 | 7-Cl-Q | —CH=CH— | H | 7-CF₃ | —OCH₂COOH |
| 1563 | 7-Cl-Q | —CH=CH— | H | 7-CF₃ | —OCH₂CH₂COOH |
| 1564 | 7-Cl-Q | —CH=CH— | H | 7-CF₃ | —SCH₂COOH |
| 1565 | 7-Cl-Q | —CH=CH— | H | 7-CF₃ | —SCH₂CH₂COOH |
| 1566 | 7-Cl-Q | —CH=CH— | H | 7-CF₃ | —SCH₂CH(CH₃)COOH |
| 1567 | 7-Cl-Q | —CH=CH— | H | 9-C≡CH | —OCH₂COOH |
| 1568 | 7-Cl-Q | —CH=CH— | H | 9-C≡CH | —OCH(CH₃)COOH |
| 1569 | 7-Cl-Q | —CH=CH— | H | 9-C≡CH | —OCH₂CH₂COOH |
| 1570 | 7-Cl-Q | —CH=CH— | H | 9-C≡CH | —OCH₂CH(CH3)COOH |
| 1571 | 7-Cl-Q | —CH=CH— | H | 9-C≡CH | —OCH₂C(CH₂CH₂)CH₂COOH |
| 1572 | 7-Cl-Q | —CH=CH— | H | 9-C≡CH | —SCH₂COOH |
| 1573 | 7-Cl-Q | —CH=CH— | H | 9-C≡CH | —SCH(CH₃)COOH |
| 1574 | 7-Cl-Q | —CH=CH— | H | 9-C≡CH | —SCH₂CH₂COOH |
| 1575 | 7-Cl-Q | —CH=CH— | H | 9-C≡CH | —SCH₂CH(CH₃)COOH |
| 1576 | 7-Cl-Q | —CH=CH— | H | 9-C≡CH | —SCH₂C(CH₂CH₂)CH₂COOH |
| 1577 | 7-Cl-Q | —CH=CH— | H | 8-C≡CH | —OCH₂COOH |
| 1578 | 7-Cl-Q | —CH=CH— | H | 8-C≡CH | —OCH₂CH₂COOH |
| 1579 | 7-Cl-Q | —CH=CH— | H | 8-C≡CH | —SCH₂COOH |
| 1580 | 7-Cl-Q | —CH=CH— | H | 8-C≡CH | —SCH₂CH₂COOH |
| 1581 | 7-Cl-Q | —CH=CH— | H | 8-C≡CH | —SCH₂CH(CH₃)COOH |
| 1582 | 7-Cl-Q | —CH=CH— | H | 8-C≡CH | —SCH₂C(CH₂CH₂)CH₂COOH |
| 1583 | 7-Cl-Q | —CH=CH— | H | 7-C≡CH | —OCH₂COOH |
| 1584 | 7-Cl-Q | —CH=CH— | H | 7-C≡CH | —OCH₂CH₂COOH |
| 1585 | 7-Cl-Q | —CH=CH— | H | 7-C≡CH | —SCH₂COOH |
| 1586 | 7-Cl-Q | —CH=CH— | H | 7-C≡CH | —SCH₂CH₂COOH |
| 1587 | 7-Cl-Q | —CH=CH— | H | 7-C≡CH | —SCH₂CH(CH₃)COOH |
| 1588 | 7-Cl-Q | —CH=CH— | H | 9-CH₂OH | —OCH₂COOH |
| 1589 | 7-Cl-Q | —CH=CH— | H | 9-CH₂OH | —SCH₂CH₂COOH |
| 1590 | 7-Cl-Q | —CH=CH— | H | 8-CH₂OH | —OCH₂COOH |
| 1591 | 7-Cl-Q | —CH=CH— | H | 8-CH₂OH | —SCH₂CH₂COOH |
| 1592 | 7-Cl-Q | —CH=CH— | H | 7-CH₂OH | —OCH₂COOH |
| 1593 | 7-Cl-Q | —CH=CH— | H | 7-CH₂OH | —SCH₂CH₂COOH |
| 1594 | 7-Cl-Q | —CH=CH— | H | 9-C(CH₃)₂OH | —OCH₂COOH |
| 1595 | 7-Cl-Q | —CH=CH— | H | 9-C(CH₃)₂OH | —SCH₂CH₂COOH |

TABLE 1-continued (I)

| No. | A | B | (R²)n | (R¹)m | X—Y—Z |
|---|---|---|---|---|---|
| 1596 | 7-Cl-Q | —CH=CH— | H | 8-C(CH₃)₂OH | —OCH₂COOH |
| 1597 | 7-Cl-Q | —CH=CH— | H | 8-C(CH₃)₂OH | —SCH₂CH₂COOH |
| 1598 | 7-Cl-Q | —CH=CH— | H | 7-C(CH₃)₂OH | —OCH₂COOH |
| 1599 | 7-Cl-Q | —CH=CH— | H | 7-C(CH₃)₂OH | —SCH₂CH₂COOH |
| 1600 | 7-Cl-Q | —CH=CH— | H | 9-OCH₃ | —OCH₂COOH |
| 1601 | 7-Cl-Q | —CH=CH— | H | 9-OCH₃ | —SCH₂CH₂COOH |
| 1602 | 7-Cl-Q | —CH=CH— | H | 8-OCH₃ | —OCH₂COOH |
| 1603 | 7-Cl-Q | —CH=CH— | H | 8-OCH₃ | —SCH₂CH₂COOH |
| 1604 | 7-Cl-Q | —CH=CH— | H | 7-OCH₃ | —OCH₂COOH |
| 1605 | 7-Cl-Q | —CH=CH— | H | 7-OCH₃ | —SCH₂CH₂COOH |
| 1606 | 7-Cl-Q | —CH=CH— | H | 9-OCHF₂ | —OCH₂COOH |
| 1607 | 7-Cl-Q | —CH=CH— | H | 9-OCHF₂ | —SCH₂CH₂COOH |
| 1608 | 7-Cl-Q | —CH=CH— | H | 8-OCHF₂ | —OCH₂COOH |
| 1609 | 7-Cl-Q | —CH=CH— | H | 8-OCHF₂ | —SCH₂CH₂COOH |
| 1610 | 7-Cl-Q | —CH=CH— | H | 7-OCHF₂ | —OCH₂COOH |
| 1611 | 7-Cl-Q | —CH=CH— | H | 7-OCHF₂ | —SCH₂CH₂COOH |
| 1612 | 7-Cl-Q | —CH=CH— | H | 9-OCF₃ | —OCH₂COOH |
| 1613 | 7-Cl-Q | —CH=CH— | H | 9-OCF₃ | —SCH₂CH₂COOH |
| 1614 | 7-Cl-Q | —CH=CH— | H | 8-OCF₃ | —OCH₂COOH |
| 1615 | 7-Cl-Q | —CH=CH— | H | 8-OCF₃ | —SCH₂CH₂COOH |
| 1616 | 7-Cl-Q | —CH=CH— | H | 7-OCF₃ | —OCH₂COOH |
| 1617 | 7-Cl-Q | —CH=CH— | H | 7-OCF₃ | —SCH₂CH₂COOH |
| 1618 | 7-Cl-Q | —CH=CH— | H | 9-SOCH₃ | —OCH₂COOH |
| 1619 | 7-Cl-Q | —CH=CH— | H | 9-SOCH₃ | —SCH₂CH₂COOH |
| 1620 | 7-Cl-Q | —CH=CH— | H | 8-SOCH₃ | —OCH₂COOH |
| 1621 | 7-Cl-Q | —CH=CH— | H | 8-SOCH₃ | —SCH₂CH₂COOH |
| 1622 | 7-Cl-Q | —CH=CH— | H | 7-SOCH₃ | —OCH₂COOH |
| 1623 | 7-Cl-Q | —CH=CH— | H | 7-SOCH₃ | —SCH₂CH₂COOH |
| 1624 | 7-Cl-Q | —CH=CH— | H | 9-SO₂CH₃ | —OCH₂COOH |
| 1625 | 7-Cl-Q | —CH=CH— | H | 9-SO₂CH₃ | —SCH₂CH₂COOH |
| 1626 | 7-Cl-Q | —CH=CH— | H | 8-SO₂CH₃ | —OCH₂COOH |
| 1627 | 7-Cl-Q | —CH=CH— | H | 8-SO₂CH₃ | —SCH₂CH₂COOH |
| 1628 | 7-Cl-Q | —CH=CH— | H | 7-SO₂CH₃ | —OCH₂COOH |
| 1629 | 7-Cl-Q | —CH=CH— | H | 7-SO₂CH₃ | —SCH₂CH₂COOH |
| 1630 | 7-Cl-Q | —CH=CH— | H | 9-CH=CH₂ | —SCH₂CH₂COOH |
| 1631 | 7-Cl-Q | —CH=CH— | H | 8-CH=CH₂ | —SCH₂CH₂COOH |
| 1632 | 7-Cl-Q | —CH=CH— | H | 7-CH=CH₂ | —SCH₂CH₂COOH |
| 1633 | 7-Cl-Q | —CH=CH— | H | 9-NO₂ | —OCH₂COOH |
| 1634 | 7-Cl-Q | —CH=CH— | H | 9-NO₂ | —SCH₂CH₂COOH |
| 1635 | 7-Cl-Q | —CH=CH— | H | 8-NO₂ | —OCH₂COOH |
| 1636 | 7-Cl-Q | —CH=CH— | H | 8-NO₂ | —SCH₂CH₂COOH |
| 1637 | 7-Cl-Q | —CH=CH— | H | 7-NO₂ | —OCH₂COOH |
| 1638 | 7-Cl-Q | —CH=CH— | H | 7-NO₂ | —SCH₂CH₂COOH |
| 1639 | 7-Cl-Q | —CH=CH— | 1-F | H | —SCH₂CH₂COOH |
| 1640 | 7-Cl-Q | —CH=CH— | 2-F | H | —SCH₂CH₂COOH |
| 1641 | 7-Cl-Q | —CH=CH— | 1-Cl | H | —SCH₂CH₂COOH |
| 1642 | 7-Cl-Q | —CH=CH— | 2-Cl | H | —SCH₂CH₂COOH |
| 1643 | 7-Cl-Q | —CH=CH— | 1-CH₃ | H | —SCH₂CH₂COOH |
| 1644 | 7-Cl-Q | —CH=CH— | 2-CH₃ | H | —SCH₂CH₂COOH |
| 1645 | 7-Cl-Q | —CH=CH— | 1-OCH₃ | H | —SCH₂CH₂COOH |
| 1646 | 7-Cl-Q | —CH=CH— | 2-OCH₃ | H | —SCH₂CH₂COOH |
| 1647 | 7-Cl-Q | —CH=CH— | 1-NO₂ | H | —SCH₂CH₂COOH |
| 1648 | 7-Cl-Q | —CH=CH— | 2-NO₂ | H | —SCH₂CH₂COOH |
| 1649 | 7-Cl-Q | —CH=CH— | 1-CN | H | —SCH₂CH₂COOH |
| 1650 | 7-Cl-Q | —CH=CH— | 2-CN | H | —SCH₂CH₂COOH |
| 1651 | 7-Cl-Q | —CH₂O— | H | H | —OCH₂COOH |
| 1652 | 7-Cl-Q | —CH₂O— | H | H | —OCH(CH₃)COOH |
| 1653 | 7-Cl-Q | —CH₂O— | H | H | —OCH₂CH₂COOH |
| 1654 | 7-Cl-Q | —CH₂O— | H | H | —OCH₂CH(CH₃)COOH |
| 1655 | 7-Cl-Q | —CH₂O— | H | H | —OCH₂C(CH₂CH₂)CH₂COOH |
| 1656 | 7-Cl-Q | —CH₂O— | H | H | —SCH₂COOH |

TABLE 1-continued (I)

| No. | A | B | (R²)n | (R¹)m | X—Y—Z |
|---|---|---|---|---|---|
| 1657 | 7-Cl-Q | —CH₂O— | H | H | —SCH(CH3)COOH |
| 1658 | 7-Cl-Q | —CH₂O— | H | H | —SCH₂CH₂COOH |
| 1659 | 7-Cl-Q | —CH₂O— | H | H | —SCH₂CH(CH₃)COOH |
| 1660 | 7-Cl-Q | —CH₂O— | H | H | —SCH₂C(CH₃)₂COOH |
| 1661 | 7-Cl-Q | —CH₂O— | H | H | —SCH₂CH(CH₂CH₃)COOH |
| 1662 | 7-Cl-Q | —CH₂O— | H | H | —SCH(CH₃)CH₂COOH |
| 1663 | 7-Cl-Q | —CH₂O— | H | H | —SC(CH₃)₂CH₂COOH |
| 1664 | 7-Cl-Q | —CH₂O— | H | H | —SCH₂CH₂CH₂COOH |
| 1665 | 7-Cl-Q | —CH₂O— | H | H | —SCH₂CH(CH₃)CH₂COOH |
| 1666 | 7-Cl-Q | —CH₂O— | H | H | —SCH₂C(CH₃)₂CH₂COOH |
| 1667 | 7-Cl-Q | —CH₂O— | H | H | —SCH₂C(CH₂CH₂)CH₂COOH |
| 1668 | 7-Cl-Q | —CH₂O— | H | H | —SCH₂CF₂COOH |
| 1669 | 7-Cl-Q | —CH₂O— | H | H | —SCH₂CF₂CH₂COOH |
| 1670 | 7-Cl-Q | —CH₂O— | H | H | —SCH₂-Tet |
| 1671 | 7-Cl-Q | —CH₂O— | H | H | —SCH₂CH₂-Tet |
| 1672 | 7-Cl-Q | —CH₂O— | H | H | —SCH₂NHSO₂CF₃ |
| 1673 | 7-Cl-Q | —CH₂O— | H | H | —SCH₂CONHSO₂CH₃ |
| 1674 | 7-Cl-Q | —CH₂O— | H | H | —SCH₂CONHSO₂CF₃ |
| 1675 | 7-Cl-Q | —CH₂O— | H | H | —SCH₂CONHSO₂Ph |
| 1676 | 7-Cl-Q | —CH₂O— | H | H | —SCH₂CONHSO₂(2-CH₃—Ph) |
| 1677 | 7-Cl-Q | —CH₂O— | H | H | —SCH₂CH₂NHSO₂CF₃ |
| 1678 | 7-Cl-Q | —CH₂O— | H | H | —SCH₂CH₂CONHSO₂CH₃ |
| 1679 | 7-Cl-Q | —CH₂O— | H | H | —SCH₂CH₂CONHSO₂CF₃ |
| 1680 | 7-Cl-Q | —CH₂O— | H | H | —SCH₂CH₂CONHSO₂Ph |
| 1681 | 7-Cl-Q | —CH₂O— | H | H | —SCH₂CH₂CONHSO₂(2-CH₃—Ph) |
| 1682 | 7-Cl-Q | —CH₂O— | H | H | —CH₂COOH |
| 1683 | 7-Cl-Q | —CH₂O— | H | H | —CH₂CH₂COOH |
| 1684 | 7-Cl-Q | —CH₂O— | H | H | —CH₂CH₂CH₂COOH |
| 1685 | 7-Cl-Q | —CH₂O— | H | 9-F | —OCH₂COOH |
| 1686 | 7-Cl-Q | —CH₂O— | H | 9-F | —OCH(CH₃)COOH |
| 1687 | 7-Cl-Q | —CH₂O— | H | 9-F | —OCH₂CH₂COOH |
| 1688 | 7-Cl-Q | —CH₂O— | H | 9-F | —OCH₂CH(CH3)COOH |
| 1689 | 7-Cl-Q | —CH₂O— | H | 9-F | —OCH₂C(CH₂CH₂)CH₂COOH |
| 1690 | 7-Cl-Q | —CH₂O— | H | 9-F | —SCH₂COOH |
| 1691 | 7-Cl-Q | —CH₂O— | H | 9-F | —SCH(CH₃)COOH |
| 1692 | 7-Cl-Q | —CH₂O— | H | 9-F | —SCH₂CH₂COOH |
| 1693 | 7-Cl-Q | —CH₂O— | H | 9-F | —SCH₂CH(CH₃)COOH |
| 1694 | 7-Cl-Q | —CH₂O— | H | 9-F | —SCH₂C(CH₂CH₂)CH₂COOH |
| 1695 | 7-Cl-Q | —CH₂O— | H | 8-F | —OCH₂COOH |
| 1696 | 7-Cl-Q | —CH₂O— | H | 8-F | —OCH₂CH₂COOH |
| 1697 | 7-Cl-Q | —CH₂O— | H | 8-F | —SCH₂COOH |
| 1698 | 7-Cl-Q | —CH₂O— | H | 8-F | —SCH₂CH₂COOH |
| 1699 | 7-Cl-Q | —CH₂O— | H | 8-F | —SCH₂CH(CH₃)COOH |
| 1700 | 7-Cl-Q | —CH₂O— | H | 8-F | —SCH₂C(CH₂CH₂)CH₂COOH |
| 1701 | 7-Cl-Q | —CH₂O— | H | 7-F | —OCH₂COOH |
| 1702 | 7-Cl-Q | —CH₂O— | H | 7-F | —OCH₂CH₂COOH |
| 1703 | 7-Cl-Q | —CH₂O— | H | 7-F | —SCH₂COOH |
| 1704 | 7-Cl-Q | —CH₂O— | H | 7-F | —SCH₂CH₂COOH |
| 1705 | 7-Cl-Q | —CH₂O— | H | 7-F | —SCH₂CH(CH₃)COOH |
| 1706 | 7-Cl-Q | —CH₂O— | H | 6-F | —OCH₂COOH |
| 1707 | 7-Cl-Q | —CH₂O— | H | 6-F | —OCH(CH₃)COOH |
| 1708 | 7-Cl-Q | —CH₂O— | H | 6-F | —OCH₂CH₂COOH |
| 1709 | 7-Cl-Q | —CH₂O— | H | 6-F | —OCH₂CH(CH3)COOH |
| 1710 | 7-Cl-Q | —CH₂O— | H | 6-F | —OCH₂C(CH₂CH₂)CH₂COOH |
| 1711 | 7-Cl-Q | —CH₂O— | H | 6-F | —SCH₂COOH |
| 1712 | 7-Cl-Q | —CH₂O— | H | 6-F | —SCH(CH₃)COOH |
| 1713 | 7-Cl-Q | —CH₂O— | H | 6-F | —SCH₂CH₂COOH |
| 1714 | 7-Cl-Q | —CH₂O— | H | 6-F | —SCH₂CH(CH₃)COOH |
| 1715 | 7-Cl-Q | —CH₂O— | H | 6-F | —SCH₂C(CH₂CH₂)CH₂COOH |
| 1716 | 7-Cl-Q | —CH₂O— | H | 9-Cl | —OCH₂COOH |
| 1717 | 7-Cl-Q | —CH₂O— | H | 9-Cl | —OCH(CH₃)COOH |
| 1718 | 7-Cl-Q | —CH₂O— | H | 9-Cl | —OCH₂CH₂COOH |
| 1719 | 7-Cl-Q | —CH₂O— | H | 9-Cl | —OCH₂CH(CH3)COOH |
| 1720 | 7-Cl-Q | —CH₂O— | H | 9-Cl | —OCH₂C(CH₂CH₂)CH₂COOH |
| 1721 | 7-Cl-Q | —CH₂O— | H | 9-Cl | —SCH₂COOH |

TABLE 1-continued (I)

$$\text{structure with } A-B \text{ attached at position 3, } (R^2)_n \text{ at positions 1/2, } X=Y-Z \text{ at position 5, } (R^1)_m \text{ at positions 7-9}$$

| No. | A | B | (R²)n | (R¹)m | X—Y—Z |
|---|---|---|---|---|---|
| 1722 | 7-Cl-Q | —CH₂O— | H | 9-Cl | —SCH(CH₃)COOH |
| 1723 | 7-Cl-Q | —CH₂O— | H | 9-Cl | —SCH₂CH₂COOH |
| 1724 | 7-Cl-Q | —CH₂O— | H | 9-Cl | —SCH₂CH(CH₃)COOH |
| 1725 | 7-Cl-Q | —CH₂O— | H | 9-Cl | —SCH₂C(CH₂CH₂)CH₂COOH |
| 1726 | 7-Cl-Q | —CH₂O— | H | 8-Cl | —SCH₂C(CH₂CH₂)CH₂COOH |
| 1727 | 7-Cl-Q | —CH₂O— | H | 8-Cl | —OCH₂COOH |
| 1728 | 7-Cl-Q | —CH₂O— | H | 8-Cl | —OCH₂CH₂COOH |
| 1729 | 7-Cl-Q | —CH₂O— | H | 8-Cl | —SCH₂COOH |
| 1730 | 7-Cl-Q | —CH₂O— | H | 8-Cl | —SCH₂CH₂COOH |
| 1731 | 7-Cl-Q | —CH₂O— | H | 8-Cl | —SCH₂CH(CH₃)COOH |
| 1732 | 7-Cl-Q | —CH₂O— | H | 7-Cl | —OCH₂COOH |
| 1733 | 7-Cl-Q | —CH₂O— | H | 7-Cl | —OCH₂CH₂COOH |
| 1734 | 7-Cl-Q | —CH₂O— | H | 7-Cl | —SCH₂COOH |
| 1735 | 7-Cl-Q | —CH₂O— | H | 7-Cl | —SCH₂CH₂COOH |
| 1736 | 7-Cl-Q | —CH₂O— | H | 7-Cl | —SCH₂CH(CH₃)COOH |
| 1737 | 7-Cl-Q | —CH₂O— | H | 9-CN | —OCH₂COOH |
| 1738 | 7-Cl-Q | —CH₂O— | H | 9-CN | —OCH(CH₃)COOH |
| 1739 | 7-Cl-Q | —CH₂O— | H | 9-CN | —OCH₂CH₂COOH |
| 1740 | 7-Cl-Q | —CH₂O— | H | 9-CN | —OCH₂CH(CH3)COOH |
| 1741 | 7-Cl-Q | —CH₂O— | H | 9-CN | —OCH₂C(CH₂CH₂)CH₂COOH |
| 1742 | 7-Cl-Q | —CH₂O— | H | 9-CN | —SCH₂COOH |
| 1743 | 7-Cl-Q | —CH₂O— | H | 9-CN | —SCH(CH₃)COOH |
| 1744 | 7-Cl-Q | —CH₂O— | H | 9-CN | —SCH₂CH₂COOH |
| 1745 | 7-Cl-Q | —CH₂O— | H | 9-CN | —SCH₂CH(CH₃)COOH |
| 1746 | 7-Cl-Q | —CH₂O— | H | 9-CN | —SCH₂C(CH₂CH₂)CH₂COOH |
| 1747 | 7-Cl-Q | —CH₂O— | H | 8-CN | —OCH₂COOH |
| 1748 | 7-Cl-Q | —CH₂O— | H | 8-CN | —OCH₂CH₂COOH |
| 1749 | 7-Cl-Q | —CH₂O— | H | 8-CN | —SCH₂COOH |
| 1750 | 7-Cl-Q | —CH₂O— | H | 8-CN | —SCH₂CH₂COOH |
| 1751 | 7-Cl-Q | —CH₂O— | H | 8-CN | —SCH₂CH(CH₃)COOH |
| 1752 | 7-Cl-Q | —CH₂O— | H | 8-CN | —SCH₂C(CH₂CH₂)CH₂COOH |
| 1753 | 7-Cl-Q | —CH₂O— | H | 7-CN | —OCH₂COOH |
| 1754 | 7-Cl-Q | —CH₂O— | H | 7-CN | —OCH₂CH₂COOH |
| 1755 | 7-Cl-Q | —CH₂O— | H | 7-CN | —SCH₂COOH |
| 1756 | 7-Cl-Q | —CH₂O— | H | 7-CN | —SCH₂CH₂COOH |
| 1757 | 7-Cl-Q | —CH₂O— | H | 7-CN | —SCH₂CH(CH₃)COOH |
| 1758 | 7-Cl-Q | —CH₂O— | H | 9-CH₃ | —OCH₂COOH |
| 1759 | 7-Cl-Q | —CH₂O— | H | 9-CH₃ | —OCH₂CH₂COOH |
| 1760 | 7-Cl-Q | —CH₂O— | H | 9-CH₃ | —SCH₂COOH |
| 1761 | 7-Cl-Q | —CH₂O— | H | 9-CH₃ | —SCH₂CH₂COOH |
| 1762 | 7-Cl-Q | —CH₂O— | H | 9-CH₃ | —SCH₂CH(CH₃)COOH |
| 1763 | 7-Cl-Q | —CH₂O— | H | 9-CH₃ | —SCH₂CH(CH₂CH₃)COOH |
| 1764 | 7-Cl-Q | —CH₂O— | H | 9-CH₃ | —SCH₂C(CH₂CH₂)CH₂COOH |
| 1765 | 7-Cl-Q | —CH₂O— | H | 8-CH₃ | —OCH₂COOH |
| 1766 | 7-Cl-Q | —CH₂O— | H | 8-CH₃ | —OCH₂CH₂COOH |
| 1767 | 7-Cl-Q | —CH₂O— | H | 8-CH₃ | —SCH₂COOH |
| 1768 | 7-Cl-Q | —CH₂O— | H | 8-CH₃ | —SCH₂CH₂COOH |
| 1769 | 7-Cl-Q | —CH₂O— | H | 8-CH₃ | —SCH₂CH(CH₃)COOH |
| 1770 | 7-Cl-Q | —CH₂O— | H | 8-CH₃ | —SCH₂C(CH₂CH₂)CH₂COOH |
| 1771 | 7-Cl-Q | —CH₂O— | H | 7-CH₃ | —OCH₂COOH |
| 1772 | 7-Cl-Q | —CH₂O— | H | 7-CH₃ | —OCH₂CH₂COOH |
| 1773 | 7-Cl-Q | —CH₂O— | H | 7-CH₃ | —SCH₂COOH |
| 1774 | 7-Cl-Q | —CH₂O— | H | 7-CH₃ | —SCH₂CH₂COOH |
| 1775 | 7-Cl-Q | —CH₂O— | H | 7-CH₃ | —SCH₂CH(CH₃)COOH |
| 1776 | 7-Cl-Q | —CH₂O— | H | 9-CF₃ | —OCH₂COOH |
| 1777 | 7-Cl-Q | —CH₂O— | H | 9-CF₃ | —OCH(CH₃)COOH |
| 1778 | 7-Cl-Q | —CH₂O— | H | 9-CF₃ | —OCH₂CH₂COOH |
| 1779 | 7-Cl-Q | —CH₂O— | H | 9-CF₃ | —OCH₂CH(CH3)COOH |
| 1780 | 7-Cl-Q | —CH₂O— | H | 9-CF₃ | —OCH₂C(CH₂CH₂)CH₂COOH |
| 1781 | 7-Cl-Q | —CH₂O— | H | 9-CF₃ | —SCH₂COOH |
| 1782 | 7-Cl-Q | —CH₂O— | H | 9-CF₃ | —SCH(CH₃)COOH |
| 1783 | 7-Cl-Q | —CH₂O— | H | 9-CF₃ | —SCH₂CH₂COOH |
| 1784 | 7-Cl-Q | —CH₂O— | H | 9-CF₃ | —SCH₂CH(CH₃)COOH |
| 1785 | 7-Cl-Q | —CH₂O— | H | 9-CF₃ | —SCH₃C(CH₂CH₂)CH₂COOH |
| 1786 | 7-Cl-Q | —CH₂O— | H | 8-CF₃ | —OCH₂COOH |

TABLE 1-continued

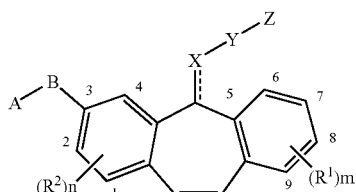

| No. | A | B | (R²)n | (R¹)m | X—Y—Z |
|---|---|---|---|---|---|
| 1787 | 7-Cl-Q | —CH₂O— | H | 8-CF₃ | —OCH₂CH₂COOH |
| 1788 | 7-Cl-Q | —CH₂O— | H | 8-CF₃ | —SCH₂COOH |
| 1789 | 7-Cl-Q | —CH₂O— | H | 8-CF₃ | —SCH₂CH₂COOH |
| 1790 | 7-Cl-Q | —CH₂O— | H | 8-CF₃ | —SCH₂CH(CH₃)COOH |
| 1791 | 7-Cl-Q | —CH₂O— | H | 8-CF₃ | —SCH₃C(CH₂CH₂)CH₂COOH |
| 1792 | 7-Cl-Q | —CH₂O— | H | 7-CF₃ | —OCH₂COOH |
| 1793 | 7-Cl-Q | —CH₂O— | H | 7-CF₃ | —OCH₂CH₂COOH |
| 1794 | 7-Cl-Q | —CH₂O— | H | 7-CF₃ | —SCH₂COOH |
| 1795 | 7-Cl-Q | —CH₂O— | H | 7-CF₃ | —SCH₂CH₂COOH |
| 1796 | 7-Cl-Q | —CH₂O— | H | 7-CF₃ | —SCH₂CH(CH₃)COOH |
| 1797 | 7-Cl-Q | —CH₂O— | H | 9-C≡CH | —OCH₂COOH |
| 1798 | 7-Cl-Q | —CH₂O— | H | 9-C≡CH | —OCH(CH₃)COOH |
| 1799 | 7-Cl-Q | —CH₂O— | H | 9-C≡CH | —OCH₂CH₂COOH |
| 1800 | 7-Cl-Q | —CH₂O— | H | 9-C≡CH | —OCH₂CH(CH3)COOH |
| 1801 | 7-Cl-Q | —CH₂O— | H | 9-C≡CH | —OCH₂C(CH₂CH₂)CH₂COOH |
| 1802 | 7-Cl-Q | —CH₂O— | H | 9-C≡CH | —SCH₂COOH |
| 1803 | 7-Cl-Q | —CH₂O— | H | 9-C≡CH | —SCH(CH₃)COOH |
| 1804 | 7-Cl-Q | —CH₂O— | H | 9-C≡CH | —SCH₂CH₂COOH |
| 1805 | 7-Cl-Q | —CH₂O— | H | 9-C≡CH | —SCH₂CH(CH₃)COOH |
| 1806 | 7-Cl-Q | —CH₂O— | H | 9-C≡CH | —SCH₂C(CH₂CH₂)CH₂COOH |
| 1807 | 7-Cl-Q | —CH₂O— | H | 8-C≡CH | —OCH₂COOH |
| 1808 | 7-Cl-Q | —CH₂O— | H | 8-C≡CH | —OCH₂CH₂COOH |
| 1809 | 7-Cl-Q | —CH₂O— | H | 8-C≡CH | —SCH₂COOH |
| 1810 | 7-Cl-Q | —CH₂O— | H | 8-C≡CH | —SCH₂CH₂COOH |
| 1811 | 7-Cl-Q | —CH₂O— | H | 8-C≡CH | —SCH₂CH(CH₃)COOH |
| 1812 | 7-Cl-Q | —CH₂O— | H | 8-C≡CH | —SCH₂C(CH₂CH₂)CH₂COOH |
| 1813 | 7-Cl-Q | —CH₂O— | H | 7-C≡CH | —OCH₂COOH |
| 1814 | 7-Cl-Q | —CH₂O— | H | 7-C≡CH | —OCH₂CH₂COOH |
| 1815 | 7-Cl-Q | —CH₂O— | H | 7-C≡CH | —SCH₂COOH |
| 1816 | 7-Cl-Q | —CH₂O— | H | 7-C≡CH | —SCH₂CH₂COOH |
| 1817 | 7-Cl-Q | —CH₂O— | H | 7-C≡CH | —SCH₂CH(CH₃)COOH |
| 1818 | 7-Cl-Q | —CH₂O— | H | 9-CH₂OH | —OCH₂COOH |
| 1819 | 7-Cl-Q | —CH₂O— | H | 9-CH₂OH | —SCH₂CH₂COOH |
| 1820 | 7-Cl-Q | —CH₂O— | H | 8-CH₂OH | —OCH₂COOH |
| 1821 | 7-Cl-Q | —CH₂O— | H | 8-CH₂OH | —SCH₂CH₂COOH |
| 1822 | 7-Cl-Q | —CH₂O— | H | 7-CH₂OH | —OCH₂COOH |
| 1823 | 7-Cl-Q | —CH₂O— | H | 7-CH₂OH | —SCH₂CH₂COOH |
| 1824 | 7-Cl-Q | —CH₂O— | H | 9-C(CH₃)₂OH | —OCH₂COOH |
| 1825 | 7-Cl-Q | —CH₂O— | H | 9-C(CH₃)₂OH | —SCH₂CH₂COOH |
| 1826 | 7-Cl-Q | —CH₂O— | H | 8-C(CH₃)₂OH | —OCH₂COOH |
| 1827 | 7-Cl-Q | —CH₂O— | H | 8-C(CH₃)₂OH | —SCH₂CH₂COOH |
| 1828 | 7-Cl-Q | —CH₂O— | H | 7-C(CH₃)₂OH | —OCH₂COOH |
| 1829 | 7-Cl-Q | —CH₂O— | H | 7-C(CH₃)₂OH | —SCH₂CH₂COOH |
| 1830 | 7-Cl-Q | —CH₂O— | H | 9-OCH₃ | —OCH₂COOH |
| 1831 | 7-Cl-Q | —CH₂O— | H | 9-OCH₃ | —SCH₂CH₂COOH |
| 1832 | 7-Cl-Q | —CH₂O— | H | 8-OCH₃ | —OCH₂COOH |
| 1833 | 7-Cl-Q | —CH₂O— | H | 8-OCH₃ | —SCH₂CH₂COOH |
| 1834 | 7-Cl-Q | —CH₂O— | H | 7-OCH₃ | —OCH₂COOH |
| 1835 | 7-Cl-Q | —CH₂O— | H | 7-OCH₃ | —SCH₂CH₂COOH |
| 1836 | 7-Cl-Q | —CH₂O— | H | 9-OCHF₂ | —OCH₂COOH |
| 1837 | 7-Cl-Q | —CH₂O— | H | 9-OCHF₂ | —SCH₂CH₂COOH |
| 1838 | 7-Cl-Q | —CH₂O— | H | 8-OCHF₂ | —OCH₂COOH |
| 1839 | 7-Cl-Q | —CH₂O— | H | 8-OCHF₂ | —SCH₂CH₂COOH |
| 1840 | 7-Cl-Q | —CH₂O— | H | 7-OCHF₂ | —OCH₂COOH |
| 1841 | 7-Cl-Q | —CH₂O— | H | 7-OCHF₂ | —SCH₂CH₂COOH |
| 1842 | 7-Cl-Q | —CH₂O— | H | 9-OCF₃ | —OCH₂COOH |
| 1843 | 7-Cl-Q | —CH₂O— | H | 9-OCF₃ | —SCH₂CH₂COOH |
| 1844 | 7-Cl-Q | —CH₂O— | H | 8-OCF₃ | —OCH₂COOH |
| 1845 | 7-Cl-Q | —CH₂O— | H | 8-OCF₃ | —SCH₂CH₂COOH |

TABLE 1-continued

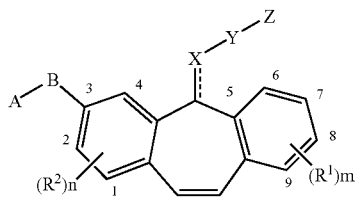

(I)

| No. | A | B | (R²)n | (R¹)m | X—Y—Z |
|---|---|---|---|---|---|
| 1846 | 7-Cl-Q | —CH₂O— | H | 7-OCF₃ | —OCH₂COOH |
| 1847 | 7-Cl-Q | —CH₂O— | H | 7-OCF₃ | —SCH₂CH₂COOH |
| 1848 | 7-Cl-Q | —CH₂O— | H | 9-SOCH₃ | —OCH₂COOH |
| 1849 | 7-Cl-Q | —CH₂O— | H | 9-SOCH₃ | —SCH₂CH₂COOH |
| 1850 | 7-Cl-Q | —CH₂O— | H | 8-SOCH₃ | —OCH₂COOH |
| 1851 | 7-Cl-Q | —CH₂O— | H | 8-SOCH₃ | —SCH₂CH₂COOH |
| 1852 | 7-Cl-Q | —CH₂O— | H | 7-SOCH₃ | —OCH₂COOH |
| 1853 | 7-Cl-Q | —CH₂O— | H | 7-SOCH₃ | —SCH₂CH₂COOH |
| 1854 | 7-Cl-Q | —CH₂O— | H | 9-SO₂CH₃ | —OCH₂COOH |
| 1855 | 7-Cl-Q | —CH₂O— | H | 9-SO₂CH₃ | —SCH₂CH₂COOH |
| 1856 | 7-Cl-Q | —CH₂O— | H | 8-SO₂CH₃ | —OCH₂COOH |
| 1857 | 7-Cl-Q | —CH₂O— | H | 8-SO₂CH₃ | —SCH₂CH₂COOH |
| 1858 | 7-Cl-Q | —CH₂O— | H | 7-SO₂CH₃ | —OCH₂COOH |
| 1859 | 7-Cl-Q | —CH₂O— | H | 7-SO₂CH₃ | —SCH₂CH₂COOH |
| 1860 | 7-Cl-Q | —CH₂O— | H | 9-CH=CH₂ | —SCH₂CH₂COOH |
| 1861 | 7-Cl-Q | —CH₂O— | H | 8-CH=CH₂ | —SCH₂CH₂COOH |
| 1862 | 7-Cl-Q | —CH₂O— | H | 7-CH=CH₂ | —SCH₂CH₂COOH |
| 1863 | 7-Cl-Q | —CH₂O— | H | 9-NO₂ | —OCH₂COOH |
| 1864 | 7-Cl-Q | —CH₂O— | H | 9-NO₂ | —SCH₂CH₂COOH |
| 1865 | 7-Cl-Q | —CH₂O— | H | 8-NO₂ | —OCH₂COOH |
| 1866 | 7-Cl-Q | —CH₂O— | H | 8-NO₂ | —SCH₂CH₂COOH |
| 1867 | 7-Cl-Q | —CH₂O— | H | 7-NO₂ | —OCH₂COOH |
| 1868 | 7-Cl-Q | —CH₂O— | H | 7-NO₂ | —SCH₂CH₂COOH |
| 1869 | 7-Cl-Q | —CH₂O— | 1-F | H | —SCH₂CH₂COOH |
| 1870 | 7-Cl-Q | —CH₂O— | 2-F | H | —SCH₂CH₂COOH |
| 1871 | 7-Cl-Q | —CH₂O— | 1-Cl | H | —SCH₂CH₂COOH |
| 1872 | 7-Cl-Q | —CH₂O— | 2-Cl | H | —SCH₂CH₂COOH |
| 1873 | 7-Cl-Q | —CH₂O— | 1-CH₃ | H | —SCH₂CH₂COOH |
| 1874 | 7-Cl-Q | —CH₂O— | 2-CH₃ | H | —SCH₂CH₂COOH |
| 1875 | 7-Cl-Q | —CH₂O— | 1-OCH₃ | H | —SCH₂CH₂COOH |
| 1876 | 7-Cl-Q | —CH₂O— | 2-OCH₃ | H | —SCH₂CH₂COOH |
| 1877 | 7-Cl-Q | —CH₂O— | 1-NO₂ | H | —SCH₂CH₂COOH |
| 1878 | 7-Cl-Q | —CH₂O— | 2-NO₂ | H | —SCH₂CH₂COOH |
| 1879 | 7-Cl-Q | —CH₂O— | 1-CN | H | —SCH₂CH₂COOH |
| 1880 | 7-Cl-Q | —CH₂O— | 2-CN | H | —SCH₂CH₂COOH |
| 1881 | TQ | —CH=CH— | H | H | —OCH₂COOH |
| 1882 | TQ | —CH=CH— | H | H | —OCH₂CH₂COOH |
| 1883 | TQ | —CH=CH— | H | H | —OCH₂CH(CH₃)COOH |
| 1884 | TQ | —CH=CH— | H | H | —SCH₂COOH |
| 1885 | TQ | —CH=CH— | H | H | —SCH₂CH₂COOH |
| 1886 | TQ | —CH=CH— | H | H | —SCH₂CH(CH₃)COOH |
| 1887 | TQ | —CH=CH— | H | H | —SCH₂C(CH₃)₂COOH |
| 1888 | TQ | —CH=CH— | H | H | —SCH₂CH(CH₂CH₃)COOH |
| 1889 | TQ | —CH=CH— | H | H | —SCH(CH₃)CH₂COOH |
| 1890 | TQ | —CH=CH— | H | H | —SC(CH₃)₂CH₂COOH |
| 1891 | TQ | —CH=CH— | H | H | —SCH₂CH₂CH₂COOH |
| 1892 | TQ | —CH=CH— | H | H | —SCH₂CH(CH₃)CH₂COOH |
| 1893 | TQ | —CH=CH— | H | H | —SCH₂C(CH₃)₂CH₂COOH |
| 1894 | TQ | —CH=CH— | H | H | —SCH₂C(CH₂CH₂)CH₂COOH |
| 1895 | TQ | —CH=CH— | H | H | —SCH₂CF₂COOH |
| 1896 | TQ | —CH=CH— | H | H | —SCH₂CF₂CH₂COOH |
| 1897 | TQ | —CH=CH— | H | H | —SCH₂CONHSO₂CH₃ |
| 1898 | TQ | —CH=CH— | H | H | —SCH₂CONHSO₂CF₃ |
| 1899 | TQ | —CH=CH— | H | H | —SCH₂CH₂NHSO₂CF₃ |
| 1900 | TQ | —CH=CH— | H | H | —SCH₂CH₂CONHSO₂CH₃ |
| 1901 | TQ | —CH=CH— | H | H | —SCH₂CH₂CONHSO₂CF₃ |
| 1902 | TQ | —CH=CH— | H | H | —CH₂CH₂COOH |
| 1903 | TQ | —CH=CH— | H | H | —CH₂CH₂CH₂COOH |
| 1904 | TQ | —CH=CH— | H | 9-F | —OCH₂COOH |
| 1905 | TQ | —CH=CH— | H | 9-F | —OCH₂CH₂COOH |
| 1906 | TQ | —CH=CH— | H | 9-F | —SCH₂COOH |
| 1907 | TQ | —CH=CH— | H | 9-F | —SCH₂CH₂COOH |
| 1908 | TQ | —CH=CH— | H | 8-F | —OCH₂COOH |
| 1909 | TQ | —CH=CH— | H | 8-F | —OCH₂CH₂COOH |
| 1910 | TQ | —CH=CH— | H | 8-F | —SCH₂COOH |

TABLE 1-continued

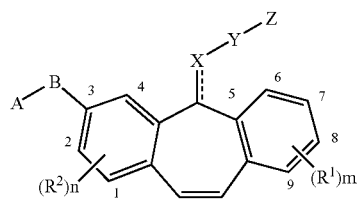

(I)

| No. | A | B | (R²)n | (R¹)m | X—Y—Z |
|---|---|---|---|---|---|
| 1911 | TQ | —CH=CH— | H | 8-F | —SCH₂CH₂COOH |
| 1912 | TQ | —CH=CH— | H | 9-CN | —OCH₂COOH |
| 1913 | TQ | —CH=CH— | H | 9-CN | —OCH₂CH₂COOH |
| 1914 | TQ | —CH=CH— | H | 9-CN | —SCH₂COOH |
| 1915 | TQ | —CH=CH— | H | 9-CN | —SCH₂CH₂COOH |
| 1916 | TQ | —CH=CH— | H | 8-CN | —OCH₂COOH |
| 1917 | TQ | —CH=CH— | H | 8-CN | —OCH₂CH₂COOH |
| 1918 | TQ | —CH=CH— | H | 8-CN | —SCH₂COOH |
| 1919 | TQ | —CH=CH— | H | 8-CN | —SCH₂CH₂COOH |
| 1920 | TQ | —CH=CH— | H | 9-CF₃ | —OCH₂COOH |
| 1921 | TQ | —CH=CH— | H | 9-CF₃ | —SCH₂CH₂COOH |
| 1922 | TQ | —CH=CH— | H | 8-CF₃ | —OCH₂COOH |
| 1923 | TQ | —CH=CH— | H | 8-CF₃ | —SCH₂CH₂COOH |
| 1924 | TQ | —CH=CH— | H | 9-C≡CH | —OCH₂COOH |
| 1925 | TQ | —CH=CH— | H | 9-C≡CH | —SCH₂CH₂COOH |
| 1926 | TQ | —CH=CH— | H | 8-C≡CH | —SCH₂CH₂COOH |
| 1927 | TQ | —CH₂O— | H | H | —OCH₂COOH |
| 1928 | TQ | —CH₂O— | H | H | —OCH₂CH₂COOH |
| 1929 | TQ | —CH₂O— | H | H | —OCH₂CH(CH₃)COOH |
| 1930 | TQ | —CH₂O— | H | H | —SCH₂COOH |
| 1931 | TQ | —CH₂O— | H | H | —SCH₂CH₂COOH |
| 1932 | TQ | —CH₂O— | H | H | —SCH₂CH(CH₃)COOH |
| 1933 | TQ | —CH₂O— | H | H | —SCH₂C(CH₃)₂COOH |
| 1934 | TQ | —CH₂O— | H | H | —SCH₂CH(CH₂CH₃)COOH |
| 1935 | TQ | —CH₂O— | H | H | —SCH(CH₃)CH₂COOH |
| 1936 | TQ | —CH₂O— | H | H | —SC(CH₃)₂CH₂COOH |
| 1937 | TQ | —CH₂O— | H | H | —SCH₂CH₂COOH |
| 1938 | TQ | —CH₂O— | H | H | —SCH₂CH(CH₃)CH₂COOH |
| 1939 | TQ | —CH₂O— | H | H | —SCH₂C(CH₃)₂CH₂COOH |
| 1940 | TQ | —CH₂O— | H | H | —SCH₂C(CH₂CH₃)CH₂COOH |
| 1941 | TQ | —CH₂O— | H | H | —SCH₂CF₂COOH |
| 1942 | TQ | —CH₂O— | H | H | —SCH₂CF₂CH₂COOH |
| 1943 | TQ | —CH₂O— | H | H | —SCH₂CONHSO₂CH₃ |
| 1944 | TQ | —CH₂O— | H | H | —SCH₂CONHSO₂CF₃ |
| 1945 | TQ | —CH₂O— | H | H | —SCH₂CH₂NHSO₂CF₃ |
| 1946 | TQ | —CH₂O— | H | H | —SCH₂CH₂CONHSO₂CH₃ |
| 1947 | TQ | —CH₂O— | H | H | —SCH₂CH₂CONHSO₂CF₃ |
| 1948 | TQ | —CH₂O— | H | H | —CH₂CH₂COOH |
| 1949 | TQ | —CH₂O— | H | H | —CH₂CH₂CH₂COOH |
| 1950 | TQ | —CH₂O— | H | 9-F | —OCH₂COOH |
| 1951 | TQ | —CH₂O— | H | 9-F | —OCH₂CH₂COOH |
| 1952 | TQ | —CH₂O— | H | 9-F | —SCH₂COOH |
| 1953 | TQ | —CH₂O— | H | 9-F | —SCH₂CH₂COOH |
| 1954 | TQ | —CH₂O— | H | 8-F | —OCH₂COOH |
| 1955 | TQ | —CH₂O— | H | 8-F | —OCH₂CH₂COOH |
| 1956 | TQ | —CH₂O— | H | 8-F | —SCH₂COOH |
| 1957 | TQ | —CH₂O— | H | 8-F | —SCH₂CH₂COOH |
| 1958 | TQ | —CH₂O— | H | 9-CN | —OCH₂COOH |
| 1959 | TQ | —CH₂O— | H | 9-CN | —OCH₂CH₂COOH |
| 1960 | TQ | —CH₂O— | H | 9-CN | —SCH₂COOH |
| 1961 | TQ | —CH₂O— | H | 9-CN | —SCH₂CH₂COOH |
| 1962 | TQ | —CH₂O— | H | 8-CN | —OCH₂COOH |
| 1963 | TQ | —CH₂O— | H | 8-CN | —OCH₂CH₂COOH |
| 1964 | TQ | —CH₂O— | H | 8-CN | —SCH₂COOH |
| 1965 | TQ | —CH₂O— | H | 8-CN | —SCH₂CH₂COOH |
| 1966 | TQ | —CH₂O— | H | 9-CF₃ | —OCH₂COOH |
| 1967 | TQ | —CH₂O— | H | 9-CF₃ | —SCH₂CH₂COOH |
| 1968 | TQ | —CH₂O— | H | 8-CF₃ | —OCH₂COOH |
| 1969 | TQ | —CH₂O— | H | 8-CF₃ | —SCH₂CH₂COOH |
| 1970 | TQ | —CH₂O— | H | 9-C≡CH | —OCH₂COOH |
| 1971 | TQ | —CH₂O— | H | 9-C≡CH | —SCH₂CH₂COOH |
| 1972 | TQ | —CH₂O— | H | 8-C≡CH | —SCH₂CH₂COOH |
| 1973 | 7-CF₃-Q | —CH=CH— | H | H | —OCH₂COOH |
| 1974 | 7-CF₃-Q | —CH=CH— | H | H | —OCH₂CH₂COOH |
| 1975 | 7-CF₃-Q | —CH=CH— | H | H | —SCH₂COOH |

TABLE 1-continued

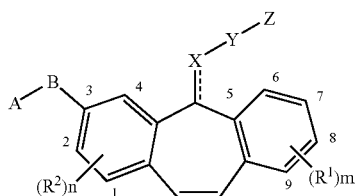

(I)

| No. | A | B | (R²)n | (R¹)m | X—Y—Z |
|---|---|---|---|---|---|
| 1976 | 7-CF₃-Q | —CH=CH— | H | H | —SCH₂CH₂COOH |
| 1977 | 7-CF₃-Q | —CH=CH— | H | H | —SCH₂CH(CH₃)COOH |
| 1978 | 7-CF₃-Q | —CH=CH— | H | H | —SCH₂C(CH₂CH₂)CH₂COOH |
| 1979 | 7-CF₃-Q | —CH₂O— | H | H | —OCH₂COOH |
| 1980 | 7-CF₃-Q | —CH₂O— | H | H | —OCH₂CH₂COOH |
| 1981 | 7-CF₃-Q | —CH₂O— | H | H | —SCH₂COOH |
| 1982 | 7-CF₃-Q | —CH₂O— | H | H | —SCH₂CH₂COOH |
| 1983 | 7-CF₃-Q | —CH₂O— | H | H | —SCH₂CH(CH₃)COOH |
| 1984 | 7-CF₃-Q | —CH₂O— | H | H | —SCH₂C(CH₂CH₂)CH₂COOH |
| 1985 | 6-F,7-CF₃-Q | —CH=CH— | H | H | —OCH₂COOH |
| 1986 | 6-F,7-CF₃-Q | —CH=CH— | H | H | —OCH₂CH₂COOH |
| 1987 | 6-F,7-CF₃-Q | —CH=CH— | H | H | —SCH₂COOH |
| 1988 | 6-F,7-CF₃-Q | —CH=CH— | H | H | —SCH₂CH₂COOH |
| 1989 | 6-F,7-CF₃-Q | —CH=CH— | H | H | —SCH₂CH(CH₃)COOH |
| 1990 | 6-F,7-CF₃-Q | —CH=CH— | H | H | —SCH₂C(CH₂CH₂)CH₂COOH |
| 1991 | 6-F,7-CF₃-Q | —CH₂O— | H | H | —OCH₂COOH |
| 1992 | 6-F,7-CF₃-Q | —CH₂O— | H | H | —OCH₂CH₂COOH |
| 1993 | 6-F,7-CF₃-Q | —CH₂O— | H | H | —SCH₂COOH |
| 1994 | 6-F,7-CF₃-Q | —CH₂O— | H | H | —SCH₂CH₂COOH |
| 1995 | 6-F,7-CF₃-Q | —CH₂O— | H | H | —SCH₂CH(CH₃)COOH |
| 1996 | 6-F,7-CF₃-Q | —CH₂O— | H | H | —SCH₂C(CH₂CH₂)CH₂COOH |
| 1997 | 6,7-diCl-Q | —CH=CH— | H | H | —OCH₂COOH |
| 1998 | 6,7-diCl-Q | —CH=CH— | H | H | —OCH₂CH₂COOH |
| 1999 | 6,7-diCl-Q | —CH=CH— | H | H | —SCH₂COOH |
| 2000 | 6,7-diCl-Q | —CH=CH— | H | H | —SCH₂CH₂COOH |
| 2001 | 6,7-diCl-Q | —CH=CH— | H | H | —SCH₂CH(CH₃)COOH |
| 2002 | 6,7-diCl-Q | —CH=CH— | H | H | —SCH₂C(CH₂CH₂)CH₂COOH |
| 2003 | 6,7-diCl-Q | —CH₂O— | H | H | —OCH₂COOH |
| 2004 | 6,7-diCl-Q | —CH₂O— | H | H | —OCH₂CH₂COOH |
| 2005 | 6,7-diCl-Q | —CH₂O— | H | H | —SCH₂COOH |
| 2006 | 6,7-diCl-Q | —CH₂O— | H | H | —SCH₂CH₂COOH |
| 2007 | 6,7-diCl-Q | —CH₂O— | H | H | —SCH₂CH(CH₃)COOH |
| 2008 | 6,7-diCl-Q | —CH₂O— | H | H | —SCH₂C(CH₂CH₂)CH₂COOH |
| 2009 | 6-Cl,7-F-Q | —CH=CH— | H | H | —OCH₂COOH |
| 2010 | 6-Cl,7-F-Q | —CH=CH— | H | H | —OCH₂CH₂COOH |
| 2011 | 6-Cl,7-F-Q | —CH=CH— | H | H | —SCH₂COOH |
| 2012 | 6-Cl,7-F-Q | —CH=CH— | H | H | —SCH₂CH₂COOH |
| 2013 | 6-Cl,7-F-Q | —CH=CH— | H | H | —SCH₂CH(CH₃)COOH |
| 2014 | 6-Cl,7-F-Q | —CH=CH— | H | H | —SCH₂C(CH₂CH₂)CH₂COOH |
| 2015 | 6-Cl,7-F-Q | —CH₂O— | H | H | —OCH₂COOH |
| 2016 | 6-Cl,7-F-Q | —CH₂O— | H | H | —OCH₂CH₂COOH |
| 2017 | 6-Cl,7-F-Q | —CH₂O— | H | H | —SCH₂COOH |
| 2018 | 6-Cl,7-F-Q | —CH₂O— | H | H | —SCH₂CH₂COOH |
| 2019 | 6-Cl,7-F-Q | —CH₂O— | H | H | —SCH₂CH(CH₃)COOH |
| 2020 | 6-Cl,7-F-Q | —CH₂O— | H | H | —SCH₂C(CH₂CH₂)CH₂COOH |
| 2021 | 5,6,7-triF-Q | —CH=CH— | H | H | —OCH₂COOH |
| 2022 | 5,6,7-triF-Q | —CH=CH— | H | H | —OCH₂CH₂COOH |
| 2023 | 5,6,7-triF-Q | —CH=CH— | H | H | —SCH₂COOH |
| 2024 | 5,6,7-triF-Q | —CH=CH— | H | H | —SCH₂CH₂COOH |
| 2025 | 5,6,7-triF-Q | —CH₂O— | H | H | —OCH₂COOH |
| 2026 | 5,6,7-triF-Q | —CH₂O— | H | H | —OCH₂CH₂COOH |
| 2027 | 5,6,7-triF-Q | —CH₂O— | H | H | —SCH₂COOH |
| 2028 | 5,6,7-triF-Q | —CH₂O— | H | H | —SCH₂CH₂COOH |
| 2029 | 4-t-Bu-T | —CH=CH— | H | H | —OCH₂COOH |
| 2030 | 4-t-Bu-T | —CH=CH— | H | H | —SCH₂COOH |
| 2031 | 4-t-Bu-T | —CH=CH— | H | H | —SCH₂CH₂COOH |
| 2032 | 4-t-Bu-T | —CH₂O— | H | H | —OCH₂COOH |
| 2033 | 4-t-Bu-T | —CH₂O— | H | H | —SCH₂COOH |
| 2034 | 4-t-Bu-T | —CH₂O— | H | H | —SCH₂CH₂COOH |
| 2035 | 5-F-BT | —CH=CH— | H | H | —OCH₂COOH |
| 2036 | 5-F-BT | —CH=CH— | H | H | —SCH₂COOH |
| 2037 | 5-F-BT | —CH=CH— | H | H | —SCH₂CH₂COOH |
| 2038 | 5-F-BT | —CH₂O— | H | H | —OCH₂COOH |
| 2039 | 5-F-BT | —CH₂O— | H | H | —SCH₂COOH |
| 2040 | 5-F-BT | —CH₂O— | H | H | —SCH₂CH₂COOH |

TABLE 1-continued

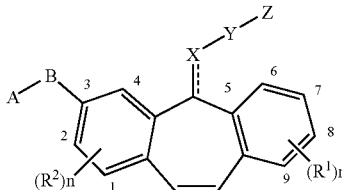

(I)

| No. | A | B | (R²)n | (R¹)m | X—Y—Z |
|---|---|---|---|---|---|
| 2041 | 5,6-diF-BT | —CH=CH— | H | H | —OCH₂COOH |
| 2042 | 5,6-diF-BT | —CH=CH— | H | H | —SCH₂COOH |
| 2043 | 5,6-diF-BT | —CH=CH— | H | H | —SCH₂CH₂COOH |
| 2044 | 5,6-diF-BT | —CH₂O— | H | H | —OCH₂COOH |
| 2045 | 5,6-diF-BT | —CH₂O— | H | H | —SCH₂COOH |
| 2046 | 5,6-diF-BT | —CH₂O— | H | H | —SCH₂CH₂COOH |
| 2047 | 6-t-Bu-Py | —CH=CH— | H | H | —OCH₂COOH |
| 2048 | 6-t-Bu-Py | —CH=CH— | H | H | —SCH₂COOH |
| 2049 | 6-t-Bu-Py | —CH=CH— | H | H | —SCH₂CH₂COOH |
| 2050 | 6-t-Bu-Py | —CH₂O— | H | H | —OCH₂COOH |
| 2051 | 6-t-Bu-Py | —CH₂O— | H | H | —SCH₂COOH |
| 2052 | 6-t-Bu-Py | —CH₂O— | H | H | —SCH₂CH₂COOH |
| 2053 | 6,7-diF-Q | —CH₂CH₂— | H | H | —OCH₂COOH |
| 2054 | 6,7-diF-Q | —CH₂CH₂— | H | H | —SCH₂COOH |
| 2055 | 6,7-diF-Q | —CH₂CH₂— | H | H | —SCH₂CH₂COOH |
| 2056 | 6,7-diF-Q | —CH₂S— | H | H | —OCH₂COOH |
| 2057 | 6,7-diF-Q | —CH₂S— | H | H | —SCH₂COOH |
| 2058 | 6,7-diF-Q | —CH₂S— | H | H | —SCH₂CH₂COOH |
| 2059 | 6,7-diF-Q | —OCH₂— | H | H | —OCH₂COOH |
| 2060 | 6,7-diF-Q | —OCH₂— | H | H | —SCH₂COOH |
| 2061 | 6,7-diF-Q | —OCH₂— | H | H | —SCH₂CH₂COOH |
| 2062 | 6,7-diF-Q | —SCH₂— | H | H | —OCH₂COOH |
| 2063 | 6,7-diF-Q | —SCH₂— | H | H | —SCH₂COOH |
| 2064 | 6,7-diF-Q | —SCH₂— | H | H | —SCH₂CH₂COOH |
| 2065 | 7-Cl,6-F-Q | —CH₂CH₂— | H | H | —OCH₂COOH |
| 2066 | 7-Cl,6-F-Q | —CH₂CH₂— | H | H | —SCH₂COOH |
| 2067 | 7-Cl,6-F-Q | —CH₂CH₂— | H | H | —SCH₂CH₂COOH |
| 2068 | 7-Cl,6-F-Q | —CH₂S— | H | H | —OCH₂COOH |
| 2069 | 7-Cl,6-F-Q | —CH₂S— | H | H | —SCH₂COOH |
| 2070 | 7-Cl,6-F-Q | —CH₂S— | H | H | —SCH₂CH₂COOH |
| 2071 | 7-Cl,6-F-Q | —OCH₂— | H | H | —OCH₂COOH |
| 2072 | 7-Cl,6-F-Q | —OCH₂— | H | H | —SCH₂COOH |
| 2073 | 7-Cl,6-F-Q | —OCH₂— | H | H | —SCH₂CH₂COOH |
| 2074 | 7-Cl,6-F-Q | —SCH₂— | H | H | —OCH₂COOH |
| 2075 | 7-Cl,6-F-Q | —SCH₂— | H | H | —SCH₂COOH |
| 2076 | 7-Cl,6-F-Q | —SCH₂— | H | H | —SCH₂CH₂COOH |
| 2077 | 7-F-Q | —CH₂CH₂— | H | H | —OCH₂COOH |
| 2078 | 7-F-Q | —CH₂CH₂— | H | H | —SCH₂COOH |
| 2079 | 7-F-Q | —CH₂CH₂— | H | H | —SCH₂CH₂COOH |
| 2080 | 7-F-Q | —CH₂S— | H | H | —OCH₂COOH |
| 2081 | 7-F-Q | —CH₂S— | H | H | —SCH₂COOH |
| 2082 | 7-F-Q | —CH₂S— | H | H | —SCH₂CH₂COOH |
| 2083 | 7-F-Q | —OCH₂— | H | H | —OCH₂COOH |
| 2084 | 7-F-Q | —OCH₂— | H | H | —SCH₂COOH |
| 2085 | 7-F-Q | —OCH₂— | H | H | —SCH₂CH₂COOH |
| 2086 | 7-F-Q | —SCH₂— | H | H | —OCH₂COOH |
| 2087 | 7-F-Q | —SCH₂— | H | H | —SCH₂COOH |
| 2088 | 7-F-Q | —SCH₂— | H | H | —SCH₂CH₂COOH |
| 2089 | 7-Cl-Q | —CH₂CH₂— | H | H | —OCH₂COOH |
| 2090 | 7-Cl-Q | —CH₂CH₂— | H | H | —SCH₂COOH |
| 2091 | 7-Cl-Q | —CH₂CH₂— | H | H | —SCH₂CH₂COOH |
| 2092 | 7-Cl-Q | —CH₂S— | H | H | —OCH₂COOH |
| 2093 | 7-Cl-Q | —CH₂S— | H | H | —SCH₂COOH |
| 2094 | 7-Cl-Q | —CH₂S— | H | H | —SCH₂CH₂COOH |
| 2095 | 7-Cl-Q | —OCH₂— | H | H | —OCH₂COOH |
| 2096 | 7-Cl-Q | —OCH₂— | H | H | —SCH₂COOH |
| 2097 | 7-Cl-Q | —OCH₂— | H | H | —SCH₂CH₂COOH |
| 2098 | 7-Cl-Q | —SCH₂— | H | H | —OCH₂COOH |
| 2099 | 7-Cl-Q | —SCH₂— | H | H | —SCH₂COOH |
| 2100 | 7-Cl-Q | —SCH₂— | H | H | —SCH₂CH₂COOH |

Incidentally, in the above-mentioned table, the respective abbreviations mean t-Bu: t-butyl group, BT: 2-benzothiazolyl group, Tet: 1H-tetrazol-5-yl group, Ph: a phenyl group, Py: 2-pyridyl group, Q: quinolin-2-yl group, T: 2-thiazolyl group, and TQ: 5,6,7,8-tetrahydroquinolin-2-yl group, and the $CH_2C(CH_2CH_2)CH_2$ portion in the $-OCH_2C(CH_2CH_2)-CH_2COOH$ or $-SCH_2C(CH_2CH_2)CH_2COOH$ represents the formula (a) wherein o=1, p=1 and q=1, and the $CH_2C(CH_2CH_2)$ portion in the $-SCH_2C(CH_2CH_2)COOH$ represents the formula (a) wherein o=1, p=0 and q=1. Also, in the above-mentioned Table 1, the numeral(s) in the formula (I) represents a substituted position(s) of the substituent(s).

As the more preferred compounds, there may be mentioned compounds of Compounds No. 1, 2, 3, 4, 5, 6, 7, 8, 9, 11, 12, 13, 14, 15, 16, 17, 24, 25, 27, 33, 34, 35, 36, 37, 38, 39, 40, 41, 42, 43, 44, 47, 49, 55, 56, 57, 58, 59, 60, 61, 62, 63, 64, 65, 66, 67, 68, 69, 70, 71, 72, 73, 74, 76, 78, 79, 87, 89, 92, 94, 97, 99, 102, 103, 104, 105, 106, 107, 110, 112, 118, 121, 122, 123, 124, 128, 136, 138, 139, 140, 141, 142, 143, 144, 145, 146, 149, 157, 159, 160, 161, 162, 163, 164, 165, 166, 167, 170, 179, 184, 185, 190, 191, 196, 197, 202, 203, 220, 223, 224, 241, 243, 244, 245, 246, 247, 248, 249, 250, 251, 257, 264, 273, 274, 275, 277, 280, 281, 282, 283, 284, 285, 288, 296, 298, 299, 300, 301, 302, 303, 304, 305, 306, 308, 309, 310, 311, 312, 313, 314, 315, 319, 320, 327, 329, 331, 332, 333, 334, 335, 336, 337, 340, 348, 351, 366, 368, 371, 372, 373, 374, 375, 376, 378, 379, 387, 392, 393, 394, 396, 397, 400, 420, 421, 426, 427, 429, 432, 433, 435, 453, 454, 455, 456, 471, 472, 473, 474, 475, 476, 477, 478, 479, 481, 482, 483, 484, 485, 486, 487, 494, 495, 497, 503, 504, 505, 506, 507, 508, 509, 510, 511, 512, 513, 514, 517, 519, 525, 526, 527, 528, 529, 530, 531, 532, 533, 534, 535, 536, 537, 538, 539, 540, 541, 542, 543, 544, 546, 548, 549, 557, 558, 559, 562, 564, 567, 569, 572, 573, 574, 575, 576, 577, 580, 582, 588, 591, 592, 593, 594, 598, 606, 608, 609, 610, 611, 612, 613, 614, 615, 616, 619, 627, 629, 630, 631, 632, 633, 634, 635, 636, 637, 640, 649, 654, 655, 660, 661, 666, 667, 672, 673, 690, 693, 694, 711, 713, 714, 715, 716, 717, 718, 719, 720, 721, 727, 734, 743, 744, 745, 747, 750, 751, 752, 753, 754, 755, 758, 766, 768, 769, 770, 771, 772, 773, 774, 775, 776, 778, 779, 780, 781, 782, 783, 784, 785, 789, 790, 797, 799, 801, 802, 803, 804, 805, 806, 807, 810, 818, 821, 836, 838, 841, 842, 843, 844, 845, 846, 848, 849, 857, 862, 863, 864, 866, 867, 870, 890, 891, 896, 897, 899, 902, 903, 905, 923, 924, 925, 926, 941, 942, 943, 944, 945, 946, 947, 948, 949, 951, 952, 953, 954, 955, 956, 957, 964, 965, 967, 973, 974, 975, 976, 977, 978, 979, 980, 981, 982, 983, 984, 987, 989, 995, 996, 997, 998, 999, 1000, 1001, 1002, 1003, 1004, 1005, 1006, 1007, 1008, 1009, 1010, 1011, 1012, 1013, 1014, 1016, 1018, 1019, 1027, 1029, 1032, 1034, 1037, 1039, 1042, 1043, 1044, 1045, 1046, 1047, 1050, 1052, 1058, 1061, 1062, 1063, 1064, 1068, 1076, 1078, 1079, 1080, 1081, 1082, 1083, 1084, 1085, 1086, 1089, 1097, 1099, 1100, 1101, 1102, 1103, 1104, 1105, 1106, 1107, 1110, 1119, 1124, 1125, 1130, 1131, 1136, 1137, 1142, 1143, 1160, 1163, 1164, 1181, 1183, 1184, 1185, 1186, 1187, 1188, 1189, 1190, 1191, 1197, 1204, 1213, 1214, 1215, 1217, 1220, 1221, 1222, 1223, 1224, 1225, 1228, 1236, 1238, 1239, 1240, 1241, 1242, 1243, 1244, 1245, 1246, 1248, 1249, 1250, 1251, 1252, 1253, 1254, 1255, 1259, 1260, 1267, 1269, 1271, 1272, 1273, 1274, 1275, 1276, 1277, 1280, 1288, 1291, 1306, 1308, 1311, 1312, 1313, 1314, 1315, 1316, 1318, 1319, 1327, 1332, 1333, 1334, 1336, 1337, 1340, 1360, 1361, 1366, 1367, 1369, 1372, 1373, 1375, 1393, 1394, 1395, 1396, 1411, 1412, 1413, 1414, 1415, 1416, 1417, 1418, 1419, 1421, 1422, 1423, 1424, 1425, 1426, 1427, 1434, 1435, 1437, 1443, 1444, 1445, 1446, 1447, 1448, 1449, 1450, 1451, 1452, 1453, 1454, 1457, 1459, 1465, 1466, 1467, 1468, 1469, 1470, 1471, 1472, 1473, 1474, 1475, 1476, 1477, 1478, 1479, 1480, 1481, 1482, 1483, 1484, 1486, 1488, 1489, 1497, 1499, 1502, 1504, 1507, 1509, 1512, 1513, 1514, 1515, 1516, 1517, 1520, 1522, 1528, 1531, 1532, 1533, 1534, 1538, 1546, 1548, 1549, 1550, 1551, 1552, 1553, 1554, 1555, 1556, 1559, 1567, 1569, 1570, 1571, 1572, 1573, 1574, 1575, 1576, 1577, 1580, 1589, 1594, 1595, 1600, 1601, 1606, 1607, 1612, 1613, 1630, 1633, 1634, 1651, 1653, 1654, 1655, 1656, 1657, 1658, 1659, 1660, 1661, 1667, 1674, 1683, 1684, 1685, 1687, 1690, 1691, 1692, 1693, 1694, 1695, 1698, 1706, 1708, 1709, 1710, 1711, 1712, 1713, 1714, 1715, 1716, 1718, 1719, 1720, 1721, 1722, 1723, 1724, 1725, 1729, 1730, 1737, 1739, 1741, 1742, 1743, 1744, 1745, 1746, 1747, 1750, 1758, 1761, 1776, 1778, 1781, 1782, 1783, 1784, 1785, 1786, 1788, 1789, 1797, 1802, 1803, 1804, 1806, 1807, 1810, 1830, 1831, 1836, 1837, 1839, 1842, 1843, 1845, 1863, 1864, 1865, 1866, 1884, 1885, 1886, 1888, 1894, 1903, 1907, 1911, 1915, 1921, 1925, 1931, 1932, 1934, 1940, 1949, 1953, 1961, 1967, 1971, 1976, 1978, 1980, 1982, 1984, 1988, 1990, 1994, 1995, 1996, 2000, 2001, 2002, 2004, 2006, 2007, 2008, 2012, 2013, 2014, 2018, 2019, 2020, 2024, 2028, 2031, 2034, 2037, 2040, 2043, 2046, 2049, 2052, 2055, 2058, 2061, 2064, 2067, 2070, 2073, 2076, 2079, 2082, 2085, 2088, 2091, 2094, 2097 or 2100, more preferably compounds are Compounds No. 1, 2, 3, 4, 6, 7, 8, 9, 11, 14, 15, 17, 35, 37, 38, 40, 41, 42, 43, 47, 49, 55, 57, 60, 62, 63, 64, 65, 66, 67, 70, 72, 73, 74, 78, 79, 87, 89, 92, 94, 97, 102, 104, 105, 106, 110, 121, 122, 123, 136, 138, 141, 143, 144, 145, 149, 157, 159, 162, 163, 164, 165, 166, 170, 191, 197, 202, 203, 220, 224, 241, 243, 246, 247, 248, 249, 251, 257, 275, 280, 282, 283, 284, 288, 296, 298, 301, 303, 304, 305, 306, 308, 311, 312, 313, 314, 315, 320, 327, 332, 334, 335, 336, 340, 351, 366, 371, 372, 373, 374, 375, 376, 379, 387, 393, 394, 400, 420, 421, 426, 427, 432, 433, 453, 456, 471, 473, 474, 476, 477, 478, 479, 481, 484, 485, 487, 505, 507, 508, 510, 511, 512, 513, 517, 519, 525, 527, 530, 532, 533, 534, 535, 536, 537, 540, 542, 543, 544, 548, 549, 557, 558, 559, 562, 564, 567, 572, 574, 575, 576, 580, 591, 592, 593, 606, 608, 611, 613, 614, 615, 619, 627, 629, 632, 633, 634, 635, 636, 640, 661, 667, 672, 673, 690, 694, 711, 713, 716, 717, 718, 719, 721, 727, 745, 750, 752, 753, 754, 758, 766, 768, 771, 773, 774, 775, 776, 778, 781, 782, 783, 784, 785, 790, 797, 802, 804, 805, 806, 810, 821, 836, 841, 842, 843, 844, 845, 846, 849, 857, 863, 864, 870, 890, 891, 896, 897, 902, 903, 923, 926, 941, 943, 944, 946, 947, 948, 949, 951, 954, 955, 957, 975, 977, 978, 980, 981, 982, 983, 987, 989, 995, 997, 1000, 1002, 1003, 1004, 1005, 1006, 1007, 1010, 1012, 1013, 1014, 1018, 1019, 1027, 1029, 1032, 1034, 1037, 1042, 1044, 1045, 1046, 1050, 1061, 1062, 1063, 1076, 1078, 1081, 1083, 1084, 1085, 1089, 1097, 1099, 1102, 1103, 1104, 1105, 1106, 1110, 1131, 1137, 1142, 1143, 1160, 1164, 1181, 1183, 1186, 1187, 1188, 1189, 1191, 1197, 1215, 1220, 1222, 1223, 1224, 1225, 1228, 1236, 1238, 1241, 1243, 1244, 1245, 1246, 1248, 1251, 1252, 1253, 1254, 1255, 1260, 1267, 1272, 1274, 1275, 1276, 1280, 1291, 1306, 1311, 1312, 1313, 1314, 1315, 1316, 1319, 1327, 1333, 1334, 1340, 1360, 1361, 1366, 1367, 1372, 1373, 1393, 1396, 1411, 1413, 1414, 1416, 1417, 1418, 1419, 1421, 1424, 1425, 1427, 1445, 1447, 1448, 1450, 1451, 1452, 1453, 1457, 1459, 1465, 1467, 1470, 1472, 1473, 1474, 1475, 1476, 1477, 1480, 1482, 1483, 1484, 1488, 1489, 1497, 1499, 1502, 1504, 1507, 1512, 1514, 1515, 1516, 1520, 1531, 1532, 1533, 1546, 1548, 1551, 1553, 1554, 1555, 1559, 1567, 1569, 1572, 1573, 1574, 1575, 1576, 1580, 1601, 1607, 1612, 1613, 1630, 1634, 1651, 1653, 1656, 1657, 1658, 1659, 1661, 1667, 1685, 1690, 1692, 1693, 1694, 1695, 1698, 1706, 1708, 1711, 1713, 1714, 1715, 1716, 1718, 1721, 1722, 1723, 1724, 1725, 1730, 1737, 1742, 1744, 1745, 1746, 1750, 1761, 1776, 1781, 1782, 1783, 1784, 1785, 1786, 1789, 1797, 1803, 1804, 1810, 1830, 1831, 1836, 1837, 1842, 1843, 1863, 1866, 1885, 1886, 1888, 1894, 1907, 1911, 1915, 1921, 1931, 1932, 1934, 1953, 1961, 1967 or 1971, further more preferably compounds of Compounds No. 1, 2, 3, 4, 6, 8, 9, 11, 15, 17, 38, 40, 41, 42, 43, 47, 62, 63, 64, 72, 73, 74, 79, 87, 89, 92, 94, 97, 104, 106, 110, 121, 136, 143, 144, 145, 149, 157, 163, 164, 165, 166, 191, 197, 203, 220, 247, 248, 249, 251, 257, 282, 283, 284, 303, 312, 313, 314, 315, 334, 372, 373, 374, 375, 393, 394, 421, 427, 433, 471, 473, 474, 476, 477, 478, 479, 481, 485, 487, 505, 508, 510, 511, 512, 513, 517, 532, 533, 534, 535, 542, 543, 544, 549, 557, 558, 559, 562, 564, 567, 574, 576, 580, 591, 606, 613, 614, 615, 619, 627, 633, 634, 635, 636, 661, 667, 673, 690, 717, 718, 719, 721, 727, 752, 753, 754, 773, 782, 783, 784, 785, 804, 842, 843, 844, 845, 863, 864, 891, 897, 903, 941, 943, 944, 946, 948, 949, 951, 955, 957, 978, 980, 981, 982, 983, 987, 1002, 1003, 1004, 1012, 1013, 1014, 1019, 1027, 1029, 1032, 1034, 1037, 1044, 1046, 1050, 1061, 1076, 1083, 1084, 1085, 1089, 1097, 1103, 1104, 1105, 1106, 1131, 1137, 1143, 1160, 1187, 1188, 1189, 1191, 1197, 1222, 1223, 1224, 1243, 1252, 1253, 1254, 1255, 1274, 1312, 1313, 1314, 1315, 1333, 1334, 1361, 1367, 1373, 1411, 1413, 1414, 1416, 1418, 1419, 1421, 1425, 1427, 1448, 1450, 1451, 1452, 1453, 1457, 1472, 1473, 1474, 1482, 1483, 1484, 1489, 1497, 1499, 1502, 1504, 1507, 1514, 1516, 1520, 1531, 1546, 1553, 1554, 1555, 1559, 1567, 1573, 1574, 1575, 1576, 1601, 1607, 1613, 1630, 1657, 1658, 1659, 1661, 1667, 1692, 1693, 1694, 1713, 1722, 1723, 1724, 1725, 1744, 1782, 1783, 1784, 1785, 1803, 1804, 1831, 1837, 1843, 1885, 1886, 1894, 1907 or 1921.

It is particularly preferably mentioned

Compound No.1; [3-[(E)-2-(6,7-difluoroquinolin-2-yl)ethenyl]-5H-dibenzo[a,d]cyclohepten-5-yl]oxyacetic acid, Compound No.4; 3-{[3-[(E)-2-(6,7-difluoroquinolin-2-yl)-ethenyl]-5H-dibenzo[a,d]cyclohepten-5-yl]oxy}-2-methyl-propionic acid, Compound No.8; 3-{[3-[(E)-2-(6,7-difluoroquinolin-2-yl)-ethenyl]-5H-dibenzo[a,d]cyclohepten-5-yl]thio}propionic acid, Compound No.9; 3-{[3-[(E)-2-(6,7-difluoroquinolin-2-yl)-ethenyl]-5H-dibenzo[a,d]cyclohepten-5-yl]thio}-2-methyl-propionic acid, Compound No.471; [3-[(E)-2-(7-chloro-6-fluoroquinolin-2-yl)-ethenyl]-5H-dibenzo[a,d]cyclohepten-5-yl]oxyacetic acid, Compound No.473; 3-{[3-[(E)-2-(7-chloro-6-fluoroquinolin-2-yl)ethenyl]-5H-dibenzo[a,d]cyclohepten-5-yl]oxy}propionic acid, Compound No.474; 3-{[3-[(E)-2-(7-chloro-6-fluoroquinolin-2-yl)ethenyl]-5H-dibenzo[a,d]cycloyhepten-5-yl]oxy}-2-methyl-propionic acid, Compound No.476; [3-[(E)-2-(7-chloro-6-fluoroquinolin-2-yl)ethenyl]-5H-dibenzo[a,d]cyclohepten-5-yl]thioacetic acid, Compound No.477; 2-{[3-[(E)-2-(7-chloro-6-fluoroquinolin-2-yl)ethenyl]-5H-dibenzo[a,d]cyclohepten-5-yl]thio}propionic acid, Compound No.478; 3-{[3-[(E)-2-(7-chloro-6-fluoroquinolin-2-yl)ethenyl]-5H-dibenzo[a,d]cyclohepten-5-yl]thio}propionic acid, Compound No.487; 3-{[3-[(E)-2-(7-chloro-6-fluoroquinolin-2-yl)ethenyl]-5H-dibenzo[a,d]cyclohepten-5-yl]thiomethyl}-cyclopropane acetic acid, Compound No.505; [3-[(E)-2-(7-chloro-6-fluoroquinolin-2-yl)ethenyl]-9-fluoro-5H-dibenzo[a,d]cyclohepten-5-yl]oxy-acetic acid, Compound No.510; 3-{[3-[(E)-2-(7-chloro-6-fluoroquinolin-2-yl)ethenyl]-9-fluoro-5H-dibenzo[a,d]cyclohepten-5-yl]thio}-propionic acid, Compound No.535; [3-[(E)-2-(7-chloro-6-fluoroquinolin-2-yl)ethenyl]-9-chloro-5H-dibenzo[a,d]cyclohepten-5-yl] oxy-acetic acid, Compound No.542; 3-{[3-[(E)-2-(7-chloro-6-fluoroquinolin-2-yl)ethenyl]-9-chloro-5H-dibenzo[a,d]cyclohepten-5-yl]thio}-propionic acid, Compound No.549; 3-{[3-[(E)-2-(7-chloro-6-fluoroquinolin-2-yl)ethenyl]-8-chloro-5H-dibenzo[a,d]cyclohepten-5-yl]thio}-propionic acid, Compound No.557; [3-[(E)-2-(7-chloro-6-fluoroquinolin-2-yl)ethenyl]-6-chloro-5H-dibenzo[a,d]cyclohepten-5-yl] oxy-acetic acid, Compound No.558; 2-{[3-[(E)-2-(7-chloro-6-fluoroquinolin-2-yl)ethenyl]-5H-dibenzo[a,d]cyclohepten-5-yl]oxy}propionic acid, Compound No.559; 3-{[3-[(E)-2-(7-chloro-6-fluoroquinolin-2-yl)ethenyl]-6-chloro-5H-dibenzo[a,d]cyclohepten-5-yl]oxy}-propionic acid, Compound No.562; [3-[(E)-2-(7-chloro-6-fluoroquinolin-2-yl)ethenyl]-6-chloro-5H-dibenzo[a,d]cyclohepten-5-yl] thio-acetic acid, Compound No.564; 3-{[3-[(E)-2-(7-chloro-6-fluoroquinolin-2-yl)ethenyl]-6-chloro-5H-dibenzo[a,d]cyclohepten-5-yl]thio}-propionic acid, Compound No.613; 3-{[3-[(E)-2-(7-chloro-6-fluoroquinolin-2-yl)ethenyl]-9-trifluoromethyl-5H-dibenzo[a,d]cyclohepten-5-yl]thio}propionic acid, Compound No.718; 3-{[3-(7-chloro-6-fluoroquinolin-2-yl) methoxy-5H-dibenzo[a,d]cyclohepten-5-yl] thio}propionic acid, Compound No.1411; [3-[(E)-2-(7-chloroquinolin-2-yl)ethenyl]-5H-dibenzo[a,d]cyclohepten-5-yl]oxyacetic acid, Compound No.1416; [3-[(E)-2-(7-chloroquinolin-2-yl)ethenyl]-5H-dibenzo[a,d]cyclohepten-5-yl]thioacetic acid, Compound No.1418; 3-{[3-[(E)-2-(7-chloroquinolin-2-yl) ethenyl]-5H-dibenzo[a,d]cyclohepten-5-yl] thio}propionic acid, Compound No.1885; 3-{[3-[(E)-2-(5,6,7,8-tetrahydroquinolin-2-yl)ethenyl]-5H-dibenzo[a,d]cyclohepten-5-yl] thio}propionic acid or Compound No.1921; 3-{[3-[(E)-2-(5,6,7,8-tetrahydroquinolin-2-yl)ethenyl]-9-trifluoromethyl-5H-dibenzo[a,d]cyclohepten-5-yl]thio} propionic acid.

The compound represented by the formula (I) of the present invention can be produced by, for example, Preparation process A, B, C, D, E or L shown below.

Preparation process A
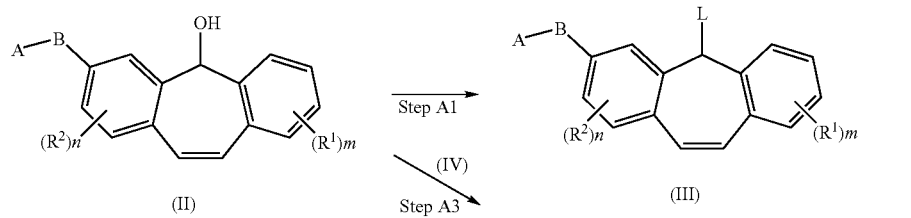
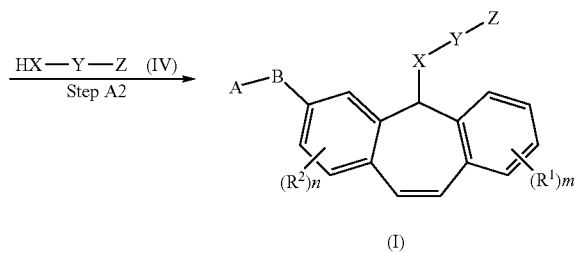
Preparation process B
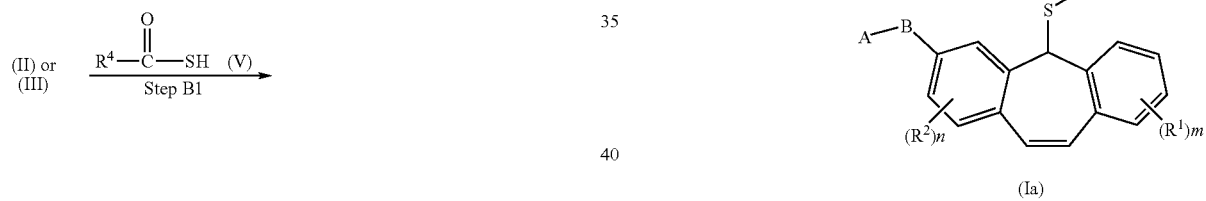
-continued
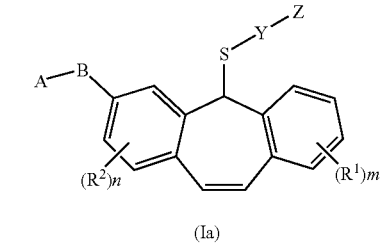
Preparation process C
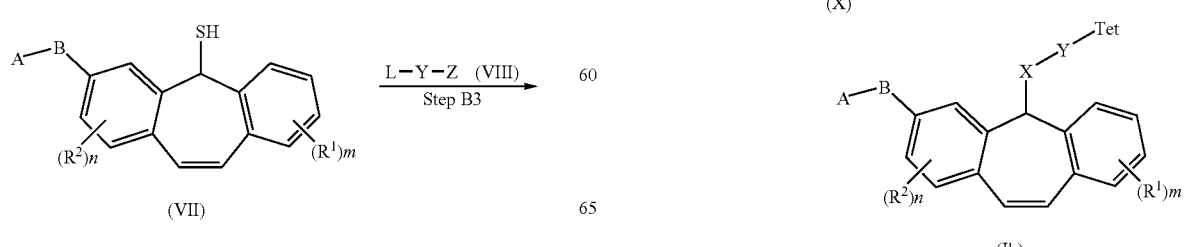
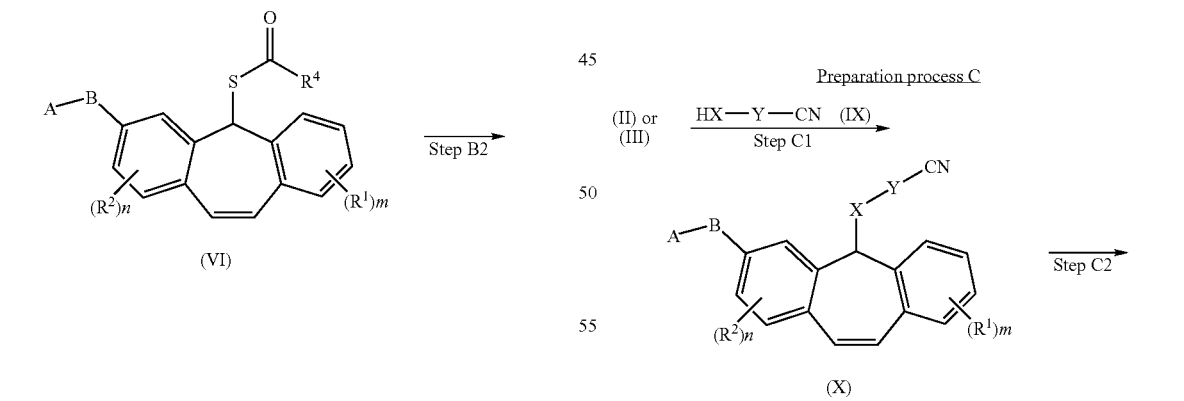
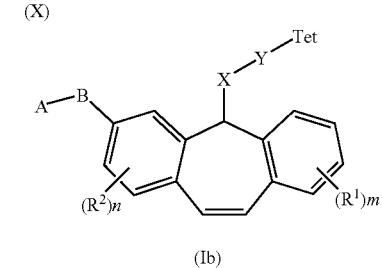

Preparation process D
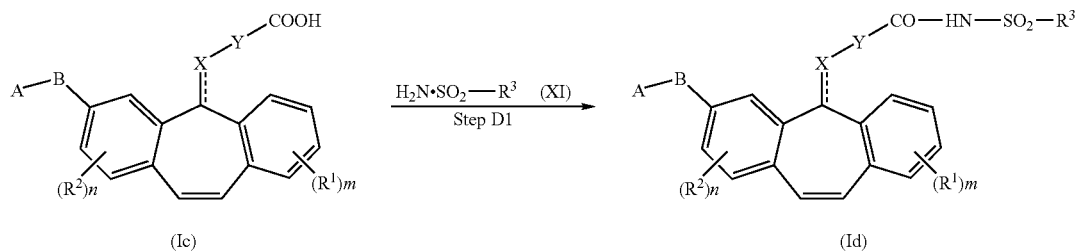
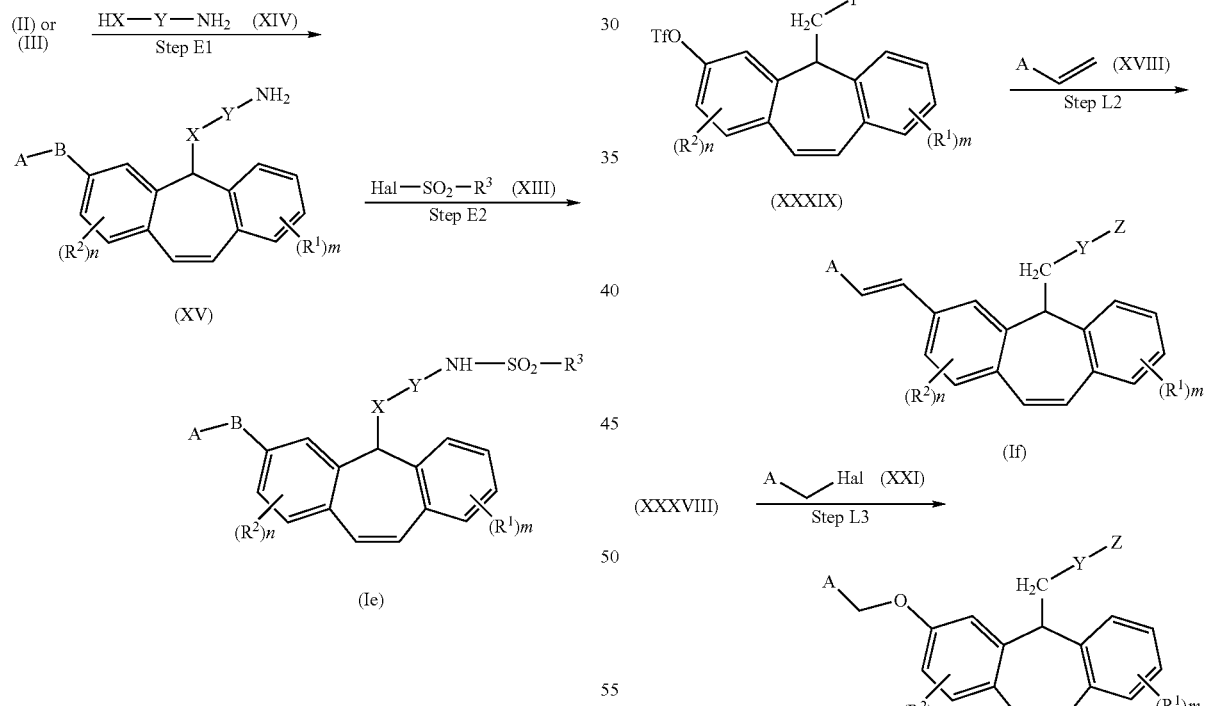
In the above reaction formulae, R¹, R², R³, A, B, X, Y, Z, m and n have the same meanings as defined above, L represents a halogen atom, a $C_1$-$C_4$ alkylsulfonyloxy group, a fluoro $C_1$-$C_4$ alkylsulfonyloxy group or a phenylsulfonyloxy group which may be substituted (said substituent is a $C_1$-$C_4$ alkyl group or a halogen atom), $R^4$ represents a $C_1$-$C_4$ alkyl group or a phenyl group which may be substituted (said substituent is a $C_1$-$C_4$ alkyl group or a halogen atom), Tet represents a 1H-tetrazol-5-yl group, and Hal represents a halogen atom.

Preparation process A is a preparation process of Compound (I).

Step A1 of Preparation process A is a step of synthesizing Compound (III) by subjecting Compound (II) to halogenation or sulfonylation.

Halogenation of Compound (II) is carried out by reacting Compound (II) and a halogenating agent in a solvent or in the absence of a solvent (preferably in a solvent).

The solvent to be used is not specifically limited so long as it does not inhibit the reaction and can dissolve the starting materials with a certain extent, and there may be mentioned, for example, halogenated hydrocarbons such as methylene chloride, chloroform, carbon tetrachloride, 1,2-dichloroethane, etc.; aromatic hydrocarbons such as benzene, toluene, etc.; or aliphatic hydrocarbons such as heptane, hexane, cyclohexane, etc., preferably halogenated hydrocarbons.

As the halogenating agent, there may be mentioned, for example, thionyl chloride, thionyl bromide, phosphorus oxychloride, phosphorus oxybromide, phosphorus pentachloride, etc., preferably thionyl chloride or phosphorus oxychloride. An amount of the halogenating agent to be used is usually 1 to 10-fold mol amount, preferably 1 to 2-fold mol amount based on the amount of Compound (II).

The reaction is carried out in the temperature range usually at −20 to 100° C., preferably at −10 to 30° C. A reaction time may vary depending on the reaction temperature and the like, and it is usually 5 minutes to 10 hours, preferably 10 minutes to 5 hours.

Sulfonylation of Compound (II) is carried out by reacting Compound (II) and a sulfonylating agent in the presence of a base in a solvent.

The solvent to be used is not specifically limited so long as it does not inhibit the reaction and can dissolve the starting materials with a certain extent, and there may be mentioned, for example, the same solvent as used in the above-mentioned halogenation reaction (for example, halogenated hydrocarbons, aromatic hydrocarbons or aliphatic hydrocarbons), etc., preferably halogenated hydrocarbons.

As the sulfonylating agent, there may be mentioned, for example, methanesulfonyl chloride, trifluoromethanesulfonyl chloride, methanesulfonic anhydride, trifluoromethanesulfonic anhydride, benzenesulfonyl chloride, toluenesulfonyl chloride, benzenesulfonyl bromide, toluenesulfonyl bromide, etc., preferably methanesulfonyl chloride, benzenesulfonyl chloride or toluenesulfonyl chloride. An amount of the sulfonylating agent to be used is usually 1 to 10-fold mol amount, preferably 1 to 3-fold mol amount based on the amount of Compound (II).

As the base, there may be mentioned, for example, amines such as triethylamine, tributylamine, diisopropylethylamine, pyridine, picoline, lutidine, 4-dimethylaminopyridine, etc., preferably triethylamine, diisopropylethylamine or pyridine. An amount of the base to be used is usually 1 to 10-fold mol amount, preferably 1 to 2-fold mol amount based on the amount of the sulfonylating agent.

The reaction is carried out in the temperature range usually at −10 to 100° C., preferably at 0 to 30° C. A reaction time may vary depending on the reaction temperature and the like, and it is usually 5 minutes to 10 hours, preferably 30 minutes to 5 hours.

Incidentally, Compound (III) can be separated and purified from the reaction mixture according to the usual method, but a crude product obtained by concentrating the reaction mixture can be used as such in the next step.

Step A2 is carried out by reacting Compound (III) and Compound (IV) in the presence or absence of a base in a solvent.

An amount of Compound (IV) to be used is usually 1 to 10-fold mol amount, preferably 1 to 5-fold mol amount based on the amount of Compound (III).

The solvent to be used is not specifically limited so long as it does not inhibit the reaction and can dissolve the starting materials with a certain extent, and there may be mentioned, for example, aprotic polar solvents such as N,N-dimethylformamide, N-methylpyrrolidone, dimethylsulfoxide, N,N-dimethylacetamide, hexamethylphosphoric acid triamide, etc.; halogenated hydrocarbons such as methylene chloride, chloroform, 1,2-dichloroethane, etc.; ketones such as acetone, methyl ethyl ketone, methyl isobutyl ketone, etc.; nitriles such as acetonitrile, etc.; esters such as ethyl acetate, etc.; or ethers such as diethyl ether, diisopropyl ether, tetrahydrofuran, dioxane,. etc. or a mixed solvent of the above-mentioned solvents, preferably aprotic polar solvents, ethers or a mixed solvent of the above-mentioned solvents.

As the base to be used, there may be mentioned, for example, alkali metal hydrides such as sodium hydride, lithium hydride, etc.; alkali metal amides such as sodium amide, etc.; amines such as triethylamine, tributylamine, diisopropylethylamine, pyridine, picoline, lutidine, 4-dimethylaminopyridine, etc.; or alkali metal carbonates such as sodium carbonate, potassium carbonate, sodium hydrogen carbonate, etc., preferably amines or alkali metal hydrides. An amount of the base to be used may vary depending on the kinds of the starting compound(s), and it is usually 1 to 10-fold mol amount, preferably 1 to 5-fold mol amount based on the amount of Compound (IV). Incidentally, in the present reaction, the base may not necessarily be used.

The reaction is carried out in the temperature range usually at −50 to 150° C., preferably at −10 to 100° C. A reaction time may vary depending on the reaction temperature and the like, and it is usually 5 minutes to 10 hours, preferably 30 minutes to 5 hours.

Step A3 is a step of separately obtaining Compound (I), and it is suitably employed particularly when X is a sulfur atom. The present step is carried out by reacting Compound (II) and Compound (IV) in the presence of an acid catalyst in a solvent.

An amount of Compound (IV) to be used is usually 1 to 5-fold mol amount, preferably 1 to 2-fold mol amount based on the amount of Compound (II).

The solvent to be used is not specifically limited so long as it does not inhibit the reaction and can dissolve the starting materials with a certain extent, and there may be mentioned, for example, halogenated hydrocarbons such as methylene chloride, chloroform, 1,2-dichloroethane, etc.; alcohols such as methanol, ethanol, propanol, isopropanol, butanol, etc.; aprotic polar solvents such as N,N-dimethylformamide, N-methylpyrrolidone, dimethylsulfoxide, N,N-dimethylacetamide, hexamethylphosphoric acid triamide, etc.; or ethers such as diethyl ether, diisopropyl ether, tetrahydrofuran, dioxane, etc., preferably halogenated hydrocarbons.

As the acid catalyst to be used, there may be mentioned, for example, mineral acids such as hydrochloric acid, sulfuric acid, phosphoric acid, etc.; organic acids such as methanesulfonic acid, trifluoroacetic acid, etc.; Lewis acids such as boron trifluoride-diethyl ether complex, zinc chloride, tin tetrachloride, aluminum chloride, etc., preferably organic acids or boron trifluoride-diethyl ether complex. An amount of the catalyst to be used is usually 0.1 to 50-fold mol amount, preferably 1 to 10-fold mol amount based on the amount of Compound (II), and when the organic acids are used, it can be used with a markedly excessive amount also as a solvent.

The reaction is carried out in the temperature range usually at −10 to 100° C., preferably at 0 to 30° C. A reaction time may vary depending on the reaction temperature and the like, and it is usually 5 minutes to 10 hours, preferably 10 minutes to 5 hours.

Incidentally, in Compound (I), a compound wherein Z is a carboxyl group (Compound Ic mentioned below) can be directly produced by using Compound (IV) wherein Z is a carboxyl group, or can be synthesized, by using Compound (IV) wherein Z is a protected carboxyl group (the protective group is preferably a $C_1$-$C_4$ alkyl group), by once leading to Compound (I) wherein Z is a protected carboxyl group, and then, hydrolyzing the protective group under acidic or alkaline conditions by the conventional manner.

Also, in Compound (I), a desired protective group can be introduced into Compound (Ic) wherein Z is a carboxyl group according to the conventoinally known method (for example, see written by W. Greene and P. G. H. Wult, "Protective Group in Organic Synthesis" $2^{nd}$ Ed., John Wiley & Sons, p. 224).

Preparation process B is a preparation process of Compound (Ia) wherein X is a sulfur atom in Compound (I).

A reaction of obtaining Compound (VI) from Compound (II) or Compound (III) and a thiocarboxylic acid (V) in Step B1 can be carried out in the same manner as in the method described in Step A2 or Step A3 in the above-mentioned Preparation process A except for using a thiocarboxylic acid (V) in place of Compound (IV).

In Step B2, Compound (VII) can be synthesized by hydrolyzing Compound (VI) under alkaline conditions according to the conventional manner.

Step B3 is carried out by reacting Compound (VII) and Compound (VIII) in the presence of a base in a solvent. The present reaction can be carried out in the same manner as in the method described in the above-mentioned Step A2 except for using Compound (VII) in place of Compound (II), and using Compound (VIII) in place of Compound (IV).

An amount of Compound (VIII) to be used is usually 1 to 10-fold mol amount, preferably 1 to 5-fold mol amount based on the amount of Compound (VII).

Preparation process C is a preparation process of Compound (Ib) wherein Z is a 1H-tetrazole group in Compound (I), and in Step C1, a reaction of obtaining Compound (X) from Compound (II) or Compound (III) and Compound (IX) can be carried out in the same manner as in the method described in the above-mentioned Process A except for using Compound (IX) in place of Compound (IV).

In Step C2, Compound (Ib) can be synthesized by reacting Compound (X) and an azide compound in a solvent.

As the azide compound to be used, there may be mentioned, for example, alkali metal azides such as sodium azide, potassium azide, lithium azide, etc.; alkaline earth metal azides such as calcium azide, magnesium azide, etc.; or organic tin azides such as trimethyl tin azide, tributyl tin azide, triphenyl tin azide, etc. An amount of the azide compound to be used, it is usually 1 to 10-fold mol amount, preferably 1 to 5-fold mol amount based on the amount of Compound (X). In the reaction, the azide compound is used singly, or may be used in combination with, for example, Lewis acids such as aluminum chloride, stannic chloride, zinc chloride, titanium chloride, boron trifluoride-diethyl ether complex, etc.; ammonium salts such as ammonium chloride, tetramethylammonium chloride, etc.; sulfonic acids such as methanesulfonic acid, ethanesulfonic acid, etc.; alkali metal chlorides such as lithium chloride, etc.; or amine salts such as triethylamine hydrochloride, etc.

The solvent to be used is not specifically limited so long as it does not inhibit the reaction and can dissolve the starting materials with a certain extent, and there may be mentioned, for example, aprotic polar solvents such as N,N-dimethylformamide, dimethylsulfoxide, N-methylpyrrolidone, N,N-dimethylacetamide, etc.; ethers such as tetrahydrofuran, dimethoxyethane, diethoxyethane, dioxane, etc.; aromatic hydrocarbons such as benzene, toluene, xylene, etc.; or aliphatic hydrocarbons such as hexane, petroleum ether, etc.

The reaction is carried out in the temperature range usually at 0 to 200° C., preferably 50 to 150° C. A reaction time may vary depending on the reaction temperature and the like, and it is usually 1 hour to 72 hours, preferably 3 hours to 48 hours.

Preparation process D is a preparation process of Compound (Id) wherein Z is a —CO—NH—$SO_2$—$R^3$ group in Compound (I). Step D1 comprises a method of reacting Compound (Ic) and Compound (XI) in the presence of a condensing agent (Step D1a), or once leading Compound (Ic) to its reactive derivative (Step D1b), and then, reacting the reactive derivative and Compound (XI) in the presence of a base (Step D1c)

As the condensing agent to be used in Step D1a, there may be mentioned, for example, N,N'-dicyclohexylcarbodiimide (DCC), 1-ethyl-3-(3-dimethylaminopropyl)carbodiimide hydrochloride (EDC), N,N'-carbonyldiimidazol (CDI), diphenylphosphoric acid azide, hexafluorophosphoric acid benzotriazol-1-yloxy-tris-(dimethylamino)phosphonium (BOP), hexafluorophosphoric acid benzotriazol-1-yloxy-tris-pyrrolidinophosphonium (PyBOP), hexafluorophosphoric acid 2-(1H-benzotriazol-1-yl)-1,1,3,3-tetramethyluronium (HBTU), tetrafluoroboric acid 2-(1H-benzotriazol-1-yl)-1,1,3,3-tetramethyluronium (TBTU), etc., preferably DCC or EDC. An amount of the condensing agent to be used is usually 1 to 5-fold mol amount, preferably 1 to 3-fold mol amount based on the amount of Compound (Ic).

The solvent to be used is not specifically limited so long as it does not inhibit the reaction and can dissolve the starting materials with a certain extent, and there may be mentioned, for example, ethers such as diethyl ether, tetrahydrofuran, dimethoxyethane, diethoxyethane, dioxane, etc.; nitriles such as acetonitrile, etc.; aprotic polar solvents such as N,N-dimethylformamide, dimethylsulfoxide, N-methylpyrrolidone, N,N-dimethylacetamide, etc.; or halogenated hydrocarbons such as methylene chloride, chloroform, 1,2-dichloroethane, etc., and these can be used singly or as a mixed solvent.

The reaction is carried out in the temperature range usually at −20 to 100° C., preferably at 0 to 50° C. A reaction time may vary depending on the reaction temperature and the like, and it is usually 30 minutes to 24 hours, preferably 1 hour to 10 hours.

As the reactive derivative of Compound (Ic) in Step D1b, there may be mentioned, for example, acid halide derivatives of Compound (Ic) such as acid bromide compound or acid chloride compound of Compound (Ic); or reactive amide derivatives such as Compound (Ic) and imidazol, 3,5-dimethylpyrazol or triazole and Compound (Ic), etc., preferably acid halide derivative.

The acid halide compound of Compound (Ic) can be produced according to the conventional manner, and for example, it can be synthesized by reacting Compound (Ic) with a halogenating agent (for example, thionyl chloride, thionyl bromide, phosphorus pentachloride, etc.) in a solvent (for example, halogenated hydrocarbons such as methylene chloride, chloroform, 1,2-dichloroethane, etc.).

Also, reactive amide derivatives of Compound (IC) can be produced according to the conventional manner, and for example, in the case of an imidazolidated compound of Compound (Ic), it can be synthesized by reacting Compound (Ic) with 1,1'-carbonyldiimidazole in a solvent (for example, ethers such as diethyl ether, tetrahydrofuran, dimethoxyethane, diethoxyethane, dioxane, etc.; nitriles such as acetonitrile, etc.; aprotic polar solvents such as N,N-dimethylformamide, dimethylsulfoxide, N-methylpyrrolidone, N,N-dimethylacetamide, etc.; or halogenated hydrocarbons such as methylene chloride, chloroform, 1,2-dichloroethane, etc.).

The reactive derivatives of Compound (Ic) can be used as such in the next Step D1c without separation after formation thereof.

Amounts of the reactive derivative of Compound (Ic) in Step D1c and Compound (XI) to be used in the reaction with Compound (XI) are each usually 1 to 10-fold mol amount, preferably 1 to 5-fold mol amount based on the amount of Compound (Ic).

As the base to be used, there may be mentioned, for example, amines such as triethylamine, tributylamine, diisopropylethylamine, pyridine, picoline, lutidine, 4-dimethylaminopyridine, 1,8-diazabicyclo[5.4.0]-7-undecene, 1,5-diazabicyclo[4.3.0]-5-nonene, etc., preferably triethylamine, tributylamine or diisopropylethylamine. An amount of the base to be used is usually 1 to 10-fold mol amount, preferably 1 to 5-fold mol amount based on the amount of Compound (Ic).

The reaction is carried out in the temperature range usually at 0 to 150° C., preferably at 10 to 100° C. A reaction time may vary depending on the reaction temperature and the like, and it is usually 5 minutes to 48 hours, preferably 30 minutes to 24 hours.

Also, Compound (Id) can be produced by a method which is through Compound (XII).

Step D2 is a step of obtaining Compound (XII) by amidating the carboxyl group of Compound (Ic), and can be carried out by optionally employing a method among the conventionally known methods. For example, Compound (XII) can be easily produced by reacting the above-mentioned reactive derivative of Compound (Ic) and ammonia.

Step D3 is carried out by reacting Compound (XII) and Compound (XIII) in the presence of a base in a solvent.

An amount of Compound (XIII) to be used is usually 1 to 10-fold mol amount, preferably 1 to 5-fold mol amount based on the amount of Compound (XII).

As the solvent and the base to be used, the same as those used in the above-mentioned Step D1 can be used, and the reaction can be carried out under the same conditions as those of Step D1.

Preparation process E is a preparation process of Compound (Ie) wherein Z is a —NH—SO$_2$—R$^3$ group in Compound (I).

In Step E1, the reaction of obtaining Compound (XV) from Compound (II) or Compound (III) and Compound (XIV) can be carried out by the same method as those mentioned in the above-mentioned method A except for using Compound (XIV) in place of Compound (IV).

Step E2 is carried out by reacting Compound (XV) and Compound (XIII) in the presence of a base in a solvent.

An amount of Compound (XIII) to be used is usually 1 to 10-fold mol amount, preferably 1 to 5-fold mol amount based on the amount of Compound (XV).

As the solvent to be used, the same solvent as those mentioned in the above-mentioned Step D1 may be mentioned, and preferably halogenated hydrocarbons or aprotic polar solvents.

As the base to be used, the same base as those mentioned in the above-mentioned Step D1 may be mentioned, and an amount of the base to be used is usually 1 to 10-fold mol amount, preferably 1 to 5-fold mol amount based on the amount of Compound (XIV). Also, in the present reaction, the base may be used in an extremely excessive amount also as a solvent.

The reaction is carried out in the temperature range usually at −20 to 100° C., preferably at 0 to 50° C. A reaction time may vary depending on the reaction temperature and the like, and it is usually 5 minutes to 10 hours, preferably 30 minutes to 5 hours.

Preparation process L is a preparation process of Compound (If) wherein X is a methylene group and B is —CH═CH— in Compound (I), and Compound (Ig) wherein X is a methylene group and B is —CH$_2$O— in Compound (I).

Step L1 is carried out in the same manner as in Step F1 mentioned below except for using Compound (XXXVIII) in place of Compound (XVI), and Step L2 is carried out in the same manner as in Step F2 mentioned below except for using Compound (XXXIX) in place of Compound (XVII).

Step L3 is carried out in the same manner as in Step G1 of preparation process G mentioned below except for using Compound (XXXVIII) in place of Compound (XVI).

In the above-mentioned respective reactions, the formed objective Compound can be collected from the reaction mixture according to the conventional manner. For example, when insoluble materials are present, the objecttive compound can be obtained by, after removing the insoluble materials by filtration, removing the solvent, or by removing the solvent under reduced pressure, adding water to the residue, extracting the mixture with a water-immiscible organic solvent such as ethyl acetate, etc., if necessary, after drying over anhydrous sodium sulfate, etc., removing the solvent, and further, if necessary, by purifying with the conventional manner, for example, recrystallization, column chromatography, etc.

Also, the compound of the formula (I) of the present invention can be converted into a pharmaceutically acceptable salt by treating with an acid or a base according to the conventional manner. For example, in an inert solvent (preferably ethers such as diethyl ether, tetrahydrofuran, dimethoxyethane, diethoxyethane, dioxane, etc.; alcohols such as methanol, ethanol, propanol, isopropanol, butanol, etc.; halogenated hydrocarbons such as methylene chloride, chloroform, etc.; or water), it is reacted with a desired acid or a base, and the solvent is removed, or else, precipitated crystals are collected by filtration to obtain a desired salt. Also, it can be directly separated as a salt from the reaction mixture in the final reaction step.

Moreover, in the compound of the formula (I), there exist optical isomer(s) (including diastereomer) due to an asymmetric carbon(s) and/or geometric (E,Z) isomers due to an unsaturated carbon. These respective isomers can be separated by treating the corresponding racemic isomers or geometric isomer mixture by usual optical resolution methods (fractional recrystallization method, optical resolution column chromatography method or diastereomer method, etc.) or separation methods (recrystallization method, column chromatography method, etc.). For example, when optical isomers are to be separated, Compound (I) which is racemic mixture is reacted with an optically active sulfonic acid compound ((S) or (R)-camphor-10-sulfonic acid, etc.), to obtain one of the diastereomer salts, and if necessary, further subjecting to purification, the resulting diastereomer salt is resolved according to the conventional manner to obtain an optical isomer. Also, when the above reaction is carried out by using the starting compound which has been subjected to optical resolution or separation, a desired optical isomer or geometric isomer can be obtained.

Compound (IV), (V), (VIII), (IX), (XI), (XIII), (XIV) and other sub-starting materials which are used as starting materials in the above-mentioned Preparation process A, B, C, D, E or L are each well known compounds or can be easily produced according to the conventionally know method. Also, Compound (II) and (XXXVIII) can be produced by using either one of or in combination with two or more of Preparation processes F, G, H, I, J, K, N, O and P shown below optionally.

Preparation process F

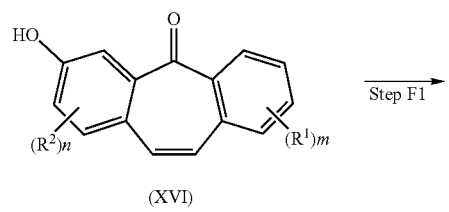

(XVI)

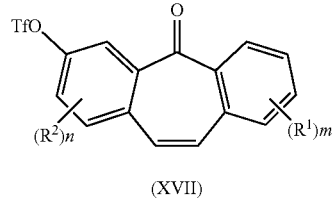

(XVII)

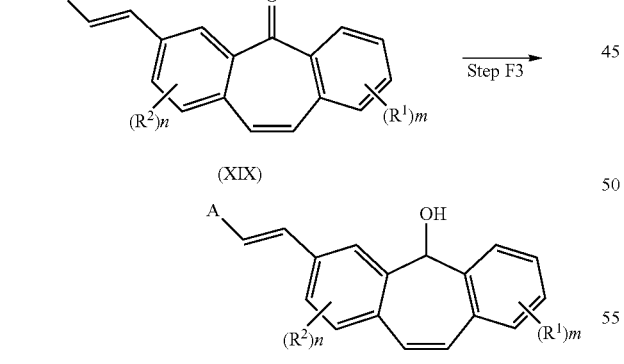

(XIX)

(IIa)

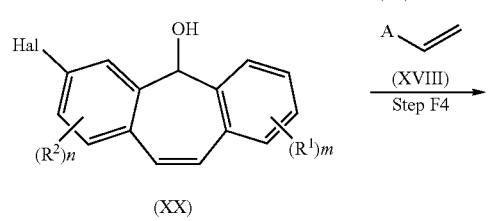

(XX)

-continued

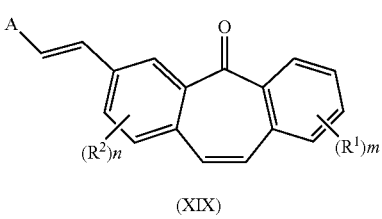

(XIX)

Preparation process G

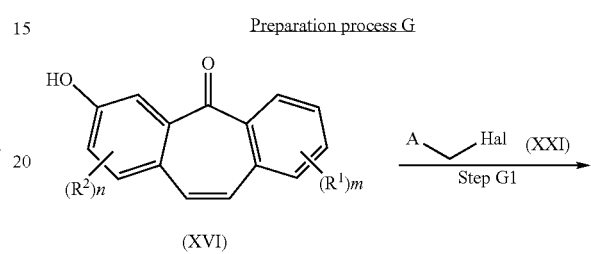

(XVI)

(XXII)

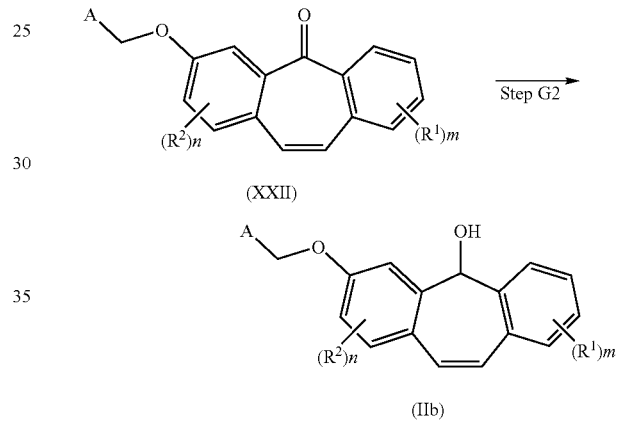

(IIb)

Preparation process H

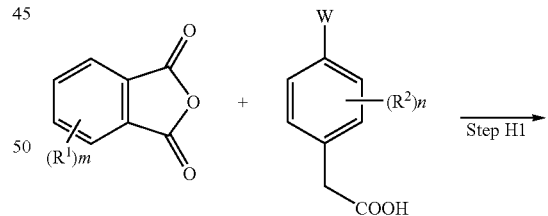

(XXIII)   (XXIV)

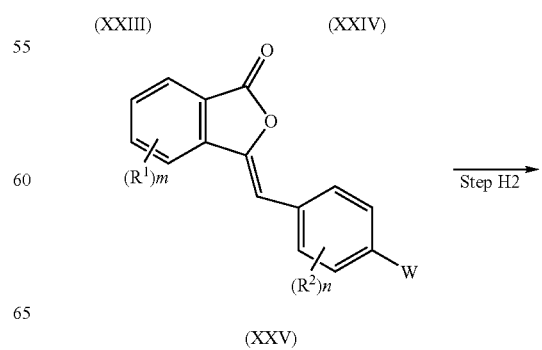

(XXV)

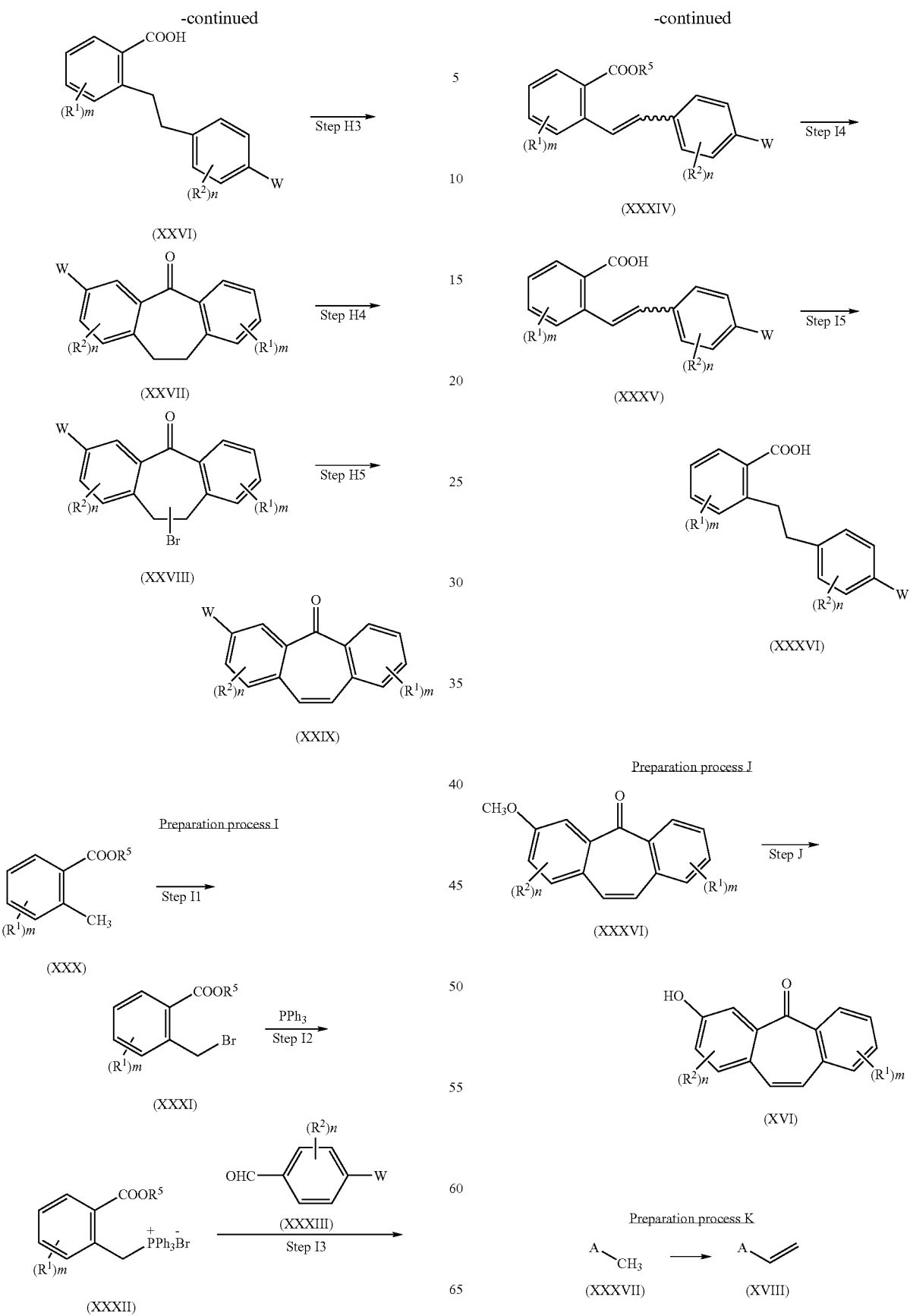

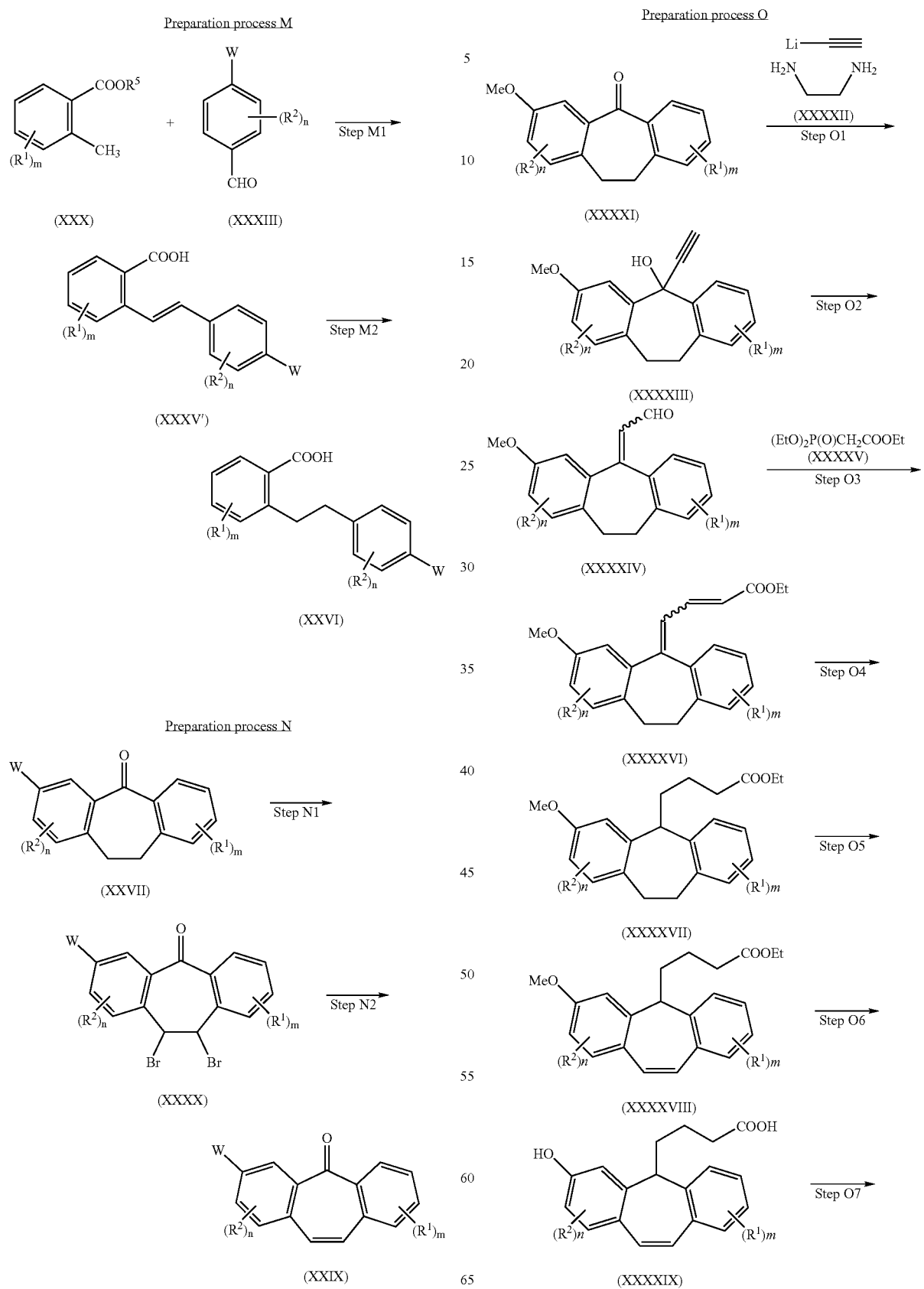

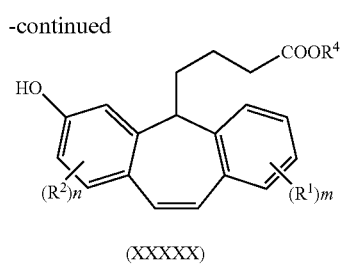

(XXXXX)

Preparation process P

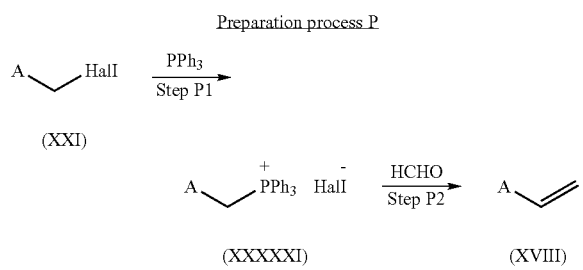

wherein R₁, R², A, Hal, m and n have the same meanings as defined above, Tf represents a trifluoromethanesulfonyl group, W represents a methoxy group or a halogen atom (preferably a bromine atom or an iodine atom), and $R^5$ represents a $C_1$-$C_4$ alkyl group.

Preparation process F is a preparation process of Compound (IIa).

Step F1 is a step of synthesizing Compound (XVII) by trifrating Compound (XVI).

Trifration of Compound (XVI) is carried out by reacting Compound (XVI) and a trifrating agent in the presence of a base in a solvent.

The solvent to be used is not specifically limited so long as it does not inhibit the reaction and can dissolve the starting materials with a certain extent, and there may be mentioned, for example, halogenated hydrocarbons such as methylene chloride, chloroform, carbon tetrachloride, 1,2-dichloroethane, etc.; aromatic hydrocarbons such as benzene, toluene, etc.; or aliphatic hydrocarbons such as heptane, hexane, cyclohexane, etc., preferably halogenated hydrocarbons.

As the trifrating agent, there may be mentioned, for example, trifluoromethanesulfonyl chloride or trifluoromethanesulfonic anhydride, preferably trifluoromethanesulfonic anhydride. An amount of the trifrating agent to be used is usually 1 to 10-fold mol amount, preferably 1 to 2-fold mol amount based on the amount of Compound (XVI).

As the base, there may be mentioned, for example, amines such as triethylamine, tributylamine, diisopropylethylamine, pyridine, picoline, lutidine, 4-dimethylaminopyridine, etc., preferably triethylamine, diisopropylethylamine or pyridine. An amount of the base to be used is usually 1 to 10-fold mol amount, preferably 1 to 2-fold mol amount based on the amount of the trifrating agent.

The reaction is carried out in the temperature range usually at −20 to 100° C., preferably at −10 to 30° C. A reaction time may vary depending on the reaction temperature and the like, and it is usually 5 minutes to 10 hours, preferably 30 minutes to 5 hours.

Step F2 is carried out by reacting Compound (XVII) and Compound (XVIII) in an inert gas atmosphere such as nitrogen, helium or argon in the presence of a catalyst (palladium catalyst) and a base, in a solvent.

The solvent to be used is not specifically limited so long as it does not inhibit the reaction and can dissolve the starting materials with a certain extent, and there may be mentioned, for example, polar solvents such as N,N-dimethylformamide, N,N-dimethylacetamide, N-methylpyrrolidone, dimethylsulfoxide, etc., or acetonitrile, etc., preferably N,N-dimethylformamide.

As the base, there may be mentioned, for example, amines such as triethylamine, tributylamine, diisopropylethylamine, pyridine, picoline, lutidine, 4-dimethylaminopyridine, etc., preferably triethylamine. An amount of the base to be used is usually 1 to 10-fold mol amount, preferably 1 to 2-fold mol amount based on the amount of Compound (XVII).

Also, in place of the amines, quaternary amines such as tetrabutyl ammonium chloride, tetrabutyl ammonium bromide, etc., and alkali metal carbonates such as potassium carbonate, sodium carbonate, sodium hydrogen carbonate, etc. may be used in combination.

As the palladium catalyst, there may be mentioned, for example, palladium acetate, palladium acetate-triphenylphosphine, dichlorobis(triphenylphosphine)palladium, tetrakis(triphenylphosphine)palladium, etc., preferably palladium acetate-triphenylphosphine or tetrakis(triphenylphosphine)palladium. An amount of the palladium catalyst to be used is usually 0.01 to 1-fold mol amount, preferably 0.01 to 0.3-fold mol amount based on the amount of Compound (XVII).

Also, lithium chloride or lithium bromide may be co-present in the reaction.

The reaction is carried out in the temperature range usually at 0° C. to 200° C., preferably at 50° C. to 150° C. A reaction time may vary depending on the reaction temperature and the like, and it is usually 30 minutes to 48 hours, preferably 1 hour to 24 hours.

Reduction from Compound (XIX) to Compound (IIa) in Step F3 can be carried out by using a reducing agent in a solvent.

As the reducing agent, there may be mentioned, for example, sodium borohydride, lithium borohydride, sodium cyanoborohydride, lithium aluminum hydride, etc., preferably lithium borohydride.

The solvent to be used may be mentioned, for example, alcohols such as methanol, ethanol, propanol, butanol, etc.; ethers such as tetrahydrofuran, dioxane, 1,2-dimethoxyethane, etc.; nitrites such as acetonitrile, etc.; amides such as N,N-dimethylformamide, N,N-dimethylacetamide, N-methylpyrrolidone, etc.; water or a mixed solvent of the above-mentioned solvents, preferably tetrahydrofuran or a mixed solvent with tetrahydrofuran.

The reaction is carried out in the temperature range usually at −10 to 150° C., preferably at 0 to 100° C. A reaction time may vary depending on the reaction temperature and the like, and it is usually 10 minutes to 10 hours, preferably 30 minutes to 6 hours.

Step F4 is another process for producing Compound (XIX), and carried out in the similar conditions as those mentioned in the above-mentioned Step F2 by using Compound (XX) (preferably a bromine atom or an iodine atom as Hal) in place of Compound (XVII) as a starting compound.

Preparation process G is a preparation process of Compound (IIb).

Step G1 is carried out by reacting Compound (XVI) and Compound (XXI) in the presence of a base in a solvent, and carried out in the similar method as those mentioned in the above-mentioned Step A2 except for using Compound (XVI) in place of Compound (III), and using Compound (XXI) in place of Compound (IV).

Reduction from Compound (XXII) to Compound (IIb) in Step G2 is carried out in a solvent by using a reducing agent. It is carried out in the similar method as those mentioned in the above-mentioned Step F3 except for using Compound (XXII) in place of Compound (XIX).

Preparation process H is a preparation process of Compound (XXIX), and includes preparation processes of Compound (XX: W=a halogen atom) and a compound (XXXVI: W=methoxy group) mentioned below.

Preparation process H can be easily carried out by referring to the conventionally known method as disclosed in, for example, Helv. Chim. Acta, 48, 1240 (1965) or U.S. Pat. No. 1,207,404 B.

Step H1 is carried out by, for example, reacting Compound (XXIII) and Compound (XXIV) in the presence of a base such as sodium acetate in the absence of a solvent or using diphenyl ether as a solvent under heating (preferably at 100° C. to 250° C.) to carry out dehydration condensation.

A step of obtaining Compound (XXVI) by reducing Compound (XXV) in Step H2 is carried out by optionally employing a reducing method in which hydrogen is used in the presence of a Raney-nickel catalyst (U.S. Pat. No. 1,207,404 B) or a reducing method in which hydroiodic acid/red phosphorus are used (Helv. Chim. Acta, 48, 1240 (1965)), and when W is a halogen atom, the latter reduction method is suitably used.

A step of obtaining Compound (XXVII) by subjecting Compound (XXVI) to dehydration and cyclization in Step H3 is carried out by reacting Compound (XXVI) in a solvent or in the absence of a solvent, and in the presence of a catalyst (a dehydrating agent).

The solvent to be used is not specifically limited so long as it does not inhibit the reaction and can dissolve the starting materials with a certain extent, and there may be mentioned, for example, halogenated hydrocarbons such as methylene chloride, chloroform, carbon tetrachloride, 1,2-dichloroethane, etc.; nitrobenzene, and carbon disulfide, preferably halogenated hydrocarbons.

As the catalyst to be used, there may be mentioned, for example, mineral acids such as sulfuric acid, phosphoric acid, polyphosphoric acid, etc.; acid anhydrides such as methanesulfonic anhydride, trifluoroacetic anhydride, etc.; Lewis acids such as boron trifluoride-diethyl ether complex, aluminum chloride, zinc chloride, etc., preferably polyphosphoric acid, methanesulfonic anhydride, trifluoroacetic anhydride or boron trifluoride-diethyl ether complex. Also, a mixture of trifluoroacetic anhydride and boron trifluoride-diethyl ether complex is suitably used. An amount of the catalyst to be used is usually 1 to 10-fold mol amount, preferably 1 to 5-fold mol amount based on the amount of Compound (XXVI).

The reaction is carried out in the temperature range usually at 0 to 150° C., preferably at 0 to 100° C. A reaction time may vary depending on the reaction temperature and the like, and it is usually 5 minutes to 10 hours, preferably 30 minutes to 5 hours.

For example, when polyphosphoric acid, etc. as the catalyst is used with a large amount, a solvent may not be specifically added. In this case, an amount thereof is 5 to 100-fold amount, preferably 10 to 30-fold amount by weight based on the amount of Compound (XXVI).

The reaction is carried out in the temperature range usually at 0 to 250° C., preferably at 100 to 200° C. A reaction time may vary depending on the reaction temperature and the like, and it is usually 10 minutes to 12 hours, preferably 30 minutes to 5 hours.

A step of obtaining Compound (XXVIII) by brominating Compound (XXVII) in Step H4 can be easily carried out by the conventionally known method, for example, in which reaction is carried out under irradiation of light using N-bromosuccineimide as a brominating agent, or reaction is carried out in the presence of a radical initiating agent such as azobisisobutyronitrile (AIBN), benzoyl peroxide (BPO), etc. The solvent to be used is not specifically limited so long as it does not inhibit the reaction and can dissolve the starting materials with a certain extent, and there may be mentioned, for example, halogenated hydrocarbons such as dichloromethane, chloroform, carbon tetrachloride, 1,2-dichloroethane, etc., preferably 1,2-dichloroethane.

When the reaction is carried out under irradiation of light, as a light source, a mercury lamp is suitably used. The N-bromosuccinimide to be-used is usually 1 to 2.5-fold mol amount, preferably 1 to 1.1-fold mol amount based on the amount of Compound (XXVII). A reaction temperature is usually in the range of 0 to 80° C., preferably 30 to 60° C.

A reaction time may vary depending on the reaction temperature and the like, and it is usually 1 hour to 12 hours, preferably 3 hours to 8 hours.

When the reaction is carried out in the presence of a radical initiator such as azobisisobutyronitrile (AIBN), benzoyl peroxide (BPO), etc., an amount of the radical initiator to be used is usually 0.001 to 0.1-fold mol amount, preferably 0.01 to 0.05-fold mol amount based on the amount of Compound (XXVII).

The N-bromosuccinimide to be used is usually 1 to 4-fold mol amount, preferably 1 to 1.1-fold mol amount based on the amount of Compound (XXVII).

The reaction is carried out in the temperature range usually at 50 to 100° C., preferably at 60 to 80° C. A reaction time may vary depending on the reaction temperature and the like, and it is usually 30 minutes to 12 hours, preferably 1 hour to 6 hours.

A step of obtaining Compound (XXIX) by removing hydrogen bromide from Compound (XXVIII) in Step H5 is carried out by treating Compound (XXVIII) with a base (preferably triethylamine or 1,5-diazabicyclo[4.3.0]-5-nonene (DBN)).

The solvent to be used is not specifically limited so long as it does not inhibit the reaction and can dissolve the starting materials with a certain extent, and there may be mentioned, for example, halogenated hydrocarbons such as dichloromethane, carbon tetrachloride, 1,2-dichloroethane, etc.; aromatic hydrocarbons such as benzene, toluene, xylene, etc.; esters such as methyl acetate, ethyl acetate, etc.; nitrites such as acetonitrile, propionitrile, etc., preferably 1,2-dichloroethane, toluene, ethyl acetate or acetonitrile.

An amount of the base to be used is 1 to 150-fold mol amount, preferably 1 to 15-fold mol amount based on the amount of Compound (XXVIII).

The reaction is carried out in the temperature range usually at 0 to 150° C., preferably at 60 to 120° C. A reaction time may vary depending on the reaction temperature and the like, and it is usually 30 minutes to 12 hours, preferably 1 hour to 3 hours.

Preparation process I is another process for producing Compound (XXVI) in Preparation process H.

Bromination reaction of Compound (XXX) in Step I1 is carried out in the same manner as in Step H4 except for using Compound (XXX) in place of Compound (XXVII).

Step I2 can be easily carried out by reacting Compound (XXXI) and triphenylphosphine in a solvent.

The solvent to be used is not specifically limited so long as it does not inhibit the reaction and can dissolve the starting materials with a certain extent, and there may be mentioned, halogenated hydrocarbons such as dichloromethane, chloroform, carbon tetrachloride, 1,2-dichloroethane, etc.; aromatic hydrocarbons such as benzene, toluene, xylene, etc.; esters such as methyl acetate, ethyl acetate, etc.; nitrites such as acetonitrile, propionitrile, etc.; amides such as N,N-dimethylformamide, N,N-dimethylacetamide, N-methylpyrrolidone, etc., ketones such as acetone, methyl ethyl ketone, etc.; or dimethylsulfoxide, preferably ethyl acetate, or acetonitrile.

An amount of the triphenylphosphine to be used is 1 to 2-fold mol amount, preferably 1 to 1.5-fold mol amount based on the amount of Compound (XXXI).

The reaction is carried out in the temperature range usually at 0 to 150° C., preferably at 60 to 100° C. A reaction time may vary depending on the reaction temperature and the like, and it is usually 30 minutes to 12 hours, preferably 1 hour to 3 hours.

A reaction of Compound (XXXII) and Compound (XXXIII) in Step I3 is a reaction known as the so-called Wittig reaction, and carried out-optionally by selecting the conventionally known conditions.

An amount of Compound (XXXIII) to be used is usually 1 to 10-fold mol amount, preferably 1 to 1.5-fold mol amount based on the amount of Compound (XXXII).

The solvent to be used is not specifically limited so long as it does not inhibit the reaction and can dissolve the starting materials with a certain extent, and there may be mentioned, halogenated hydrocarbons such as dichloromethane, carbon tetrachloride, chloroform, 1,2-dichloroethane, etc.; ethers such as diethyl ether, tetrahydrofuran, dioxane, dimethoxyethane, etc.; aromatic hydrocarbons such as benzene, toluene, xylene, etc.; esters such as methyl acetate, ethyl acetate, etc.; nitrites such as acetonitrile, propionitrile, etc.; amides such as N,N-dimethylformamide, N,N-dimethylacetamide, N-methylpyrrolidone, etc.; dimethylsulfoxide or a mixed solvent of the above-mentioned solvents, and further, a mixed solvent of the above solvents and water may be also used.

The base to be used may include alkali metal hydroxides such as lithium hydroxide, sodium hydroxide, potassium hydroxide, etc.; alkali metal carbonates such as sodium carbonate, potassium carbonate, etc.; alkali metal alkoxides such as sodium methoxide, sodium ethoxide, sodium t-butoxide, potassium t-butoxide, etc.; alkali metal hydrides such as sodium hydride, potassium hydride, etc.; alkyl lithium such as methyl lithium, butyl lithium, etc.; metal amides such as sodium amide, lithium diisopropyl amide, etc.; and organic amines such as triethylamine, diisopropylethylamine, tripropylamine, 1,5-diazabicyclo-[4.3.0]-5-nonene (DBN), etc. An amount of the base to be used is usually 1 to 5-fold mol amount, preferably 1 to 2-fold mol amount based on the amount of is Compound (XXXII).

The reaction is carried out in the temperature range usually at 0 to 150° C., preferably at 15 to 80° C. A reaction time may vary depending on the reaction temperature and the like, and it is usually 1 hour to 24 hours, preferably 1 hour to 6 hours.

Incidentally, in this step, a mixture of cis and trans geometric isomer can be usually obtained and it can be applied to the next step in the state of a mixture.

Hydrolysis reaction of Compound (XXXIV) to the carboxyl group in Step I4 may be also carried out, for example, by a typical alkali hydrolysis reaction using sodium hydroxide or potassium hydroxide, or a method disclosed in "Protective Group in Organic Synthesis" written by W. Greene and P. G. H. Wult, $2^{nd}$ Ed., John Wiley & Sons, p. 229.

Reduction of Compound (XXXV) in Step I5 can be carried out by a catalytic hydrogenation reaction or a reduction using hydroiodic acid/red phosphorus, and when W is a halogen atom, the reduction using hydroiodic acid/red phosphorus is suitable.

In the case of the catalytic hydrogenation reaction, Compound (XXXV) is subjected to catalytic reduction by hydrogen in the presence of a catalyst whereby Compound (XXVI) can be synthesized.

The solvent to be used is not specifically limited so long as it does not inhibit the reaction and can dissolve the starting materials with a certain extent, and there may be mentioned, for example, alcohols such as methanol, ethanol, etc., or ethers such as tetrahydrofuran, dioxane, etc., preferably alcohols.

As the catalyst to be used, there may be mentioned, for example, palladium-carbon, platinum-carbon, platinum black, rhodium-carbon or Raney nickel, preferably palladium-carbon.

In the catalytic hydrogenation reaction, a partial pressure of hydrogen is usually 1 atm. to 10 atm., preferably 1 atm. to 5 atm.

The reaction is carried out in the temperature range usually at 0° C. to 100° C., preferably at 20° C. to 80° C. A reaction time may vary depending on the reaction temperature and the like, and it is usually 15 minutes to 72 hours, preferably 30 minutes to 48 hours.

In the case of the reduction using hydroiodic acid/red phosphorus, the solvent to be used is not specifically limited so long as it does not inhibit the reaction and can dissolve the starting materials with a certain extent, and there may be mentioned, for example, water, acetic acid or propionic acid, preferably acetic acid. The hydroiodic acid to be used is 3 to 15-fold mol amount, preferably 4 to 8-fold mol amount based on 1 mol of Compound (XXXV).

The red phosphorus to be used is 1 to 10-fold mol amount, preferably 2 to 5-fold mol amount based on the amount of Compound (XXXV). A method of addition thereof may be once or divided into several times.

The reaction is carried out in the temperature range usually at 90 to 150° C., preferably at 100 to 130° C. A reaction time may vary depending on the reaction temperature and the like, and it is usually 1 hour to 48 hours, preferably 6 hours to 24 hours.

Preparation process J is a process for producing Compound (XVI) by demethylating Compound (XXXVI). Demethylation of Compound (XXXVI) is carried out by optionally employing a conventionally known method (see "Protective Group in Organic Synthesis" written by W. Greene and P. G. H. Wult, $2^{nd}$ Ed., John Wiley & Sons, p. 146), for example, a method of using hydrobromic acid or hydroiodic acid, or a method of using boron tribromide and trimethylsilane iodide, and the like.

Preparation process K is a preparation process of Compound (XVIII), and carried out easily by employing a conventionally known method, for example, a method as disclosed in J. Org. Chem., 61, 3398 (1996).

Preparation process M is another process for producing Compound (XXVI).

Step M1 is a process for producing Compound (XXXV') by condensation reaction of Compound (XXX) and Compound (XXXIII) in the presence of a base.

The solvent to be used is not specifically limited so long as it does not inhibit the reaction and can dissolve the starting materials with a certain extent, and there may be mentioned, for example, alcohols such as methanol, ethanol, propanol, butanol, t-butanol, etc.; ethers such as tetrahydrofuran, dioxane, 1,2-dimethoxyethane, etc.; amides such as N,N-dimethylformamide, N,N-dimethylacetamide, N-methylpyrrolidone, etc., preferably N,N-dimethylformamide.

An amount of Compound (XXXIII) to be used is usually 1 to 1.5-fold mol amount, preferably 1 to 1.2-fold mol amount based on the amount of Compound (XXX).

The base to be used may be mentioned alkali metal alkoxides such as sodium methoxide, sodium ethoxide, sodium t-butoxide, potassium t-butoxide, etc.; or alkali metal hydrides such as sodium hydride, potassium-hydride, etc., preferably sodium t-butoxide. An amount thereof to be used is usually 1 to 2-fold mol amount, preferably 1 to 1.5-fold mol amount based on the amount of Compound (XXX).

The reaction is carried out in the temperature range usually at 0 to 100° C., preferably at 10 to 40° C. A reaction time may vary depending on the reaction temperature and the like, and it is usually 1 to 24 hours, preferably 3 to 12 hours.

Step M2 is a hydrogenation reaction of olefin and can be carried out in the same manner as in Step I5 of Preparation process I.

Preparation process N is another process for producing Compound (XXIX).

Step N1 is a step of obtaining Compound (XXXX) by reacting Compound (XXVII) and N-bromosuccinimide under irradiation of light, preferably under irradiation of light using a mercury lamp light source.

The solvent to be used is not specifically limited so long as it does not inhibit the reaction and can dissolve the starting materials with a certain extent, and there may be mentioned, for example, halogenated hydrocarbons such as dichloromethane, chloroform, carbon tetrachloride, 1,2-dichloroethane, etc., preferably 1,2-dichloroethane. An amount of the N-bromosuccinimide to be used is usually 1.8 to 2.5-fold mol amount, preferably 2.0 to 2.1-fold mol amount based on the amount of Compound (XXVII).

The reaction is carried out in the temperature range usually at 0 to 80° C., preferably at 30 to 60° C. A reaction time may vary depending on the reaction temperature and the like, and it is usually 1 hour to 12 hours, preferably 3 hours to 8 hours.

Step N2 is a step of converting from vicinal dibromide to olefin and is carried our easily by a method as disclosed in, for example, Synth., Comm., 26, 3791 (1996) or the like.

Preparation process O is a preparation process of an intermediate Compound (XXXXX) for the exemplary Compounds (If) and (Ig) wherein X=a methylene group among the compounds represented by the formula (I).

Step O1 is a step of producing Compound (XXXXIII) by reacting an acetylene compound (XXXXII) to Compound (XXXXI).

The solvent to be used is not specifically limited so long as it does not inhibit the reaction and can dissolve the starting materials with a certain extent, and there may be preferably mentioned, for example, ethers such as tetrahydrofuran, dioxane, 1,2-dimethoxyethane, etc.

An amount of the acetylene compound (XXXXII) to be used is usually 1 to 2-fold mol amount, preferably 1 to 1.5-fold mol amount based on the amount of Compound (XXXXI).

The reaction is carried out in the temperature range usually at 0 to 100° C., preferably at 0 to 30° C. A reaction time may vary depending on the reaction temperature and the like, and it is usually 5 minutes to 12 hours, preferably 30 minutes to 6 hours.

The reaction of producing Compound (XXXXIV) from Compound (XXXXIII) in Step O2 is carried out by subjecting to conversion reaction in a solvent in the presence of an acid catalyst.

The solvent to be used is not specifically limited so long as it does not inhibit the reaction and can dissolve the starting materials with a certain extent, and there may be mentioned, for example, alcohols such as methanol, ethanol, propanol, butanol, etc.; ethers such as tetrahydrofuran, dioxane, 1,2-dimethoxyethane, etc.; nitrites such as acetonitrile, etc.; and a mixed solvent of amides such as N,N-dimethylformamide, N,N-dimethylacetamide, N-methylpyrrolidone, etc. and water, preferably methanol, ethanol, tetrahydrofuran or a mixed solvent of N,N-dimethylformamide and water.

As the acid catalyst to be used, there may be mentioned, for example, mineral acids such as hydrochloric acid, sulfuric acid, phosphoric acid, etc.; or organic acids such as methanesulfonic acid, trifluoroacetic acid, etc., preferably trifluoroacetic acid. An amount of the catalyst to be used is usually 1 to 100-fold mol amount, preferably 1 to 50-fold mol amount based on the amount of Compound (XXXXIII).

The reaction is carried out in the temperature range usually at 0 to 100° C., preferably at 0 to 30° C. A reaction time may vary depending on the reaction temperature and the like, and it is usually 5 minutes to 48 hours, preferably 30 minutes to 24 hours.

Step O3 is a step of obtaining Compound (XXXXVI) by reacting Compound (XXXXIV) and Compound (XXXXV) in the presence of a base in a solvent.

An amount of Compound (XXXXV) to be used is usually 1 to 10-fold mol amount, preferably 1 to 5-fold mol amount based on the amount of Compound (XXXXIV).

As the base to be used, there may be mentioned, for example, alkali metal hydrides such as sodium hydride, lithium hydride, etc.; alkali metal alkoxides such as sodium methoxide, sodium ethoxide, potassium t-butoxide, etc.; alkyl lithiums such as methyl lithium, butyl lithium, etc.; metal amides such as sodium amide, lithium diisopropyl amide, etc., preferably alkali metal hydride. An amount of the base to be used is usually 1 to 5-fold mol amount, preferably 1 to 2-fold mol amount based on the amount of Compound (XXXXV).

The solvent to be used is not specifically limited so long as it does not inhibit the reaction and can dissolve the starting materials with a certain extent, and there may be mentioned, for example, aromatic hydrocarbons such as benzene, toluene, etc.; ethers such as tetrahydrofuran, dioxane, dimethoxyethane, dimethoxyethane, etc.; or aprotic polar solvents such as N,N-dimethylformamide, N,N-dimethylacetamide, N-methylpyrrolidone, dimethylsulfoxide, etc., preferably ethers.

The reaction is carried out in the temperature range usually at −50° C. to 100° C., preferably at −10° C. to 50° C. A reaction time may vary depending on the reaction temperature and the like, and it is usually 15 minutes to 12 hours, preferably 30 minutes to 5 hours.

In Step O4, Compound (XXXXVII) can be synthesized by subjecting Compound (XXXXVI) to catalytic reduction with hydrogen in a solvent in the presence of a base, and the step is carried out in the same manner as in the catalytic hydrogenation of Step I5.

Step O5 is a conversion to olefin by dehydrogenation and, for example, it is carried out in the same manner as in the above-mentioned Preparation process N except for using Compound (XXXXVII) in place of Compound (XXVII).

Step O6 is demethylation of a methoxy group and hydrolysis of an ester group.

Demethylation of the methyl group and hydrolysis of the ester group are simultaneously accomplished by carrying out in the same manner as in, for example, Preparation process J except for using Compound (XXXXVIII) in place of Compound (XXXVI).

Step O7 is a protection step for a carboxyl group by esterification, and can be easily converted by a conventionally known method (for example, see "Protective Group in Organic Synthesis" written by W. Greene and P. G. H. Wult, $2^{nd}$ Ed., John Wiley & Sons, p. 224).

Preparation process P is another process for producing Compound (XVIII).

Step P1 is a step of producing Compound (XXXXXI) by reacting Compound (XXI) and triphenylphosphine, and Step P2 is a step of producing Compound (XVIII) by reacting Compound (XXXXXI) and formaldehyde in the presence of a base.

Step P1 is carried out in the same manner as in Step I2 except for using Compound (XXI) in place of Compound (XXXI).

Step P2 is carried out in the same manner as in Step I3 except for using Compound (XXXXXI) in place of Compound (XXXII), and using formaldehyde in place of Compound (XXXIII).

The compound represented by the present invention has a potent leukotriene antagonistic action, and extremely useful as an antiazma agent, an antiallergic agent and anti-inflammatory agent.

When used as a prophylactic or therapeutic medicament for the desiases described above, Compound (I) or a pharmaceutically acceptable salt thereof of the present invention can be administered alone or can be presented as part of a pharmaceutical formulation. The pharmaceutical formulation is prepared by blending the active ingredient with appropriate pharmaceutically acceptable excipient, diluent, etc., followed by formulation in the form of tablets, capsules, granules, powders or syrups, etc. for oral administration or in the form of injections, etc. for parenteral administration (preferably oral administration).

The production of such pharmaceutical formulation is carried out according to general technique known to those skilled in the art using additives such as an excipient (for example, a sugar derivative such as lactose, sucrose, glucose, mannitol, or sorbitol; a starch derivative such as corn starch, potato starch, α-starch, dextrin, or carboxymethyl starch; a cellulose derivative such as crystalline cellulose, low-substituted hydroxypropyl cellulose, hydroxypropylmethyl cellulose, carboxymethyl cellulose, calcium carboxymethyl cellulose, or internally bridged sodium carboxymethyl cellulose; acacia; dextran; pullulan; a silicate derivative such as light silicic acid anhydride, synthetic aluminum silicate, or magnesium aluminate metasilicate; a phosphate derivative such as calcium phosphate; a carbonate derivative such as calcium carbonate; a sulfate derivative such as calcium sulfate; etc.), a binder (for example, one of the excipients described above; gelatin; polyvinylpyrrolidone; Macrogol (tradename), etc.), a disintegrator (for example, one of the excipients described above; a chemically modified starch, cellulose derivative such as sodium croscarmellose, sodium carboxymethyl starch; bridged polyvinylpyrrolidone, etc.), a lubricant (for example, talc; stearic acid; a metal salt of stearic acid such as calcium stearate, or magnesium stearate; colloidal silica; a wax such as bee gum and spermaceti; boric acid; glycol; a carboxylic acid such as fumaric acid, or adipic acid; a sodium carboxylate such as sodium benzoate; a sulfate such as sodium sulfate; leucine; a laurylsulfate such as sodium laurylsulfate, or magnesium laurylsulfate; a silicic acid such as silicic acid anhydride,or a silicic acid hydrate; one of the starch derivatives described above in relation to the excipient, etc.), a stabilizer (for example, a p-hydroxybenzoate derivative such as methylparaben, or propylparaben; an alcohol such as chlorobutanol, benzyl alcohol, or phenylethyl alcohol; benzalkonium chloride; a phenol derivative such as phenol, or cresol; thimerosal; acetic anhydride; sorbic acid, etc.), a corrigent (for example, a sweetening, souring, or flavoring agent, which are conventionally used, etc.), a diluent, a solvent for injection (for example, water, ethanol, glycerin, etc.), etc. A dose for administration may vary depending on symptom, an age, etc, and in the case of oral. administration, it is desirably administered 1 mg (preferably 5 mg) as a lower limit and 1000 mg (preferably 500 mg) as an upper limit once per day, and in the case of intravenous administration, it is desirably administered 0.1 mg (preferably 1 mg) as a lower limit and 500 mg (preferably 300 mg) as an upper limit once per day to an adult person with one to six times per day depending on the symptom.

Utilizability in Industry

The compound represented by the formula (I) or a pharmaceutically acceptable salt thereof according to the present invention has leukotriene $C_4$ antagonistic action and leukotriene $E_4$ antagonistic action in addition to potent leukotriene $D_4$ antagonistic action, and is extremely useful as an anti-asthmatic agent, an antiallergic agent and an anti-inflammatory agent.

EXAMPLE

In the following, the present invention is explained by referring to Test examples and Examples, but the scope of the present invention is not limited to these.

Test Example 1

Leukotriene $D_4$ Receptor Binding Test

<Preparation of Receptor Sample>

As a receptor sample, a lung cell membrane fraction from guinea pigs was used. Preparation of the membrane fraction was carried out according to the method of Ahn et al. (Eur. J. Pharmacol., 127, 153-155 (1986)). Lungs of Hartley male guinea pigs (400 to 500 g body weight, Japan SLC Inc.) were isolated, and perfused with a physiological saline, and then, adding 10 mM of PIPES, 10 mM of $MgCl_2$ and 10 mM of $CaCl_2$ buffer (pH 7.5) to the lung tissue and the mixture was homogenized. This homogenate was centrifuged at 70,000×g for 10 minutes to obtain a membrane fraction.

<Leukotriene $D_4$ Receptor Binding Test>

Leukotriene $D_4$ ($LTD_4$) receptor binding test was carried out according to the method of Aharony, et al. (J. Pharmacol. Expl. Ther., 243, 921-926 (1987)). To 0.42 mg of the receptor sample were added 10 mM of PIPES, 10 mM of MgCl$_2$ and 10 mM of CaCl$_2$ buffer (pH 7.5) to make the total amount of 480 µl, and 10 µl of [$^3$H] LTD$_4$ (NEN Life Science Products Inc.) and 10 µl of a test compound in dimethylsulfoxide were added to the mixture, and the resulting mixture was incubated at 25° C. for 30 minutes. The mixtures thus incubated were filtered through a glass fiber filter (Whatman International Ltd., GF/C) using cell harvester (Biomedical Research & Development Laboratories, Inc., M-30R). The filter paper was washed with 10 mM of Tris and 100 mM of NaCl buffer (pH 7.5), and 5 ml of a liquid scintillator (nacalai tesque inc., clearsol I) was added thereto, and radioactivity was measured by a liquid scintillation analyzer (Packard Instrument Co., 2000CA). When a dissociation constant (Kd) of LTD$_4$ was to be obtained, [$^3$H] LTD$_4$ with 0.03 to 0.5 nM was used, and 1 µM of non-radioactive LTD$_4$ was added. When a binding inhibition constant (Ki) of the Test compound is to be measured, [$^3$H] LTD$_4$ with 0.2 nM was used. Kd and Ki are calculated according to the method of Bennett et al. (Neurotransmitter Receptor Binding, 2$^{nd}$ ed., edited by H. I. Yamamura et al., pp. 61-89, Raven Press (1985)).

TABLE 2

Results of leukotriene D$_4$ receptor binding test

| Compound to be tested | pKi |
|---|---|
| Example Compound 3 | 10.0 |
| Example Compound 4 | 9.7 |
| Example Compound 7 | 9.7 |
| Example Compound 9 | 9.8 |
| Example Compound 10 | 10.0 |
| Example Compound 11 | 9.9 |
| Example Compound 12 | 9.7 |
| Example Compound 13 | 9.9 |
| Example Compound 17 | 9.8 |
| Example Compound 29 | 9.6 |
| Example Compound 30 | 9.7 |
| Example Compound 31 | 9.7 |
| Compound A | 9.5 |

Compound A; 3-[2-(7-chloro-6-fluoroquinolin-2-yl) methoxy-6,11-dihydrobenz[b,e]oxepin-11-yl]thio-propionic acid (see WO 94/193445 publication)

Test Example 2

Leukotriene D$_4$ Induced Respiratory Constriction Test

Respiratory constriction was measured by modifying the method of Konzett and Rossler (Arch. Exp. Pathol. Pharmakol., 195, pp. 71-74 (1940)). Hartley male guinea pigs (400 to 500 g body weight, Japan SLC Inc.) were anesthetized with pentobarbital (50 mg/kg, s.c.), and a cannula was inserted into the trachea to carry out artificial ventilation with an artificial ventilator (manufactured by Harvard Apparatus, Model 683). An inner pressure of the respiratory tract was measured by a differential pressure transducer (Nihon Kohden, TP-603T) connected to the respiratory cannula and it is used as an index of respiratory constriction.

LTD$_4$ (0.03, 0.06, 0.13, 0.25, 0.5, 1 and 2 µg/kg, Simga-Aldrich) was intravenously administered from a cannula inserted into the right jugular vein from a low dose with an interval of 5 minutes to cause a respiratory constricttion reaction and an increased amount of a respiratory inner pressure was measured. Test compound was suspended in 0.5% sodium carboxymethyl cellulose aqueous solution or dissolved in 30% propylene glycol aqueous solution, and orally administered 24 hours before administration of LTD$_4$. Animals were fasted for 24 hours before administration of the Test compound. From a dose-reaction curve of LTD$_4$, 50% reaction dose (ED$_{50}$) was measured, and a dose of the Test compound required for shifting two-times of a dose-reaction curve of a control group to a higher dose side was calculated from the formula shown below and it was made as LTD$_4$ inhibitory activity. LTD$_4$ inhibitory activity=(Dose of Compound administered)/{(ED$_{50}$ of group to which Compound was added)/(ED$_{50}$ of control group)-1}

TABLE 3

Results of leukotriene D$_4$ induced respiratory constriction test

| Compound to be tested | LTD$_4$ inhibitory activity (µg/kg, p.o. 24 h) |
|---|---|
| Example Compound 3 | 4.71 |
| Example Compound 4 | 1.91 |
| Example Compound 7 | 0.85 |
| Example Compound 8 | 5.30 |
| Example Compound 10 | 9.93 |
| Example Compound 14 | 4.85 |
| Example Compound 16 | 0.79 |
| Example Compound 18 | 1.12 |
| Example Compound 19 | 2.43 |
| Example Compound 20 | 0.70 |
| Example Compound 28 | 1.70 |
| Compound A | 25.52 |

Compound A; 3-[2-(7-chloro-6-fluoroquinolin-2-yl)-methoxy-6,11-dihydrobenz[b,e]oxepin-11-yl]thio-propionic acid (see WO 94/193445 publication)

Preparation Example 1

| Tablet | |
|---|---|
| Compound of Example 7 | 30.0 mg |
| Lactose | 144.0 |
| Corn starch | 25.0 |
| Magnesium stearate | 1.0 |
| | 200 mg |

A tablet is prepared using the ingredients above. The components are blended and compressed by a tablet machine to form a tablet weighing 200 mg. The tablet may be coated if necessary, for example, to form a sugar-coated tablet or a coated tablet.

Example 1

Methyl [3-[(E)-2-(6,7-difluoroquinolin-2-yl)-ethenyl]-5H-dibenzo[a,d]cyclohepten-5-yl]oxyacetate (methyl ester of Exemplary compound 1)

After a solution of 1.19 g (2.99 mmol) of 3-[(E)-2(6,7-difluoroquinolin-2-yl)ethenyl]-5H-dibenzo[a,d]cyclohepten-5-ol dissolved in 10 ml of tetrahydrofuran was cooled to 0° C. with ice, 0.85 ml (5.98 mmol) of triethylamine and 0.30 ml (3.89 mmol) of methanesulfonyl chloride were added to the solution, and the mixture was stirred at 0° C. for 1 hour, and further at room temperature for 3 hours.

After completion of the reaction, the solvent was removed from the mixture under reduced pressure. The residue was dissolved in 15 ml of N,N-dimethylformamide, then, 0.54 g (5.98 mmol) of methyl glycolate was added to the mixture, and the resulting mixture was stirred at room temperature overnight.

After completion of the reaction, water was added to the reaction mixture, and extracted with chloroform. The organic layer was washed with water, dried over anhydrous sodium sulfate, and the solvent was removed under reduced pressure. The residue was applied to silica gel column chromatography (solvent: hexane/ethyl acetate=2/1 (volume ratio)) to obtain 0.38 g of the title compound as yellowish solid.

EI-MS (m/z); 469 (M$^+$). CI-MS (m/z); 470 (M$^+$+1).

Example 2

[3-[(E)-2-(6,7-difluoroquinolin-2-yl)ethenyl]-5H-dibenzo[a,d]cyclohepten-5-yl]oxyacetic acid (Exemplary compound 1)

To mixed solution comprising 15 ml of methanol and 5 ml of tetrahydrofuran was dissolved 0.38 g (0.81 mmol) of methyl [3-[(E)-2-(6,7-difluoroquinolin-2-yl)ethenyl]-5H-dibenzo[a,d]cyclohepten-5-yl]oxyacetate, 2.4 ml (2.4 mmol) of an aqueous 1N sodium hydroxide solution was added to the solution and the resulting mixture was stirred at room temperature for 5 hours.

After completion of the reaction, the reaction mixture was adjusted to pH 6.5 by using an aqueous diluted acetic acid solution, and then, the mixture was concentrated under reduced pressure. Water was added to the residue, and the precipitated solid was collected by filtration. The solid was applied to silica gel column chromatography (solvent: chloroform/methanol=9/1 (volume ratio)) to obtain 0.21 g of the title compound as yellowish solid.

FAB-MS (m/z); 456 (M$^+$+1). $^1$H-NMR ($\delta$, DMSO-d$_6$); 4.14 (s, 2H), 4.93 (s, 1H), 7.18-7.67 (m, 9H), 7.89-8.07 (m, 5H), 8.37 (d, J=8.5 Hz, 1H).

Example 3

Sodium [3-[(E)-2-(6,7-difluoroquinolin-2-yl)ethenyl]-5H-dibenzo[a,d]cyclohepten-5-yl]oxyacetate (sodium salt of Exemplary compound 1)

In a mixed solution of 15 ml of tetrahydrofuran and 5 ml of methanol was dissolved 0.20 g (0.44 mmol) of [3[(E)-2-(6,7-difluoroquinolin-2-yl)ethenyl]-5H-dibenzo[s,d]-cyclohepten-5-yl]oxyacetic acid, 0.44 ml (0.44 mmol) of an aqueous 0.1N sodium hydroxide solution was added to the solution and the mixture was stirred at room temperature for 1 hour.

After completion of the reaction, the reaction mixture was concentrated, ethanol was added to the residue, and the precipitated solid was collected by filtration to obtain 0.14 g of the title compound as pale yellowish solid.

m.p.; 213 to 227° C. FAB-MS (m/z); 478 (M$^+$+1). $^1$H-NMR ($\delta$, DMSO-d$_6$); 3.81 (s, 2H), 5.03 (s, 1H), 7.15-7.65 (m, 9H), 7.89-8.06 (m, 5H), 8.37 (d, J=8.8 Hz, 1H).

Example 4

Sodium 3-{[3-[(E)-2-(6,7-difluoroquinolin-2-yl)ethenyl]-5H-dibenzo[a,d]cyclohepten-5-yl]thio}propionate (sodium salt of Exemplary compound 8)

(a) In a mixed solution of 0.4 ml of trifluoroacetic acid and 40 ml of methylene chloride was dissolved 0.33 g (0.83 mmol) of 3-[(E)-2-(6,7-difluoroquinolin-2-yl)ethenyl]-5H-dibenzo[a,d]cyclohepten-5-ol, 0.08 ml (0.92 mmol) of 3-mercaptopropionic acid was added to the solution and the mixture was stirred at room temperature for 3 hours.

After completion of the reaction, the reaction mixture was concentrated, and the residue was applied to silica gel column chromatography (eluent: chloroform/methanol=19/1 (volume ratio)) to obtain 0.17 g (0.35 mmol) of 3-{[3-[(E)-2-(6,7-difluoroquinolin-2-yl)ethenyl]-5H-dibenzo[a,d]cyclohepten-5-yl]thio}propionic acid as brown solid.

(b) 3-{[3-[(E)-2-(6,7-difluoroquinolin-2-yl)ethenyl]-5H-dibenzo[a,d]cyclohepten-5-yl]thio}propionic acid obtained in Example 4(a) was dissolved as such in a mixed solution of 10 ml of tetrahydrofuran and 20 ml of methanol, 0.35 ml (0.35 mmol) of an aqueous 1N sodium hydroxide solution was added to the solution and the mixture was stirred at room temperature for 1 hour.

After completion of the reaction, the reaction mixture was concentrated, the residue was washed with diethyl ether, and dried under reduced pressure to obtain 0.14 g of the title compound as pale yellowish solid.

m.p.; 213 to 216° C. FAB-MS (m/z); 508 (M$^+$+1). $^1$H-NMR ($\delta$, DMSO-d$_6$); 1.90-2.10 (m, 2H), 2.30-2.45 (m, 2H), 5.48 (s, 1H), 7.00 (s, 2H), 7.20-7.60 (m, 6H), 7.33 (d, J=8.8 Hz, 1H), 7.37 (d, J=7.3 Hz, 1H), 7.48 (d, J=8.5 Hz, 1H), 7.54 (d, J=16.4 Hz, 1H), 7.66 (d, J=7.8 Hz, 1H), 7.80-8.20 (m, 3H), 7.87 (d, J=16.1 Hz, 1H), 8.04 (dd, J=9.0 Hz, 2.2 Hz, 1H), 8.38 (d, J=8.8 Hz, 1H).

Reaction was carried out in the same manner as in Example 4 to obtain compounds of the following Examples 5 to 9.

Example 5

Sodium 3-{[3-(7-chloro-6-fluoroquinolin-2-yl)methoxy-5H-dibenzo[a,d]cyclohepten-5-yl]thiol}propionate (sodium salt of Exemplary compound 718)

Appearance; pale yellowish solid m.p.; 229 to 232° C. $^1$H-NMR ($\delta$, DMSO-d$_6$); 2.00-2.20 (m, 2H), 2.25-2.45 (m, 2H), 5.38 (s, 1H), 5.41 (s, 2H), 6.83 (d, J=12.0 Hz, 1H), 6.90 (d, J=12.2 Hz, 1H), 7.00 (dd, J=8.5 Hz, 2.7 Hz, 1H), 7.20-7.55 (m, 6H), 7.75 (d, J=8.5 Hz, 1H), 8.05 (d, J=9.8 Hz, 1H), 8.29 (d, J=7.3 Hz, 1H), 8.44 (d, J=8.3 Hz, 1H).

Example 6

Sodium 3-{[3-[(E)-2-(6,7-difluoroquinolin-2-yl)ethenyl]-5H-dibenzo[a,d]cyclohepten-5-yl]thio}-2-(S)-methylpropionate (sodium salt of Exemplary compound 9)

Appearance; pale yellowish solid m.p.; 240 to 249° C. FAB-MS (m/z); 522(M$^+$+1). $^1$H-NMR ($\delta$, DMSO-d$_6$); 0.89 (d, J=6.6 Hz, 3H), 2.10-2.89 (m, 2H), 2.51-2.58 (m, 1H), 5.45 (s, 1H), 7.00 (s, 2H), 7.31-7.49 (m, 5H), 7.54 (d, J=16.4 Hz, 1H), 7.66 (d, J=8.1 Hz, 1H), 7.85 (d, J=6.8 Hz, 1H), 7.86-7.98 (m, 2H), 7.98 (d, J=3.9 Hz, 1H), 8.04 (dd, J=11.0 Hz, 8.8 Hz, 1H), 8.38 (d, J=8.8 Hz, 1H).

Example 7

Sodium 3-{[3-[(E)-2-(7-chloro-6-fluoroquinolin-2-yl)ethenyl]-5H-dibenzo[a,d]cyclohepten-5-yl]thio}propionate (sodium salt of Exemplary compound 478)

Appearance; yellowish solid m.p.; 228 to 238° C. FAB-MS (m/z); 524 (M$^+$+1). $^1$H-NMR ($\delta$, DMSO-d$_6$); 1.96-2.01 (m, 2H), 2.34-2.37 (m, 2H), 5.48 (s, 1H), 7.00 (s, 2H), 7.29-7.50 (m, 5H), 7.55 (d, J=16.4 Hz, 1H), 7.66 (dd, J=8.8 Hz, 1.5 Hz, 1H), 7.88 (d, J=16.4 Hz, 1H), 7.89 (d, J=1.5 Hz, 1H), 8.00 (d, J=8.8 Hz, 1H), 8.01 (d, J=10.0 Hz, 1H). 8.23 (d, J=7.1 Hz, 1H), 8.39 (d, J=8.5 Hz, 1H).

Example 8

Sodium 3-{[3-[(E)-2-(7-chloroquinolin-2-yl)ethenyl]-5H-dibenzo[a,d]cyclohepten-5-yl]thio}propionate (sodium salt of Exemplary compound 1418)

Appearance; orange solid m.p.; 193 to 203° C. FAB-MS (m/z); 506 (M$^+$+1). $^1$H-NMR (δ, DMSO-d$_6$); 2.02-2.08 (m, 2H), 2.35-2.41 (m, 2H), 5.49 (s, 1H), 7.00 (s, 2H), 7.29-7.49 (m, 5H), 7.53-7.61 (m, 2H), 7.67 (d, J=8.1 Hz, 1H), 7.86-7.94 (m, 3H), 7.99-8.03 (m, 2H), 8.41 (d, J=8.5 Hz, 1H).

Example 9

Sodium 3-{[3-[(E)-2-(5,6,7,8-tetrahydroquinolin-2-yl)ethenyl]-5H-dibenzo[a,d]cyclohepten-5-yl]thio}propionate (sodium salt of Exemplary compound 1885)

Appearance; pale yellowish solid m.p.; 175 to 185° C. FAB-MS (m/z); 508 (M$^+$+1). $^1$H-NMR (δ, DMSO-d$_6$); 1.76-1.85 (m, 4H), 2.08-2.13 (m, 2H), 2.35-2.40 (m, 2H), 2.74-2.84 (m, 4H), 5.44 (s, 1H), 6.97 (s, 2H), 7.28-7.46 (m, 8H), 7.54-7.59 (m, 2H), 7.78 (s, 1H).

Reaction was carried out in the same manner as in Examples 1 to 3 to obtain compounds of the following Examples 10 to 13.

Example 10

Sodium 3-{[3-[(E)-2-(6,7-difluoroquinolin-2-yl)ethenyl]-5H-dibenzo[a,d]cyclohepten-5-yl]oxy}-2-(R)-methyl-propionate (sodium salt of Exemplary compound 4)

Appearance; yellowish solid $^1$H-NMR (δ, DMSO-d$_6$); 0.74, 1.20 (each b, 3H in total), 2.44 (b, 1H), 3.53, 3.77 (each b, 2H in total), 4.68, 5.55 (each s, 1H in total), 7.00-7.70 (m, 9H), 7.87-8.07 (m, 5H), 8.37 (d, J=8.8 Hz, 1H).

Example 11

Sodium [3-[(E)-2-(7-chloro-6-fluoroquinolin-2-yl)ethenyl]-5H-dibenzo[a,d]cyclohepten-5-yl]oxyacetate (sodium salt of Exemplary compound 471)

Appearance; yellowish solid $^1$H-NMR (δ, DMSO-d$_6$); 3.81 (bs, 2H), 5.04 (bs, 1H), 7.15 (bs, 2H), 7.26-7.66 (m, 7H), 7.90-8.02 (m, 4H), 8.22 (d, J=7.3 Hz, 1H), 8.38 (d, J=8.6 Hz, 1H).

Example 12

Sodium 3-{[3-[(E)-2-(7-chloro-6-fluoroquinolin-2-yl)ethenyl]-5H-dibenzo[a,d]cyclohepten-5-yl]oxy}propionate (sodium salt of Exemplary compound 473)

Appearance; yellowish solid $^1$H-NMR (δ, DMSO-d$_6$); 2.37 (bs, 2H), 3.72, 3.82 (each bs, 2H in total), 4.70 (bs, 1H), 7.18 (bs, 2H), 7.28-7.66 (m, 8H), 7.88-8.04 (m, 4H), 8.27 (d, J=7.1 Hz, 1H), 8.38 (d, J=8.5 Hz, 1H).

Example 13

Sodium 3-{[3-[(E)-2-(7-chloro-6-fluoroquinolin-2-yl)ethenyl]-5H-dibenzo[a,d]cyclohepten-5-yl]oxy}-2-(R)-methylpropionate (sodium salt of Exemplary compound 474)

Appearance; yellowish solid $^1$H-NMR (δ, DMSO-d$_6$); 0.73, 1.20, 1.52 (each b, 3H in total), 2.45 (b, 1H), 3.33-3.86 (each m, 2H), 4.68, 5.55 (each s, 1H in total), 7.19-7.63 (m, 9H), 7.88-8.27 (m, 5H), 8.38 (d, J=8.8 Hz, 1H).

Reaction was carried out in the same manner as in Example 4 to obtain compounds of the following Examples 14 to 16.

Example 14

Sodium [3-[(E)-2-(7-chloro-6-fluoroquinolin-2-yl)-ethenyl]-5H-dibenzo[a,d]cyclohepten-5-yl]thioacetate (sodium salt of Exemplary compound 476)

Appearance; orange solid $^1$H-NMR (δ, DMSO-d$_6$); 2.61 (d, J=13.7 Hz, 2H), 2.66 (d, J=13.7 Hz, 2H), 5.63 (s, 1H), 6.98 (s, 2H), 7.31 (td, J=9.0 Hz, 2.0 Hz, 1H), 7.33-7.42 (m, 3H), 7.45 (d, J=7.8 Hz, 1H), 7.52 (d, J=16.4 Hz, 1H), 7.67 (dd, J=8.1 Hz, 1.5 Hz, 1H), 7.75 (d, J=2.0 Hz, 1H), 7.88 (d, J=16.1 Hz, 1H), 7.98 (d, J=9.8 Hz, 1H), 8.02 (d, J=10.0 Hz, 1H), 8.24 (d, J=7.6 Hz, 1H), 8.39 (d, J=8.6 Hz, 1H).

Example 15

Sodium 2-{[3-[(E)-2-(7-chloro-6-fluoroquinolin-2-yl)ethenyl]-5H-dibenzo[a,d]cyclohepten-5-yl]thio}propionate (sodium salt of Exemplary compound 477)

Appearance; pale yellowish solid $^1$H-NMR (δ, DMSO-d$_6$); 1.10-1.14 (m, 3H), 2.68-2.76 (m, 3H), 5.67 (d, J=6.4 Hz, 1H), 6.98 (s, 2H), 7.23-7.54 (m, 6H), 7.67 (dd, J=8.1 Hz, 1.5 Hz, 1H), 7.31-7.90 (m, 2H), 7.98 (d, J=7.6 Hz, 1H), 8.01 (d, J=9.8 Hz, 1H), 8.23 (d, J=7.3 Hz, 1H), 8.39 (d, J=8.6 Hz, 1H).

Example 16

Sodium 3-{[3-[(E)-2-(7-chloro-6-fluoroquinolin-2-yl)ethenyl]-5H-dibenzo[a,d]cyclohepten-5-yl]thiomethyl}-cyclopropaneacetate (sodium salt of Exemplary compound 487)

Appearance; pale yellowish solid $^1$H-NMR (δ, DMSO-d$_6$); 0.15 (bs, 2H), 0.33 (bs, 2H), 1.95 (d, J=14.2 Hz, 1H), 2.06 (d, J=14.2 Hz, 1H), 2.43 (d, J=13.4 Hz, 1H), 2.60 (d, J=13.4 Hz, 1H), 5.69 (s, 1H), 7.00 (s, 2H), 7.31 (td, J=7.3 Hz, 1.2 Hz, 1H), 7.34-7.42 (m, 2H), 7.45 (d, J=8.1 Hz, 1H), 7.55-7.61 (m, 2H), 7.66 (d, J=8.1 Hz, 1H), 7.88 (d, J=16.4 Hz, 1H), 7.96-8.03 (m, 3H), 8.26 (d, J=7.3 Hz, 1H), 8.39 (d, J=8.8 Hz, 1H).

Reaction was carried out in the same manner as in Examples 1 to 3 to obtain compounds of the following Example 17.

Example 17

Sodium [3-[(E)-2-(7-chloro-6-fluoroquinolin-2-yl)ethenyl]-9-fluoro-5H-dibenzo[a,d]cyclohepten-5-yl]oxy-acetate (sodium salt of Exemplary compound 505)

Appearance; pale yellowish solid
$^1$H-NMR (δ, DMSO-$d_6$); 3.79 (bs, 2H), 5.08 (bs, 1H), 7.06-7.35 (m, 3H), 7.40-7.55 (m, 4H), 7.62-7.72 (m, 1H), 7.92-7.97 (m, 1H), 7.93 (d, J=16.4 Hz, 1H), 8.00 (d, J=9.8 Hz, 1H), 8.01 (d, J=8.5 Hz, 1H), 8.23 (d, J=7.3 Hz, 1H), 8.38 (d, J=8.8 Hz, 1H).

Reaction was carried out in the same manner as in Example 4 to obtain a compound of the following Example 18.

Example 18

Sodium 3-{[3-[(E)-2-(7-chloro-6-fluoroquinolin-2-yl)ethenyl]-9-fluoro-5H-dibenzo[a,d]cyclohepten-5-yl]thio}-propionate (sodium salt of Exemplary compound 510)

Appearance; pale yellowish solid
$^1$H-NMR (δ, DMSO-$d_6$); 1.96-2.01 (m, 2H), 2.36-2.42 (m, 2H), 5.56 (s, 1H), 7.06-7.20 (m, 3H), 7.3.3 (d, J=6.6 Hz, 1H), 7.41 (td, J=13.4 Hz, 5.5 Hz, 1H), 7.47 (d, J=8.1 Hz, 1H), 7.55 (d, J=16.4 Hz, 1H), 7.67 (dd, J=9.4 Hz, 1.5 Hz, 1H), 7.83-7.89 (m, 2H), 7.96 (d, J=8.6 Hz, 1H), 8.01 (d, J=9.7 Hz, 1H), 8.21 (d, J=7.3 Hz, 1H), 8.38 (d, J=8.8 Hz, 1H).

Reaction was carried out in the same manner as in Examples 1 to 3 to obtain a compound of the following Example 19.

Example 19

Sodium [3-[(E)-2-(7-chloro-6-fluoroquinolin-2-yl)ethenyl]-9-chloro-5H-dibenzo[a,d]cyclohepten-5-yl]oxy-acetate (sodium salt of Exemplary compound 535)

Appearance; pale yellowish solid
$^1$H-NMR (δ, DMSO-$d_6$); 3.79 (s, 2H), 5.07 (s, 1H), 7.35-7.51 (m, 6H), 7.66 (bs, 2H), 7.90-8.03 (m, 4H), 8.23 (d, J=7.3 Hz, 1H), 8.38 (d, J=8.5 Hz, 1H).

Reaction was carried out in the same manner as in Example 4 to obtain compounds of the following Examples 20 to 21.

Example 20

Sodium 3-{[3-[(E)-2-(7-chloro-6-fluoroquinolin-2-yl)ethenyl]-9-chloro-5H-dibenzo[a,d]cyclohepten-5-yl]thio}-propionate (sodium salt of Exemplary compound 542)

Appearance; yellowish solid
$^1$H-NMR (δ, DMSO-$d_6$); 1.97-2.09 (m, 2H), 2.41-2.46 (m, 2H), 5.56 (s, 1H), 7.20 (d, J=12.5 Hz, 1H), 7.26 (d, J=12.5 Hz, 1H), 7.36-7.52 (m, 4H), 7.56 (d, J=16.4 Hz, 1H), 7.69 (dd, J=8.1 Hz, 1.5 Hz, 1H), 7.88 (d, J=16.4 Hz, 1H), 7.91 (d, J=1.5 Hz, 1H), 7.98 (d, J=8.8 Hz, 1H), 8.02 (d, J=9.8 Hz, 1H), 8.23 (d, J=7.3 Hz, 1H), 8.40 (d, J=8.6 Hz, 1H).

Example 21

Sodium 3-{[3-[(E)-2-(7-chloro-6-fluoroquinolin-2-yl)ethenyl]-8-chloro-5H-dibenzo[a,d]cyclohepten-5-yl]thio}-propionate (sodium salt of Exemplary compound 549)

Appearance; yellowish solid
$^1$H-NMR (δ, DMSO-$d_6$); 1.96-2.01 (m, 2H), 2.35-2.40 (m, 2H), 5.54 (s, 1H), 6.98 (d, J=12.0 Hz, 1H), 7.07 (d, J=12.2 Hz, 1H), 7.43 (dd, J=8.3 Hz, 2.2 Hz, 1H), 7.47 (d, J=8.1 Hz, 1H), 7.50-7.58 (m, 2H), 6.68 (d, J=7.8 Hz, 1H), 7.84-7.90 (m, 2H), 7.98 (d, J=8.8 Hz, 1H), 8.02 (d, J=9.8 Hz, 1H), 8.02 (d, J=7.8 Hz, 1H), 8.39 (d, J=8.8 Hz, 1H).

Reaction was carried out in the same manner as in Examples 1 to 3 to obtain compounds of the following Examples 22 to 25.

Example 22

Sodium [3-[(E)-2-(7-chloro-6-fluoroquinolin-2-yl)ethenyl]-6-chloro-5H-dibenzo[a,d]cyclohepten-5-yl]oxy-acetate (sodium salt of Exemplary compound 557)

Appearance; pale yellowish solid
$^1$H-NMR (δ, DMSO-$d_6$); 3.06 (d, J=15.0 Hz, 1H), 3.12 (d, J=15.0 Hz, 1H), 6.52 (s, 1H), 7.07 (d, J=12.0 Hz, 1H), 7.11 (d, J=12.5 Hz, 1H), 7.36 (t, J=7.8 Hz, 1H), 7.48-7.58 (m, 4H), 7.78-7.82 (m, 2H), 7.94 (d, J=16.4 Hz, 1H), 7.99-8.02 (m, 2H), 8.22 (d, J=7.3 Hz, 1H), 8.39 (d, J=8.8 Hz, 1H).

Example 23

Sodium 2-(R)-{[3-[(E)-2-(7-chloro-6-fluoroquinolin-2-yl)ethenyl]-5H-dibenzo[a,d]cyclohepten-5-yl]oxy}propionate (sodium salt of Exemplary compound 558).

Appearance; yellowish solid
$^1$H-NMR (δ, DMSO-$d_6$); 0.84-0.86, 1.46-1.50 (each m, 1H in total), 3.00-3.04, 3.75-3.79 (each m, 1H in total), 5.01, 5.95 (each s, 1H in total), 7.03, 7.15 (each s, 1H in total), 7.20-8.01 (m, 11H), 8.04 (d, J=10.0 Hz, 1H), 8.23 (d, J=7.3 Hz, 1H), 8.37 (dd, J=8.8 Hz, 2.4 Hz, 1H)

Example 24

Sodium 2-(S)-{[3-[(E)-2-(7-chloro-6-fluoroquinolin-2-yl)ethenyl]-5H-dibenzo[a,d]cyclohepten-5-yl]oxy}propionate (sodium salt of Exemplary compound 558)

Appearance; pale yellowish solid
$^1$H-NMR (δ, DMSO-$d_6$); 0.82-0.84, 1.44-1.48 (each m, 1H in total), 3.33-3.42, 3.69-3.78 (each m, 1H in total), 5.00, 5.94 (each s, 1H in total), 7.03, 7.15 (each s, 1H in total), 7.20-7.99 (m, 11H), 8.04 (d, J=10.0 Hz, 1H), 8.23 (d, J=7.3 Hz, 1H), 8.37 (dd, J=8.8 Hz, 2.4 Hz, 1H).

Example 25

Sodium 3-{[3-[(E)-2-(7-chloro-6-fluoroquinolin-2-yl)ethenyl]-6-chloro-5H-dibenzo[a,d]cyclopheten-5-yl]oxy}-propionate (sodium salt of Exemplary compound 559)

Appearance; pale yellowish solid
$^1$H-NMR (δ, DMSO-$d_6$); 1.86-1.92 (m, 2H), 3.09-3.22 (m, 2H), 6.26 (s, 1H), 7.08 (d, J=12.0 Hz, 1H), 7.13 (d, J=12.2 Hz, 1H), 7.38 (t, J=7.6 Hz, 1H), 7.51 (dd, J=7.8 Hz, 1.2 Hz, 1H), 7.53-7.62 (m, 3H), 7.80 (dd, J=8.1 Hz, 1.5 Hz, 1H), 7.92 (s, 1H), 7.95 (d, J=16.4 Hz, 1H), 7.99-8.03 (m, 2H), 8.22 (d, J=7.3 Hz, 1H), 8.39 (d, J=8.5 Hz, 1H).

Reaction was carried out in the same manner as in Example 4 to obtain compounds of the following Examples 26 to 28.

Example 26

Sodium [3-[(E)-2-(7-chloro-6-fluoroquinolin-2-yl)ethenyl]-6-chloro-5H-dibenzo[a,d]cyclohepten-5-yl]thio-acetate (sodium salt of Exemplary compound 562)

Appearance; orange solid $^1$H-NMR ($\delta$, DMSO-$d_6$); 2.77 (d, J=13.4 Hz, 1H), 2.85 (d, J=13.7 Hz, 1H), 6.17 (s, 1H), 7.04 (d, J=12.0 Hz, 1H), 7.08 (d, J=12.0 Hz, 1H), 7.30 (t, J=7.8 Hz, 1H), 7.41 (d, J=7.1 Hz, 1H), 7.47-7.58 (m, 3H), 7.72 (d, J=8.1 Hz, 1H), 7.79 (s, 1H), 7.91 (d, J=16.4 Hz, 1H), 7.98-8.03 (m, 2H), 8.22 (d, J=7.7 Hz, 1H), 8.39 (d, J=8.8 Hz, 1H).

Example 27

Sodium 3-{[3-[(E)-2-(7-chloro-6-fluoroquinolin-2-yl)ethenyl]-6-chloro-5H-dibenzo[a,d]cyclohepten-5-yl]thio}-propionate (sodium salt of Exemplary compound 564)

Appearance; yellowish solid $^1$H-NMR ($\delta$, DMSO-$d_6$); 1.93-2.07 (m, 2H), 2.49-2.55 (m, 2H), 6.02 (s, 1H), 7.06 (d, J=12.2 Hz, 1H), 7.11 (d, J=12.0 Hz, 1H), 7.32 (t, J=7.6 Hz, 1H), 7.42 (dd, J=7.8 Hz, 1.2 Hz, 1H), 7.51 (d, J=8.1 Hz, 1H), 7.52-7.62 (m, 2H), 7.75 (dd, J=8.1 Hz, 1.5 Hz, 1H), 7.82 (d, J=1.5 Hz, 1H), 7.92 (d, J=16.4 Hz, 1H), 7.99-8.03 (m, 2H), 8.22 (d, J=7.3 Hz, 1H), 7.39 (d, J=8.8 Hz, 1H).

Example 28

Sodium 3-{[3-[(E)-2-(7-chloro-6-fluoroquinolin-2-yl)ethenyl]-9-trifluoromethyl-5H-dibenzo[a,d]cyclohepten-5-yl]thio}propionate (sodium salt of Exemplary compound 613)

Appearance; pale yellowish solid

FAB-MS (m/z): 492 (M$^+$+1). $^1$H-NMR ($\delta$, DMSO-$d_6$); 1.99-2.09 (m, 2H), 2.43-2.53 (m, 2H), 5.65 (s, 1H), 7.69-7.30 (m, 2H), 7.50-7.59 (m, 3H), 7.67-7.74 (m, 2H), 7.85-8.03 (m, 5H), 8.23 (d, J=7.3 Hz, 1H), 8.40 (d, J=8.8 Hz, 1H).

Reaction was carried out in the same manner as in Examples 1 to 3 to obtain a compound of the following Example 29.

Example 29

Sodium [3-[(E)-2-(7-chloroquinolin-2-yl)ethenyl]-5H-dibenzo[a,d]cyclohepten-5-yl]oxyacetate (sodium salt of Exemplary compound 1411)

Appearance; orange solid $^1$H-NMR ($\delta$, DMSO-$d_6$); 3.80 (bs, 2H), 5.04 (bs, 1H), 7.16 (bs, 2H), 7.27-7.66 (m, 8H), 7.92-8.02 (m, 4H), 8.04 (d, J=2.2 Hz, 1H), 8.40 (d, J=8.5 Hz, 1H).

Reaction was carried out in the same manner as in Example 4 to obtain compounds of the following Examples 30 to 31.

Example 30

Sodium [3-[(E)-2-(7-chloroquinolin-2-yl)ethenyl]-5H-dibenzo[a,d]cyclohepten-5-yl]thioacetate (sodium salt of Exemplary compound 1416)

Appearance; pale yellowish solid

FAB-MS (m/z); 492 (M$^+$+1). $^1$H-NMR ($\delta$, DMSO-$d_6$); 2.65 (d, J=13.9 Hz, 2H), 2.68 (d, J=13.9 Hz, 2H), 5.64 (s, 1H), 6.98 (s, 2H), 7.22-7.46 (m, 5H), 7.53 (d, J=16.4 Hz, 1H), 7.59 (dd, J=8.8 Hz, 2.2 Hz, 1H), 7.67 (dd, J=8.1 Hz, 1.5 Hz, 1H), 7.77 (d, J=1.5 Hz, 1H), 7.87-8.04 (m, 4H), 8.41 (d, J=8.5 Hz, 1H).

Example 31

Sodium 3-{[3-[(E)-2-(5,6,7,8-tetrahydroquinolin-2-yl)ethenyl]-9-trifluoromethyl-5H-dibenzo[a,d]cyclohepten-5-yl]thio}propionate (sodium salt of Exemplary compound 1921)

Appearance; pale yellowish solid

FAB-MS (m/z): 544 (M$^+$+1). $^1$H-NMR ($\delta$, DMSO-$d_6$); 1.75-1.85 (m, 4H), 2.00-2.05 (m, 2H), 2.42-2.47 (m, 2H), 2.72-2.87 (m, 4H), 5.60 (s, 1H), 7.14-7.32 (m, 4H), 7.44-7.47 (m, 2H), 7.53-7.61 (m, 3H), 7.72 (d, J=7.6 Hz, 1H), 7.81-7.83 (m, 2H).

Reference Example 1

(a) 7-Chloro-2-vinyl quinolin

The title compound was obtained by the method as described in J. Org. Chem., 61, 3398 (1996).

Appearance; ocherous solid $^1$H-NMR ($\delta$, DMSO-$d_6$); 5.69 (dd, J=11.0 Hz, 1.0 Hz, 1H), 6.31 (dd, J=17.6 Hz, 0.7 Hz, 1H), 7.00 (dd, J=17.8 Hz, 11.0 Hz, 1H), 7.45 (dd, J=8.8 Hz, 2.0 Hz, 1H), 7.60 (d, J=8.5 Hz, 1H), 7.71 (d, J=8.5 Hz, 1H), 8.06-8.10 (m, 2H).

(b) 3-Trifluoromethanesulfonyloxy-5H-dibenzo[a,d]-cyclohepten-5-one

In 30 ml of methylene chloride was dissolved 0.23 g (1.0 mmol) of 3-hydroxy-5H-dibenzo[a,d]cyclohepten-5-one and after cooling the solution with ice-water, 0.33 ml (2.0 mmol) of trifluoromethanesulfonic anhydride and 0.27 ml (2.0 mmol) of triethylamine were added to the solution and the resulting mixture was stirred under ice-cooling for 4 hours.

After completion of the reaction, the reaction mixture was concentrated, and the residue was applied to silica gel column chromatography (eluent: chloroform) to obtain 0.30 g of the title compound as brown oily product.

CI-MS (m/z); 355 (M$^+$+1). EI-MS; 354 (M$^+$). $^1$H-NMR ($\delta$, DMSO-$d_6$); 7.31 (d, J=12.2 Hz, 1H), 7.37 (d, J=12.2 Hz, 1H), 7.50-8.40 (m, 7H).

(c) 3-[(E)-2-(7-chloroquinolin-2-yl)ethenyl]-5H-dibenzo[a,d]cyclohepten-5-one

In 30 ml of N,N-dimethylformamide were dissolved 0.89 g (2.5 mmol) of 3-trifluoromethanesulfonyloxy-5H-dibenzo[a,d]cyclohepten-5-one and 0.48 g (2.5 mmol) of 7-chloro-2-vinyl quinoline, and then, 100 mg (0.5 mmol) of palladium acetate, 420 mg (1.6 mmol) of triphenylphosphine and 2.1 g (24 mmol) of lithium bromide were added to the mixture and the atmosphere thereof was made nitrogen. Then, 5.0 ml (36 mmol) of triethylamine was added to the mixture, and the resulting mixture was stirred under nitrogen atmosphere at 120° C. for 10 hours.

After completion of the reaction, the reaction mixture was concentrated, and the residue was applied to silica gel column chromatography (eluent: toluene/ethyl acetate=9/1 (volume ratio)) to obtain 0.53 g of the title compound as pale brown solid.

CI-MS (m/z); 394 (M$^+$+1). $^1$H-NMR ($\delta$, DMSO-d$_6$); 7.28 (s, 2H), 7.59-7.69 (m, 3H), 7.78-7.83 (m, 3H), 7.97-8.06 (m, 4H), 8.13-8.20 (m, 2H), 8.38 (s, 1H), 8.44 (d, J=9.3 Hz, 1H).

(d) 3-[(E)-2-(7-chloroquinolin-2-yl)ethenyl]-5H-dibenzo[a,d]cyclohepten-5-ol

In a mixed solution of 40 ml of tetrahydrofuran and 10 ml of methanol was dissolved 0.53 g (1.3 mmol) of 3-[(E)-2-(7-chloroquinolin-2-yl)ethenyl]-5H-debenxo[a,d]-cyclohepten-5-one, and 0.11 g (2.6 mmol) of sodium borohydride was added to the mixture and the resulting mixture was stirred at room temperature for 3 hours.

After completion of the reaction, water was added to the reaction mixture, a pH of the mixture was adjusted to about 2.0 with 1N hydrochloric acid and the mixture was extracted with ethyl acetate. The organic layer was washed with a saturated aqueous sodium chloride solution, dried over anhydrous magnesium sulfate and concentrated. The residue was dried under reduced pressure to obtain 0.33 g of the title compound as ocherous solid.

CI-MS (m/z); 396 (M$^+$+1). $^1$H-NMR ($\delta$, DMSO-d$_6$); 5.10 (d, J=3.4 Hz, 1H), 6.20 (s, 1H), 7.18 (s, 2H), 7.26 (td, J=8.8 Hz, 1.2 Hz, 1H), 7.37-7.52 (m, 4H), 7.59 (dd, J=8.5 Hz, 2.2 Hz, 1H), 7.64 (dd, J=8.1 Hz, 1.7 Hz, 1H), 7.76 (d, J=7.6 Hz, 1H), 7.91-8.04 (m, 5H), 8.40 (d, J=8.3 Hz, 1H).

Reference Example 2

Reaction was carried out in the same manner as in Reference Example 1(a) to obtain a compound of the following Reference Example 2(a).

(a) 7-Chloro-6-fluoro-2-vinylquinoline

Appearance; yellowish solid

CI-MS (m/z); 208 (M$^+$+1). EI-MS; 207 (M$^+$). $^1$H-NMR ($\delta$, DMSO-d$_6$); 5.73 (dd, J=11.0 Hz, 1.0 Hz, 1H), 6.43 (dd, J=17.6 Hz, 1.0 Hz, 1H), 6.98 (dd, J=17.8 Hz, 11.0 Hz, 1H), 7.89 (d, J=8.8 Hz, 1H), 8.01 (d, J=9.8 Hz, 1H), 8.21 (d, J=7.3 Hz, 1H). 8.37 (d, J=9.0 Hz, 1H).

Reaction was carried out in the same manner as in Reference Example 1(c) to obtain a compound of the following Reference Example 2(b).

(b) 3-[(E)-2-(7-chloro-6-fluoroquinolin-2-yl)ethenyl]-5H-dibenzo[a,d]cyclohepten-5-one Appearance; pale yellowish solid $^1$H-NMR ($\delta$, DMSO-d$_6$); 7.29 (s, 2H), 7.63-7.70 (m, 2H), 7.78-7.84 (m, 3H), 8.00-8.05 (m, 3H), 8.13-8.21 (m, 2H), 8.23 (d, J=7.6 Hz, 1H), 8.38 (d, J=1.7 Hz, 1H), 8.42 (d, J=9.3 Hz, 1H).

Reaction was carried out in the same manner as in Reference Example 1(d) to obtain a compound of the following Reference Example 2(c).

(c) 3-[(E)-2-(7-chloro-6-fluoroquinolin-2-yl)ethenyl]-5H-dibenzo[a,d]cyclohepten-5-ol Appearance; yellowish solid $^1$H-NMR ($\delta$, DMSO-d$_6$); 5.09 (d, J=3.9 Hz, 1H), 6.20 (s, 1H), 7.18 (s, 2H), 7.26 (td, J=7.3 Hz, 1.2 Hz, 1H), 7.37-7.50 (m, 4H), 7.60 (d, J=7.6 Hz, 1H), 7.63 (dd, J=7.8 Hz, 1.7 Hz, 1H), 7.93 (d, J=16.4 Hz, 1H), 7.98-8.02 (m, 3H), 8.21 (d, J=7.3 Hz, 1H), 8.38 (d, J=8.5 Hz, 1H).

Reference Example 3

Reaction was carried out in the same manner as in Reference Example 1(a) to obtain a compound of the following Reference Example 3(a).

(a) 6,7-Difluoro-2-vinylquinoline

Appearance; pale yellowish solid

CI-MS (m/z); 192 (M$^+$+1). EI-MS; 191 (M$^+$). $^1$H-NMR ($\delta$, DMSO-d$_6$); 5.69 (dd, J=11.0 Hz, 1.0 Hz, 1H), 6.39 (dd, J=17.6 Hz, 1.0 Hz, 1H), 6.93 (dd, J=8.1 Hz, 3.9 Hz, 1H), 6.95 (dd, J=17.6 Hz, 11.0 Hz, 1H), 7.82 (d, J=8.8 Hz, 1H), 8.00 (dd, J=9.0 Hz, 2.2 Hz, 1H), 8.33 (d, J=8.5 Hz, 1H).

Reaction was carried out in the same manner as in Reference Example 1(c) to obtain a compound of the following Reference Example 3(b).

(b) 3-[(E)-2-(6,7-difluoroquinolin-2-yl)ethenyl]-5H-dibenzo[a,d]cyclohepten-5-one Appearance; brown solid CI-MS (m/z); 396 (M$^+$+1). EI-MS; 395 (M$^+$). $^1$H-NMR ($\delta$, DMSO-d$_6$); 7.29 (s, 2H), 7.50-7.90 (m, 7H), 7.95-8.30 (m, 5H), 8.41 (d, J=8.5 Hz, 1H).

Reaction was carried out in the same manner as in Reference Example 1(d) to obtain a compound of the following Reference Example 3(c).

(c) 3-[(E)-2-(6,7-difluoroquinolin-2-yl)ethenyl]-5H-dibenzo[a,d]cyclohepten-5-ol Appearance; brown solid CI-MS (m/z); 398 (M$^+$+1). EI-MS; 397 (M$^+$). $^1$H-NMR ($\delta$, DMSO-d$_6$); 5.09 (s, 1H), 7.18 (s, 2H), 7.20-7.70 (m, 2H), 7.28 (d, J=7.3 Hz, 1H), 7.38 (d, J=7.6 Hz, 1H), 7.43 (d, J=7.8 Hz, 1H), 7.49 (d, J=7.6 Hz, 1H), 7.76 (d, J=7.6 Hz, 1H), 7.80-8.20 (m, 4H), 7.93 (d, J=16.6 Hz, 1H), 8.36 (d, J=8.5 Hz, 1H).

Reference Example 4

(a) 5,6,7,8-Tetrahydro-2-vinylquinoline

In 300 ml of acetonitrile was dissolved 14.7 g (65 mmol) of (5,6,7,8-tetrahydroquinolin-2-yl)methyl bromide, and 25.5 g (97.5 mmol) of triphenylphosphine was added to the mixture and the resulting mixture was refluxed for 2 hours. After cooling the mixture with an ice-bath, precipitates were collected by filtration and washed with diethyl ether to obtain (5,6,7,8-tetrahydroquinolin-2-yl)methyltriphenylphosphonium bromide as pale yellowish solid. Then, the obtained solid was dissolved in 250 ml of chloroform, 9.50 g (117 mmol) of 37% formaldehyde and 8.10 g (76 mmol)

of an aqueous sodium carbonate solution (20 ml) were added to the solution and the mixture was stirred at room temperature for 2 hours.

After completion of the reaction, water was added to the reaction mixture and the mixture was extracted with chloroform. The organic layer was dried over potassium carbonate and concentrated. The residue was applied to silica gel column chromatography (eluent: hexane/ethyl acetate=9/1 (volume ratio)) to obtain 6.01 g of the title compound as yellowish oily product.

CI-MS (m/z); 160 (M$^+$+1). EI-MS; 159 (M$^+$). $^1$H-NMR (δ, CDCl$_3$); 1.85 (m, 4H), 2.75 (dd, J=17.6 Hz, 1.0 Hz, 2H), 2.91 (dd, J=8.1 Hz, 3.9 Hz, 2H), 5.41 (dd, J=10.7 Hz, 1.2 Hz, 1H), 6.06 (dd, J=17.6 Hz, 1.2 Hz, 1H), 6.75 (dd, J=17.6 Hz, 10.7 Hz, 1H), 7.14 (d, J=7.8 Hz, 1H), 7.31 (d, J=7.8 Hz, 1H).

Reaction was carried out in the same manner as in Reference Example 1(c) to obtain a compound of the following Reference Example 4(b).

(b) 3-[(E)-2-(5,6,7,8-tetrahydroquinolin-2-yl)ethenyl]-5H-dibenzo[a,d]cyclohepten-5-one Appearance; pale yellowish solid
$^1$H-NMR (δ, CDCl$_3$); 1.81-1.95 (m, 4H), 2.79 (t, J=6.1, 2H), 2.96 (t, J=6.4 Hz, 2H), 7.05 (s, 2H), 7.15-7.37 (m, 4H), 7.52-7.64 (m, 4H), 7.81-7.85 (m, 1H), 8.23-8.26 (m, 1H), 8.40 (d, J=2.0 Hz, 1H).

Reaction was carried out in the same manner as in Reference Example 1(d) to obtain a compound of the following Reference Example 4(c).

(c) 3-[(E)-2-(5,6,7,8-tetrahydroquinolin-2-yl)-ethenyl]-5H-dibenzo[a,d]cyclohepten-5-ol Appearance; pale yellowish solid
$^1$H-NMR (δ, CDCl$_3$); 1.80-2.00 (m, 4H), 2.77 (m, 2H), 2.95 (m, 2H), 5.45 (s, 1H), 7.09 (s, 1H), 7.20-7.70 (m, 10H), 7.89 (s, 1H).

Reference Example 5

(a) 3-(7-chloro-6-fluoroquinolin-2-yl)methoxy-5H-dibenzo[a,d]cyclohepten-5-one

In 30 ml of N,N-dimethylformamide were dissolved 0.37 g (1.4 mmol) of 2-bromomethyl-7-chloro-6-fluoroquinoline and 0.30 g (1.4 mmol) of 3-hydroxy-5H-dibenzo-[a,d]cyclohepten-5-one, and 0.37 g (2.8 mmol) of potassium carbonate was added to the mixture and the resulting mixture was stirred at room temperature for 6 hours.

After completion of the reaction, water was added to the reaction mixture and the mixture was extracted with ethyl acetate. The organic layer was washed with a saturated aqueous sodium chloride solution, dried over anhydrous magnesium sulfate and concentrated. The residue was dried under reduced pressure to obtain 0.47 g of the title compound as dark brown solid.

CI-MS (m/z); 416 (M$^+$+1). EI-MS; 415 (M$^+$). $^1$H-NMR (δ, DMSO-d$_6$); 5.53 (s, 2H), 7.13 (d, J=12.2 Hz, 1H), 7.21 (d, J=12.2 Hz, 1H), 7.51 (dd, J=8.5 Hz, 2.7 Hz, 1H), 7.55-7.90 (m, 6H), 8.00-8.35 (m, 2H), 8.31 (d, J=7.3 Hz, 1H), 8.46 (d, J=8.5 Hz, 1H).

(b) 3-(7-chloro-6-fluoroquinolin-2-yl)methoxy-5H-dibenzo[a,d]cyclohepten-5-ol

Reaction was carried out in the same manner as in Reference Example 1(d) except for using 3-(7-chloro-6-fluoroquinolin-2-yl)methoxy-5H-dibenzo[a,d]cyclohepten-5-one in place of 3-[(E)-2-(6,7-difluoroquinolin-2-yl)ethenyl]-5H-dibenzo[a,d]cyclohepten-5-one to obtain the title compound.

Appearance; brown solid
CI-MS (m/z); 418 (M$^+$+1). EI-MS; 418 (M$^+$). $^1$H-NMR (δ, DMSO-d$_6$); 5.38 (s, 1H), 5.41 (s, 2H), 6.80-7.90 (m, 9H), 7.95-8.35 (m, 3H), 8.42 (d, J=8.8 Hz, 1H).

Reference Example 6

(a) 2-methoxycarbonylbenzyltriphenylphosphonium bromide

In 300 ml of acetonitrile were dissolved 86.32 g (377 mmol) of methyl 2-(bromomethyl)benzoate and 98.84 g (377 mmol) of triphenylphosphine, and the solution was refluxed for 2 hours.

After completion of the reaction, 700 ml of diethyl ether was added to the reaction mixture. The precipitated white precipitates were collected by filtration and washed with diethyl ether. The precipitates were dried under reduced pressure to obtain 117.42 g of the title compound as pale brown solid.

CI-MS (m/z); 410 (M$^+$–Br). $^1$H-NMR (δ, DMSO-d$_6$); 3.46 (s, 3H), 5.53 (d, J=15.4 Hz, 2H), 7.30-7.40 (m, 1H), 7.45-7.63 (m, 8H), 7.65-7.80 (m, 6H), 7.82-7.95 (m, 4H).

(b) Methyl 2-[2-(4-methoxyphenyl)ethenyl]benzoate

In 50 ml of acetonitrile were dissolved 4.91 g (10 mmol) of 2-methoxycarbonylbenzyltriphenylphosphonium bromide and 1.77 g (13 mmol) of 4-methoxybenzaldehyde, and 2.48 g (20 mmol) of 1,5-diazabicyclo[4.3.0]-5-nonene was added to the solution and the mixture was refluxed for 5 hours.

After completion of the reaction, the reaction mixture was concentrated, and the residue was applied to silica gel column chromatography (eluent: toluene) to obtain 1.25 g of the title compound (E,Z mixture) as pale yellowish oily product.

CI-MS (m/z); 269 (M$^+$+1). EI-MS; 268 (M$^+$).

Cis isomer (Z isomer)
$^1$H-NMR (δ, DMSO-d$_6$); 3.79 (s, 3H), 3.87 (s, 3H), 6.74 (d, J=9.0 Hz, 1H), 6.90-7.00 (m, 2H), 7.10-7.73 (m, 5H), 7.75-7.95 (m, 2H).

Trans isomer (E isomer)
$^1$H-NMR (δ, DMSO-d$_6$); 3.69 (s, 3H), 3.87 (s, 3H), 6.56 (d, J=12.2 Hz, 1H), 6.74 (d, J=9.0 Hz, 1H), 6.84 (d, J=12.2 Hz, 1H), 6.90-7.00 (m, 2H), 7.10-7.73 (m, 3H), 7.75-7.95 (m, 2H).

(c) 2-[2-(4-Methoxyphenyl)ethenyl]benzoic acid

To 2 ml of a methanol solution containing 1.20 g (4.5 mmol) of methyl 2-[2-(4-methoxyphenyl)ethenyl]benzoic acid was added 1.5 g (26.7 mmol) of an aqueous potassium hydroxide solution (20 ml), and the mixture was refluxed for 6 hours.

After completion of the reaction, the reaction mixture was cooled and a 1N aqueous hydrochloric acid solution was added to the mixture to adjust a pH thereof to 3. Formed white precipitates were collected by filtration, washed with water and dried under reduced pressure to obtain 1.12 g of the title compound (E,Z mixture) as white solid.

CI-MS (m/z); 255 (M$^+$+1). EI-MS; 254 (M$^+$).

Cis isomer (Z isomer)

$^1$H-NMR (δ, DMSO-d$_6$); 3.78 (s, 3H), 6.53 (d, J=12.2 Hz, 1H), 6.74 (d, J=8.8 Hz, 1H), 6.89 (d, J=12.2 Hz, 1H), 6.96 (d, J=8.8 Hz, 1H), 6.97 (d, J=8.8 Hz, 1H), 7.15-7.60 (m, 3H), 7.70-7.95 (m, 2H), 12.93 (br, 1H).

Trans isomer (E isomer)

$^1$H-NMR (δ, DMSO-d$_6$); 3.69 (s, 3H), 6.74 (d, J=8.8 Hz, 1H), 6.96 (d, J=8.8 Hz, 1H), 6.97 (d, J=8.8 Hz, 1H), 7.12 (d, J=16.1 Hz, 1H), 7.15-7.60 (m, 4H), 7.70-7.95 (m, 2H), 12.93 (br, 1H).

(d) 2-[2-(4-Methoxyphenyl)ethyl]benzoic acid

To 20 ml of a methanol solution containing 0.20 g (1.3 mmol) of 2-[2-(4-methoxyphenyl)ethenyl]benzoic acid was added 0.10 g of 10% palladium-activated charcoal, and then, the mixture was stirred at room temperature for 5 hours under hydrogen atmosphere (normal pressure).

After completion of the reaction, 10% palladium-activated charcoal was removed from the reaction mixture by filtration by using Celite (tradename), and the filtrate was concentrated to obtain 0.18 g of the title compound as pale yellowish solid.

CI-MS (m/z); 257 (M$^+$+1). EI-MS; 256 (M$^+$). $^1$H-NMR (δ, DMSO-d$_6$); 2.70-2.80 (m, 2H), 3.10-3.20 (m, 2H), 3.67 (s, 3H), 6.80-6.90 (m, 2H), 7.10-7.20 (m, 2H), 7.22-7.35 (m, 2H), 7.40-7.50 (m, 1H), 7.75-7.85 (m, 1H), 12.88 (br, 1H).

(e) 3-Methoxy-10,11-dihydro-5H-dibenzo[a,d]cyclohepten-5-one

To 50 ml of a methylene chloride solution containing 1.80 g (7.0 mmol) of 2-[2-(4-methoxyphenyl)ethyl]benzoic acid were added 1.83 ml (13 mmol) of trifluoroacetic anhydride and 0.8 ml (6.3 mmol) of boron trifluoride ethyl ether complex and the mixture was stirred at room temperature for 5 hours.

After completion of the reaction, the reaction mixture was concentrated, and the residue was applied to silica gel column chromatography (eluent: toluene) to obtain 0.65 g of the title compound as yellow oily product.

CI-MS (m/z); 239 (M$^+$+1). EI-MS; 238 (M$^+$). $^1$H-NMR (δ, DMSO-d$_6$); 3.12 (s, 4H), 3.79 (s, 3H), 7.12 (dd, J=8.3 Hz, 2.9 Hz, 1H), 7.28 (d, J=8.3 Hz, 1H), 7.35 (d, J=7.8 Hz, 2H), 7.40 (d, J=2.9 Hz, 1H), 7.51 (dd, J=7.3 Hz, 1.5 Hz, 1H), 7.84 (d, J=8.1 Hz, 1H).

(f) 3-Methoxy-5H-dibenzo[a,d]cyclohepten-5-one

To 20 ml of a 1,2-dichloroethane solution containing 0.65 g (2.7 mmol) of 3-methoxy-10,11-dihydro-5H-dibenzo-[a,d]cyclohepten-5-one were added 0.80 g (4.5 mmol) of N-bromosuccineimide and 0.14 g (0.6 mmol) of benzoyl peroxide, and the mixture was refluxed for 3 hours.

After completion of the reaction, 100 ml of chloroform was added to the reaction mixture and the resulting mixture was washed with 50 ml of an aqueous 1N sodium hydroxide solution. The organic layer was washed with a saturated aqueous sodium chloride solution, dried over anhydrous magnesium sulfate and concentrated. The residue was dissolved in 50 ml of 1,2-dichloroethane, 50 ml of triethylamine was added thereto and the resulting mixture was refluxed for 2 hours.

After completion of the reaction, the reaction mixture was concentrated, and the residue was applied to silica gel column chromatography (eluent: toluene/ethyl acetate=9/1 (volume ratio)) to obtain 0.57 g of the title compound as brown solid.

CI-MS (m/z); 237 (M$^+$+1). EI-MS; 236 (M$^+$). $^1$H-NMR (δ, DMSO-d$_6$); 3.90 (s, 3H), 7.12 (d, J=12.2 Hz, 1H), 7.22 (d, J=12.2 Hz, 1H), 7.38 (dd, J=8.5 Hz, 2.9 Hz, 1H), 7.55-7.68 (m, 2H), 7.70-7.80 (m, 3H), 8.13 (d, J=7.6 Hz, 1H).

(g) 3-Hydroxy-5H-dibenzo[a,d]cyclohepten-5-one

In 100 ml of acetic acid was dissolved 2.03 g (8.6 mmol) of 3-methoxy-5H-dibenzo[a,d]cyclohepten-5-one, 20 ml of 48% hydrobromic acid was added to the solution and the resulting mixture was refluxed for 10 hours.

After completion of the reaction, the reaction mixture was poured into 200 ml of ice-water and the formed solid was collected by filtration, washed with water and dried to obtain 1.48 g of the title compound as dark brown solid.

CI-MS (m/z); 223 (M$^+$+1). EI-MS; 222 (M$^+$). $^1$H-NMR (δ, DMSO-d$_6$); 7.04 (d, J=12.0 Hz, 1H), 7.12 (d, J=12.0 Hz, 1H), 7.19 (dd, J=8.5 Hz, 2.9 Hz, 1H), 7.50-7.64 (m, 3H), 7.67-7.80 (m, 2H), 8.11 (d, J=7.6 Hz, 1H).

Reference Example 7

(a) 3-(4-Methoxybenzylidene)phthalide 22.28 g (150 mmol) of phthalic anhydride, 25.0 g (150 mmol) of 4-methoxyphenyl acetate and 2.0 g (24 mmol) of sodium acetate were mixed and the mixture was stirred at 220° C. for 8 hours.

After completion of the reaction, ethanol was added to the reaction mixture and insoluble material was removed by filtration, and the filtrate was concentrated. The obtained residue was applied to silica gel column chromatography (eluent: toluene/ethyl acetate=9/1 (volume ratio)) to obtain 13.15 g of the title compound as yellowish solid.

CI-MS (m/z); 253 (M$^+$+1). EI-MS; 252 (M$^+$). $^1$H-NMR (δ, DMSO-d$_6$); 3.81 (s, 3H), 6.90 (s, 1H), 7.06 (d, J=8.8 Hz, 1H), 7.64 (t, J=7.3 Hz, 1H), 7.78 (d, J=8.8 Hz, 1H), 7.87 (t, J=7.3 Hz, 1H), 7.95 (d, J=7.8 Hz, 1H), 8.09 (d, J=7.8 Hz, 1H).

(b) 2-[2-(4-Methoxyphenyl)ethyl]benzoic acid

To 280 ml of an ethanol solution containing 20.0 g (79.3 mmol) of 3-(4-methoxybenzylidene)phthalide were added 16.6 ml (119 mmol) of triethylamine and Raney nickel (available from Kawaken Finechemical, developed nickel catalyst NTD-65, 24 ml), and the resulting mixture was stirred at 80° C. for 2.5 hours under pressure with hydrogen (10 atm).

After completion of the reaction, the catalyst was removed from the reaction mixture by filtration using Celite (tradename), and the filtrate was concentrated. The obtained residue was dissolved in 200 ml of methylene chloride, washed successively with 100 ml of a 1N aqueous hydrochloric acid solution, and a saturated aqueous sodium chloride solution, dried over anhydrous magnesium sulfate and concentrated. The residue was dried under reduced pressure to obtain 17.2 g of the title compound as white solid. The obtained compound was the same as the compound of Reference Example 6(d).

Reference Example 8

(a) 2-[2-(4-Bromophenyl)ethenyl]-3-fluorobenzoic acid

To a liquor in which 11.6 g (121 mmol) of sodium t-butoxide had been suspended in 200 ml of N,N-dimethylformamide were added dropwise a solution in which 20.2 g (120 mmol) of methyl 3-fluoro-2-methylbenzoate and 22.3 g (120 mmol) of p-bromobenzaldehyde had been dissolved in 100 ml of dimethylformamide at 5° C. over 1 hour. After completion of dropwise addition, the mixture was stirred at 10° C. for 1 hour, and further stirred at at room temperature overnight.

After completion of the reaction, 1.0 liter of water was added to the reaction mixture and the resulting mixture was adjusted with conc. hydrochloric acid to pH 3. Precipitated solid was collected by filtration, washed with water and dried under reduced pressure to obtain 25.3 g of the title compound as pale yellowish solid.

$^1$H-NMR ($\delta$, CDCl$_3$); 7.06 (dd, J=16.9 Hz, 1.7 Hz, 1H), 7.38-7.61 (m, 7H), 7.67 (dd, J=7.1 Hz, 1.7 Hz, 1H), 13.28 (b, 1H).

(b) 2-[2-(4-Bromophenyl)ethyl]-3-fluorobenzoic acid

To 25.3 g (78.8 mmol) of 2-[2-(4-bromophenyl)ethenyl]-3-fluorobenzoic acid were added 6.2 g (199.4 mmol) of red phosphorus, 60 ml of 57% hydroiodic acid and 150 ml of acetic acid, and the mixture was refluxed for 10 hours.

After cooling by allowing to stand, red phosphorus was further added to the mixture and the mixture was refluxed. Addition of red phosphorus was carried out further two times.

After completion of the reaction, 1.0 liter of water was added to the reaction mixture, precipitated solid was collected by filtration, water was added to the solid and the mixture was adjusted to pH 12 with an aqueous sodium hydroxide solution, and insoluble material was filtered off. The filtrate was adjusted to pH 3 with conc. hydrochloric acid, precipitated solid was collected by filtration, washed with water and dried under reduced pressure to obtain 23.9 g of the title compound as colorless solid.

$^1$H-NMR ($\delta$, CDCl$_3$); 2.76-2.81 (m, 2H), 3.15-3.20 (m, 2H), 7.16 (d, J=8.3 Hz, 2H), 7.35-7.39 (m, 2H), 7.47 (d, J=8.3 Hz, 2H), 7.65-7.68 (m, 1H), 13.4 (b, 1H).

(c) 3-Bromo-9-fluoro-10,11-dihydro-5H-dibenzo[a,d]-cyclohepten-5-one

To 25.8 g (80 mmol) of 2-[2-(4-bromophenyl)ethyl]-3-fluorobenzoic acid was added 550 g of polyphosphoric acid, and the mixture was stirred at 170° C. for 3 hours. After cooling the mixture to 80° C. by allowing to stand, water was added to the mixture and the resulting mixture was cooled to room temperature under stirring by allowing to stand.

After completion of the reaction, the reaction mixture was extracted with chloroform. The extract was washed successively with water, an aqueous sodium hydroxide solution, and water. The organic layer was dried over anhydrous sodium sulfate, concentrated and the residue was applied to silica gel column chromatography (eluent: hexane/ethyl acetate=9/1(volume ratio)) to obtain 18.6 g of the title compound as brown solid.

CI-MS (m/z); 305 (M$^+$+1). $^1$H-NMR ($\delta$, CDCl$_3$); 3.11-3.23 (m, 4H), 7.17 (d, J=8.5 Hz, 1H), 7.19-7.34 (m, 2H), 7.55 (dd, J=8.3 Hz, 2.2 Hz, 1H), 7.79 (d, J=7.1 Hz, 1H), 7.99 (m, J=2.2 Hz, 1H).

(d) 3,10,11-Tribromo-9-fluoro-5H-dibenzo[a,d]cyclohepten-5-one

To 18.1 g (59.2 mmol) of 3-bromo-9-fluoro-10,11-dihydro-5H-dibenzo[a,d]cyclohepten-5-one and 21.4 g (120.2 mmol) of N-bromosuccineimide was added 120 ml of 1,2-dichloroethane, and the mixture was stirred at 40° C. for 6 hours under mercury lamp irradiation.

After completion of the reaction, chloroform was added to the reaction mixture, and the resulting mixture was washed with a saturated aqueous sodium hydrogen carbonate solution. The organic layer was dried over anhydrous magnesium sulfate, and concentrated under reduced pressure to obtain 28.9 g of the title compound as yellowish solid.

$^1$H-NMR ($\delta$, CDCl$_3$); 5.70 (d, J=5.6 Hz, 1H), 6.14 (d, J=5.9 Hz, 1H), 7.27-7.38 (m, 2H), 7.46-7.53 (m, 1H), 7.69 (dd, J=8.3 Hz, 2.2 Hz, 1H), 7.89-7.92 (m, 1H), 8.17 (d, J=2.2 Hz, 1H).

(e) 3-Bromo-9-fluoro-5H-dibenzo[a,d]cyclohepten-5-one

After dissolving 8.9 g (20 mmol) of 3,10,11-tribromo-9-fluoro-5H-dibenzo[a,d]cyclohepten-5-one in 50 ml of N,N-dimethylformamide under heating, the solution was cooled, and 14.4 g of sodium hydrosulfite and 18.5 g of sodium hydrogen carbonate was added to the solution and the resulting mixture was stirred at 40° C. for 2 hours.

After completion of the reaction, warm water was added to the reaction mixture and the mixture was stirred until a temperature thereof became room temperature, and precipitated solid was collected by filtration. The filtrated product was washed with water and dried under reduced pressure to obtain 5.1 g of the title compound as yellowish solid.

$^1$H-NMR ($\delta$, CDCl$_3$); 7.08 (d, J=12.5 Hz, 1H), 7.34-7.44 (m, 3H), 7.47-7.54 (m, 1H), 7.48 (dd, J=8.3 Hz, 2.2 Hz, 1H), 7.93-7.96 (m, 1H), 8.29 (d, J=2.2 Hz, 1H).

(f) 3-[(E)-2-(7-chloro-6-fluoroquinolin-2-yl)-ethenyl]-9-fluoro-5H-dibenzo[a,d]cyclohepten-5-one In 30 ml of N,N-dimethylformamide were dissolved 2.7 g (13 mmol) of 7-chloro-6-fluoro-2-vinyl quinoline and 3.0 g (10 mmol) of 3-bromo-9-fluoro-5H-dibenzo[a,d]cyclohepten-5-one, and then, 1.0 g (4.6 mmol) of palladium acetate (II), 0.52 g (4.6 mmol) of triphenylphosphine and 2.2 ml (16 mmol) of triethylamine were added to the solution and the resulting mixture was stirred at 100° C. for 4 hours under argon atmosphere.

After completion of the reaction, the reaction mixture was cooled to room temperature by allowing to stand, 50 ml of ethanol was added to the mixture and the resulting mixture was stirred, and then, precipitated solid was collected by filtration. The collected product by filtration was washed with ethanol to obtain 2.2 g of the title compound as pale green yellowish brown solid.

CI-MS (m/z); 430 (M$^+$+1). EI-MS (m/z); 429 (M$^+$). $^1$H-NMR ($\delta$, DMSO-d$_6$); 7.40 (s, 2H), 7.66-7.71 (m, 2H), 7.67 (d, J=16.1 Hz, 1H), 7.84 (d, J=8.3 Hz, 1H), 7.91-7.94 (m, 1H), 8.02 (d, J=16.1 Hz, 1H), 8.02 (d, J=9.1 Hz, 1H), 8.03 (d, J=9.8 Hz, 1H), 8.20 (dd, J=8.3 Hz, 1.7 Hz, 1H), 8.23 (d, J=7.8 Hz, 1H), 8.31 (d, J=1.7 Hz, 1H), 8.42 (d, J=8.8 Hz, 1H).

(g) 3-[(E)-2-(7-chloro-6-fluoroquinolin-2-yl)-ethenyl]-9-fluoro-5H-dibenzo[a,d]cyclohepten-5-ol In 153 ml of tetrahydrofuran was suspended 2.20 g (5.1 mmol) of 3-[(E)-2-(7-chloro-6-fluoroquinolin-2-yl)ethenyl]-9-fluoro-5H-dibenzo[a,d]cyclohepten-5-one, 100 mg (4.6 mmol) of lithium borohydride was added to the suspension under ice-cooling, and the mixture was returned to room temperature and stirred for 1 hour.

After completion of the reaction, the reaction mixture was ice-cooled and 50 ml of a saturated aqueous sodium hydrogen carbonate solution was poured to the mixture little by little, and after stirring at room temperature for 10 minutes, the resulting mixture was extracted with ethyl acetate. The organic layer was washed with water and further washed with a saturated aqueous sodium chloride solution one time. Then, the organic layer was dried over anhydrous magnesium sulfate and concentrated under reduced pressure to obtain 1.52 g of the title compound as yellowish solid.

CI-MS (m/z); 432 (M$^+$+1). EI-MS (m/z); 431 (M$^+$). $^1$H-NMR (δ, DMSO-d$_6$); 5.09 (bs, 1H), 6.36 (bs, 1H), 7.09-7.16 (m, 1H), 7.24 (dd, J=11.5 Hz, 1.5 Hz, 1H), 7.32 (d, J=11.7 Hz, 1H), 7.44-7.52 (m, 3H), 7.59 (d, J=7.8 Hz, 1H), 7.67 (dd, J=8.1 Hz, 1.9 Hz, 1H), 7.93 (d, J=16.1 Hz, 1H), 7.99-8.03 (m, 3H), 8.22 (d, J=7.6 Hz, 1H), 8.38 (d, J=8.5 Hz, 1H).

Reference Example 9

The reaction was carried out in the same manner as in Reference Example 8(a-g) to obtain the following compounds of Reference Example 9(a-g).

(a) 2-[2-(4-Bromophenyl)ethenyl]-3-chlorobenzoic acid

Appearance; white solid
$^1$H-NMR (δ, CDCl$_3$); 6.72 (d, J=16.6 Hz, 1H), 7.31-7.44 (m, 2H), 7.51-7.61 (m, 4H), 7.66-7.70 (m, 2H), 13.25 (b, 1H).

(b) 2-[2-(4-Bromophenyl)ethyl]-3-chlorobenzoic acid

Appearance; white solid
CI-MS (m/z); 341 (M$^+$+1). $^1$H-NMR (δ, CDCl$_3$); 2.77-2.83 (m, 2H), 3.22-3.27 (m, 2H), 7.21 (d, J=8.3 Hz, 1H), 7.36 (t, J=7.8 Hz, 1H), 7.50 (d, J=8.5 Hz, 1H), 7.66 (dd, J=8.1 Hz, 2.2 Hz, 1H), 7.75 (dd, J=7.8 Hz, 1.2 Hz, 1H), 13.28 (b, 1H).

(c) 3-Bromo-9-chloro-10,11-dihydro-5H-dibenzo[a,d]-cyclohepten-5-one

Appearance; yellowish brown solid
CI-MS (m/z); 323 (M$^+$+1). $^1$H-NMR (δ, CDCl$_3$); 3.13-3.17 (m, 2H), 3.31-3.35 (m, 2H), 7.12 (d, J=8.3 Hz, 1H), 7.26 (t, J=8.1 Hz, 1H), 7.52-7.56 (m, 2H), 7.62 (dd, J=7.8 Hz, 1.5 Hz, 1H), 7.97 (d, J=2.2 Hz, 1H).

(d) 3,10,11-Tribromo-9-chloro-5H-dibenzo[a,d]cyclohepten-5-one

Appearance; pale yellowish solid
$^1$H-NMR (δ, CDCl$_3$); 5.78 (d, J=5.9 Hz, 1H), 6.35 (d, J=5.9 Hz, 1H), 7.31 (d, J=8.3 Hz, 1H), 7.43 (t, J=7.8 Hz, 1H), 7.65 (dd, J=7.8 Hz, 1.2 Hz, 1H), 7.70 (dd, J=8.3 Hz, 2.2 Hz, 1H), 7.92 (dd, J=7.8 Hz, 1.5 Hz, 1H), 8.21 (d, J=2.2 Hz, 1H)

(e) 3-Bromo-9-chloro-5H-dibenzo[a,d]cyclohepten-5-one

Appearance; pale yellowish solid
CI-MS (m/z); 321 (M$^+$+1). EI-MS (m/z); 320 (M$^+$). $^1$H-NMR (δ, CDCl$_3$); 7.10 (d, J=12.5 Hz, 1H), 7.39-7.48 (m, 2H), 7.59 (d, J=12.7 Hz, 1H), 7.70-7.74 (m, 2H), 7.97 (dd, J=8.1 Hz, 1.2 Hz, 1H), 8.18 (d, J=1.7 Hz, 1H).

(f) 3-[(E)-2-(7-chloro-6-fluoroquinolin-2-yl)ethenyl]-9-chloro-5H-dibenzo[a,d]cyclohepten-5-one Appearance; green yellowish solid
CI-MS (m/z); 448 (M$^+$+1). EI-MS (m/z); 445 (M$^+$). $^1$H-NMR (δ, DMSO-d$_6$); 7.52 (d, J=12.5 Hz, 1H), 7.56 (d, J=12.7 Hz, 1H), 7.62-7.69 (m, 2H), 8.82 (d, J=8.3 Hz, 1H), 7.91-8.05 (m, 5H), 8.18-8.25 (m, 3H), 8.42 (d, J=9.0 Hz, 1H).

(g) 3-[(E)-2-(7-chloro-6-fluoroquinolin-2-yl)-ethenyl]-9-fluoro-5H-dibenzo[a,d]cyclohepten-5-ol Appearance; orange solid
CI-MS (m/z); 448 (M$^+$+1). $^1$H-NMR (δ, DMSO-d$_6$); 5.05 (bs, 1H), 6.45 (bs, 1H), 7.37-7.52 (m, 7H), 7.67 (dd, J=8.1 Hz, 1.7 Hz, 1H), 7.69 (d, J=7.3 Hz, 1H), 7.93 (d, J=16.1 Hz, 1H), 7.90-8.02 (m, 2H), 8.21 (d, J=7.3 Hz, 1H), 8.38 (d, J=8.8 Hz, 1H)

Reference Example 10

The reaction was carried out in the same manner as in Reference Example 8(a-e) to obtain the following compounds of Reference Example 10(a-e).

(a) 2-[2-(4-Bromophenyl)ethenyl]-3-iodobenzoic acid

Appearance; pale yellowish solid
CI-MS (m/z): 428 (M$^+$+1). EI-MS (m/z): 429 (M$^+$). $^1$H-NMR (δ, CDCl$_3$); 6.51 (d, J=16.6 Hz, 1H), 7.15 (t, J=7.8 Hz, 1H), 7.29 (d, J=16.4 Hz, 1H), 7.53 (d, J=8.5 Hz, 1H), 7.59 (d, J=8.5 Hz, 1H), 7.69 (dd, J=7.8 Hz, 1.2 Hz, 1H), 8.07 (dd, J=7.8 Hz, 1.2 Hz, 1H), 13.28 (b, 1H).

(b) 2-[2-(4-Bromophenyl)ethyl]-3-iodobenzoic acid

Appearance; white solid
CI-MS (m/z); 431 (M$^+$+1). $^1$H-NMR (δ, CDCl$_3$); 2.75-2.83 (m, 2H), 3.20-3.25 (m, 2H), 7.09 (t, J=7.8 Hz, 1H), 7.24 (d, J=8.3 Hz, 1H), 7.52 (d, J=8.3 Hz, 1H), 7.78 (dd, J=7.8 Hz, 1.5 Hz, 1H), 8.06 (dd, J=7.8 Hz, 1.2 Hz, 1H), 13.3 (b, 1H).

(c) 3-Bromo-9-iodo-10,11-dihydro-5H-dibenzo[a,d]-cyclohepten-5-one

Appearance; yellowish solid
CI-MS (m/z); 413 (M$^+$+1). $^1$H-NMR (δ, CDCl$_3$); 3.13-3.17 (m, 2H), 3.31-3.33 (m, 2H), 7.01 (t, J=7.8 Hz, 1H), 7.11 (d, J=8.3 Hz, 1H), 7.55 (dd, J=8.1 Hz, 2.2 Hz, 1H), 7.75 (dd, J=7.8 Hz, 1.5 Hz, 1H), 7.98-8.01 (m, 2H).

(d) 3,10,11-Tribromo-9-iodo-5H-dibenzo[a,d]cyclohepten-5-one

Appearance; yellowish solid
$^1$H-NMR (δ, CDCl$_3$); 5.80 (d, J=5.9 Hz, 1H), 6.17 (d, J=6.1 Hz, 1H), 7.14 (t, J=7.8 Hz, 1H), 7.31 (d, J=8.1 Hz, 1H), 7.71 (dd, J=8.3 Hz, 2.2 Hz, 1H), 8.10 (dd, J=7.8 Hz, 1.2 Hz, 1H), 7.24 (d, J=2.2 Hz, 1H).

(e) 3-Bromo-9-iodo-5H-dibenzo[a,d]cyclohepten-5-one

CI-MS (m/z); 413 (M$^+$+1). $^1$H-NMR ($\delta$, CDCl$_3$); 7.05 (d, J=12.5 Hz, 1H), 7.18 (t, J=7.8 Hz, 1H), 7.35-7.42 (m, 2H), 7.72 (dd, J=8.3 Hz, 2.2 Hz, 1H), 8.00 (dd, J=8.1 Hz, 1.0 Hz, 1H), 8.13 (d, J=2.2 Hz, 1H), 8.21 (dd, J=7.8 Hz, 1.2 Hz, 1H).

(f) 3-Bromo-9-trifluoromethyl-5H-dibenzo[a,d]cyclohepten-5-one

In 28 ml of N,N-dimethylformamide were suspended 6.2 g (15.1 mmol) of 3-bromo-9-iodo-5H-dibenzo[a,d]cyclohepten-5-one obtained in Reference Example 10(e) and 1.15 g (0.60 mmol) of copper (I) iodide, 11.61 g (60.4 mmol) of fluorosulfonyl(difluoro)methyl acetate was added to the suspension, and the resulting mixture was stirred at 80° C. for 21 hours under argon atmosphere.

After completion of the reaction, the reaction mixture was cooled to room temperature by allowing to stand, diluted with ethyl acetate and precipitated material was filtered off, and the filtrate was successively washed with water and a saturated aqueous sodium chloride solution. The organic layer was dried over anhydrous sodium sulfate, concentrated and the residue was applied to silica gel column chromatography (eluent: hexane/ethyl acetate=9/1(volume ratio)) to obtain 4.0 g of the title compound as pale yellowish solid.

CI-MS (m/z); 355 (M$^+$+1). EI-MS (m/z); 354 (M$^+$). $^1$H-NMR ($\delta$, DMSO-d$_6$); 7.14 (d, J=12.5 Hz, 1H), 7.39-7.43 (m, 2H), 7.61 (t, J=8.3 Hz, 1H), 7.75 (dd, J=8.3 Hz, 2.2 Hz, 1H), 7.99 (d, J=7.8 Hz, 1H), 8.15 (d, J=2.2 Hz, 1H) 8.19 (d, J=8.5 Hz, 1H).

The reaction was carried out in the same manner as in Reference Example 8(f) to obtain the following compound of Reference Example 10(g).

(g) 3-[(E)-2-(7-chloro-6-fluoroquinolin-2-yl)-ethenyl]-9-trifluoromethyl-5H-dibenzo[a,d]cyclohepten-5-one Appearance; yellowish solid CI-MS (m/z); 482 (M$^+$+1). EI-MS (m/z); 479 (M$^+$). $^1$H-NMR ($\delta$, DMSO-d$_6$); 7.35 (dd, J=12.5 Hz, 1.7 Hz, 1H), 7.50 (d, J=12.7 Hz, 1H), 7.67 (d, J=16.4 Hz, 1H), 7.79-7.87 (m, 2H), 7.97-8.04 (m, 3H), 8.16-8.24 (m, 5H), 8.42 (d, J=8.8 Hz, 1H).

The reaction was carried out in the same manner as in Reference Example 8(g) to obtain the following compound of Reference Example 10(h).

(h) 3-[(E)-2-(7-chloro-6-fluoroquinolin-2-yl)-ethenyl]-9-trifluoromethyl-5H-dibenzo[a,d]cyclohenpten-5-ol Appearance; pale yellowish solid CI-MS (m/z): 482 (M$^+$+1). $^1$H-NMR ($\delta$, DMSO-d$_6$); 5.05 (bs, 1H), 6.53 (bs, 1H), 7.32-7.69 (m, 7H), 7.94 (d, J=16.4 Hz, 1H), 7.99-8.02 (m, 3H), 8.10 (d, J=6.8 Hz, 1H), 8.21 (d, J=7.6 Hz, 1H), 8.79 (d, J=8.8 Hz, 1H).

Reference Example 11

The reaction was carried out in the same manner as in Reference Example 8(f) to obtain the following compound of Reference Example 11(a).

(a) 3-[(E)-2-(5,6,7,8-tetrahydroquinolin-2-yl)-ethenyl]-9-trifluoromethyl-5H-dibenzo[a,d]cyclohepten-5-one Appearance; brown solid CI-MS (m/z); 432 (M$^+$+1). $^1$H-NMR ($\delta$, DMSO-d$_6$); 1.74-1.92 (m, 4H), 2.72-2.87 (m, 4H), 7.31 (dd, J=12.7 Hz, 2.2 Hz, 1H), 7.36-7.53 (m, 4H), 7.66-7.83 (m, 3H), 8.07 (dd, J=8.0 Hz, 1.7 Hz, 1H), 8.11-8.21 (m, 3H).

The reaction was carried out in the same manner as in Reference Example 8(g) to obtain the following compound of Reference Example 11(b).

(b) 3-[(E)-2-(5,6,7,8-tetrahydroquinolin-2-yl)-ethenyl]-9-trifluoromethyl-5H-dibenzo[a,d]cyclohepten-5-ol Appearance; gray solid CI-MS (m/z); 434 (M$^+$+1). $^1$H-NMR ($\delta$, DMSO-d$_6$); 1.75-1.85 (m, 4H), 2.72-2.86 (m, 4H), 5.03 (bs, 1H), 6.46 (bs, 1H), 7.27 (d, J=16.1 Hz, 1H), 7.33-7.46 (m, 4H), 7.54-7.67 (m, 3H), 7.94 (s, 1H) 8.08 (d, J=7.3 Hz, 1H).

Reference Example 12

(a) 2-Chloro-6-methylbenzoic acid

To a liquid in which 42.5 g (0.43 mol) of copper (I) chloride had been suspended in 700 ml of acetonitrile was: added 39.9 g (0.39 mol) of t-butyl nitrite, and the mixture was warmed to 55° C. To the liquor was added 40.0 g (0.26 mol) of 2-amino-6-methylbenzoic acid by dividing into portions. After stirring at 60° C. for 3 hours, the mixture was cooled to room temperature by allowing to stand.

After completion of the reaction, the reaction mixture was poured into a mixed solution of 1.5 liters of conc. hydrochloric acid and 1.5 liters of water, and extracted with chloroform. The organic layer was washed with a saturated aqueous ammonium chloride solution, and dried over anhydrous magnesium sulfate. The concentrate concentrated under reduced pressure was recrystallized from cyclohexane to obtain 21.8 g of the title compound as beige color solid.

CI-MS (m/z); 171 (M$^+$+1). $^1$H-NMR ($\delta$, CDCl$_3$); 2.45 (s, 3H), 7.15 (t, J=4.2 Hz, 1H), 7.26-7.28 (m, 2H), 9.94 (bs, 1H).

(b) Methyl 2-chloro-6-methylbenzoate

In 10 ml of N,N-dimethylformamide was dissolved 1.8 g (10.6 mmol) of 2-chloro-6-methylbenzoic acid, and then, 1.49 g (10.8 mmol) of potassium carbonate and 2.7 ml of methyl iodide were added to the solution, and the mixture was stirred at room temperature for 3 hours.

After completion of the reaction, water was added to the reaction mixture and the mixture was extracted with diethyl ether. The organic layer was successively washed with water and a saturated aqueous sodium chloride solution, dried over anhydrous magnesium sulfate, and concentrated under reduced pressure. The residue was applied to silica gel column chromatography (eluent: hexane/ethyl acetate=9/1 (volume ratio)) to obtain 1.69 g of the title compound as pale yellowish liquid.

CI-MS (m/z); 171 (M$^+$+1). $^1$H-NMR ($\delta$, CDCl$_3$); 2.32 (s, 3H), 3.95 (s, 3H), 7.10 (t, J=4.3 Hz, 1H), 7.22-7.23 (m, 2H).

(c) Methyl 2-chloro-6-bromomethylbenzoate

To 20.0 g (108 mmol) of methyl 2-chloro-6-methylbenzoate and 19.3 g (108 mmol) of N-bromosuccineimide was added 100 ml of 1,2-dichloroethane, and the mixture was stirred at 50° C. for 5 hours under mercury lamp irradiation.

After completion of the reaction, chloroform was added to the reaction mixture and the resulting mixture was washed with a saturated aqueous sodium hydrogen carbonate solution. The organic layer was dried over anhydrous magnesium sulfate and concentrated under reduced pressure, and hexane was added to the residue and precipitated material was removed by filtration. The filtrate was concentrated under reduced pressure to obtain 27.6 g of the title compound as pale yellowish liquid.

$^1$H-NMR ($\delta$, CDCl$_3$); 4.00 (s, 3H), 4.50 (s, 2H), 7.32-7.39 (m, 3H).

(d) 3-Chloro-2-methoxycarbonylbenzyltriphenylphosphonium bromide

To a mixture of 27.6 g of methyl 2-chloro-6-bromomethylbenzoate and 39.0 g of triphenylphosphine was added 200 ml of acetonitrile, and the mixture was stirred at 80° C. for 3 hours.

After completion of the reaction, the reaction mixture was concentrated under reduced pressure and diethyl ether was added to the residue. The precipitated solid was collected by filtration and dried under reduced pressure to obtain 44.6 g of the title compound as beige color solid.

$^1$H-NMR ($\delta$, CDCl$_3$); 3.66 (s, 3H), 5.62 (d, J=2.0 Hz, 2H), 7.32-7.39 (m, 18H).

(e) Methyl 6-[2-(4-bromophenyl)ethenyl]-2-chlorobenzoate

To a mixture of. 44.6 g (84.9 mmol) of 3-chloro-2-methoxycarbonylbenzyltriphenylphosphonium bromide and 16.7 g (90.4 mmol) of 4-bromobenzaldehyde was added 150 ml of acetonitrile, and then, 14.8 g (119 mmol) of 1,5-diazabicyclo[4,3,0]-5-nonene was added dropwise to the mixture. Thereafter, the mixture was refluxed for 3 hours.

After completion of the reaction, the reaction mixture was concentrated under reduced pressure, ethyl acetate was added to the residue and insoluble material was removed by filtration. The filtrate was successively washed with a 5% aqueous potassium hydrogen sulfate solution, a saturated aqueous sodium hydrogen carbonate solution and a saturated aqueous sodium chloride solution in this order. The organic layer was dried over anhydrous magnesium sulfate and concentrated under reduced pressure, and the residue was applied to silica gel column chromatography (eluent: hexane/ethyl acetate=9/1 (volume ratio)) to obtain 27.6 g of the title compound as colorless liquid.

$^1$H-NMR ($\delta$, CDCl$_3$); 3.95, 4.08 (each s, 3H in total), 6.61 (dd, J=12.2 Hz, 2.2 Hz, 1H), 6.97-7.17 (m, 3H), 7.28-7.58 (m, 6H).

Reaction was carried out in the same manner as in Reference Example 8(b) to obtain a compound of the following Reference Example 12(f).

(f) 6-[2-(4-Bromophenyl)ethyl]-2-chlorobenzoic acid

Appearance; white solid

CI-MS (m/z); 339 (M$^+$+1). $^1$H-NMR ($\delta$, CDCl$_3$); 2.84-2.98 (m, 4H), 6.99-7.06 (m, 2H), 7.26-7.29 (m, 3H), 7.35-7.39 (m, 2H).

The reaction was carried out in the same manner as in Reference Example 8(c) to obtain the following compound of Reference Example 12(g).

(g) 3-Bromo-6-chloro-10,11-dihydro-5H-dibenzo[a,d]-cyclohepten-5-one

Appearance; beige color solid

CI-MS (m/z): 323 (M$^+$+1). $^1$H-NMR ($\delta$, CDCl$_3$); 3.06-3.11 (m, 2H), 3.16-3.20 (m, 2H), 7.08 (d, J=8.3 Hz, 1H), 7.14 (dd, J=6.8 Hz, 1.7 Hz, 1H), 7.26-7.31 (m, 2H), 7.54 (dd, J=8.3 Hz, 2.4 Hz, 1H), 8.01 (d, J=2.2 Hz, 1H).

The reaction was carried out in the same manner as in Reference Example 8(d) to obtain the following compound of Reference Example 12 (h).

(h) 3,11-Dibromo-6-chloro-10-hydro-5H-dibenzo[a,d]-cyclohepten-5-one

Appearance; yellowish brown foamy solid.

$^1$H-NMR ($\delta$, CDCl$_3$); 3.37 (dd, J=14.9 Hz, 6.6 Hz, 1H), 3.74 (dd, J=14.9 Hz, 2.4 Hz, 1H), 5.56-5.74 (m, 1H), 7.19 (dd, J=7.3 Hz, 1.2 Hz, 1H), 7.33-7.43 (m, 3H), 7.68 (dd, J=8.3 Hz, 2.2 Hz, 1H), 8.98 (d, J=2.0 Hz, 1H).

(i) 3-Bromo-6-chloro-5H-dibenzo[a,d]cyclohepten-5-one

In 300 ml of ethyl acetate was dissolved 33.0 g of 3,11-dibromo-6-chloro-10-hydro-5H-dibenzo[a,d]cyclohepten-5-one obtained in Reference Example 12(h), and 150 ml of triethylamine was added to the solution and the resulting mixture was stirred at 80° C. for 90 minutes.

After completion of the reaction, the reaction mixture was cooled to room temperature by allowing to stand, and the mixture was concentrated under reduced pressure. Ethyl acetate was added to the residue, and the mixture was successively washed with a 5% aqueous potassium hydrogen sulfate solution, a saturated aqueous sodium hydrogen carbonate solution and a saturated aqueous sodium chloride solution in this order. The organic layer was dried over anhydrous magnesium sulfate. The solvent was removed under reduced pressure, and the residue was applied to silica gel column chromatography (eluent: toluene) to obtain 8.91 g of the title compound as brown solid.

CI-MS (m/z); 321 (M$^+$+1). $^1$H-NMR ($\delta$, CDCl$_3$); 6.98 (d, J=12.0 Hz, 1H), 7.04 (d, J=12.2 Hz, 1H), 7.35 (d, J=8.3 Hz, 1H), 7.41-7.47 (m, 2H), 7.57 (dd, J=7.3 Hz, 2.0 Hz, 1H), 7.68 (dd, J=8.3 Hz, 2.2 Hz, 1H), 8.98 (d, J=2.0 Hz, 1H).

The reaction was carried out in the same manner as in Reference Example 8(f) to obtain a compound of the following Reference Example 12(j).

(j) 3-[(E)-2-(7-chloro-6-fluoroquinolin-2-yl)-ethenyl]-6-chloro-5H-dibenzo[a,d]cyclohepten-5-one Appearance; yellowish brown solid $^1$H-NMR ($\delta$, DMSO-d$_6$); 7.25 (d, J=12.0 Hz, 1H), 7.30 (d, J=12.2 Hz, 1H), 7.62-7.77 (m, 5H), 8.00-8.04 (m, 4H), 8.13 (dd, J=8.3 Hz, 2.0 Hz, 1H), 8.22 (d, J=7.3 Hz, 1H), 8.41 (d, J=8.8 Hz, 1H).

The reaction was carried out in the same manner as in Reference Example 8(g) to obtain the following compound of Reference Example 12(k).

(k) 3-[(E)-2-(7-chloro-6-fluoroquinolin-2-yl)-ethenyl]-6-chloro-5H-dibenzo[a,d]cyclohepten-5-ol Appearance; beige color solid
$^1$H-NMR (δ, DMSO-$d_6$); 5.19 (d, J=3.7 Hz, 1H), 6.49-6.53 (m, 2H), 7.10 (d, J=11.7 Hz, 1H), 7.15 (d, J=12.0 Hz, 1H), 7.35 (t, J=7.8 Hz, 1H), 7.48-7.56 (m, 3H), 7.59 (d, J=2.4 Hz, 1H), 7.70 (dd, J=8.1 Hz, 1.5 Hz, 1H), 7.85 (s, 1H), 7.95 (d, J=16.4 Hz, 1H), 7.97-8.03 (m, 3H), 8.22 (d, J=7.3 Hz, 1H), 8.40 (d, J=8.8 Hz, 1H).

Reference Example 13

(a) 3-Bromo-8-chloro-10,11-dihydro-5H-dibenzo[a,d]-cyclohepten-5-one

The title compound was obtained as a by-product of Reference Example 12(g).

Appearance; beige color solid
CI-MS (m/z): 323 (M$^+$+1). $^1$H-NMR (δ, CDCl$_3$); 3.16 (s, 4H), 7.12 (d, J=8.3 Hz, 1H), 7.24 (d, J=2.2 Hz, 1H), 7.32 (dd, J=8.5 Hz, 2.0 Hz, 1H), 7.55 (dd, J=8.1 Hz, 2.2 Hz, 1H), 7.98 (d, J=8.3 Hz, 1H), 8.15 (d, J=2.2 Hz, 1H).

The reaction was carried out in the same manner as in Reference Example 8(d) to obtain the following compound of Reference Example 13(b).

(b) 3,10,11-Tribromo-8-chloro-5H-dibenzo[a,d]cyclohepten-5-one

Appearance; yellowish brown solid
$^1$H-NMR (δ, CDCl$_3$); 5.66 (d, J=5.6 Hz, 1H), 5.70 (d, J=5.6 Hz, 1H), 7.27 (d, J=8.3 Hz, 1H), 7.40 (d, J=2.2 Hz, 1H), 7.47 (dd, J=8.3 Hz, 2.0 Hz, 1H), 7.69 (dd, J=8.1 Hz, 2.2 Hz, 1H), 8.06 (d, J=8.5 Hz, 1H), 8.23 (d, J=2.2 Hz, 1H).

The reaction was carried out in the same manner as in Reference Example 8(e) to obtain the following compound of Reference Example 13(c).

(c) 3-Bromo-8-chloro-5H-dibenzo[a,d]cyclohepten-5-one

Appearance; beige color solid
1H-NMR (δ, CDCl$_3$); 6.96 (d, J=12.1 Hz, 1H), 7.03 (d, J=12.1 Hz, 1H), 7.41 (d, J=8.3 Hz, 1H), 7.51 (dd, J=8.3 Hz, 2.0 Hz, 1H), 7.53 (d, J=2.0 Hz, 1H), 7.74 (dd, J=8.3 Hz, 2.2 Hz, 1H), 8.16 (d, J=8.4 Hz, 1H), 8.36 (d, J=2.2 Hz, 1H).

The reaction was carried out in the same manner as in Reference Example 8(f) to obtain the following compound of Reference Example 13(d).

(d) 3-[(E)-2-(7-chloro-6-fluoroquinolin-2-yl)-ethenyl]-8-chloro-5H-dibenzo[a,d]cyclohepten-5-one Appearance; green-yellowish brown solid
$^1$H-NMR (δ, DMSO-$d_6$); 7.25 (d, J=12.0 Hz, 1H), 7.35 (d, J=12.2 Hz, 1H), 7.66 (d, J=6.4 Hz, 1H), 7.71 (dd, J=8.5 Hz, 2.2 Hz, 1H), 7.84 (d, J=8.3 Hz, 1H), 7.93 (d, J=2.2 Hz, 1H), 7.99-8.04 (m, 3H), 8.15 (d, J=8.8 Hz, 1H), 8.19-8.24 (m, 2H), 8.38 (d, J=1.7 Hz, 1H), 8.41 (d, J=9.0 Hz, 1H).

The reaction was carried out in the same manner as in Reference Example 8(g) to obtain the following compound of Reference Example 13(e).

(e) 3-[(E)-2-(7-chloro-6-fluoroquinolin-2-yl)-ethenyl]-8-chloro-5H-dibenzo[a,d]cyclohepten-5-ol Appearance; orange solid
$^1$H-NMR (δ, DMSO-$d_6$); 5.08 (d, J=4.2 Hz, 1H), 6.32 (b, 1H), 7.15 (d, J=11.5 Hz, 1H), 7.24 (d, J=11.7 Hz, 1H), 7.44-7.52 (m, 4H), 7.66 (dd, J=8.1 Hz, 2.0 Hz, 1H), 7.75 (d, J=9.0 Hz, 1H), 7.59 (d, J=16.4 Hz, 1H), 7.99-8.02 (m, 3H), 8.21 (d, J=7.3 Hz, 1H), 8.38 (d, J=8.8 Hz, 1H).

The invention claimed is:
1. A dibenzocycloheptene compound represented by the formula (I):

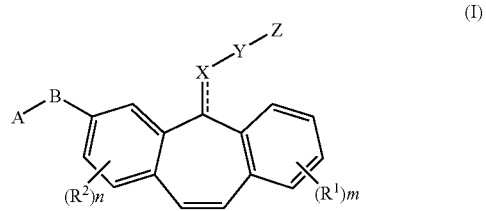

wherein R$^1$ represents a hydrogen atom, a halogen atom, a hydroxy group, a nitro group, a cyano group, a carbamoyl group, a formyl group, a carboxyl group, 1H-tetrazol-5-yl group, C$_1$-C$_4$ alkyl group, fluoro C$_1$-C$_4$ alkyl group, hydroxy C$_1$-C$_4$ alkyl group, C$_2$-C$_4$ alkenyl group, C$_2$-C$_4$ alkynyl group, C$_1$-C$_4$ alkoxy group, fluoro C$_1$-C$_4$ alkoxy group, C$_1$-C$_4$ alkylthio group, C$_1$-C$_4$ alkylsulfinyl group or C$_1$-C$_4$ alkylsulfonyl group,
R$^2$ represents a hydrogen atom, a halogen atom, a nitro group, a cyano group, C$_1$-C$_4$ alkyl group or C$_1$-C$_4$ alkoxy group,
A represents a 5-membered or 6-membered heteroaromatic ring group having 1 to 3 hetero atom(s) selected from the group consisting of a nitrogen atom, an oxygen atom and a sulfur atom or a heteroaromatic ring-fused group in which the heteroaromatic ring group and a benzene ring are fused, and the heteroaromatic ring group or fused heteroaromatic ring group may have a halogen atom, a nitro group, a cyano group, C$_1$-C$_4$ alkyl group, fluoro C$_1$-C$_4$ alkyl group, C$_1$-C$_4$ alkoxy group, fluoro C$_1$-C$_4$ alkoxy group, C$_1$-C$_4$ alkylthio group or C$_3$-C$_4$ alkylene group as a substituent(s),
B represents a formula: —CH═CH—,
X represents a sulfur atom,
Y represents a C$_1$-C$_{10}$ alkylene group which may have a halogen atom, C$_1$-C$_4$ alkyl group or C$_1$-C$_4$ alkoxy group as a substituent(s), or a group (a) of the formula:

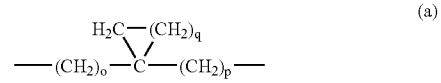

where o and p are each an integer of 0 to 2, and q is an integer of 1 to 4,
Z represents a carboxyl group which may be protected; 1H-tetrazol-5-yl group; a formula: —NH—SO$_2$—R$^3$; or a formula: —CO—NH—SO$_2$—R$^3$
where R$^3$ represents a C$_1$-C$_4$ alkyl group, a fluoro-C$_1$-C$_4$ alkyl group or a phenyl group which may have a halogen atom, a C$_1$-C$_4$ alkyl group, a fluoro-C$_1$-C$_4$ alkyl group, a $C_1$-$C_4$ alkoxy group, a fluoro-$C_1$-$C_4$ alkoxy group, a nitro group or a cyano group as a substituent(s), m is an integer of 1 to 4, when m is 2 or more, a plural number of $R^1$ may be different from each other, n is an integer of 1 to 3, and when n is 2 or more, a plural number of $R^2$ may be different from each other, ------ represents a single bond or a double bond, or a pharmaceutically acceptable salt thereof.

2. The dibenzocycloheptene compound or a pharmaceutically acceptable salt thereof according to claim 1, wherein $R^1$ of the compound represented by the formula (I) is selected from the group consisting of a hydrogen atom, a fluorine atom, a chlorine atom, a nitro group, a cyano group, a formyl group, a 1H-tetrazol-5-yl group, a methyl group, a difluoromethyl group, a trifluoromethyl group, a hydroxymethyl group, a 1-hydroxy-1-methylethyl group, a vinyl group, an ethynyl group, a methoxy group, a difluoromethoxy group, a trifluoromethoxy group, a methylthio group, a methylsulfinyl group and a methylsulfonyl group.

3. The dibenzocycloheptene compound or a pharmaceutically acceptable salt thereof according to claim 1, wherein $R^1$ of the compound represented by the formula (I) is selected from the group consisting of a hydrogen atom, a fluorine atom, a chlorine atom, a cyano group, a trifluoromethyl group, a hydroxymethyl group, a 1-hydroxy-1-methylethyl group, an ethynyl group, a methoxy group, a difluoromethoxy group, a trifluoromethoxy group, a methylsulfinyl group and a methylsulfonyl group.

4. The dibenzocycloheptene compound or a pharmaceutically acceptable salt thereof according to any one of claims 1 to 3, wherein $R^2$ of the compound represented by the formula (I) is selected from the group consisting of a hydrogen atom, a fluorine atom, a chlorine atom, a methyl group and a methoxy group.

5. The dibenzocycloheptene compound or a pharmaceutically acceptable salt thereof according to any one of claims 1 to 3, wherein $R^2$ of the compound represented by the formula (I) is a hydrogen atom.

6. The dibenzocycloheptene compound or a pharmaceutically acceptable salt thereof according to any one of claims 1 to 3, wherein A of the compound represented by the formula (I) is selected from the group consisting of 2-pyridyl, 2-benzothiazolyl, quinolin-2-yl, 5,6-difluoro-2-pyridyl, 5,6-dichloro-2-pyridyl, 5,6-dimethyl-2-pyridyl, 5,6,7,8-tetrahydroquinolin-2-yl, 6-fluoro-2-benzothiazolyl, 5-fluoro-2-benzothiazolyl, 5,6-difluoro-2-benzothiazolyl, 6-chloro-2-benzothiazolyl, 5-chloro-2-benzothiazolyl, 5,6-dichloro-2-benzothiazolyl, 5-chloro-6-fluoro-2-benzothiazolyl, 5-methyl-2-benzothiazolyl, 5-cyano-2-benzothiazolyl, 5-trifluoromethyl-2-benzothiazolyl, 5-methylthio-2-benzothiazolyl, 5-fluoroquinolin-2-yl, 6-fluoroquinolin-2-yl, 7-fluoroquinolin-2-yl, 5-chloroquinolin-2-yl, 6-chloroquinolin-2-yl, 7-chloroquinolin-2-yl, 7-methylquinolin-2-yl, 7-trifluoromethylquinolin-2-yl, 7-methoxyquinolin-2-yl, 7-difluoromethoxyquinolin-2-yl, 7-trifluoromethoxyquinolin-2-yl, 5,7-difluoroquinolin-2-yl, 6,7-difluoroquinolin-2-yl, 5,7-dichloroquinolin-2-yl, 6,7-dichloroquinolin-2-yl, 5-chloro-7-fluoroquinolin-2-yl, 6-chloro-7-fluoroquinolin-2-yl, 7-chloro-5-fluoroquinolin-2-yl, 7-chloro-6-fluoroquinolin-2-yl, 7-chloro-6-cyanoquinolin-2-yl, 7-cyano-6-fluoroquinolin-2-yl, 6-fluoro-7-trifluoromethylquinolin-2-yl and 5,6,7-trifluoroquinolin-2-yl group.

7. The dibenzocycloheptene compound or a pharmaceutically acceptable salt thereof according to any one of claims 1 to 3, wherein A of the compound represented by the formula (I) is selected from the group consisting of 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl and 7-chloro-6-fluoroquinolin-2-yl group.

8. The dibenzocycloheptene compound or a pharmaceutically acceptable salt thereof according to any one of claims 1 to 3, wherein Y of the compound represented by the formula (I) is selected from the group consisting of methylene, ethylene, trimethylene, difluoromethylene, 1-fluoroethylene, 2-fluoroethylene, 1,1-difluoroethylene, 2,2-difluoroethylene, ethylidene, 1-methylethylene, 2-methylethylene, 2,2-difluorotrimethylene, 1-methyltrimethylene, 2-methyltrimethylene, 1,1-dimethyltrimethylene, 2,2-dimethyltrimethylene, 3,3-dimethyltrimethylene and a group (a) of the formula:

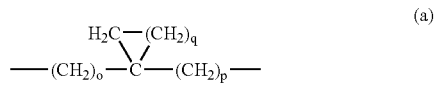

wherein o, p and q are each an integer of 1.

9. The dibenzocycloheptene compound or a pharmaceutically acceptable salt thereof according to any one of claims 1 to 3, wherein Y of the compound represented by the formula (I) is selected from the group consisting of methylene, ethylene, trimethylene, ethylidene, 1-methylethylene, 2-methylethylene and a group (a) of the formula:

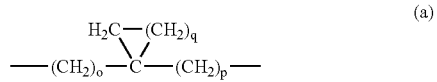

wherein o, p and q are each an integer of 1.

10. The dibenzocycloheptene compound or a pharmaceutically acceptable salt thereof according to any one of claims 1 to 3, wherein Z of the compound represented by the formula (I) is selected from the group consisting of carboxyl, methanesulfonylamino, trifluoromethanesulfonylamino, methanesulfonylaminocarbonyl and trifluoromethanesulfonylaminocarbonyl group.

11. The dibenzocycloheptene compound or a pharmaceutically acceptable salt thereof according to any one of claims 1 to 3, wherein Z of the compound represented by the formula (I) is a carboxyl group.

12. The dibenzocycloheptene compound or a pharmaceutically acceptable salt thereof according to any one of claims 1 to 3, wherein m of the compound represented by the formula (I) is 1 or 2.

13. The dibenzocycloheptene compound or a pharmaceutically acceptable salt thereof according to any one of claims 1 to 3, wherein n of the compound represented by the formula (I) is 1.

14. The dibenzocycloheptene compound or a pharmaceutically acceptable salt thereof according to claim 1, wherein $R^1$ of the compound represented by the formula (I) is selected from the group consisting of a hydrogen atom, a fluorine atom, a chlorine atom, a nitro group, a cyano group, a formyl group, a 1H-tetrazol-5-yl group, a methyl group, a difluoromethyl group, a trifluoromethyl group, a hydroxymethyl group, a 1-hydroxy-1-methylethyl group, a vinyl group, an ethynyl group, a methoxy group, a difluoromethoxy group, a trifluoromethoxy group, a methylthio group, a methylsulfinyl group and a methylsulfonyl group, $R^2$ is selected from the group consisting of a hydrogen atom, a fluorine atom, a chlorine atom, a methyl group and a methoxy group, A is selected from the group consisting of 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl and 7-chloro-6-fluoroquinolin-2-yl group, B is a formula: —CH=CH—, X is a sulfur atom, Y is selected from the group consisting of methylene, ethylene, trimethylene, difluoromethylene, 1-fluoroethylene, 2-fluoroethylene, 1,1-difluoroethylene, 2,2-difluoroethylene, ethylidene, 1-methylethylene, 2-methylethylene, 2,2-difluorotrimethylene, 1-methyltrimethylene, 2-methyltrimethylene, 1,1-dimethyltrimethylene, 2,2-dimethyltrimethylene, 3,3-dimethyltrimethylene and a group (a) of the formula:

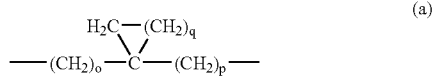

(a)

wherein o, p and q are each an integer of 1, Z is selected from the group consisting of carboxy, methanesulfonylamino, trifluoromethanesulfonylamino, methanesulfonylaminocarbonyl and trifluoromethanesulfonylaminocarbonyl group, m is 1 or 2, and n is 1.

15. The dibenzocycloheptene compound or a pharmaceutically acceptable salt thereof according to claim 1, wherein $R^1$ of the compound represented by the formula (I) is selected from the group consisting of a hydrogen atom, a fluorine atom, a chlorine atom, a cyano group, a trifluoromethyl group, a hydroxymethyl group, a 1-hydroxy-1-methylethyl group, an ethynyl group, a methoxy group, a difluoromethoxy group, a trifluoromethoxy group, a methylsulfinyl group and a methylsulfonyl group, $R^2$ is a hydrogen atom, A is selected from the group consisting of a 5,6,7,8-tetrahydroquinolin-2-yl, 7-fluoroquinolin-2-yl, 7-chloroquinolin-2-yl, 6,7-difluoroquinolin-2-yl, 6,7-dichloroquinolin-2-yl and 7-chloro-6-fluoroquinolin-2-yl group, B is a formula: —CH=CH—, X is a sulfur atom, Y is selected from the group consisting of a methylene, ethylene, trimethylene, ethylidene, 1-methylethylene, 2-methylethylene and a group (a) of the formula:

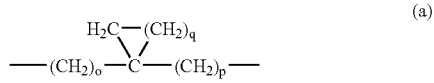

(a)

wherein o, p and q are each an integer of 1, Z is a carboxy group, m is 1 or 2, and n is 1.

16. The dibenzocycloheptene compound or a pharmaceutically acceptable salt thereof according to claim 1, wherein the compound represented by the formula (I) is selected from the group consisting of:

3-{[3-[(E)-2-(6,7-difluoroquinolin-2-yl)ethenyl]-5H-dibenzo[a,d]cyclohepten-5-yl]thio}propionic acid, 3-{[3-[(E)-2-(6,7-difluoroquinolin-2-yl)ethenyl]-5H-dibenzo[a,d]cyclohepten-5-yl]thio}-2-methylpropionic acid,

[3-[(E)-2-(7-chloro-6-fluoroquinolin-2-yl)ethenyl]-5H-dibenzo[a,d]cyclohepten-5-yl]thioacetic acid, 2-{[3-[(E)-2-(7-chloro-6-fluoroquinolin-2-yl)ethenyl]-5H-dibenzo[a,d]cyclohepten-5-yl]thio}propionic acid, 3-{[3-[(E)-2-(7-chloro-6-fluoroquinolin-2-yl)ethenyl]-5H-dibenzo[a,d]cyclohepten-5-yl]thio}propionic acid, 3-{[3-[(E)-2-(7-chloro-6-fluoroquinolin-2-yl)ethenyl]-5H-dibenzo[a,d]cyclohepten-5-yl]thiomethyl}cyclopropane acetic acid, 3-{[3-[(E)-2-(7-chloro-6-fluoroquinolin-2-yl)ethenyl]-9-fluoro-5H-dibenzo[a,d]cyclohepten-5yl]thio}propionic acid, 3-{[3-[(E)-2-(7-chloro-6-fluoroquinolin-2-yl)ethenyl]-9-chloro-5H-dibenzo[a,d]cyclohepten-5-yl]thio}propionic acid, 3-{[3-[(E)-2-(7-chloro-6-fluoroquinolin-2-yl)ethenyl]-8-chloro-5H-dibenzo[a,d]cyclohepten-5-yl]thio}propionic acid,

[3-[(E)-2-(7-chloro-6-fluoroquinolin-2-yl)ethenyl]-6-chloro-5H-dibenzo[a,d]cyclohepten-5-yl]thioacetic acid, 3-{[3-[(E)-2-(7-chloro-6-fluoroquinolin-2-yl)ethenyl]-6-chloro-5H-dibenzo[a,d]cyclopten-5yl]thio}propionic acid, 3-{[3-[(E)-2-(7-chloro-6-fluoroquinolin-2-yl)ethenyl]-9-trifluoromethyl-5H-dibenzo[a,d]cyclohepten-5-yl]-thio}propionic acid,

[3-[(E)-2-(7-chloroquinolin-2-yl)ethenyl]-5H-dibenzo[a,d]cyclohepten-5-yl]thioacetic acid, 3-{[3-[(E)-2-(7-chloroquinolin-2-yl)ethenyl]-5H-dibenzo[a,d]cyclohepten-5-yl]thio}propionic acid, 3-{[3-[(E)-2-(5,6,7,8-tetrahydroquinolin-2-yl)ethenyl]-5H-dibenzo[a,d]cyclohepten-5-yl]thio}propionic acid and 3-{[3-[(E)-2-(5,6,7,8-tetrahydroquinolin-2-yl)ethenyl]-9-trifluoromethyl-5H-dibenzo[a,d]cyclohepten-5yl]thio}-propionic acid.

17. A medical composition containing the dibenzocycloheptene compound or a pharmaceutically acceptable salt thereof according to any one of claims 1 to 3 as an effective ingredient.

18. The medical composition according to claim 17, wherein the medical composition is a composition for treatment of asthma.

19. A method of treatment of asthma which comprises administering the dibenzocycloheptene compound or a pharmaceutically acceptable salt thereof according to any one of claims 1 to 3 to a warm-blooded animal with a pharmaceutically effective amount.

20. The method according to claim 19, wherein the warm-blooded animal is human.

* * * * *